(12) United States Patent
Paek et al.

(10) Patent No.: US 9,222,073 B2
(45) Date of Patent: Dec. 29, 2015

(54) IMMORTALIZED MESENCHYMAL STROMAL CELL FROM ADIPOSE TISSUE

(71) Applicant: SNU R&DB Foundation, Seoul (KR)

(72) Inventors: Sun Ha Paek, Seoul (KR); Hyo Eun Moon, Seoul (KR); Hyung Woo Park, Incheon (KR); Hye Young Shin, Seoul (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 14/629,042

(22) Filed: Feb. 23, 2015

(65) Prior Publication Data
US 2015/0166959 A1 Jun. 18, 2015

Related U.S. Application Data

(63) Continuation of application No. 12/972,315, filed on Dec. 17, 2010, now abandoned.

(30) Foreign Application Priority Data

Jun. 18, 2010 (KR) .......................... 10-2010-0058273

(51) Int. Cl.
| | |
|---|---|
| C12N 5/0775 | (2010.01) |
| C12Q 1/68 | (2006.01) |
| G01N 33/50 | (2006.01) |
| C12N 5/077 | (2010.01) |

(52) U.S. Cl.
CPC ............ *C12N 5/0667* (2013.01); *C12N 5/0653* (2013.01); *C12Q 1/6883* (2013.01); *G01N 33/5023* (2013.01); *C12N 2510/04* (2013.01); *C12Q 2600/136* (2013.01); *C12Q 2600/158* (2013.01); *G01N 2800/2835* (2013.01)

(58) Field of Classification Search
None
See application file for complete search history.

(56) References Cited

U.S. PATENT DOCUMENTS

2001/0051344 A1 12/2001 Shalon et al.

OTHER PUBLICATIONS

Wolbank et al. Telomerase immortalized human amnion- and adipose-derived mesenchymal stem cells: Maintenance of differentiation and immunomodulatory characteristics. Tissue Engineering: Part A, vol. 15, No. 7, Jul. 2009, published online Jan. 6, 2009.*
Huang et al. Stabilization of cellular properties and differentiation multipotential of human mesenchymal stem cells transduced with hTERT gene in a long-term culture. Journal of Cellular Biochemistry, vol. 103, pp. 1256-1269, 2008.*
Kobune et al. Telomerized human multipotent mesenchymal cells can differentiate into hematopoietic and cobblestone area—supporting cells. Experimental Hematology, vol. 31, pp. 715-722, 2003.*
Hung et al. Establishment of immortalized mesenchymal stromal cells with red fluorescence protein expression for in vivo transplantation and tracing in the rat model with traumatic brain injury. Cytotherapy, vol. 12, pp. 455-465, 2010.*
Park et al. Disease-specific induced pluripotent stem cells. Cell, vol. 134, pp. 877-886, Sep. 2008.*
Bueler, H. Impaired mitochondrial dynamics and function in the pathogenesis of Parkinson's disease. Experimental Neurology, vol. 218, pp. 235-246, Mar. 18, 2009.*
Capeau, J. et al., Human Lipodystrophies: Genetic and Acquired Diseases of Adipose Tissue, Levy-Marchal C. Peinicaud L (eds): Adipose Tissue Development: From Animal Models to Clinical Conditions. *Endocr Dev. Basel, Karger*, vol. 19, (2010) pp. 1-20.
Dominici, M. et al., Minimal Criteria for Defining Multipotent Mesenchymal Stromal Cells, *The International Society for Cellular Therapy Position Statement, Cytotherapy*, vol. 8, No. 4 (2006) 315-317.
Eisen, M. B. et al., Cluster Analysis and Display of Genome-Wide Expression Patterns, *Genetics*, vol. 95, Issue 25 (1998) 14863-14868.
Huang, D. W. et al., Systematic and Integrative Analysis of Large Gene Lists Using DAVID Bioinformatics Resources, *Nature Procotols*, vol. 4, No. 1 (2009), 44-57.
Moon, H. et al., Genetic Profiling in Human Adipose Tissue-Derived Mesenchymal Stromal Cells from the Iodopathic and Familial Parkin-Deficient Patients of Parkinson's Disease in Comparison with Non-PD Patients, *Tissue Engineering and Regenerative Medicine*, vol. 7; No. 2, (2010) 237-247.
Moon, H. et al., Genetic Profiling and Mitochondria Dysfunction of Human Adipose Tissue-Derived Mesenchymal Stromal Cells From the Patients with Idiopathic and Parkin Defect Parkinson's Disease in Comparison with Non-PD Patients, *The Korean Society for Neurodegenerative Disease*, 2009, p. 88.
Saeed, A. I. et al., TM4: A Free, Open-Source System for Microarray Data Management and Analysis, *BioTechniques*, vol. 34, No. 2, (Feb. 2003) 374-378.
Soukas, A. et al., Leptin-specific Patterns of Gene Expression in White Adipose Tissue, *Genes Dev*, 14 (2000) 963-980.
Zuk, P. A. et al., Human Adipose Tissue Is a Source of Multipotent Stem Cells, *Molecular Biology of the Cell*, vol. 13, Dec. 2002, pp. 4279-4295.
Simon et al.; "Pitfalls in the Use of DNA Microarray Data for Diagnostic and Prognostic Classification"; *Journal of the National Cancer Institute*; vol. 95, No. 1; pp. 14-18; Jan. 2003.

(Continued)

*Primary Examiner* — Jennifer Dunston
(74) *Attorney, Agent, or Firm* — Alston & Bird LLP

(57) ABSTRACT

The present invention relates to a composition for diagnosing a Parkinson's disease comprising mesenchymal stromal cells derived from adipose tissue, a method of providing information for diagnosing Parkinson's disease and/or the extent of the disease progression, a biomarker for diagnosing a Parkinson's disease, a method of screening a drug candidate treating Parkinson's disease where the drug candidate is a target of the biomarker, and an immortalized mesenchymal stromal cell from adipose tissue.

5 Claims, 25 Drawing Sheets

(56) References Cited

OTHER PUBLICATIONS

Scherzer et al.; "Molecular Markers of Early Parkinson's Disease Based on Gene Expression in Blood"; *Proceedings of the National Academy of Sciences*, USA; vol. 104, No. 3; pp. 955-960; Jan. 2007.

Lee et al.; "Characterizaton and Expression Analysis of Mesenchymal Stem Cells from Human Bone Marrow and Adipose Tissue"; *Cellular Physiology and Biochemistry*; vol. 14; pp. 311-324; 2004.

Pradervand et al.; "Affymetrix Whole—Transcript Human Gene 1.0 ST Array is Highly Concordant with Standard 3' Expression Arrays"; *Biotechniques*; vol. 44; pp. 759-762; May 2008.

Pusztai and Hess; "Clinical Trial Design for Microarray Predictive Marker Discovery and Assessement"; *Annals of Oncology*; vol. 15; pp. 1731-1737; 2004.

Golub et al.; "Molecular Classification of Cancer: Class Discovery and Class Prediction by Gene Expression Monitoring"; *Science*; vol. 286; pp. 531-537; Oct. 1999.

Affymetrix [online] [retrieved Mar. 26, 2015]. Retrieved from the Internet: <URL: http://www.affymetrix.com/estore/. 1 page.

TM4: Microarray Software Suite [online] [retrieved Mar. 26, 2015]. Retrieved from the Internet: <URL: http://www.tm4.org/. 2 pages.

DAVID Functional Annotation Bioinformatics Microarray Analysis [online] [retrieved Mar. 26, 2015]. Retrieved from the Internet: <URL: http://david.abcc.ncifcrf.gov/home.jsp. 1 page.

Home—PubMed—NCBI [online] [retrieved Mar. 26, 2015]. Retrieved from the Internet: <URL: http://www.ncbi.nlm.nih.gov/pubmed. 1 page.

ImageJ [online] [retrieved Mar. 26, 2015]. Retrieved from the Internet: <URL: http://rsb.info.nih.gov/ij/. 1 page.

GEO Accession Viewer [online] [Retrieved Nov. 3, 2014]. Retrieved from the Internet: <URL: http://www.ncbi.nlm.nih.gov/geo/query/acc.cgi?acc=GSM511148>. (Dated Feb. 15, 2011). 2 pages.

GEO Accession Viewer [online] [Retrieved Nov. 3, 2014]. Retrieved from the Internet: <URL: http://www.ncbi.nlm.nih.gov/geo/query/acc.cgi?acc=GSM572410>. (Dated Jul. 13, 2011). 2 pages.

GEO Accession Viewer [online] [Retrieved Nov. 3, 2014]. Retrieved from the Internet: <URL: http://www.ncbi.nlm.nih.gov/geo/query/acc.cgi?acc=GSM572422>. (Dated Jul. 13, 2011). 2 pages.

GEO Accession Viewer [online] [Retrieved Nov. 3, 2014]. Retrieved from the Internet: <URL: http://www.ncbi.nlm.nih.gov/geo/query/acc.cgi?acc=GSM770571>. (Dated Nov. 22, 2011). 2 pages.

\* cited by examiner

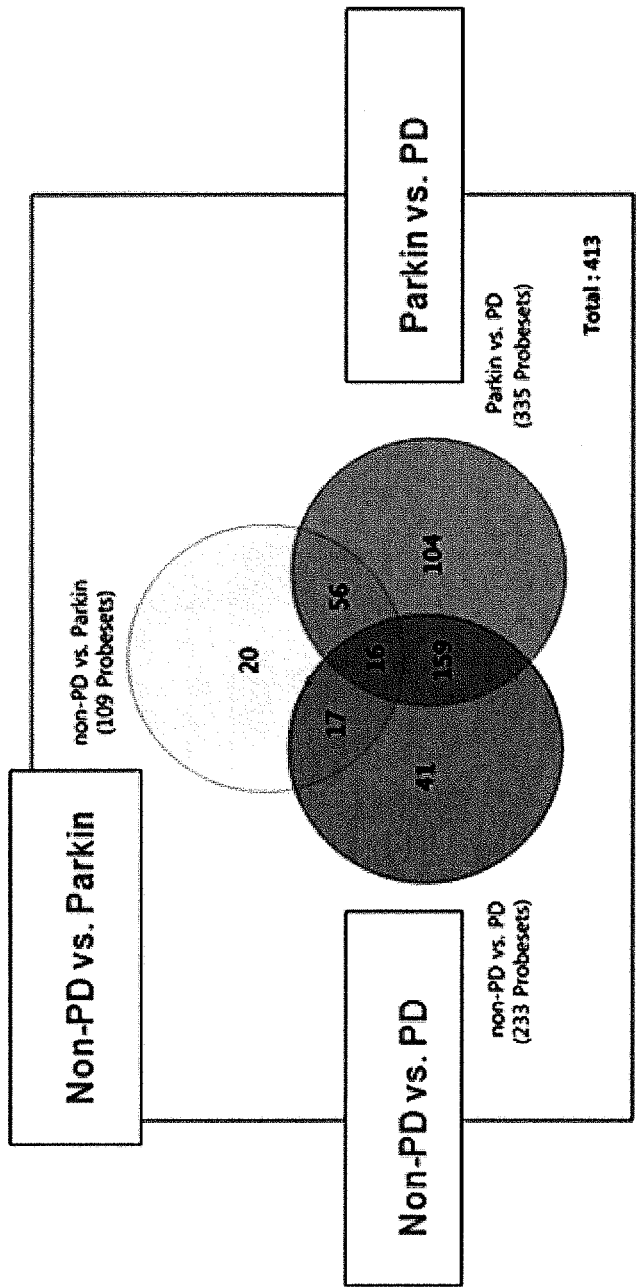

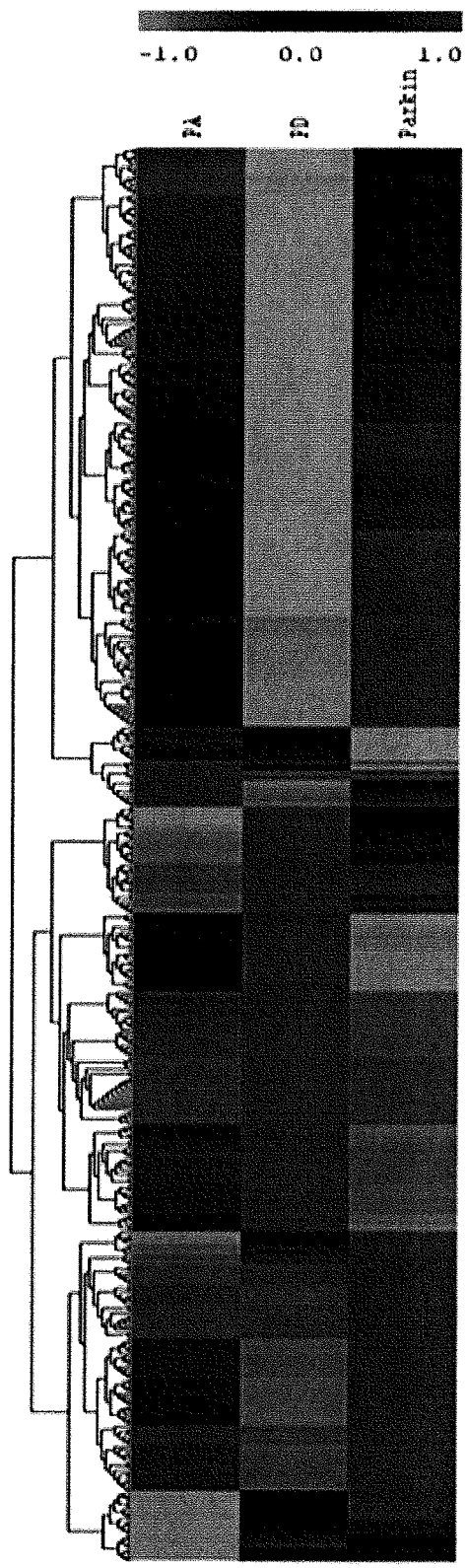

*non-PD* vs. *PD* Up-regulation

Complex I (NADH dehydrogenase)

Complex II (Succinate dehydrogenase)

Complex IV (Cytochrome C oxidase)

Fig. 15b
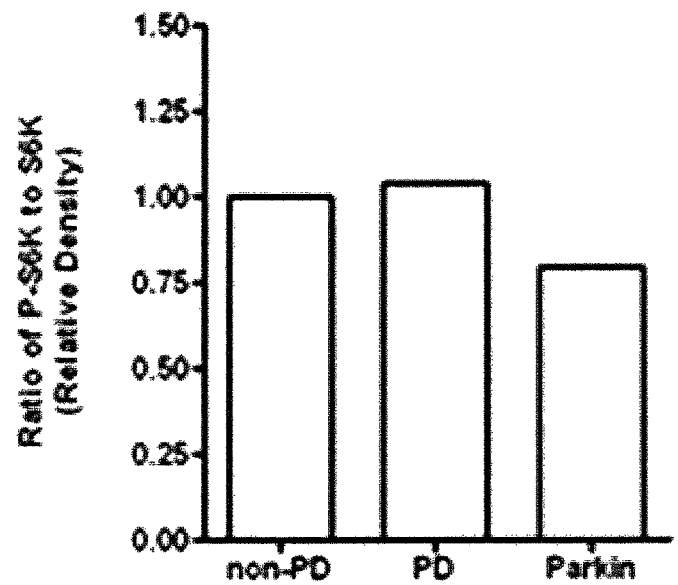
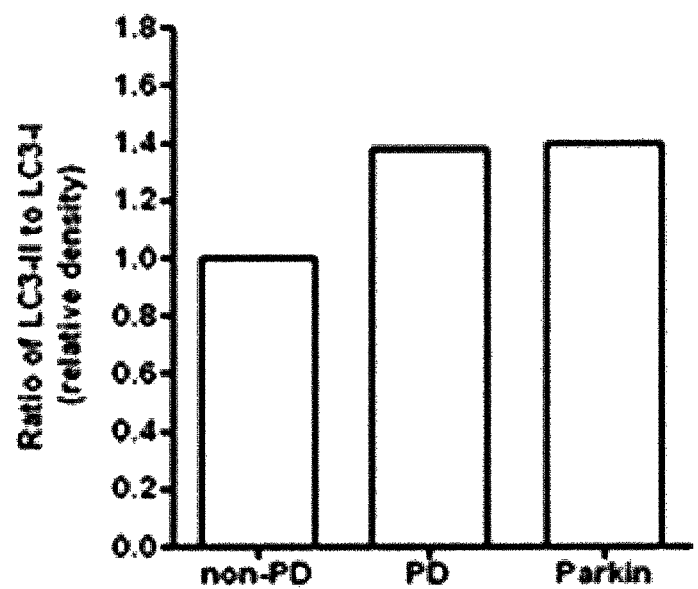

Fig. 16b
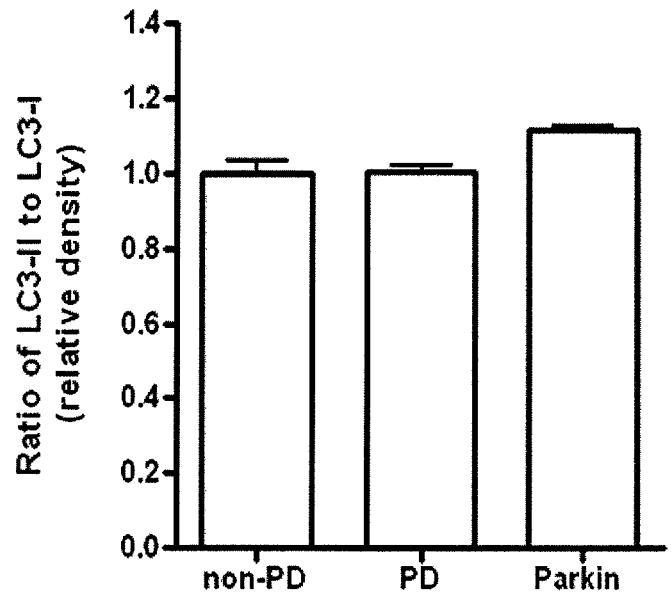
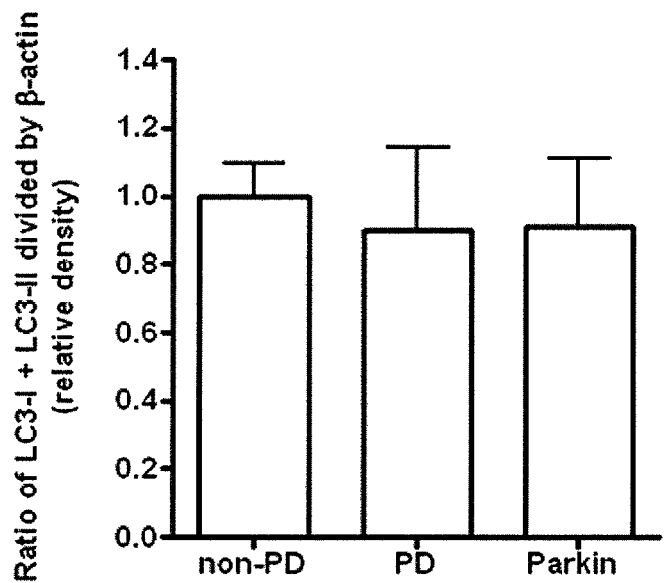

SEQUENCE LISTING

<160> NUMBER OF SEQ ID NOS: 54

<210> SEQ ID NO 1
<211> LENGTH: 3261
<212> TYPE: DNA
<213> ORGANISM: Artificial Sequence
<220> FEATURE:
<223> OTHER INFORMATION: ITGA8 (Genbank accession No: NM_003638)

<400> SEQUENCE: 1

| | | | | | |
|---|---|---|---|---|---|
| atgtcgcccg | gggccagccg | cggtccccgg | ggaagccagg | cgccgctgat | cgcgccctc | 60 |
| tgctgcgccg | cggccgcgct | ggggatgttg | ctgtggtccc | ccgcctgtca | ggcgttcaac | 120 |
| ctggacgtgg | aaaagctcac | agtgtacagc | ggccccaagg | gcagctactt | cggctacgcc | 180 |
| gtggacttcc | acatacccga | cgcccgcaca | gcgagtgtct | tggtggggc | gcccaaagcc | 240 |
| aacaccagcc | agcccgatat | cgtggaaggg | ggagccgtct | attactgtcc | ttggcccgcg | 300 |
| gagggtctg | cgcagtgcag | gcagataccg | tttgacacca | ccaacaacag | aaagatcaga | 360 |
| gttaatggaa | ccaaagaacc | tatcgagttc | aaatccaatc | agtggtttgg | agcaacagtg | 420 |
| aaagctcaca | aggaaaagt | tgtggcctgt | gctcctttat | atcactggag | aactcttaaa | 480 |
| ccgacaccag | aaaaggaccc | agttggcacc | tgctatgtag | caattcagaa | cttcagcgcc | 540 |
| tatgccgagt | tctctccttg | ccggaacagc | aatgctgatc | ggaaggcca | gggttactgc | 600 |
| caagcaggat | ttagtctgga | tttttataag | aatggagacc | ttattgtggg | aggacctggg | 660 |
| agtttctact | ggcaaggaca | agtgatcact | gccagtgttg | cagatatcat | tgcaaattac | 720 |
| tcattcaagg | atatcctcag | gaaactggca | ggagaaaagc | agacggaagt | ggctccagct | 780 |
| tcctatgatg | acagttacct | tggatactca | gttgctgctg | gggagtttac | tggggattct | 840 |
| cagcaagaat | tggttgctgg | aattccaaga | ggagcacaga | ttttggata | tgtttccatc | 900 |
| attaactcta | cggatatgac | gtttattcag | aatttcacgg | agaacagat | ggcatcttat | 960 |
| tttggatata | ccgttgtcgt | atcagatgtt | aacagtgatg | gactggatga | tgtcctggtt | 1020 |
| ggggcacctc | tctttatgga | acgtgaattt | gagagcaacc | ccagagaagt | agggcaaatc | 1080 |
| tacctgtatt | tgcaagtgag | ctctctcctc | ttcagagacc | cccagatcct | cactggcacc | 1140 |
| gagacgtttg | ggagattcgg | tagtgctatg | gcacacttag | agacctgaa | ccaagatgga | 1200 |
| tacaatgaca | ttgccatcgg | agtgcctttt | gcaggcaagg | atcaaagagg | caaagtgctc | 1260 |
| atttataatg | ggaacaaaga | tggcttaaac | accaagcctt | cccaagttct | gcaaggagtg | 1320 |
| tgggcctcac | atgctgtccc | ttccggattt | ggctttactt | taagaggaga | ttcagacata | 1380 |
| gacaagaatg | attacccaga | tttgattgtg | ggtgcatttg | aacaggaaa | agtcgctgtt | 1440 |
| tacagagcaa | gaccggttgt | gactgtagat | gcccagcttc | tgctgcaccc | aatgattatc | 1500 |
| aatcttgaaa | ataaaacttg | ccaggttcca | gactctatga | catctgctgc | ctgcttttct | 1560 |
| ttaagagtat | gtgcatctgt | cacaggccag | agcattgcaa | acacaatagt | cttgatggca | 1620 |
| gaggtgcaat | tagattccct | gaaacagaaa | ggagctatta | acggacgct | cttccttgat | 1680 |
| aaccatcagg | ctcatcgcgt | cttccctctt | gtgataaaaa | ggcagaaatc | ccaccagtgc | 1740 |
| caggatttca | tcgtttacct | tcgagatgaa | actgaattcc | gagataaatt | atctccaatc | 1800 |
| aacattagtt | tgaattacag | tttggacgaa | tccaccttta | agaaggcct | ggaagtgaaa | 1860 |
| ccaatattga | actactacag | agaaaacatt | gttagtgaac | aggctcacat | tctggtggac | 1920 |
| tgtggagaag | acaatctgtg | tgttcctgac | ttgaagctgt | cggctagacc | agataagcat | 1980 |
| caggtaatca | ttggagatga | aaatcacctt | atgctcataa | taaatgcaag | aaatgaaggg | 2040 |

| | |
|---|---|
| gaaggagcat atgaagctga actctttgta atgataccag aagaggcaga ttatgttgga | 2100 |
| atcgaacgca acaacaaggg atttcgacca ctgagctgtg agtacaagat ggaaaatgta | 2160 |
| accaggatgg tggtgtgtga ccttgggaac cctatggtgt ctggaacaaa ttattccctg | 2220 |
| ggcctccgat ttgcagttcc acgtcttgag aaaacaaaca tgagcattaa cttcgatctc | 2280 |
| caaatcagaa gttccaacaa ggacaatcca gacagcaatt ttgtgagcct gcaaatcaac | 2340 |
| atcactgctg tagcgcaggt ggaaataaga ggagtgtcac accctccgca gattgttctg | 2400 |
| cccattcata actgggaacc agaagaggag ccccacaaag aggaggaggt tggaccattg | 2460 |
| gtggaacata tttatgagct gcacaatatt ggaccaagta ccatcagtga caccatcctg | 2520 |
| gaggtgggct ggcctttctc tgcccgggat gaatttcttc tctatatttt ccatattcaa | 2580 |
| actctgggac tctgcagtg ccaaccaaat cctaatatca atccacagga tataaagcct | 2640 |
| gctgcctccc cagaggacac ccctgagctc agcgcctttt tgcgaaactc tactattcct | 2700 |
| catcttgtca ggaagaggga tgtacatgtg gtcgaattcc acagacagag ccctgcaaaa | 2760 |
| atactgaatt gtacaaatat cgagtgttta caaatctcct gtgcagtggg acgactcgaa | 2820 |
| ggaggagaaa gcgcagtcct gaaagtcagg tcacgattat gggcccacac cttcctccag | 2880 |
| agaaaaaatg atccctatgc tcttgcatcc ctggtgtcct ttgaagttaa aagatgcct | 2940 |
| tatacagatc agccagcaaa actcccagaa ggaagcatag caattaagac atcagttatt | 3000 |
| tgggcaactc cgaatgtttc cttctcaatc ccattatggg taataatact agcaatactt | 3060 |
| cttggattgt tggttctcgc cattttaacc ttagctttat ggaagtgtgg attcttttgac | 3120 |
| agagccagac ctcctcagga ggacatgacc gacagggaac agctgacaaa tgacaagacc | 3180 |
| cctgaggcat gacaagaaaa aaaaagaaga ccaaagacct caaacactgg tcctgttcaa | 3240 |
| agaaaaagaa agaacatgag g | 3261 |

<210> SEQ ID NO 2
<211> LENGTH: 1494
<212> TYPE: DNA
<213> ORGANISM: Artificial Sequence
<220> FEATURE:
<223> OTHER INFORMATION: CTSH (Genbank accession No: NM_004390)

<400> SEQUENCE: 2

| | |
|---|---|
| ccacgctcgt gccgctcccc ccccgcgctc ccagttgacg ctctgggccg ccacctccgc | 60 |
| ggaccctgag cgcaagagcc aagccgccag cgctgcgatg tgggccacgc tgccgctgct | 120 |
| ctgcgccggg gcctggctcc tgggagtccc cgtctgcggt gccgccgaac tgtgcgtgaa | 180 |
| ctccttagag aagtttcact tcaagtcatg gatgtctaag caccgtaaga cctacagtac | 240 |
| ggaggagtac caccacaggc tgcagacgtt tgccagcaac tggaggaaga taaacgccca | 300 |
| caacaatggg aaccacacat ttaaaatggc actgaaccaa ttttcagaca tgagctttgc | 360 |
| tgaaataaaa cacaagtatc tctggtcaga gcctcagaat tgctcagcca ccaaaagtaa | 420 |
| ctaccttcga ggtactggtc cctacccacc ttccgtggac tggcggaaaa aaggaaattt | 480 |
| tgtctcacct gtgaaaaatc agggtgcctg cggcagttgc tggacttct ccaccactgg | 540 |
| ggccctgag tctgcgatcg ccatcgcaac cggaaagatg ctgtccttgg cggaacagca | 600 |
| gctggtggac tgcgcccagg acttcaataa tcacggctgc caaggggtc tccccagcca | 660 |
| ggctttcgag tatatcctgt acaacaaggg gatcatgggt gaagacacct accccctacca | 720 |
| gggcaaggat ggttattgca agttccaacc tggaaaggcc atcggctttg tcaaggatgt | 780 |

| | |
|---|---|
| agccaacatc acaatctatg acgaggaagc gatggtggag gctgtggccc tctacaaccc | 840 |
| tgtgagcttt gcctttgagg tgactcagga cttcatgatg tatagaacgg gcatctactc | 900 |
| cagtacttcc tgccataaaa ctccagataa agtaaaccat gcagtactgg ctgttgggta | 960 |
| tggagaaaaa aatgggatcc cttactggat cgtgaaaaac tcttgggtc cccagtgggg | 1020 |
| aatgaacggg tacttcctca tcgagcgcgg aaagaacatg tgtggcctgg ctgcctgcgc | 1080 |
| ctcctacccc atccctctgg tgtgagccgt ggcagccgca gcgcagactg gcggagaagg | 1140 |
| agaggaacgg gcagcctggg cctgggtgga atcctgccc tggaggaagt tgtggggaga | 1200 |
| tccactggga cccccaacat tctgccctca cctctgtgcc cagcctggaa acctacagac | 1260 |
| aaggaggagt tccaccatga gctcacccgt gtctatgacg caaagatcac cagccatgtg | 1320 |
| ccttagtgtc cttcttaaca gactcaaacc acatggacca cgaatattct ttctgtccag | 1380 |
| aagggctact ttccacatat agagctccag ggactgtctt ttctgtattc gctgttcaat | 1440 |
| aaacattgag tgagcacctc cccagatgga gcatgctggt cctggaaaaa aaaa | 1494 |

<210> SEQ ID NO 3
<211> LENGTH: 2402
<212> TYPE: DNA
<213> ORGANISM: Artificial Sequence
<220> FEATURE:
<223> OTHER INFORMATION: CCRL1 (Genbank accession No: NM_178445)

<400> SEQUENCE: 3

| | |
|---|---|
| ttatgtttat tgtcctgttc aaatccaagc tctttcacac agaattgtac aagcaaagtt | 60 |
| tgagtaacta atcttggggt catattccaa tgtggctccc attaaagcat ttcaaagagt | 120 |
| gctagattca ggctcacata tgttacagca acaggctata ctctagggaa agaacaaaac | 180 |
| agcttgataa aaactgtttc cttttaagca tatttagaca aatatctatc ctgtattctc | 240 |
| tttgccatct agattggagc catggctttg gaacagaacc agtcaacaga ttattattat | 300 |
| gaggaaaatg aaatgaatgg cacttatgac tacagtcaat atgaactgat ctgtatcaaa | 360 |
| gaagatgtca gagaatttgc aaaagttttc ctccctgtat tcctcacaat agttttcgtc | 420 |
| attggacttg caggcaattc catggtagtg gcaatttatg cctattacaa gaaacagaga | 480 |
| accaaaacag atgtgtacat cctgaatttg gctgtagcag atttactcct tctattcact | 540 |
| ctgcctttt gggctgttaa tgcagttcat gggtgggttt tagggaaaat aatgtgcaaa | 600 |
| ataacttcag ccttgtacac actaaacttt gtctctggaa tgcagtttct ggcttgtatc | 660 |
| agcatagaca gatatgtggc agtaactaaa gtccccagcc aatcaggagt gggaaaacca | 720 |
| tgctggatca tctgtttctg tgtctggatg gctgccatct tgctgagcat accccagctg | 780 |
| gttttttata cagtaaatga caatgctagg tgcattccca ttttccccg ctacctagga | 840 |
| acatcaatga aagcattgat tcaaatgcta gagatctgca ttggatttgt agtacccttt | 900 |
| cttattatgg gggtgtgcta ctttatcaca gcaaggacac tcatgaagat gccaaacatt | 960 |
| aaaatatctc gacccctaaa agttctgctc acagtcgtta tagttttcat tgtcactcaa | 1020 |
| ctgccttata acattgtcaa gttctgccga gccatagaca tcatctactc cctgatcacc | 1080 |
| agctgcaaca tgagcaaacg catggacatc gccatccaag tcacagaaag catcgcactc | 1140 |
| tttcacagct gcctcaaccc aatcctttat gtttttatgg agcatctttt caaaaactac | 1200 |
| gttatgaaag tggccaagaa atatgggtcc tggagaagac agagacaaag tgtggaggag | 1260 |
| tttcctttg attctgaggg tcctacagag ccaaccagta cttttagcat ttaaaggtaa | 1320 |
| aactgctctg ccttttgctt ggatacatat gaatgatgct ttcccctcaa ataaaacatc | 1380 |

```
tgcattattc tgaaactcaa atctcagacg ccgtggttgc aacttataat aaagaatggg    1440
ttgggggaag ggggagaaat aaaagccaag aagaggaaac aagataataa atgtacaaaa    1500
catgaaaatt aaaatgaaca atataggaaa ataattgtaa caggcataag tgaataacac    1560
tctgctgtaa cgaagaagag ctttgtggtg ataattttgt atcttggttg cagtggtgct    1620
tatacaaatc tacacaagtg ataaaatgac acagaactat atacacacat tgtaccaatt    1680
tcaatttcct ggttttgaca ttatagtata attatgtaag atggaaccat tggggaaaac    1740
tgggtgaagg gtacccagga ccactctgta ccatctttgt aacttcctgt gaatttataa    1800
taatttcaaa ataaaacaag ttaaaaaaaa acccactatg ctataagtta ggccatctaa    1860
aacagattat taaagaggtt catgttaaaa ggcatttata attattttta attatctaag    1920
ttttaataca agaacgattt ccctgcataa ttttagtact tgaataagta tgcagcagaa    1980
ctccaactat cttttttcct gttttttta aatttgtaag taatttatata aaatccacct     2040 cctccaaaaa agcaataaaa aaaaaacaaa ctataataag cttttctgat tcttttcaaa    2100
acattcctgg taagttccta aagacataat ttgcttctat gatgtcaact ttcttactaa    2160
taactggtta tcatgacaaa tgttaggttt atcatatata gtctaggtgt aatcctcaga    2220
ctatcatttt catctgggtt ccaatttctt aacttcctaa agaattcatc tgtttataca    2280
agtctaccac tgccgattga ctaaaaaata cattatccca tgcataaaat gtcctatttt    2340
catttaaaca ctttattttt gagtaataaa aatatgtacc acaataaatt attgttaatt    2400
aa                                                                   2402

<210> SEQ ID NO 4
<211> LENGTH: 3183
<212> TYPE: DNA
<213> ORGANISM: Artificial Sequence
<220> FEATURE:
<223> OTHER INFORMATION: TGFB3 (Genbank accession No: NM_003239)

<400> SEQUENCE: 4
gacagaagca atggccgagg cagaagacaa gccgaggtgc tggtgaccct gggcgtctga     60
gtggatgatt ggggctgctg cgctcagagg cctgcctccc tgccttccaa tgcatataac    120
cccacacccc agccaatgaa gacgagaggc agcgtgaaca aagtcattta gaaagccccc    180
gaggaagtgt aaacaaaaga gaaagcatga atggagtgcc tgagagacaa gtgtgtcctg    240
tactgccccc acctttagct gggccagcaa ctgcccggcc ctgcttctcc ccacctactc    300
actggtgatc ttttttttt tacttttttt tccctttct tttccattct cttttcttat     360
tttctttcaa ggcaaggcaa ggattttgat tttgggaccc agccatggtc cttctgcttc    420
ttctttaaaa tacccacttt ctccccatcg ccaagcggcg tttggcaata tcagatatcc    480
actctattta ttttacccta aggaaaaact ccagctccct tcccactccc agctgccttg    540
ccacccctcc cagccctctg cttgccctcc acctggcctg ctgggagtca gagcccagca    600
aaacctgttt agacacatgg acaagaatcc cagcgctaca aggcacacag tccgcttctt    660
cgtcctcagg gttgccagcg cttcctggaa gtcctgaagc tctcgcagtg cagtgagttc    720
atgcaccttc ttgccaagcc tcagtctttg ggatctgggg aggccgcctg gttttcctcc    780
ctccttctgc acgtctgctg gggtctcttc ctctccaggc cttgccgtcc cctggcctc     840 tcttcccagc tcacacatga agatgcactt gcaaagggct ctggtggtcc tggccctgct    900
gaactttgcc acggtcagcc tctctctgtc cacttgcacc accttggact cggccacat    960
```

```
caagaagaag agggtggaag ccattagggg acagatcttg agcaagctca ggctcaccag    1020
cccccctgag ccaacggtga tgacccacgt cccctatcag gtcctggccc tttacaacag    1080
cacccgggag ctgctggagg agatgcatgg ggagagggag gaaggctgca cccaggaaaa    1140
caccgagtcg gaatactatg ccaaagaaat ccataaattc gacatgatcc aggggctggc    1200
ggagcacaac gaactggctg tctgccctaa aggaattacc tccaaggttt ccgcttcaa     1260 tgtgtcctca gtggagaaaa atagaaccaa cctattccga gcagaattcc gggtcttgcg    1320
ggtgcccaac cccagctcta agcggaatga gcagaggatc gagctcttcc agatccttcg    1380
gccagatgag cacattgcca aacagcgcta tatcggtggc aagaatctgc ccacacgggg    1440
cactgccgag tggctgtcct tgatgtcac tgacactgtg cgtgagtggc tgttgagaag     1500
agagtccaac ttaggtctag aaatcagcat tcactgtcca tgtcacacct tcagcccaa     1560 tggagatatc ctggaaaaca ttcacgaggt gatggaaatc aaattcaaag gcgtggacaa    1620
tgaggatgac catggccgtg gagatctggg gcgcctcaag aagcagaagg atcaccacaa    1680
ccctcatcta atcctcatga tgattccccc acaccggctc gacaacccgg gccagggggg    1740
tcagaggaag aagcgggctt tggacaccaa ttactgcttc cgcaacttgg aggagaactg    1800
ctgtgtgcgc cccctctaca ttgacttccg acaggatctg ggctggaagt gggtccatga    1860
acctaagggc tactatgcca acttctgctc aggcccttgc ccatacctcc gcagtgcaga    1920
cacaacccac agcacggtgc tgggactgta caacactctg aaccctgaag catctgcctc    1980
gccttgctgc gtgccccagg acctggagcc cctgaccatc ctgtactatg ttgggaggac    2040
ccccaaagtg gagcagctct ccaacatggt ggtgaagtct tgtaaatgta gctgagaccc    2100
cacgtgcgac agagagaggg gagagagaac caccactgcc tgactgcccg ctcctcggga    2160
aacacacaag caacaaacct cactgagagg cctggagccc acaaccttcg gctccgggca    2220
aatggctgag atggaggttt ccttttggaa catttctttc ttgctggctc tgagaatcac    2280
ggtggtaaag aaagtgtggg tttggttaga ggaaggctga actcttcaga acacacagac    2340
tttctgtgac gcagacagag gggatgggga tagaggaaag ggatggtaag ttgagatgtt    2400
gtgtggcaat gggatttggg ctaccctaaa gggagaagga agggcagaga atggctgggt    2460
cagggccaga ctggaagaca cttcagatct gaggttggat ttgctcattg ctgtaccaca    2520
tctgctctag ggaatctgga ttatgttata caaggcaagc attttttttt tttttttaaa    2580
gacaggttac gaagacaaag tcccagaatt gtatctcata ctgtctggga ttaagggcaa    2640
atctattact tttgcaaact gtcctctaca tcaattaaca tcgtgggtca ctacaggag     2700 aaaatccagg tcatgcagtt cctggcccat caactgtatt gggccttttg gatatgctga    2760
acgcagaaga aagggtggaa atcaacccte tcctgtctgc cctctgggtc cctcctctca    2820
cctctccctc gatcatattt cccctttggac acttggttag acgccttcca ggtcaggatg    2880
cacatttctg gattgtggtt ccatgcagcc ttggggcatt atgggttctt cccccacttc    2940
ccctccaaga ccctgtgttc atttggtgtt cctggaagca ggtgctacaa catgtgaggc    3000
attcggggaa gctgcacatg tgccacacag tgacttggcc ccagacgcat agactgaggt    3060
ataaagacaa gtatgaatat tactctcaaa atctttgtat aaataaatat ttttggggca    3120
tcctggatga tttcatcttc tggaatattg tttctagaac agtaaaagcc ttattctaag    3180
gtg                                                                   3183

<210> SEQ ID NO 5
<211> LENGTH: 3373
```

```
<212> TYPE: DNA
<213> ORGANISM: Artificial Sequence
<220> FEATURE:
<223> OTHER INFORMATION: DRD1 (Genbank accession No: NM_000794)

<400> SEQUENCE: 5
```

| | | | | | |
|---|---|---|---|---|---|
| ggctcgctgc | ctcgcattgc | cacaggctcc | tgagaggtcg | cgggcagtgc | ctgcggggag | 60 |
| gcgcggggcc | ctgctctgta | gggctgaagg | ccgcccgagg | ttcgccaagg | ctctgggctc | 120 |
| tcgaaaggaa | gccaagaaaa | gaagctgccc | aggtgaccag | tcctgggagt | gctctctccc | 180 |
| aaggaagctc | cgagcgccca | ggagccctta | gccgggtct | agtgcccttt | gaacaatctc | 240 |
| cagctcttca | aggaagtggg | ctgccgccgc | ctctcttggg | acctggcctg | ggatcctttc | 300 |
| cccaaacgca | ccccggcgat | ttttgcgcac | cgggagccga | accctgctg | cgcgcagctg | 360 |
| gctgggctca | ggcgcgcttc | ctcaacgttt | cggagccgct | gccccagcg | aagtccacat | 420 |
| tccaagctcc | aggggctttg | agagagacga | ccccaaggca | aggcgtttgg | agagctgctg | 480 |
| aggagccagg | ggcttggagg | agcgagaaga | catgtatttt | cagctgagtc | tcagaagggg | 540 |
| agaatctcct | gtcaccacca | gaaaagcaac | agccccgaaa | tgtgattgca | actgactagc | 600 |
| agagcagagg | cccaggagtc | actggattga | tgatttagaa | tatgctaaaa | agccagtgct | 660 |
| ttatttgggg | aattcagggg | cttttctggtg | cccaagacag | tgacctgcag | caagggagtc | 720 |
| agaagacaga | tgtagaaatc | aagagtgacc | atccacggga | ttgacttgga | ttgccactca | 780 |
| agcggtcctc | tcatggaatg | ttggtgaggc | cctctgccag | ggaagcaatc | tggctgtgca | 840 |
| aagtgctgcc | tggtggggag | gactcctgga | aatctgactg | accctattc | cctgcttggg | 900 |
| aacttgaggg | gtgtcagagc | ccctgatgtg | ctttctctta | ggaagatgag | gactctgaac | 960 |
| acctctgcca | tggacgggac | tgggctggtg | gtggagaggg | acttctctgt | tcgtatcctc | 1020 |
| actgcctgtt | tcctgtcgct | gctcatcctg | tccacgctcc | tggggaacac | gctggtctgt | 1080 |
| gctgccgtta | tcaggttccg | acacctgcgg | tccaaggtga | ccaacttctt | tgtcatctcc | 1140 |
| ttggctgtgt | cagatctctt | ggtggccgtc | ctggtcatgc | cctggaaggc | agtggctgag | 1200 |
| attgctggct | tctggccctt | tgggtccttc | tgtaacatct | gggtggcctt | tgacatcatg | 1260 |
| tgctccactg | catccatcct | caacctctgt | gtgatcagcg | tggacaggta | ttgggctatc | 1320 |
| tccagccctt | tccggtatga | gagaaagatg | acccccaagg | cagccttcat | cctgatcagt | 1380 |
| gtggcatgga | ccttgtctgt | actcatctcc | ttcatcccag | tgcagctcag | ctggcacaag | 1440 |
| gcaaaaccca | caagcccctc | tgatggaaat | gccacttccc | tggctgagac | catagacaac | 1500 |
| tgtgactcca | gcctcagcag | gacatatgcc | atctcatcct | ctgtaataag | ctttacatc | 1560 |
| cctgtggcca | tcatgattgt | cacctacacc | aggatctaca | ggattgctca | gaaacaaata | 1620 |
| cggcgcattg | cggccttgga | gagggcagca | gtccacgcca | agaattgcca | gaccaccaca | 1680 |
| ggtaatggaa | agcctgtcga | atgttctcaa | ccggaaagtt | cttttaagat | gtccttcaaa | 1740 |
| agagaaacta | aagtcctgaa | gactctgtcg | gtgatcatgg | gtgtgtttgt | gtgctgttgg | 1800 |
| ctacctttct | tcatcttgaa | ctgcattttg | cccttctgtg | gtctggggga | gacgcagccc | 1860 |
| ttctgcattg | attccaacac | ctttgacgtg | tttgtgtggt | ttgggtgggc | taattcatcc | 1920 |
| ttgaacccca | tcatttatgc | ctttaatgct | gattttcgga | aggcatttc | aaccctctta | 1980 |
| ggatgctaca | gactttgccc | tgcgacgaat | aatgccatag | agacggtgag | tatcaataac | 2040 |
| aatgggccg | cgatgttttc | cagccatcat | gagccacgag | gctccatctc | caaggagtgc | 2100 |
| aatctggttt | acctgatccc | acatgctgtg | ggctcctctg | aggacctgaa | aaaggaggag | 2160 |

| | |
|---|---:|
| gcagctggca tcgccagacc cttggagaag ctgtccccag ccctatcagt catattggac | 2220 |
| tatgacactg acgtctctct ggagaagatc caacccatca cacaaaacgg tcagcaccca | 2280 |
| acctgaactc gcagatgaat cctgccacac atgctcatcc caaaagctag aggagattgc | 2340 |
| tctggggctt gctattaaga aactaaggta cggtgagact ctgaggtgtc aggagagccc | 2400 |
| tctgctgctt tccaacacac aattaactcc gtttccaaat acattccagt gtattttctg | 2460 |
| tgttgttcat agtcaatcaa acagggacac tacaaacatg gggagccata agggacatgt | 2520 |
| ctttggcttc agaattgttt ttagaaattt attcttatct taggatttac caaatagggc | 2580 |
| aaagaatcaa cagtgaacag cttcacttaa aatcaaattt ttctgggaag aaaatgagat | 2640 |
| gggttgagtt tgctgtatac aaacaggtgc taacactgtt cccagcaaag ttttcagatt | 2700 |
| gtaaaggtag gtgcatgcct tcataaatta tttctaaaac attaattgag cttacagta | 2760 |
| ggagtgagaa attttttttcc agaattgaga gatgttttgt tgatattggt tctatttatt | 2820 |
| tattgtatat atggatattt ttaatttatg atataataaa tatatattta tcatatttaa | 2880 |
| taggataaat taatgagttt tatccaagac cttacaacca catttctggc catttaacta | 2940 |
| gcactttata agccaatgaa gcaaacacac agactctgtg agattctaaa tgttcatgtg | 3000 |
| taacttctag aaacacagca gaaactgata gataagggaa taaagttgaa atgattcctt | 3060 |
| aaaattcatg gacacagata aatgcaaggt gagaattgac aaatgctata aatgctttct | 3120 |
| ttttctgaaa agattttgaa aaatttaaaa aagtatagct actactgtgt tcaaaacgtt | 3180 |
| ttaaatgaca aatgactttc ccaggggaat ttgcagttct gtaaatatct taaataaaag | 3240 |
| ccaacttaag aagagcccag cattaaattt acgatcttag gtggtaatga aaagtatatg | 3300 |
| ctgctttgta tttatgtaaa ataattggcc ctctccatct tttctcattt catgtgtcag | 3360 |
| gtagttttttc tga | 3373 |

<210> SEQ ID NO 6
<211> LENGTH: 2492
<212> TYPE: DNA
<213> ORGANISM: Artificial Sequence
<220> FEATURE:
<223> OTHER INFORMATION: GNA14 (Genbank accession No: NM_004297)

<400> SEQUENCE: 6

| | |
|---|---:|
| agtcttagtc tgcggtcact gctgaggttt tcagaacttt ccaggcaaag gccagccagg | 60 |
| tcctttgcct ccaacccact ccgcgcctac ctcccgcctg gggacacccc taggcccagg | 120 |
| agatcctact ctcccccgag caccgacgtt ccaactcgtc tgcgccccg actgctgtcc | 180 |
| ggctcctgtg ccaaggggcg cgcgcatctt cccggggcca gcaacgctcc caacttctcg | 240 |
| actcgccctc ctcctcccca gagcgagagt ggggcgggct gagcccggat ccggggtgca | 300 |
| ctcgagcgtt cccagcgctc ggcattcacc ccgcctcaga gccgactttc gaaggggat | 360 |
| tgagcctcgg aggtccaggc gtcttactcc aaagctcaag tcggccccg tcttttcttt | 420 |
| ccacacccct gtgcccgtcg catgctggcc gggtgagcgg ccgggccgag gattcgggtg | 480 |
| cccgggccg cgtcgccccg tcgggtactg agctgagcgc accatggccg gctgctgctg | 540 |
| cctgtccgcg gaggagaagg agtcgcagcg catcagcgcg gagatcgagc gacagcttcg | 600 |
| tcgggacaag aaggacgcgc gccgtgagct taagctgctg ctgctgggaa ctggtgaaag | 660 |
| tgggaaaagc acctttatca agcagatgag aattatccat gggtctggtt acagcgacga | 720 |
| agacagaaag gggttcacga agctggttta ccaaaacata ttcaccgcca tgcaagccat | 780 |
| gatcagagcg atggacacgc taaggataca gtatgtgtgt gaacagaata aggaaaatgc | 840 |

-continued

```
ccagataatc agagaagtgg aagtggacaa ggtctccatg ctctccaggg agcaggtgga        900
ggccatcaag cagctctggc aagatccagg catccaggag tgttacgaca ggaggaggga        960
gtaccagctg tcggactctg ccaaatatta cctgactgac attgaccgca tcgccacacc       1020
atcattcgtg cctacccaac aagatgtgct tcgcgtccga gtgccaccaa ccggcatcat       1080
tgagtatcca tttgacttgg aaaacatcat ctttcggatg gtggatgttg gtggccaacg       1140
atcggaaaga cggaagtgga ttcactgctt tgagagtgtc acctccatta ttttcttggt       1200
tgctctgagt gaatatgacc aggtcctggc tgagtgtgac aacgagaatc gcatggaaga       1260
gagcaaagcc ttatttaaaa ccatcatcac ctaccctgg tttctgaatt cgtctgtgat        1320
tttattcttg aacaagaagg atcttttgga agagaaaatc atgtactctc atctaattag       1380
ctatttccca gaatacacag gaccgaaaca ggatgtcaga gctgccagag acttatcct        1440
gaagctttac caagatcaga atcctgacaa agagaaagtc atctactctc acttcacatg       1500
tgctacagat acagacaata ttcgctttgt gtttgctgct gtcaaagaca caattctaca       1560
gctaaaccta agggaattca accttgtcta aaagctgctg cccactcctc ccctataaca       1620
gaagatgtga tttgcaaact ccttgtttta tttgcaagtg cttctgacat caccagagcc       1680
agccccatgc caggaactaa ggatgtcatg tagatcgtgg ggacagagat gggtgatgga       1740
acttggaaga tatttgagtt taccaacata ctttaaaagt ccttcatcc caaattgtgt        1800
ttataattat tttcttgact tttggctata agattttgtg taattttga atttggtgtt        1860
ttctagaatt tttaaaagcc actttgattt agtttaaat atgtttaaaa atagcgatta        1920
aaattatgta agcaaggagc ctgttagttt atagatcatg ccttcaaacc tctagagtta       1980
atttgggtga cttttttaaa aataagaatg ttaatgggtt tgaagctttt tattaaacct       2040
tgtaatttag agacattttt aattgtgttt ctcacctcat gctgaagggt gactccttta       2100
acatgccacc aaagattttt tttaaacact tggttctttt tgtgtgttaa ctttctaagc       2160
caaattaatg gatatataag tatatctaat ttagctttgc cacagtttga tcaccaagaa       2220
gccaaagctg acatagagta aatgggctct agatagcata tatgttttat tggtgaaaaa       2280
tgtgtgtgtg tgcacgtgtg tgtgtgtgta cattttacc cccaatgtat atgaccagat        2340
cttaaaaatg tatgaaatgg ctagaagtcc acattgtttg acaaatgtta cgtaaccctg       2400
ccaaagttct gatggccacc acagatttgc tgtttgaatt atgtatgctg tgcctttctg       2460
aggaggctaa gaatatacca ttctgctatt aa                                     2492
```

<210> SEQ ID NO 7
<211> LENGTH: 1221
<212> TYPE: DNA
<213> ORGANISM: Artificial Sequence
<220> FEATURE:
<223> OTHER INFORMATION: PENK (Genbank accession No: NM_006211)

<400> SEQUENCE: 7

```
gtcgcggcga gggtcctgcc gagggacccc gttctgcgcc caggcaggct cgaagcacgc         60
gtccctctct cctcgcagtc catggcgcgg ttcctgacac tttgcacttg gctgctgttg       120
ctcggccccg ggtcctggc gaccgtgcgg gccaatgca gccaggattg cgcgacgtgc          180
agctaccgcc tagtgcgccc ggccgacatc aacttcctgg cttgcgtaat ggaatgtgaa       240
ggtaaactgc cttctctgaa aatttgggaa acctgcaagg agctcctgca gctgtccaaa       300
ccagagcttc tcaagatgg caccagcacc ctcagagaaa atagcaaacc ggaagaaagc        360
```

| | |
|---|---|
| catttgctag ccaaaaggta tgggggcttc atgaaaaggt atggaggctt catgaagaaa | 420 |
| atggatgagc tttatcccat ggagccagaa gaagaggcca atggaagtga gatcctcgcc | 480 |
| aagcggtatg ggggcttcat gaagaaggat gcagaggagg acgactcgct ggccaattcc | 540 |
| tcagacctgc taaaagagct tctggaaaca ggggacaacc gagagcgtag ccaccaccag | 600 |
| gatggcagtg ataatgagga agaagtgagc aagagatatg ggggcttcat gagaggctta | 660 |
| aagagaagcc cccaactgga agatgaagcc aaagagctgc agaagcgata tgggggcttc | 720 |
| atgagaagag taggtcgccc agagtggtgg atggactacc agaaacggta tggaggtttc | 780 |
| ctgaagcgct ttgccgaggc tctgccctcc gacgaagaag gcgaaagtta ctccaaagaa | 840 |
| gttcctgaaa tggaaaaaag atacggagga tttatgagat tttaatatct tttcccacta | 900 |
| gtggccccag gccccagcaa gcctccctcc atcctccagt gggaaactgt tgatggtgtt | 960 |
| ttattgtcat gtgttgcttg ccttgtatag ttgacttcat tgtctggata actatacaac | 1020 |
| ctgaaaactg tcatttcagg ttctgtgctc tttttggagt ctttaagctc agtattagtc | 1080 |
| tattgcagct atctcgtttt catgctaaaa tagttttgt tatcttgtct cttatttttg | 1140 |
| acaaacatca ataatgctt acttgtatat agagataata aacctattac cccaagtgca | 1200 |
| taaaaaaaaa aaaaaaaaa a | 1221 |

<210> SEQ ID NO 8
<211> LENGTH: 5059
<212> TYPE: DNA
<213> ORGANISM: Artificial Sequence
<220> FEATURE:
<223> OTHER INFORMATION: PRG4 (Genbank accession No: NM_005807)

<400> SEQUENCE: 8

| | |
|---|---|
| aaactcatct atcctttacg gcaagggtac ctacggtacc tgaaaacaac gatggcatgg | 60 |
| aaaacacttc ccatttacct gttgttgctg ctgtctgttt tcgtgattca gcaagtttca | 120 |
| tctcaagatt tatcaagctg tgcagggaga tgtggggaag ggtattctag agatgccacc | 180 |
| tgcaactgtg attataactg tcaacactac atggagtgct gccctgattt caagagagtc | 240 |
| tgcactgcgg agctttcctg taaggccgc tgctttgagt ccttcgagag agggagggag | 300 |
| tgtgactgcg acgcccaatg taagaagtat gacaagtgct gtcccgatta tgagagtttc | 360 |
| tgtgcagaag tgcataatcc cacatcacca ccatcttcaa agaaagcacc tccaccttca | 420 |
| ggagcatctc aaaccatcaa atcaacaacc aaacgttcac ccaaaccacc aaacaagaag | 480 |
| aagactaaga agttatag atcagaggaa ataacagaag aacattctgt ttctgaaaat | 540 |
| caagagtcct cctcctcctc ctcctcttcc tcttcttctt caacaattcg gaaaatcaag | 600 |
| tcttccaaaa attcagctgc taatagaaa ttacagaaga aactcaaagt aaaagataac | 660 |
| aagaagaaca gaactaaaaa gaaacctacc cccaaaccac cagttgtaga tgaagctgga | 720 |
| agtggattgg acaatggtga cttcaaggtc acaactcctg cacgtctac cacccaacac | 780 |
| aataaagtca gcacatctcc caagatcaca acagcaaaac caataaatcc cagacccagt | 840 |
| cttccaccta ttctgatac atctaaagag acgtctttga cagtgaataa agagacaaca | 900 |
| gttgaaacta agaaactac tacaacaaat aaacagactt caactgatgg aaaagagaag | 960 |
| actacttccg ctaaagagac acaaagtata gagaaaacat ctgctaaaga tttagcaccc | 1020 |
| acatctaaag tgctggctaa acctacaccc aaagctgaaa ctacaaccaa aggccctgct | 1080 |
| ctcaccactc ccaaggagcc cacgccacc actcccaagg agcctgcatc taccacaccc | 1140 |
| aaagagccca cacctaccac catcaagtct gcacccacca ccccaagga gcctgcaccc | 1200 |

```
accaccacca agtctgcacc caccactccc aaggagcctg cacccaccac caccaaggag    1260
cctgcaccca ccactcccaa ggagcctgca cccaccacca ccaaggagcc tgcacccacc    1320
accaccaagt ctgcacccac cactcccaag gagcctgcac ccaccacccc caagaagcct    1380
gccccaacta cccccaagga gcctgcaccc accactccca aggagcctac acccaccact    1440
cccaaggagc ctgcacccac caccaaggag cctgcaccca ccactcccaa agagcctgca    1500
cccactgccc caagaagcc tgccccaact accccaagg agcctgcacc caccactccc    1560
aaggagcctg cacccaccac caaggagcc cttcaccca ccactcccaa ggagcctgca    1620
cccaccacca ccaagtctgc acccaccact accaaggagc tgcacccac cactaccaag    1680 tctgcaccca ccactcccaa ggagccttca cccaccacca ccaaggagcc tgcacccacc    1740
actcccaagg agcctgcacc caccacccc aagaagcctg ccccaactac ccccaaggag    1800
cctgcaccca ccactcccaa ggaacctgca cccaccacca caagaagcc tgcacccacc    1860 actcccaaag agcctgcccc aactaccccc aaggagactg cacccaccac cccaagaag    1920 ctcacgccca ccacccccga gaagctcgca cccaccaccc ctgagaagcc cgcacccacc    1980 accccctgagg agctcgcacc caccaccct gaggagccca cacccaccac ccctgaggag    2040
cctgctccca ccactcccaa ggcagcggct cccaacaccc taaggagcc tgctccaact    2100 accccctaagg agcctgctcc aactacccct aaggagcctg ctccaactac ccctaaggag    2160
actgctccaa ctaccctaa agggactgct ccaactaccc tcaaggaacc tgcacccact    2220
actcccaaga gcctgccccc aaggagcctt gcacccacca ccaccaagga gcccacatcc    2280
accacctgtg acaagccgcc tccaactacc cctaaggga ctgctccaac taccctaag    2340 gagcctgctc caactaccc taaggagcct gctccaacta cccctaaggg gactgctcca    2400
actaccctca aggaacctgc acccactact cccaagaagc ctgcccccaa ggagcttgca    2460
cccaccacca ccaagggggcc cacatccacc acctctgaca agcctgctcc aactacacct    2520
aaggagactg ctccaactac ccccaaggag cctgcaccca ctaccccaa gaagcctgct    2580 ccaactactc ctgagacacc tcctccaacc acttcagagg tctctactcc aactaccacc    2640
aaggagccta ccactatcca caaaagccct gatgaatcaa ctcctgagct ttctgcagaa    2700
cccacaccaa aagctcttga aaacagtccc aaggaacctg gtgtacctac aactaagact    2760
cctgcagcga ctaaacctga aatgactaca acagctaaag acaagacaac agaaagagac    2820
ttacgtacta caactgaaac tacaactgct gcacctaaga tgacaaaaga dacagcaact    2880
acaacagaaa aaaactaccga atccaaaata acagctacaa ccacacaagt aacatctacc    2940
acaactcaag ataccacacc attcaaaatt actactctta aaacaactac tcttgcaccc    3000
aaagtaacta caacaaaaaaa gacaattact accactgaga ttatgaacaa acctgaagaa    3060
acagctaaac caaagacag agctactaat tctaaagcga caactcctaa acctcaaaag    3120
ccaaccaaag cacccaaaaa acccacttct accaaaaagc caaaacaat gcctagagtg    3180 agaaaaccaa agacgacacc aactcccgc aagatgacat caacaatgcc agaattgaac    3240
cctacctcaa gaatagcaga agccatgctc caaaccacca ccagacctaa ccaaactcca    3300
aactccaaac tagttgaagt aaatccaaag agtgaagatg caggtggtgc tgaaggagaa    3360
acacctcata tgcttctcag gccccatgtg ttcatgcctg aagttactcc cgacatggat    3420
tacttaccga gagtacccaa tcaaggcatt atcatcaatc ccatgctttc cgatgagacc    3480
aatatatgca atggtaagcc agtagatgga ctgactactt tgcgcaatgg gacattagtt    3540
```

-continued

```
gcattccgag gtcattattt ctggatgcta agtccattca gtccaccatc tccagctcgc      3600
agaattactg aagtttgggg tattccttcc cccattgata ctgttttac taggtgcaac       3660 tgtgaaggaa aaactttctt ctttaaggat tctcagtact ggcgttttac caatgatata      3720
aaagatgcag ggtaccccaa accaattttc aaaggatttg gaggactaac tggacaaata     3780
gtggcagcgc tttcaacagc taaatataag aactggcctg aatctgtgta ttttttcaag     3840
agaggtggca gcattcagca gtatatttat aaacaggaac ctgtacagaa gtgccctgga    3900
agaaggcctg ctctaaatta tccagtgtat ggagaaacga cacaggttag gagacgtcgc    3960
tttgaacgtg ctataggacc ttctcaaaca cacaccatca gaattcaata ttcacctgcc     4020
agactggctt atcaagacaa aggtgtcctt cataatgaag ttaaagtgag tatactgtgg     4080
agaggacttc caaatgtggt tacctcagct atatcactgc ccaacatcag aaaacctgac    4140
ggctatgatt actatgcctt ttctaaagat caatactata acattgatgt gcctagtaga    4200
acagcaagag caattactac tcgttctggg cagaccttat ccaaagtctg gtacaactgt   4260
ccttagactg atgagcaaag gaggagtcaa ctaatgaaga aatgaataat aaattttgac    4320
actgaaaaac atttttattaa taaagaatat tgacatgagt ataccagttt atatataaaa    4380 atgttttaa acttgacaat cattacacta aaacagattt gataatctta ttcacagttg     4440
ttattgttta cagaccattt aattaatatt tcctctgttt attcctcctc tccctcccat     4500
tgcatggctc acacctgtaa aagaaaaaag aatcaaattg aatatatctt ttaagaattc    4560
aaaactagtg tattcactta ccctagttca ttataaaaaa tatctaggca ttgtggatat    4620
aaaactgttg ggtattctac aacttcaatg gaaattatta caagcagatt aatccctctt   4680
tttgtgacac aagtacaatc taaaagttat attggaaaac atggaaatat taaaatttta   4740
cacttttact agctaaaaca taatcacaaa gctttatcgt gttgtataaa aaaattaaca   4800
atataatggc aataggtaga gatacaacaa atgaatataa cactataaca cttcatattt    4860
tccaaatctt aatttggatt taaggaagaa atcaataaat ataaaatata agcacatatt    4920
tattatatat ctaaggtata caaatctgtc tacatgaagt ttacagattg gtaaatatca    4980
cctgctcaac atgtaattat ttaataaaac tttggaacat taaaaaaata aattggaggc    5040
ttaaaaaaaa aaaaaaaa                                                   5059
```

<210> SEQ ID NO 9
<211> LENGTH: 2880
<212> TYPE: DNA
<213> ORGANISM: Artificial Sequence
<220> FEATURE:
<223> OTHER INFORMATION: LGR5 (Genbank accession No: NM_003667)

<400> SEQUENCE: 9

```
tgctgctctc cgcccgcgtc cggctcgtgg cccctactt cgggcaccat ggacacctcc      60
cggctcggtg tgctcctgtc cttgcctgtg ctgctgcagc tggcgaccgg ggcagctct     120 cccaggtctg gtgtgttgct gaggggctgc cccacacact gtcattgcga gcccgacggc   180
aggatgttgc tcagggtgga ctgctccgac ctggggctct cggagctgcc ttccaacctc   240
agcgtcttca cctcctacct agacctcagt atgaacaaca tcagtcagct gctcccgaat    300 ccctgccca gtctccgctt cctggaggag ttacgtcttg cgggaaacgc tctgacatac   360
attcccaagg gagcattcac tggcctttac agtcttaaag ttcttatgct gcagaataat   420
cagctaagac acgtacccac agaagctctg cagaatttgc gaagccttca atccctgcgt   480
ctggatgcta accacatcag ctatgtgccc ccaagctgtt tcagtggcct gcattccctg   540
```

```
aggcacctgt ggctggatga caatgcgtta acagaaatcc ccgtccaggc ttttagaagt      600
ttatcggcat tgcaagccat gaccttggcc ctgaacaaaa tacaccacat accagactat      660
gcctttggaa acctctccag cttggtagtt ctacatctcc ataacaatag aatccactcc      720
ctgggaaaga aatgctttga tgggctccac agcctagaga ctttagatttt aaattacaat     780 aaccttgatg aattccccac tgcaattagg acactctcca accttaaaga actaggattt      840
catagcaaca atatcaggtc gatacctgag aaagcatttg taggcaaccc ttctcttatt      900
acaatacatt tctatgacaa tcccatccaa tttgttggga gatctgcttt tcaacattta      960
cctgaactaa gaacactgac tctgaatggt gcctcacaaa taactgaatt tcctgattta     1020
actggaactg caaacctgga gagtctgact ttaactggag cacagatctc atctcttcct     1080
caaaccgtct gcaatcagtt acctaatctc caagtgctag atctgtctta caacctatta     1140
gaagatttac ccagttttc agtctgccaa aagcttcaga aaattgacct aagacataat      1200
gaaatctacg aaattaaagt tgacactttc cagcagttgc ttagcctccg atcgctgaat     1260
ttggcttgga acaaaattgc tattattcac cccaatgcat tttccacttt gccatccta      1320 ataaagctgg acctatcgtc caacctcctg tcgtcttttc ctataactgg gttacatggt     1380
ttaactcact taaaattaac aggaaatcat gccttacaga gcttgatatc atctgaaaac     1440
tttccagaac tcaaggttat agaaatgcct tatgcttacc agtgctgtgc atttggagtg     1500
tgtgagaatg cctataagat ttctaatcaa tggaataaag gtgacaacag cagtatggac     1560
gaccttcata agaagatgc tggaatgttt caggctcaag atgaacgtga ccttgaagat     1620
ttcctgcttg actttgagga agacctgaaa gcccttcatt cagtgcagtg ttcaccttcc     1680
ccaggcccct tcaaaccctg tgaacacctg cttgatggct ggctgatcag aattggagtg     1740
tggaccatag cagttctggc acttacttgt aatgctttgg tgacttcaac agttttcaga     1800
tcccctctgt acatttcccc cattaaactg ttaattgggg tcatcgcagc agtgaacatg     1860
ctcacgggag tctccagtgc cgtgctggct ggtgtggatg cgttcacttt tggcagcttt     1920
gcacgacatg gtgcctggtg ggagaatggg gttggttgcc atgtcattgg ttttttgtcc     1980
atttttgctt cagaatcatc tgttttcctg cttactctgg cagccctgga gcgtgggttc     2040
tctgtgaaat attctgcaaa atttgaaacg aaagctccat tttctagcct gaaagtaatc     2100
attttgctct gtgccctgct ggccttgacc atggccgcag ttcccctgct gggtggcagc     2160
aagtatggcg cctcccctct ctgcctgcct ttgcctttg gggagccag caccatgggc      2220 tacatggtcg ctctcatctt gctcaattcc ctttgcttcc tcatgatgac cattgcctac     2280
accaagctct actgcaattt ggacaaggga gacctggaga atatttggga ctgctctatg     2340
gtaaaacaca ttgccctgtt gctcttcacc aactgcatcc taaactgccc tgtggctttc     2400
ttgtccttct cctctttaat aaaccttaca tttatcagtc ctgaagtaat aagtttatc     2460 cttctggtgg tagtcccact tcctgcatgt ctcaatcccc ttctctacat cttgttcaat     2520
cctcacttta aggaggatct ggtgagcctg agaaagcaaa cctacgtctg acaagatca     2580 aaacacccaa gcttgatgtc aattaactct gatgatgtcg aaaaacagtc ctgtgactca     2640
actcaagcct tggtaacctt taccagctcc agcatcactt atgacctgcc tcccagttcc     2700
gtgccatcac cagcttatcc agtgactgag agctgccatc tttcctctgt ggcatttgtc     2760
ccatgtctct aattaatatg tgaaggaaaa tgttttcaaa ggttgagaac ctgaaaatgt     2820
gagattgagt atatcagagc agtaattaat aagaagagct gaggtgaaac tcggtttaaa     2880
```

<210> SEQ ID NO 10
<211> LENGTH: 1697
<212> TYPE: DNA
<213> ORGANISM: Artificial Sequence
<220> FEATURE:
<223> OTHER INFORMATION: HLA-DPA1 (Genbank accession No: NM_033554)

<400> SEQUENCE: 10

```
atttccagtg ctagaggccc acagtttcag tctcatctgc ctccactcgg cctcagttcc      60
tcatcactgt tcctgtgctc acagtcatca attatagacc ccacaacatg cgccctgaag     120
acagaatgtt ccatatcaga gctgtgatct tgagagccct ctccttggct ttcctgctga     180
gtctccgagg agctggggcc atcaaggcgg accatgtgtc aacttatgcc gcgtttgtac     240
agacgcatag accaacaggg gagtttatgt ttgaatttga tgaagatgag atgttctatg     300
tggatctgga caagaaggag accgtctggc atctggagga gtttggccaa gccttttcct     360
ttgaggctca gggcgggctg gctaacattg ctatattgaa caacaacttg aataccttga     420
tccagcgttc caaccacact caggccacca acgatccccc tgaggtgacc gtgtttccca     480
aggagcctgt ggagctgggc cagcccaaca ccctcatctg ccacattgac aagttcttcc     540
caccagtgct caacgtcacg tggctgtgca cggggagct ggtcactgag ggtgtcgctg     600
agagcctctt cctgcccaga acagattaca gcttccacaa gttccattac ctgacctttg     660
tgccctcagc agaggacttc tatgactgca gggtggagca ctgggcttg gaccagccgc     720
tcctcaagca ctgggaggcc aagagccaa tccagatgcc tgagacaacg gagactgtgc     780
tctgtgccct gggcctggtg ctgggcctag tcggcatcat cgtgggcacc gtcctcatca     840
taaagtctct gcgttctggc catgaccccc gggcccaggg gaccctgtga aatactgtaa     900
aggtgacaaa atatctgaac agaagaggac ttaggagaga tctgaactcc agctgcccta     960
caaactccat ctcagctttt cttctcactt catgtgaaaa ctactccagt ggctgactga    1020
attgctgacc cttcaagctc tgtccttatc cattacctca aagcagtcat tccttagtaa    1080
agtttccaac aaatagaaat taatgacact ttggtagcac taatatggag attatccttt    1140
cattgagcct tttatcctct gttctccttt gaagaacccc tcactgtcac cttcccgaga    1200
atacccctaag accaataaat acttcagtat ttcagagcgg ggagactctg agtcattctt    1260
actggaagtc taggaccagg tcacatgtga atactatttc ttgaaggtgt ggtttcaacc    1320
tctgttgccg atgtggttac taaaggttct gatcccactt gaacggaaag gtctgaggat    1380
attgattcag tcctgggttt ttccctaact acaggatagg gtggggtaga gaaaggatat    1440
ttgggggaaa ttttacttgg atgaagattt tcttggatgt agtttgaaga ctgcagtgtt    1500
tgaagtctct gagggaagag atttggtctg tctggatcaa gatttcaggc agattaggat    1560
tccattcaca gccctgagc ttccttccca aggctgtatt gtaattatag caatatttca    1620
tggaggattt ttctacatga taaactaaga gccaagaaat aaaatttta aaatgcccta    1680
aaaaaaaaa aaaaaa                                                   1697
```

<210> SEQ ID NO 11
<211> LENGTH: 5115
<212> TYPE: DNA
<213> ORGANISM: Artificial Sequence
<220> FEATURE:
<223> OTHER INFORMATION: SCUBE3 (Genbank accession No: NM_152753)

<400> SEQUENCE: 11

```
ccagccatgg gctcggggcg cgtacccggg ctctgcctgc ttgtcctgct ggtccacgcc      60
```

-continued

```
cgcgccgccc agtacagcaa agccgcgcaa gatgtggatg agtgtgtgga ggggactgac    120
aactgccaca tcgatgctat ctgccagaac accccgaggt catacaagtg catctgcaag    180
tctggctaca caggggacgg caaacactgc aaagacgtgg atgagtgcga gcgagaggat    240
aatgcaggtt gtgtgcatga ctgtgtcaac atccctggca attaccggtg tacctgctat    300
gatggattcc acctggcaca tgacggacac aactgtctgg atgtggacga gtgtgccgag    360
ggcaacggcg gctgtcagca gagctgtgtc aacatgatgg gcagctatga gtgccactgc    420
cgggaaggct tcttcctcag cgacaaccag catacctgta tccagcggcc agaagaagga    480
atgaattgca tgaacaagaa ccacggctgt gcccacattt gccgggagac acccaagggg    540
ggtattgcct gtgaatgccg tcctggcttt gagcttacca agaaccaacg ggactgtaaa    600
ttgacatgca actatggtaa cggcggctgc cagcacacgt gtgatgacac agagcagggt    660
ccccggtgcg gctgccatat caagtttgtg ctccataccg acgggaagac atgcatcgag    720
acctgtgctg tcaacaacgg gggctgtgac agtaagtgcc atgatgcagc gactggtgtc    780
cactgcacct gccctgtggg cttcatgctg cagccagaca ggaagacgtg caaagatata    840
gatgagtgcc gcttaaacaa cggggggctgt gaccatattt gccgcaacac agtgggcagc    900
ttcgaatgca gttgcaagaa aggctataag cttctcatca atgagaggaa ctgccaggat    960
atagacgagt gttcctttga tcgaacctgt gaccacatat gtgtcaacac accaggaagc   1020
ttccagtgtc tctgccatcg tggctacctg ttgtatggta tcacccactg tggggatgtg   1080
gatgaatgca gcatcaaccg gggaggttgc gcctttggct gcatcaacac tcctggcagc   1140
taccagtgta cctgcccagc aggccagggt cggctgcact ggaatggcaa agattgcaca   1200
gagccactga agtgtcaggg cagtcctggg gcctcgaaag ccatgctcag ctgcaaccgg   1260
tctggcaaga aggacacctg tgccctgacc tgtccctcca gggcccgatt tttgccagag   1320
tctgagaatg gcttcacggt gagctgtggg accccagcc ccagggctgc tccagcccga   1380
gctggccaca atgggaacag caccaactcc aaccactgcc atgaggctgc agtgctgtcc   1440
attaaacaac gggcctcctt caagatcaag gatgccaaat gccgtttgca cctgcgaaac   1500
aaaggcaaaa cagaggaggc tggcagaatc acagggccag tggtgccccc tgctctgaa    1560
tgccaggtca ccttcatcca ccttaagtgt gactcctctc ggaagggcaa gggccgacgg   1620
gcccggaccc ctccaggcaa agaggtcaca aggctcaccc tggaactgga ggcagaggtc   1680
agagccgaag aaaccacagc cagctgtggg ctgccctgcc tccgacagcg aatggaacgg   1740
cggctgaaag gatccctgaa gatgctcaga agtccatca accaggaccg cttcctgctg   1800
cgcctggcag ccttgattta tgagctggcc cacaagccgg gcctggtagc cgggagcga   1860
gcagagccga tggagtcctg taggcccggg cagcaccgtg ctgggaccaa gtgtgtcagc   1920
tgcccgcagg gaacgtatta ccacggccag acggagcagt gtgtgccatg cccagcgggc   1980
accttccagg agagagaagg gcagctctcc tgcgaccttt gccctgggag tgatgcccac   2040
gggcctcttg gagccaccaa cgtcaccacg tgtgcaggtc agtgcccacc tggccaacac   2100
tctgtagatg ggttcaagcc ctgtcagcca tgcccacgtg gcacctacca acctgaagca   2160
ggacggaccc tatgcttccc ttgtggtggg ggcctcacca ccaagcatga aggggccatt   2220
tccttccaag actgtgacac caaagtccag tgctcccag ggcactacta caacaccagc   2280
atccaccgct gtattcgctg tgccatgggc tcctatcagc ccgacttccg tcagaacttc   2340
tgcagccgct gtccaggaaa cacaagcaca gactttgatg gctctaccag tgtggcccaa   2400
```

-continued

```
tgcaagaatc gtcagtgtgg tggggagctg ggtgagttca ctggctatat tgagtcccccc    2460
aactacccgg gcaactaccc agctggtgtg gagtgcatct ggaacatcaa ccccccaccc    2520
aagcgcaaga tccttatcgt ggtaccagag atcttcctgc catctgagga tgagtgtggg    2580
gacgtcctgg tcatgagaaa gaactcatcc ccatcctcca ttaccactta tgagacctgc    2640
cagacctacg agcgtcccat tgccttcact gcccgttcca ggaagctctg gatcaacttc    2700
aagacaagcg aggccaacag cgcccgtggc ttccagattc cctatgttac ctatgatgag    2760
gactatgagc agctggtaga agacattgtg cgagatggcc ggctctatgc ctctgaaaac    2820
caccaggaga tttttaaagga caagaagctc atcaaggcct tctttgaggt gctagcccac    2880
ccccagaact acttcaagta cacagagaaa cacaaggaga tgctgccaaa atccttcatc    2940
aagctgctcc gctccaaagt ttccagcttc ctgaggccct acaaatagta accctaggct    3000
cagagaccca attttttaag cccccagact ccttagccct cagagccggc agcccctac    3060
cctcagacaa ggaactctct cctctctttt tggagggaaa aaaaaatat cactacacaa    3120
accaggcact ctccctttct gtcttttctag tttcctttcc ttgtctctct ctgcctgcct    3180
ctctactgtt ccccctttc taacacacta cctagaaaag ccattcagta ctggctctag    3240
tccccgtgag atgtaaagaa acagtacagc cccttccact gcccatttta ccagctcaca    3300
ttcccgaccc catcagcttg aagggtgct agaggcccat caaggaagtg ggtctggtgg    3360
gaaacgggga ggggaaagaa gggcttctgc cattataggg ttgtgccttg ctagtcaggg    3420
gccaaaatgt cccctggctc tgctccctag ggtgattcta acagcccagg gtcctgccaa    3480
agaagccttt gatttacagg cttaatgcca gcaccagtcc tctggggcac atggtttgag    3540
ctctggactt cccacatggc cagctttctt gtctatacag atcctctctt tctttcccta    3600
cgtctgcctg gggtctactc cataagggtt tacaaatggc ccacaacact gagttagtgg    3660
acaccggcta aatgaggaag agcagcaggc attgtcatgg tgaatgcccc gctgtagctc    3720
cctgagagaa agactgtaac tctgcaggac agaaacaagg ttttaaagca ttgccaaaaa    3780
aaagaaaaca gaaagaaaaa atgtatcatc taaaggacta gacacagaac aattggaagt    3840
caacttcaaa cactaatccc ttttcttgtc ttccctggcc cagccacctc ctcagcccca    3900
tgtgatgctc cctggggag ccctactccc cttgctacat gttgtccta aacatggtta    3960
ttgacctgaa gccagcctag gccttgccct acagttgttt ttccttgta gccccagctg    4020
gcttgtgggc ttcaccaaag aggaccccac tctgaagcca gctggagcc acctacctct    4080
ggcctcaggc tgtgggcagc aaaaggaatg tgtgtgcact tggcgagcct cctgcccacc    4140
ctgtccacac ctaataagtg caatcatttt gagtctttct atgttgtcta gacggagggg    4200
ttttttgtttt ctgggtttgt ttttttgtttt tgtttcttct tcctctatta gcaaaaccct    4260
atttatagct gcccaagaga aaagagtgta tgtttggagt ggaagaaaat cggttttgaa    4320
tctcatgaac cttgagtgct ggagcatctg atctgtctct atgccaccac tggccaccta    4380
gagcccttgg ctgtggtaat ccagggtaat tgcgcagagg catctgatgt gtaggaaagt    4440
aattctgggg atttgatgga gcagaaagga gagagaccta tgtttgctaa accaatcttg    4500
ctatccctat gcctctccat ggagtcagtg tggacctcat gattatagag gccaatggaa    4560
ctggtcagtg attctctacc ccaagtaggg aaaacctcca tcttttcccct gtcttcatcc    4620
tgttatcccc tggtgtacac atggaagagg accaggacat accacctggg gatgggctga    4680
ctcagggtcc cgaggccaga gacaaagctg tgggagccaa gaataagaca gaaggcatca    4740
gatatttgcc tggctctggt cacttccctt tgaagttgac ttcaagctta gcttcctcaa    4800
```

```
ctactgtttt tcagaaggaa gaaagaatca aatggaagaa gaatcaagtc catgcccaag    4860
cccaaagcct gcacacattc tgcccttaat ccaagtgttg cctataaaat tattttctgt    4920
tttctcactc tagttccccc aaagctgtag tcccaatcaa tcaaaggcta ccaactgagt    4980
cctcaggttc atttctttt ttttttttt tcttttaac tctcctggta actcacagaa      5040
cagctcaggt tcatttctag gtgactgtcc taggctactg ctcccccagg agactcaaca    5100
ctaaataaag gagtc                                                    5115
```

<210> SEQ ID NO 12
<211> LENGTH: 2802
<212> TYPE: DNA
<213> ORGANISM: Artificial Sequence
<220> FEATURE:
<223> OTHER INFORMATION: HSPA2 (Genbank accession No: NM_021979)

<400> SEQUENCE: 12

```
ccagcagcag gaggcgcgcg aggcaccacg gcctggcggc cgagagtcag ggaggaacct      60
catttacata acggccgccc ctctgtctcc tggcgggggc cggagtcccg cccctcgtcc     120
aacttgaaat ctgttgggtc acgggccagt cactccgacc taggcaagcc tgtggtggag     180
ctggaagagt ttgtgagggc ggtcccggga gcggattggg tctgggagtt cccagaggcg     240
gctataagaa ccgggaactg gcgcggggga gctgagttgc tggtagtgcc cgtggtgctt     300
ggttcgaggt ggccgttagt tgactccgcg gagttcatct ccctggtttt cccgtcctaa     360
cgtcgctcgc ctttcagtca ggatgtctgc ccgtggcccg gctatcggca tcgacctggg     420
caccacctat tcgtgcgtcg gggtcttcca acatggcaag gtggagatca tcgccaacga     480
ccagggcaat cgcaccaccc ccagctacgt ggccttcacg gacaccgagc gcctcatcgg     540
cgacgccgcc aagaaccagg tggccatgaa ccccaccaac accatcttcg acgccaagag     600
gctgattgga cggaaattcg aggatgccac agtgcagtcg gatatgaaac actggccgtt     660
ccgggtggtg agcgagggag gcaagcccaa agtgcaagta gagtacaagg gggagaccaa     720
gaccttcttc ccagaggaga tatcctccat ggtcctcacg aagatgaagg agatcgcgga     780
agcctacctg gggggcaagg tgcacagcgc ggtcataacg gtcccggcct atttcaacga     840
ctcgcagcgc caggccacca aggacgcagg caccatcacg gggctcaatg tgctgcgcat     900
catcaacgag cccacggcgg cggccatcgc ctacggcctg gacaagaagg gctgcgcggg     960
cggcgagaag aacgtgctca tctttgacct gggcggtggc actttcgacg tgtccatcct    1020
gaccatcgag gatggcatct tcgaggtgaa gtccacggcc ggcgacaccc acctgggcgg    1080
tgaggacttc gacaaccgca tggtgagcca cctggcggag gagttcaagc gcaagcacaa    1140
gaaggacatt gggcccaaca gcgcgccgt gaggcggctg cgcaccgctt gcgagcgcgc    1200
caagcgcacc ctgagctcgt ccacgcaggc gagcatcgag atcgactcgc tctacgaggg    1260
cgtggacttc tatacgtcca tcacgcgcgc ccgcttcgag gagctcaatg ccgacctctt    1320
tcgcgggacc ctggagccgg tggagaaggc gctgcgcgac gccaagctgg acaagggcca    1380
gatccaggag atcgtgctgg tgggcggctc cactcgtatc cccaagatcc agaagctgct    1440
gcaggatttc ttcaacggca aggagctgaa caagagcatc aaccccgacg aggcggtggc    1500
ctatggcgcc gcggtgcagg cggccatcct catcggcgac aaatcagaga atgtgcagga    1560
cctgctgcta ctcgacgtga ccccgttgtc gctgggcatc gagacagctg gcggtgtcat    1620 gacccccactc atcaagagga acaccacgat ccccaccaag cagacgcaga ccttcaccac    1680
```

| | |
|---|---|
| ctactcggac aaccagagca gcgtactggt gcaggtatac gagggcgaac gggccatgac | 1740 |
| caaggacaat aacctgctgg gcaagttcga cctgaccggg attcccctg cgcctcgcgg | 1800 |
| ggtcccccaa atcgaggtta ccttcgacat tgacgccaat ggcatcctta acgttaccgc | 1860 |
| cgccgacaag agcaccggta aggaaaacaa aatcaccatc accaatgaca aggtcgtct | 1920 |
| gagcaaggac gacattgacc ggatggtgca ggaggcggag cggtacaaat cggaagatga | 1980 |
| ggcgaatcgc gaccgagtcg cggccaaaaa cgccctggag tcctatacct acaacatcaa | 2040 |
| gcagacggtg gaagacgaga aactgagggg caagattagc gagcaggaca aaaacaagat | 2100 |
| cctcgacaag tgtcaggagg tgatcaactg gctcgaccga aaccagatgg cagagaaaga | 2160 |
| tgagtatgaa cacaagcaga aagagctcga aagagtttgc aaccccatca tcagcaaact | 2220 |
| ttaccaaggt ggtcctggcg gcggcagcgg cggcggcggt tcaggagcct ccgggggacc | 2280 |
| caccatcgaa gaagtggact aagcttgcac tcaagtcagc gtaaacctct ttgcctttct | 2340 |
| ctctctctct ttttttttgt ttgtttcttt gaaatgtcct tgtgccaagt acgagatcta | 2400 |
| ttgttggaag tctttggtat atgcaaatga aggagaggt gcaacaactt agtttaatta | 2460 |
| taaaagttcc aaagtttgtt ttttaaaaac attattcgag gtttctcttt aatgcatttt | 2520 |
| gcgtgtttgc tgacttgagc atttttgatt agttcgtgca tggagatttg tttgagatga | 2580 |
| gaaaccttaa gtttgcacac ctgttctgta gaagcttgga aacagtaaaa tatataggag | 2640 |
| cttaaattgt ttatttttat gtactacttt aaaactaaac tgaacattgc agtaatgtta | 2700 |
| aggacaggta tacttttgc aaacaaatgc ataaatgcaa atgtaaagta aagctgaaat | 2760 |
| tgatctcaaa aaaaaaaaaa aaaaaaaaaa aaaaaaaaaa aa | 2802 |

<210> SEQ ID NO 13
<211> LENGTH: 11571
<212> TYPE: DNA
<213> ORGANISM: Artificial Sequence
<220> FEATURE:
<223> OTHER INFORMATION: RELN (Genbank accession No: NM_005045)

<400> SEQUENCE: 13

| | |
|---|---|
| ctcggcgggg gcccgctccc aggcccgctc ccgagcccgt tccgctcccg tccgccttct | 60 |
| tctcgccttc tctccgcgtg gctcctccgt cccggcgtct ccaaaactga atgagcgagc | 120 |
| ggcgcgtagg gcgcgcggcg gcggcggcgg cggcggcggc atggagcgca gtggctgggc | 180 |
| ccggcagact ttcctcctag cgctgttgct gggggcgacg ctgagggcgc gcgcggcggc | 240 |
| tggctattac ccccgctttt cgcccttctt tttcctgtgc acccaccacg gggagctgga | 300 |
| aggggatggg gagcagggcg aggtgctcat ttccctgcat attgcgggca accccaccta | 360 |
| ctacgttccg ggacaagaat accatgtgac aatttcaaca agcacctttt ttgacggctt | 420 |
| gctggtgaca ggactataca catctacaag tgttcaggca tcacagagca ttggaggttc | 480 |
| cagtgctttc ggatttggga tcatgtctga ccaccagttt ggtaaccagt ttatgtgcag | 540 |
| tgtggtagcc tctcacgtga gtcacctgcc cacaaccaac ctcagtttca tctggattgc | 600 |
| tccacctgcg ggcacaggct gtgtgaattt catggctaca gcaacacacc ggggccaggt | 660 |
| tattttcaaa gatgctttag cccagcagtt gtgtgaacaa ggagctccaa cagatgtcac | 720 |
| tgtgcaccca catctagctg aaatacatag tgacagcatt atcctgagag atgactttga | 780 |
| ctcctaccac caactgcaat taaatccaaa tatatgggtt gaatgtaaca actgtgagac | 840 |
| tggagaacag tgtggcgcga ttatgcatgg caatgccgtc accttctgtg aaccatatgg | 900 |
| cccacgagaa ctgattacca caggccttaa tacaacaaca gcttctgtcc tccaatttc | 960 |

```
cattgggtca ggttcatgtc gctttagtta ttcagacccc agcatcatcg tgttatatgc    1020
caagaataac tctgcggact ggattcagct agagaaaatt agagccccctt ccaatgtcag    1080 cacaatcatc catatcctct accttcctga ggacgccaaa ggggagaatg tccaatttca    1140
gtggaagcag gaaaatcttc gtgtaggtga agtgtatgaa gcctgctggg ccttagataa    1200
catcttgatc atcaattcag ctcacagaca agtcgtttta aagatagtc tcgacccagt     1260 ggacacaggc aactggcttt tcttcccagg agctacagtt aagcatagct gtcagtcaga    1320
tgggaactcc atttatttcc atggaaatga aggcagcgag ttcaattttg ccaccaccag    1380
ggatgtagat ctttccacag aagatattca agagcaatgg tcagaagaat ttgagagcca    1440
gcctacagga tgggatgtct tgggagctgt cattggtaca gaatgtggaa cgatagaatc    1500
aggcttatca atggtcttcc tcaaagatgg agagaggaaa ttatgcactc catccatgga    1560
cactaccggt tatgggaacc tgaggtttta ctttgtgatg ggaggaattt gtgaccctgg    1620
aaattctcat gaaaatgaca taatcctgta tgcaaaaatt gaaggaagaa aagagcatat    1680
aacactggat acccttcct attcctcata taaggttccg tctttggttt ctgtggtcat     1740
caatcctgaa cttcagactc ctgctaccaa attttgtctc aggcaaaaga accatcaagg    1800
acataatagg aatgtctggg ctgtagactt tttccatgtc ttgcctgttc tcccttctac    1860
aatgtctcac atgatacagt tttccatcaa tctgggatgt ggaacgcatc agcctggtaa    1920
cagtgtcagc ttggaatttt ctaccaacca tgggcgctcc tggtccctcc ttcacactga    1980
atgcttacct gagatctgtg ctggaccca cctcccccac agcactgtct actcctctga     2040
aaactacagt gggtggaacc gaataacaat tccccttcct aacgcagcac taacccggaa    2100
caccaggatt cgctggagac aaacaggacc aatccttgga acatgtggg caattgataa     2160 tgtttatatt ggcccgtcat gtctcaaatt ctgttctggc agaggacagt gcactagaca    2220
tggttgcaag tgtgaccctg gattttctgg cccagcttgt gagatggcat cccagacatt    2280
cccaatgttt atttctgaaa gctttggcag ttccaggctc tcctcttacc ataacttta    2340 ctctatccgt ggtgctgaag tcagcttggg ttgtggtgtc ttggccagtg gtaaggccct    2400
ggttttcaac aaagatgggc ggcgtcagct aattacatct tccttgaca gctcacaatc    2460 caggtttctc cagttcacac tgagactggg gagcaaatct gttctgagca cgtgcagagc    2520
ccctgatcag cctggtgaag gagttttgtt gcattattct tatgataatg ggataacttg    2580
gaaactcctg gagcattatt catatctcag ctatcatgag cccagaataa tctccgtaga    2640
actaccaggt gatgcaaagc agtttggaat tcagttcaga tggtggcaac cgtatcattc    2700
ttcccagaga gaagatgtat gggctattga tgagattatc atgacatctg tgcttttcaa    2760
cagcattagt cttgactta ccaatcttgt ggaggtcact cagtctctgg gattctacct     2820
tggaaatgtt cagccatact gtggccacga ctggacccctt tgttttacag gagattctaa    2880
acttgcctca gtatgcgct atgtggaaac acaatcaatg cagataggag catcctatat     2940
gattcagttc agtttggtga tgggatgtgg ccagaaatac accccacaca tggacaacca    3000
ggtgaagctg gagtactcaa ccaaccacgg ccttacctgg cacctcgtcc aagaagaatg    3060
ccttccaagt atgccaagtt gtcaggaatt tacatcagca agtatttacc atgccagtga    3120
gtttacacag tggaggagag tcatagtgct tcttccccag aaaacttggt ccagtgctac    3180
ccgtttccgc tggagccaga gctattacac agctcaagac gagtgggctt tggacagcat    3240
ttacattggg cagcagtgcc ccaacatgtg cagtgggcat ggctcatgcg atcatggcat    3300
```

```
atgcaggtgt gaccaggggt accaaggcac tgaatgccac ccagaagctg cccttccgtc   3360
cacaattatg tcagattttg agaaccagaa tggctgggag tctgactggc aagaagttat   3420
tgggggagaa attgtaaaac cagaacaagg gtgtggtgtc atctcttctg gatcatctct   3480
gtacttcagc aaggctggga aaagacagct ggtgagttgg gacctggata cttcttgggt   3540
ggactttgtc cagttctaca tccagatagg cggagagagt gcttcatgca acaagcctga   3600
cagcagagag gagggcgtcc tccttcagta cagcaacaat gggggcatcc agtggcacct   3660
gctagcagag atgtactttt cagacttcag caaacccaga tttgtctatc tggagcttcc   3720
agctgctgcc aagacccctt gcaccaggtt ccgctggtgg cagcccgtgt ctcaggggga   3780
ggactatgac cagtgggcag tcgatgacat catcattctg tccgagaagc agaagcagat   3840
catcccagtt atcaatccaa ctttacctca gaactttat gagaagccag cttttgatta   3900
ccctatgaat cagatgagtg tgtggttgat gttggctaat gaaggaatgg ttaaaaatga   3960
aaccttctgt gctgccacac catcagcaat gatatttgga aaatcagatg gagatcgatt   4020
tgcagtaact cgagatttga ccctgaaacc tggatatgtg ctacagttca agctaaacat   4080
aggttgtgcc aatcaattca gcagtactgc tccagttctt cttcagtact ctcatgatgc   4140
tggtatgtcc tggtttctgg tgaaagaagg ctgttacccg gcttctgcag caaaggatg   4200 cgaaggaaac tccagagaac taagtgagcc caccatgtat cacacagggg actttgaaga   4260
atggacaaga atcaccattg ttattccaag gtctcttgca tccagcaaga ccagattccg   4320
atggatccag gagagcagct cacagaaaaa cgtgcctcca tttggtttag atggagtgta   4380
catatccgag ccttgtccca gttactgcag tggccatggg gactgcattt caggagtgtg   4440
tttctgtgac ctgggatata ctgctgcaca aggaacctgt gtgtcaaatg tccccaatca   4500
caatgagatg ttcgataggt ttgaggggaa gctcagccct ctgtggtaca agataacagg   4560
tgcccaggtt ggaactggct gtggaacact aacgatggc aaatctctct acttcaatgg   4620
ccctgggaaa agggaagccc ggacggtccc tctggacacc aggaatatca gacttgttca   4680 atttatata caaattggaa gcaaaacttc aggcattacc tgcatcaaac caagaactag   4740
aaatgaaggg cttattgttc agtattcaaa tgacaatggg atactctggc atttgcttcg   4800
agagttggac ttcatgtcct cctggaacc acagatcatt tccattgacc tgccacagga   4860
cgcgaagaca cctgcaacgg catttcgatg gtggcaaccg caacatggga agcattcagc   4920
ccagtgggct ttggatgatg ttcttatagg aatgaatgac agctctcaaa ctggatttca   4980
agacaaattt gatggctcta tagatttgca agccaactgg tatcgaatcc aaggaggtca   5040
agttgatatt gactgtctct ctatggatac tgctctgata ttcactgaaa acataggaaa   5100
acctcgttat gctgagacct gggattttca tgtgtcagca tctaccttt tgcagtttga   5160 aatgagcatg ggctgtagca agcccttcag caactcccac agtgtacagc tccagtattc   5220
tctgaacaat ggcaaggact ggcatcttgt caccgaagag tgtgttcctc caaccattgg   5280
ctgtctgcat tacacggaaa gttcaattta cacctcggaa agattccaga attggaagcg   5340
gatcactgtc taccttccac tctccaccat ttctcccagg acccggttca gatggattca   5400
ggccaactac actgtggggg ctgattcctg ggcgattgat aatgttgtac tggcctcagg   5460
gtgcccttgg atgtgctcag gacgagggat tgtgatgct ggacgctgtg tgtgtgaccg   5520
gggctttggt ggaccctatt gtgttcctgt tgttcctctg ccctcgattc ttaaagacga   5580
tttcaatggg aatttacatc ctgacccttg gcctgaagtg tatggtgcag agagggggaa   5640
tctgaatggt gaaaccatca aatctggaac atctctaatt tttaaagggg aaggactaag   5700
```

```
gatgcttatt tcaagagatc tagattgtac aaatacaatg tatgtccagt tttcacttag    5760
atttatagca aaaagtaccc cagagagatc tcactctatt ctgttacaat tctccatcag    5820
tggaggaatc acttggcacc tgatggatga attttacttt cctcaaacaa cgaatatact    5880
tttcatcaat gttcccttgc catacactgc ccaaaccaat gctacaagat tcagactctg    5940
gcaaccttat aataacggta agaaagaaga aatctggatt gttgatgact tcattatcga    6000
tggaaataat gtaaacaacc ctgtgatgct cttggataca tttgattttg ggcccagaga    6060
agacaattgg tttttctatc ctggtggtaa catcggtctt tattgtccat attcttcaaa    6120
gggggcacct gaagaagatt cagctatggt gtttgtttca aatgaagttg gtgagcattc    6180
cattaccacc cgtgacctaa atgtgaatga aacaccatc atacaatttg agatcaacgt    6240
tggctgttcg actgatagct catccgcgga tccagtgaga ctggaatttt caagggactt    6300
cggggcgacc tggcaccttc tgctgcccct ctgctaccac agcagcagcc acgtcagctc    6360
tttatgctcc accgagcacc accccagcag cacctactac gcaggaacca tgcagggctg    6420
gaggagggag tcgtgcact ttgggaagct gcacctttgt ggatctgtcc gtttcagatg    6480
gtaccaggga ttttaccctg ccggctctca gccagtgaca tgggccattg ataatgtcta    6540
catcggtccc cagtgtgagg agatgtgtaa tggacagggg agctgtatca atggaaccaa    6600
atgtatatgt gaccctggct actcaggtcc aacctgtaaa ataagcacca aaaatcctga    6660
ttttctcaaa gatgatttcg aaggtcagct agaatctgat agattcttat taatgagtgg    6720
tgggaaacca tctcgaaagt gtggaatcct ttctagtgga aacaacctct ttttcaatga    6780
agatggcttg cgcatgttga tgacacgaga cctggattta tcacatgcta gatttgtgca    6840
gttcttcatg agactgggat gtggtaaagg cgttcctgac cccaggagtc aacccgtgct    6900
cctacagtat tctctcaacg gtggcctctc gtggagtctt cttcaggagt tccttttcag    6960
caattccagc aatgtgggca ggtacattgc cctggagata cccttgaaag cccgttctgg    7020
ttctactcgc cttcgctggt ggcaaccgtc tgagaatggg cacttctaca gccctgggt    7080 tatcgatcag attcttattg gaggaaatat ttctggtaat acggtcttgg aagatgattt    7140
cacaaccctt gatagtagga aatggctgct tcacccagga ggcaccaaga tgcccgtgtg    7200
tggctctact ggtgatgccc tggtcttcat tgaaaaggcc agcacccgtt acgtggtcag    7260
cacagacgtt gccgtgaatg aggattcctt cctacagata gacttcgctg cctcctgctc    7320
agtcacagac tcttgttatg cgattgaatt ggaatactca gtagatcttg gattgtcatg    7380
gcacccattg gtaagggact gtctgcctac caatgtggaa tgcagtcgct atcatctgca    7440
acggatcctg gtgtcagaca ctttcaacaa gtggactaga atcactctgc ctctccctcc    7500
ttataccagg tcccaagcca ctcgtttccg ttggcatcaa ccagctcctt ttgacaagca    7560
gcagacatgg gcaatagata atgtctatat cggggatggc tgcatagaca tgtgcagtgg    7620
ccatgggaga tgcatccagg gaaactgcgt ctgtgatgaa cagtggggtg gcctgtactg    7680
tgatgacccc gagacctctc ttccaaccca actcaaagac aacttcaatc gagctccatc    7740
cagtcagaac tggctgactg tgaacggagg gaaattgagt acagtgtgtg gagccgtggc    7800
gtcgggaatg gctctccatt tcagtggggg ttgtagtcga ttattagtca ctgtggatct    7860
aaacctcact aatgctgagt tcatccaatt ttacttcatg tatgggtgcc tgattacacc    7920
aaacaaccgt aaccaaggtg ttctcttgga atattctgtc aatggaggca ttacctggaa    7980
cctgctcatg gagattttct atgaccagta cagtaagccc ggatttgtga atatccttct    8040
```

```
ccctcctgat gctaaagaga ttgccactcg cttccgctgg tggcagccaa gacatgacgg    8100
cctggatcag aacgactggg ccattgacaa tgtcctcatc tcaggctctg ctgaccaaag    8160
gaccgttatg ctggacacct tcagcagcgc cccagtaccc cagcatgagc gctcccctgc    8220
agatgccggc cctgtcggga ggatcgcctt tgacatgttt atggaagaca aaacttcagt    8280
gaatgagcac tggctattcc atgatgattg tacagtagaa agattctgtg actcccctga    8340
tggtgtgatg ctctgtggca gtcatgatgg acgggaggtg tatgcagtga cccatgacct    8400
gactcccact gaaggctgga ttatgcaatt caagatctca gttggatgta aggtgtctga    8460
aaaaattgcc cagaatcaaa ttcatgtgca gtattctact gacttcggtg tgagttggaa    8520
ttatctggtc cctcagtgct tgcctgctga cccaaaatgc tctggaagtg tttctcagcc    8580
atctgtattc tttccaacta aagggtggaa aaggatcacc tacccacttc ctgaaagctt    8640
agtgggaaat ccggtaaggt ttaggttcta tcagaagtac tcagacatgc agtgggcaat    8700
cgataatttc tacctgggcc ctggatgctt ggacaactgc aggggccatg gagattgctt    8760
aagggaacag tgcatctgtg atccgggata ctcagggcca aactgctact tgacccacac    8820
tctgaagact ttcctgaagg aacgctttga cagtgaagaa atcaaacctg acttatggat    8880
gtccttagaa ggtggaagta cttgcactga gtgtggaatt cttgccgagg acactgcact    8940
ctattttggg ggatccactg tgagacaagc ggttacacaa gatttggatc ttcgaggtgc    9000
aaagttcctg caatactggg ggcgcatcgg tagtgagaac aacatgacct cttgccatcg    9060
tcccatctgc cggaaggaag gcgtgctgtt ggactactct accgatggag gaattacctg    9120
gactttgctc catgagatgg attaccagaa atacatttct gttagacacg actacatact    9180
tcttcctgaa gatgccctca ccaacacaac tcgacttcgc tggtggcagc cttttgtgat    9240
cagcaatgga attgtggtct ctggggtgga gcgtgctcag tgggcactgg acaacatttt    9300
gattggtgga gcagaaatca atcccagcca attggtggac acttttgatg atgaaggcac    9360
ttcccatgaa gaaaactgga gtttttaccc taatgctgta aggacagcag gattttgtgg    9420
caatccatcc tttcacctct attggccaaa taaaagaag gacaagactc acaatgctct    9480
ctcctcccga gaactcatta tacagccagg atacatgatg cagtttaaaa ttgtggtggg    9540
ttgtgaagcc acttcttgtg gtgaccttca ttccgtaatg ctggaataca ctaaggatgc    9600
aagatcggat tcctggcagc tcgtacagac ccagtgcctt ccttcctctt ctaacagcat    9660
tggctgctcc ccttttccagt tccatgaagc caccatctac aactctgtca acagctcaag    9720
ctggaaaaga atcaccatcc agctgcctga ccatgtctcc tctagtgcaa cacagttccg    9780
ctggatccag aagggagaag aaactgagaa gcaaagctgg gcaattgacc acgtgtacat    9840
tggagaggct tgccccaagc tctgcagcgg gcacggatac tgcacgaccg gtgccatctg    9900
catctgcgac gagagcttcc aaggtgatga ctgctctgtt ttcagtcacg accttcccag    9960
ttatattaaa gataatttg agtccgcaag agtcaccgag gcaaactggg agaccattca   10020
aggtggagtc ataggaagtg gctgtgggca gctggccccc tacgcccatg agactcact    10080 gtactttaat ggctgtcaga tcaggcaagc agctaccaag cctctggatc tcactcgagc   10140
aagcaaaatc atgtttgttt tgcaaattgg gagcatgtcg cagacggaca gctgcaacag   10200
tgacctgagt ggcccccacg ctgtggacaa ggcagtgctg ctgcaataca gcgtcaacaa   10260
cgggatcacc tggcatgtca tcgcccagca ccagccaaag gacttcacac aagctcagag   10320
agtgtcttac aatgtccccc tggaggcacg gatgaaagga gtcttactgc gctggtggca   10380
accacgccac aatggaacag gtcatgatca atgggctttg gaccatgtgg aggtcgtcct   10440
```

```
agtaagcact cgcaaacaaa attacatgat gaatttttca cgacaacatg ggctcagaca    10500
tttctacaac agaagacgaa ggtcacttag gcgataccca tgaagaatca aaagtttat    10560 ttttttcctt ccaacatgtg atgtgttgct ctccattctt ttaaatctcg cactacatct    10620
gatatcagga aatatctgtg aaggacttgg tgattacctg aaagcccttc tcaagaccga    10680
gtgtacacca ctttcccaca ctgtgaacta atgcaagtg acttatttgc tcataagtaa    10740
atgtcttcat gttgatgtgt ccgtgaaagt tgtgatctgt tgtaatatca gttacagtgg    10800
cagtattgac aataagaaac agtttaacag aaaaatgaaa tttaagcaca aaaaatttaa    10860
gagattttat gtttaaaatg gcatttagca cagtatttaa cattcttggt cacaaagcta    10920
tttaagtgga ctgtatttcg gctatgtctc atgttttata tgattaaatt atcattgttt    10980
gtcctttatg tattctcttc tacaatacaa cacattgaaa ctgtatttac ttgttatgtt    11040
gtaatatttt gctgctgaat ttggggctac ttatattctg cagaaaatta attgaaatac    11100
ctattcaaga agatagttgt aaagatattg tatctccttt aatatactcc ttaaaaatgt    11160
atgttggttt agcgttgttt tgtggataag aaaaatgctt gaccctgaaa tattttctac    11220
tttaaattgt ggatgaagac cctatctccc acaaataagt tcccatttcc ttgtctaaag    11280 atctttttttt aagtgttctg tggctgattt actaacagta actgccattt tttgtctgtg    11340
ataacagagt gatttgtaaa acagtggttg ttttttcatt gtgttttctt cgtggattgt    11400 ttttctgcg ggtcatattc ataccttctg atgaagttgt acaacaccag caacattata    11460
atggccctgt agctctgaat gctatttgtg taactgaaag gttgcactct agggtgaacc    11520
aagctataaa agcccatgct taaataaaaa ttatgtccaa aagccattga a            11571
```

<210> SEQ ID NO 14
<211> LENGTH: 4296
<212> TYPE: DNA
<213> ORGANISM: Artificial Sequence
<220> FEATURE:
<223> OTHER INFORMATION: EDNRB (Genbank accession No: NM_000115)

<400> SEQUENCE: 14

```
acattccggt gggggactct ggccagcccg agcaacgtgg atcctgagag cactcccagg     60
taggcatttg ccccggtggg acgccttgcc agagcagtgt gtggcaggcc cccgtggagg    120
atcaacacag tggctgaaca ctgggaagga actggtactt ggagtctgga catctgaaac    180
ttggctctga aactgcggag cggccaccgg acgccttctg gagcaggtag cagcatgcag    240
ccgcctccaa gtctgtgcgg acgcgccctg gttgcgctgg ttcttgcctg cggcctgtcg    300
cggatctggg gagaggagag aggcttcccg cctgacaggg ccactccgct tttgcaaacc    360
gcagagataa tgacgccacc cactaagacc ttatggccca aggggttccaa cgccagtctg    420 gcgcggtcgt tggcacctgc ggaggtgcct aaaggagaca ggacggcagg atctccgcca    480
cgcaccatct cccctccccc gtgccaagga cccatcgaga tcaaggagac tttcaaatac    540
atcaacacgg ttgtgtcctg ccttgtgttc gtgctgggga tcatcgggaa ctccacactt    600
ctgagaatta tctacaagaa caagtgcatg cgaaacggtc ccaatatctt gatcgccagc    660
ttggctctgg gagacctgct gcacatcgtc attgacatcc ctatcaatgt ctacaagctg    720
ctggcagagg actggccatt tggagctgag atgtgtaagc tggtgccttt catacagaaa    780
gcctccgtgg gaatcactgt gctgagtcta tgtgctctga gtattgacag atatcgagct    840
gttgcttctt ggagtagaat taaaggaatt ggggttccaa aatggacagc agtagaaatt    900
```

```
gttttgattt gggtggtctc tgtggttctg gctgtccctg aagccatagg ttttgatata    960
attacgatgg actacaaagg aagttatctg cgaatctgct tgcttcatcc cgttcagaag   1020
acagctttca tgcagtttta caagacagca aaagattggt ggctattcag tttctatttc   1080
tgcttgccat tggccatcac tgcattttt tatacactaa tgacctgtga aatgttgaga    1140
aagaaaagtg gcatgcagat tgctttaaat gatcacctaa agcagagacg ggaagtggcc   1200
aaaaccgtct tttgcctggt ccttgtcttt gccctctgct ggcttcccct tcacctcagc   1260
aggattctga agctcactct ttataatcag aatgatccca atagatgtga acttttgagc   1320
tttctgttgg tattggacta tattggtatc aacatggctt cactgaattc ctgcattaac   1380
ccaattgctc tgtatttggt gagcaaaaga ttcaaaaact gctttaagtc atgcttatgc   1440
tgctggtgcc agtcatttga agaaaaacag tccttggagg aaaagcagtc gtgcttaaag   1500
ttcaaagcta atgatcacgg atatgacaac ttccgttcca gtaataaata cagctcatct   1560
tgaaagaaga actattcact gtatttcatt ttctttatat tggaccgaag tcattaaaac   1620
aaaatgaaac atttgccaaa acaaaacaaa aaactatgta tttgcacagc acactattaa   1680
aatattaagt gtaattattt taacactcac agctacatat gacattttat gagctgttta   1740
cggcatggaa agaaaatcag tgggaattaa gaaagcctcg tcgtgaaagc acttaattt    1800
ttacagttag cacttcaaca tagctcttaa caacttccag gatattcaca caacacttag   1860
gcttaaaaat gagctcactc agaatttcta ttctttctaa aaagagattt ttttttaaat   1920
caatgggact ctgatataaa ggaagaataa gtcactgtaa aacagaactt ttaaatgaag   1980
cttaaattac tcaattttaa attttaaaat cctttaaaac aacttttcaa ttaatattat   2040
cacactatta tcagattgta attagatgca aatgagagag cagtttagtt gttgcatttt   2100
tcggacactg gaaacattta aatgatcagg agggagtaac agaaagagca aggctgtttt   2160
tgaaaatcat tacacttcca ctagaagccc aaacctcagc attctgcaat atgtaaccaa   2220
catgtcacaa acaagcagca tgtaacagac tggcacatgt gccagctgaa tttaaaatat   2280
aatactttta aaaagaaaat tattacatcc tttacattca gttaagatca aacctcacaa   2340
agagaaatag aatgtttgaa aggctatccc aaaagacttt tttgaatctg tcattcacat   2400
accctgtgaa gacaatacta tctacaattt tttcaggatt attaaaatct tcttctttca   2460
ctatcgtagc ttaaactctg tttggttttg tcatctgtaa atacttacct acatacactg   2520
catgtagatg attaaatgag ggcaggccct gtgctcatag ctttacgatg gagagatgcc   2580
agtgacctca taataaagac tgtgaactgc ctggtgcagt gtccacatga caaaggggca   2640
ggtagcaccc tctctcaccc atgctgtggt taaaatggtt tctagcatat gtataatgct   2700
atagttaaaa tactattttt caaaatcata cagattagta catttaacag ctacctgtaa   2760
agcttattac taattttgt attattttg taaatagcca atagaaaagt ttgcttgaca    2820
tggtgctttt ctttcatcta gaggcaaaac tgcttttga gaccgtaaga acctcttagc    2880
tttgtgcgtt cctgcctaat ttttatatct tctaagcaaa gtgccttagg atagcttggg   2940
atgagatgtg tgtgaaagta tgtacaagag aaaacggaag agagaggaaa tgaggtgggg   3000
ttggaggaaa cccatgggga cagattccca ttcttagcct aacgttcgtc attgcctcgt   3060
cacatcaatg caaaaggtcc tgattttgtt ccagcaaaac acagtgcaat gttctcagag   3120
tgactttcga aataaattgg gcccaagagc tttaactcgg tcttaaaata tgcccaaatt   3180
tttactttgt ttttctttta ataggctggg ccacatgttg gaaataagct agtaatgttg   3240
ttttctgtca atattgaatg tgatggtaca gtaaaccaaa acccaacaat gtggccagaa   3300
```

```
agaaagagca ataataatta attcacacac catatggatt ctatttataa atcacccaca    3360
aacttgttct ttaatttcat cccaatcact ttttcagagg cctgttatca tagaagtcat    3420
tttagactct caattttaaa ttaattttga atcactaata ttttcacagt ttattaatat    3480
atttaatttc tatttaaatt ttagattatt tttattacca tgtactgaat ttttacatcc    3540
tgatacccgt tccttctcca tgtcagtatc atgttctcta attatcttgc caaattttga    3600
aactacacac aaaaagcata cttgcattat ttataataaa attgcattca gtggcttttt    3660
aaaaaaatgt ttgattcaaa actttaacat actgataagt aagaaacaat tataatttct    3720
ttacatactc aaaaccaaga tagaaaaagg tgctatcgtt caacttcaaa acatgtttcc    3780
tagtattaag gactttaata tagcaacaga caaaattatt gttaacatgg atgttacagc    3840
tcaaaagatt tataaaagat tttaacctat tttctcccct attatccact gctaatgtgg    3900
atgtatgttc aaacacccttt tagtattgat agcttacata tggccaaagg aatacagttt    3960
atagcaaaac atgggtatgc tgtagctaac tttataaaag tgtaatataa caatgtaaaa    4020
aattatatat ctgggaggat ttttggttg cctaaagtgg ctatagttac tgattttta    4080 ttatgtaagc aaaaccaata aaatttaag tttttttaac aactaccta ttttcactg    4140 tacagacact aattcattaa atactaattg attgtttaaa agaaatataa atgtgacaag    4200
tggacattat ttatgttaaa tatacaatta tcaagcaagt atgaagttat tcaattaaaa    4260
tgccacattt ctggtctctg ggaaaaaaaa aaaaaa                              4296

<210> SEQ ID NO 15
<211> LENGTH: 7878
<212> TYPE: DNA
<213> ORGANISM: Artificial Sequence
<220> FEATURE:
<223> OTHER INFORMATION: ITGA2 (Genbank accession No: NM_002203)

<400> SEQUENCE: 15
ttttccctgc tctcaccggg cggggagag aagccctctg acagcttct agagtgtgca       60 ggttctcgta tccctcggcc aagggtatcc tctgcaaacc tctgcaaacc cagcgcaact   120
acggtccccc ggtcagaccc aggatggggc cagaacggac aggggccgcg ccgctgccgc   180
tgctgctggt gttagcgctc agtcaaggca ttttaaattg ttgtttggcc tacaatgttg   240
gtctcccaga agcaaaaata ttttccggtc cttcaagtga acagtttggc tatgcagtgc   300
agcagtttat aaatccaaaa ggcaactggt tactggttgg ttcaccctgg agtggctttc   360
ctgagaaccg aatgggagat gtgtataaat gtcctgttga cctatccact gccacatgtg   420
aaaaactaaa tttgcaaact tcaacaagca ttccaaatgt tactgagatg aaaaccaaca   480
tgagcctcgg cttgatcctc accaggaaca tgggaactgg aggttttctc acatgtggtc   540
ctctgtgggc acagcaatgt gggaatcagt attacacaac gggtgtgtgt tctgacatca   600
gtcctgattt tcagctctca gccagcttct cacctgcaac tcagccctgc ccttccctca   660
tagatgttgt ggttgtgtgt gatgaatcaa atagtattta tccttgggat gcagtaaaga   720
atttttggga aaaatttgta caaggcctgg atataggccc cacaaagaca caggtgggt   780 taattcagta tgccaataat ccaagagttg tgtttaactt gaacacatat aaaaccaaag   840
aagaaatgat tgtagcaaca tcccagacat cccaatatgg tgggacctc acaaacacat   900 tcggagcaat tcaatatgca agaaaatatg cttattcagc agcttctggt gggcgacgaa   960
gtgctacgaa agtaatggta gttgtaactg acggtgaatc acatgatggt tcaatgttga  1020
```

```
aagctgtgat tgatcaatgc aaccatgaca atatactgag gtttggcata gcagttcttg    1080
ggtacttaaa cagaaacgcc cttgatacta aaaatttaat aaaagaaata aaagcaatcg    1140
ctagtattcc aacagaaaga tacttttca atgtgtctga tgaagcagct ctactagaaa    1200
aggctgggac attaggagaa caaattttca gcattgaagg tactgttcaa ggaggagaca    1260
actttcagat ggaaatgtca caagtgggat tcagtgcaga ttactcttct caaaatgata    1320
ttctgatgct gggtgcagtg ggagcttttg gctggagtgg gaccattgtc cagaagacat    1380
ctcatggcca tttgatcttt cctaaacaag cctttgacca aattctgcag gacagaaatc    1440
acagttcata tttaggttac tctgtggctg caatttctac tggagaaagc actcactttg    1500
ttgctggtgc tcctcgggca aattataccg gccagatagt gctatatagt gtgaatgaga    1560
atggcaatat cacggttatt caggctcacc gaggtgacca gattggctcc tattttggta    1620
gtgtgctgtg ttcagttgat gtggataaag acaccattac agacgtgctc ttggtaggtg    1680
caccaatgta catgagtgac ctaaagaaag aggaaggaag agtctacctg tttactatca    1740
aagagggcat tttgggtcag caccaatttc ttgaaggccc cgagggcatt gaaaacactc    1800
gatttggttc agcaattgca gctctcttcag acatcaacat ggatggcttt aatgatgtga    1860
ttgttggttc accactagaa aatcagaatt ctggagctgt atacatttac aatggtcatc    1920
agggcactat ccgcacaaag tattcccaga aaatctgggg atccgatgga gcctttagga    1980
gccatctcca gtactttggg aggtcctgg atggctatgg agatttaaat ggggattcca    2040
tcaccgatgt gtctattggt gcctttggac aagtggttca actctggtca caaagtattg    2100
ctgatgtagc tatagaagct tcattcacac cagaaaaaat cactttggtc aacaagaatg    2160
ctcagataat tctcaaactc tgcttcagtg caaagttcag acctactaag caaaacaatc    2220
aagtggccat tgtatataac atcacacttg atgcagatgg atttcatcc agagtaacct    2280 ccaggggggtt atttaaagaa aacaatgaaa ggtgcctgca gaagaatatg gtagtaaatc    2340
aagcacagag ttgccccgag cacatcattt atatacagga gccctctgat gttgtcaact    2400
ctttggattt gcgtgtggac atcagtctgg aaaaccctgg cactagccct gcccttgaag    2460
cctattctga gactgccaag gtcttcagta ttccttttcca caaagactgt ggtgaggacg    2520
gactttgcat ttctgatcta gtcctagatg tccgacaaat accagctgct caagaacaac    2580
cctttattgt cagcaaccaa acaaaaaggt taacattttc agtaacgctg aaaaataaaa    2640
gggaaagtgc atacaacact ggaattgttg ttgattttc agaaaacttg ttttttgcat    2700
cattctccct gccggttgat gggacagaag taacatgcca ggtggctgca tctcagaagt    2760
ctgttgcctg cgatgtaggc taccctgctt taaagagaga acaacaggtg acttttacta    2820
ttaactttga cttcaatctt caaaaccttc agaatcaggc gtctctcagt ttccaagcct    2880
taagtgaaag ccaagaagaa acaaggctg ataatttggt caacctcaaa attcctctcc    2940
tgtatgatgc tgaaattcac ttaacaagat ctaccaacat aaatttttat gaaatctctt    3000
cggatgggaa tgttccttca atcgtgcaca gttttgaaga tgttggtcca aaattcatct    3060 tctcctgaa ggtaacaaca ggaagtgttc cagtaagcat ggcaactgta atcatccaca    3120
tccctcagta taccaaagaa aagaacccac tgatgtacct aactggggtg caaacagaca    3180
aggctggtga catcagttgt aatgcagata tcaatccact gaaaatagga caaacatctt    3240
cttctgtatc tttcaaaagt gaaaatttca ggcacaccaa agaattgaac tgcagaactg    3300
cttcctgtag taatgttacc tgctggtgga aagacgttca catgaaagga gaatactttg    3360
ttaatgtgac taccagaatt tggaacggga ctttcgcatc atcaacgttc cagacagtac    3420
```

```
agctaacggc agctgcagaa atcaacacct ataaccctga gatatatgtg attgaagata   3480
acactgttac gattcccctg atgataatga aacctgatga gaaagccgaa gtaccaacag   3540
gagttataat aggaagtata attgctggaa tccttttgct gttagctctg gttgcaattt   3600
tatggaagct cggcttcttc aaaagaaaat atgaaaagat gaccaaaaat ccagatgaga   3660
ttgatgagac cacagagctc agtagctgaa ccagcagacc tacctgcagt gggaaccggc   3720
agcatcccag ccagggtttg ctgtttgcgt gaatggatt cttttaaat cccatatttt      3780
ttttatcatg tcgtaggtaa actaacctgg tattttaaga gaaaactgca ggtcagtttg    3840
gaatgaagaa attgtggggg gtgggggagg tgcggggggc aggtagggaa ataatagggga   3900
aaatacctat tttatatgat gggggaaaaa aagtaatctt taaactggct ggcccagagt   3960
ttacattcta atttgcattg tgtcagaaac atgaaatgct tccaagcatg acaactttta   4020
aagaaaaata tgatactctc agattttaag ggggaaaact gttctcttta aaatatttgt   4080
ctttaaacag caactacaga agtggaagtg cttgatatgt aagtacttcc acttgtgtat   4140
attttaatga atattgatgt taacaagagg ggaaaacaaa acacaggttt tttcaattta    4200
tgctgctcat ccaaagttgc cacagatgat acttccaagt gataatttta tttataaact   4260
aggtaaaatt tgttgttggt tcctttaga ccacggctgc ccttccaca ccccatcttg      4320
ctctaatgat caaaacatgc ttgaataact gagcttagag tatacctcct atatgtccat   4380
ttaagttagg agaggggcg atatagagaa taaggcacaa aattttgttt aaaactcaga    4440
atataacatg taaatccca tctgctagaa gcccatcctg tgccagagga aggaaaagga     4500
ggaaatttcc tttctctttt aggaggcaca acagttctct tctaggattt gtttggctga   4560
ctggcagtaa cctagtgaat ttctgaaaga tgagtaattt ctttggcaac cttcctcctc   4620
ccttactgaa ccactctccc acctcctggt ggtaccatta ttatagaagc cctctacagc   4680
ctgactttct ctccagcggt ccaaagttat cccctccttt accctcatc caaagttccc    4740
actccttcag gacagctgct gtgcattaga tattaggggg gaaagtcatc tgtttaattt   4800
acacacttgc atgaattact gtatataaac tccttaactt cagggagcta ttttcattta   4860
gtgctaaaca agtaagaaaa ataagctcga gtgaatttct aaatgttgga atgttatggg   4920
atgtaaacaa tgtaaagtaa gacatctcag gatttcacca gaagttacag atgaggcact   4980
ggaagccacc aaaattagcag gtgcaccttc tgtggctgtc ttgtttctga agtacttaaa   5040
cttccacaag agtgaatttg acctaggcaa gtttgttcaa aaggtagatc ctgagatgat   5100
ttggtcagat tgggataagg cccagcaatc tgcattttaa caagcacccc agtcactagg   5160
atgcagatgg accacacttt gagaaacacc acccatttct acttttgca ccttatttc     5220
tctgttcctg agcccccaca ttctctagga gaaacttaga ggaaaagggc acagacacta   5280
catatctaaa gctttggaca agtccttgac ctctataaac ttcagagtcc tcattataaa   5340
atgggaagac tgagctggag ttcagcagtg atgcttttag ttttaaaagt ctatgatctg   5400
gacttcctat aatacaaata cacaatcctc caagaatttg acttggaaaa aaatgtcaaa   5460
ggaaaacagg ttatctgccc atgtgcatat ggacaacctt gactaccctg gcctggcccg   5520
tggtggcagt ccagggctat ctgtactgtt tacagaatta ctttgtagtt gacaacacaa   5580
aacaaacaaa aaaggcataa aatgccagcg gttatagaa aaaacagcat ggtattctcc      5640
agttaggtat gccagagtcc aattcttta acagctgtga gaatttgctg cttcattcca     5700
acaaaatttt atttaaaaaa aaaaaaaaaa gactggagaa actagtcatt agcttgataa   5760
```

```
agaatattta acagctagtg gtgctggtgt gtacctgaag ctccagctac ttgagagact    5820
gagacaggaa gatcgcttga gcccaggagt tcaagtccag cctaagcaac atagcaagac    5880
cctgtctcaa aaaatgact atttaaaaag acaatgtggc caggcacggt ggctcacacc    5940
tgtaatccca acactttggg aggctgaggc cggtggatca cgaggtcagg agtttgagac    6000
tagcctggcc aacatggtga accccatct ctaataatat aaaaattagc tgggcgtagt    6060
agcaggtgcc tgtaatccca gttactcggg aagctgaggc aggagaatca cttgaacccg    6120
ggaggcagag gtttcagtga gccgagatcg cgccactgca ctccagcctg ggtgacaggg    6180
caagactctg tctcaaacaa acaaacaaaa aaaagttag tactgtatat gtaaatacta    6240
gcttttcaat gtgctataca aacaattata gcacatcctt cctttactc tgtctcacct    6300
cctttaggtg agtacttcct taaataagtg ctaaacatac atatacgaaa cttgaaagct    6360
ttggttagcc ttgccttagg taatcagcct agtttacact gtttccaggg agtagttgaa    6420
ttactataaa ccattagcca cttgtctctg caccattat cacaccagga cagggtctct    6480
caacctgggc gctactgtca tttggggcca ggtgattctt ccttgcaggg gctgtcctgt    6540
accttgtagg acagcagccc tgtcctagaa ggtatgttta gcagcattcc tggcctctag    6600
ctacccgatg ccagagcatg ctcccccgc agtcatgaca atcaaaaaat gtctccagac    6660
attgtcaaat gcctcctggg gggcagtatt tctcaagcac ttttaagcaa aggtaagtat    6720
tcatacaaga aatttagggg gaaaaaacat tgtttaaata aaagctatgt gttcctattc    6780
aacaatattt ttgctttaaa agtaagtaga gggcataaaa gatgtcatat tcaaatttcc    6840
atttcataaa tggtgtacag acaaggtcta tagaatgtgg taaaaacttg actgcaacac    6900
aaggcttata aaatagtaag atagtaaaat agcttatgaa gaaactacag agatttaaaa    6960
ttgtgcatga ctcatttcag cagcaaaata agaactccta actgaacaga aatttttcta    7020
cctagcaatg ttattcttgt aaaatagtta cctattaaaa ctgtgaagag taaaactaaa    7080
gccaattttat atagtcaca caagtgatta tactaaaaat tattataaag gttataattt    7140
tataatgtat ttacctgtcc tgatatatag ctataaccca atatatgaaa atctcaaaaa    7200
ttaagacatc atcatacaga aggcaggatt ccttaaactg agatccctga tccatctta    7260
atatttcaat ttgcacacat aaaacaatgc ccttttgtgt acattcaggc atacccattt    7320
taatcaattt gaaaggttaa tttaaaccctc tagaggtgaa tgagaaacat gggggaaaag    7380
tatgaaatag gtgaaaatct taactatttc tttgaactct aaagactgaa actgtagcca    7440
ttatgtaaat aaagtttcat atgtacctgt ttattttggc agattaagtc aaaatatgaa    7500
tgtatatatt gcataactat gttagaattg tatatatttt aaagaaattg tcttggatat    7560
tttcctttat acataataga taagtctttt ttcaaatgtg gtgtttgatg tttttgatta    7620
aatgtgtttt gcctctttcc acaaaaactg taaaaataaa tgcatgtttg tacaaaaagt    7680
tgcagaattc atttgattta tgagaaacaa aaattaaatt gtagtcaaca gttagtagtt    7740
tttctcatat ccaagtataa caaacagaaa agtttcatta ttgtaaccca cttttttcat    7800
accacattat tgaatattgt tacaattgtt ttgaaaataa agccattttc tttgggcttt    7860
tataagttaa aaaaaaaa                                                 7878
```

<210> SEQ ID NO 16
<211> LENGTH: 6516
<212> TYPE: DNA
<213> ORGANISM: Artificial Sequence
<220> FEATURE:
<223> OTHER INFORMATION: SLC6A6 (Genbank accession No: NM_003043)

<400> SEQUENCE: 16

```
gagagctgcc tgctcagaca acagacacgc gaggtcagga agaagccgct tataaattac    60
cgcttccttc gcgccgccgc caacgccgag ccccgaggac cgcaagccca gaggacaagc   120
tgcgccaaga gggagtgcgg agcgttcacc cagcgggtca gagagcgagc gggcaggcag   180
cccccggccg gcggaacccg gcacagccga gcagagcgcg ggcggcgccg cagccacccc   240
agatccagaa ccagaaccac agcccttctg aggagctccc aaacaaagca aggagatggc   300
caccaaggag aagctgcagt gtctgaaaga tttccacaag gacatcctga agccctcacc   360
agggaagagc ccaggcacgc ggcctgagga cgaggctgag ggaaaacctc cgcagaggga   420
gaagtggtct agcaagatcg actttgtgct ctctgtggct ggcggcttcg tgggcttggg   480
caacgtctgg cgcttcccgt acctctgcta caagaatggt ggaggtgcgt ttctcatacc   540
gtattttatt ttcctgtttg ggagcggcct gcctgtgttt ttcttggaga tcatcatagg   600
ccagtacacc tctgaagggg gcatcacctg ctgggaaaag atctgcccct tgttctctgg   660
tatcggctat gcctccgttg taattgtgtc cctcctgaat gtctactaca tcgtcatcct   720
ggcctgggcc acatactacc tgttccagtc cttccagaag gagctgccct gggcacactg   780
caaccacagc tggaacacac ctcactgcat ggaggacacc atgcgcaaga acaagagtgt   840
ctggatcacc atcagctcca ccaacttcac ctcccctgtc atcgagttct gggagcgcaa   900
cgtgctgagc ttgtcccctg gaatcgacca cccaggctct ctgaaatggg acctcgctct   960
ctgccttctt ttagtctggc tagtgtgttt cttctgcatc tggaagggcg tcaggtccac  1020
tgggaaggtc gtctacttca cagccacttt tccattcgcc atgctcctgg tgctgctggt  1080
ccgagggctg acgctgccgg gcgcgggcgc aggcatcaag ttctatctgt atcctgacat  1140
caccccgcctt gaggacccac aggtgtggat tgacgctggg actcagatat tcttctctta  1200
tgccatctgc ctgggggcta tgacctcgct ggggagctac aacaagtaca gtataactc   1260
gtacagggac tgtatgctgc tgggatgcct gaacagtggg accagttttg tgtctggctt  1320
cgcaattttt tccatcctgg gcttcatggc acaagagcaa ggggtggaca ttgctgatgt  1380
ggctgagtca ggtcctggcc tggccttcat tgcctaccca aaagctgtga caatgatgcc  1440
gctgcccaca ttttggtcca ttctttttttt tattatgctt ctcttgcttg gactggatag  1500
ccagtttgtt gaagttgaag acagatcac atccttggtt gatctttacc catccttcct  1560
aaggaagggt tatcgtcggg aaatcttcat cgccttcgtg tgtagcatca gctacctgct  1620
ggggctgacg atggtgacgg agggtggcat gtatgtgttt cagctctttg actactatgc  1680
agctagcggt gtatgccttt tgtgggttgc attctttgaa tgttttgtta ttgcctggat  1740
atatggaggt gataaccttt atgatggtat tgaggacatg attggctatc ggcccgggcc  1800
ctggatgaag tacagctggg ctgtgatcac tccagttctc tgtgttggat gtttcatctt  1860
ctcgctcgtc aagtacgtac ccctgaccta caacaaaaca tacgtgtacc caactgggc  1920
cattgggctg ggctggagcc tggccctttc ctccatgctc tgcgttccct tggtcatcgt  1980
catccgcctc tgccagactg agggggccgtt ccttgtgaga gtcaagtacc tgctgacccc  2040
aagggaaccc aaccgctggg ctgtggagcg cgagggagcc acaccttaca actctcgcac  2100
cgtcatgaac ggcgctctcg tgaaaccgac ccacatcatt gtggagacca tgatgtgagc  2160
tctctcgggt cgacggggcc ggcggctttc ctgctgttta ctaacattag attctcatag  2220
gaccaggttt acagagcttt atatttgcac taggatttt ttttttttgt aattgtcaca  2280
```

```
gaaaatgtaa ttgtgggtat gtgtgcgtgc gtgtgtgtgt gtgtgtgtat cgtgtgtgtg    2340
tgttttgttt tgatttgggg gatattttgt acaaaaagaa aacccacggg aagatgtccg    2400
tggagaggca gagctttcat actgaattag atgtatttta tgggaatttg gtaaatttttt   2460 ctttgtattt ttttttttac atataagtat atatacactt agagattgtc atatacttttt   2520 accacttgaa ttgatcttct tgccagcaat agatctcatt ttcaaaagca attcttcggt    2580
gctgtgtagc tggcagaaag ttctgtccag taaacgcagg atggaatttt cctgggactc    2640
tacacccatc ttaaggtggt ataccttcca aatcctggtt cagatggaag aaatagcagg    2700
agagaggacc cattagctgg cagacccagg gggaagaaag gagggctgtg aggagatacc    2760
tcattaaact tggcttagtg aagaagagag atgccaaagg aatgaaccaa cccttcacat    2820
aaaggagact ggctgaagct gaatgaggag gccctatagc agaagtctga ttctaagagc    2880
agtagaaact tgtaccagaa gcaaaatccc acttttaatt ttgagatggt gagtggatag    2940
tcagtagacc gtcagaacca ctggccagag agggagctgc tagagatcca agaaggctgg    3000
caggagtgag gctcacaact cagcctcgca agaggtggca gaggcacagg aggccacagt    3060
ccttcctggg gcattccagg cagagaagga gcagaggctc tcccggcagg agctggggtc    3120
tcagggctca gatgagtctg ttgcatttga atggggtcat agcaggttct ggtcattccc    3180
caagcaacat ctcagcatct cttaaagttg cctgcaggaa tgaagcatga catacctgtt    3240
gagggactag gggagtggtg gggaggtgag tggaccaaag gatataggcc ccaggcatgc    3300
agatgggccc ggtgtcgggg aggggtgctt tctttcctca tctccccact ccccactctc    3360
agcctgggag actcctgcca agccctcatt aaagatgcca ccctgggctg ccctggcacc    3420
tagcaaggca caccaagaac agcttttgag tctgtatcct ccactggggg aagtgctccc    3480
agttcagaac aagggcagcc cgtggtgctg acctaggata taacaaagct cttcacttca    3540
aaacccctgc aatagctggg tttacagaca tttaccacct gcggacccaa aagagaaggc    3600
ctaggagagt tttctagaag gttgggattg tcagggtcct ggcccctcag aactggcttg    3660
atcaagggcc ttatgtggag cagaggttgt ctctgaacca ggagagaagg tactatacct    3720
ttcaaatccc cagggcagac acaccccac ccagccccta tttggaccta aactgtgcca    3780
tttgaacagt cacttccaag ctcagtctaa atgaaaccga aacgtgacca cgcacaaagg    3840
cagtcactgc ctcgaggggt gcagaccgca gaattttcac agcaggggct cttgaaccc     3900 tggaaacccc cttcttaaat ttgggaggag gagtatgcct ttggtgtccc cctcccaagg    3960
ggcaattctg aacccatct ttggcaggca tacatatttc actgtttcca aagctatcta    4020
ctctgccaaa caacacccag tcctattcca aactctcaac gattctatct tgttcctgtt    4080
tttctatgta tttatggttg ccgtttgtgt ctgatttgat tttactgttt tttccctgat    4140
tttatggagt agcattgtga cctgtttcc tttgtcttat ataactttag taaactaacc     4200
actgtcaatg attgagggca ggtggcacgt ggggaagagg ggacttggca cgcagtggct    4260
acctgggcat ttgtggtcat ttcagtttcc atctccccag cgggggctcc ctgggtgaaa    4320
ggccacagta ttttggggttg gtaggcaaat tgcaacattc tggacatggc ctgaggaagg    4380
cctcttctta taagattctc agaccaaatt ctagaccaaa gacacaggca gaccaagtcc    4440
ccaggccccg cctggaagga agtcgttcct caactctccc caaggcacct gtctccaatc    4500
agagccctct cgcccagcca gcctggctc tgtgtgcaga gcatagctct gcgagtacct    4560
gtgtaataat gctcaacctt catgtctccg tataaacgaa actttccatg agagctcatg    4620
actctggtcc acctgtctat agagaatggg caaagtcctt cacctgcttt ctgcttggga    4680
```

```
tgggtcagaa atgctgatgc ccgcacatag cccagccagc cagatctgga aaggaagcga   4740
gggggttgtt taaatcaatt ttttaagatg aagaagtggg agacactgcg ttgagatggg   4800
ccatgctagg gccacagaga tttcctgacg gtcagggaga aagggcctc cagggtcccc    4860 taacccaacg cccttgttgt aaatgaggta actgaggctc agggaggcac tgtgagccag   4920
gaatggattt tcttgaaaca gctctagctg caggttctcc gaggtaggtg cagggaatgg   4980
tgagtgtcta accagggcta catccagcaa catcctcaag gtcttcctga caaccaaaga   5040 caagcccttta tggaaaagga aatgcgctcc cctccatgtt cagggatgag gggagcagca   5100
gcagccacac tcccaccatc ctcacagaat tcctggaccc atgcggtggc tccgtgagct   5160
gggtgactcc agcctcacct gcacacccca gccctgcacg gggccctcct tcctcccagc   5220
agcccttggt gagctaggaa ttgagatccc tgtttgtgaa agagggaact gaggtgcaga   5280
gaagccagag gtgtgccaga tccttaggca ggatttagat gaagtcgccc tggctccaga   5340
ctgaccccga ggctctgcgg ggagtttcca ggcagcagga agtggccttg gatgctctcc   5400
ttccaggaca gcataacccc tgggccatgt gcagctcctt cactgccccc tggatcccca   5460 gcatacccccc aaagacagtg gggaaacaca aggggagagc acagcatggc ccctccagcc   5520
cacttcaggg cactcttgta tcacccgggt accgccacac tggtccccca cccagccagc   5580
atctcccagc acagcccctc tccctgggga aatgctctgg gtagccagtc taaaggcaga   5640
ggcacctaac tgctccccgc agcccacccc acccaagatt cagacacaag ccaggaaagg   5700
acccaagaga aaatccttca aggtggcctg aggtcccatc cctccctcag acccatgtgg   5760
tcccaggcca ggctgcctgg gacacggtaa ataccactgt gtgcaaaaat cgaagtacaa   5820
aaccacaaga ctaaacaaaa caaacccaga gagccaaact tgtagaggtg ggcagtccag   5880
aaagcagggg gcagccctcc ccctttcctt ctctccctga tcctcagaat atatattgtt   5940
gtaataggaa gcattttgc attgttctct tgtgggtgtc actacagaca tgttctggcg   6000
tgttctccga gggatggagc atcctgttat atatttgact tcaaattgag atgttggctt   6060
catttttttt ttttacccaa ttaatctccc aatccctagc aactgtgact ctgtatttag   6120
cacaagagaa agctgagaat gtgggtcttg cctccttcca gaaatatgtc tggctcatca   6180 ggacatttt ttaaaacttc aaaatatttt taagatattt taaactttta taaaaaaaa     6240 atcaaccaac aagagacttt tctgaggagg aacatttgta tttgaacaag atccttggtg   6300
tgtagttcag tcttgcagta tacaagcttt tgtgtataaa tgttttatga tatgattccc   6360 tgtatttgc aggggttttt ttctcttttg ctttttagat aaatatgtat atcaatattt    6420
taaattcatc tttgcttttt ttagaggagt ttgtaatcac cttataacat gaaaataaac   6480
atttcctttt taacatccaa aaaaaaaaa aaaaaa                              6516
```

<210> SEQ ID NO 17
<211> LENGTH: 3446
<212> TYPE: DNA
<213> ORGANISM: Artificial Sequence
<220> FEATURE:
<223> OTHER INFORMATION: F2RL2 (Genbank accession No: NM_004101)

<400> SEQUENCE: 17

```
atgcttactg aagcatcgag tggattacat ccttccctg cggaggacca gggcaagttt      60
cctgcctgca cggcacagga gagcaaactt ctacagacag accaaggctt ccatttgctg    120
ctgacacatg gaactgaggt gaaattgtgc tccatgattt tacagatttc ataacgttta    180
```

-continued

```
agagacggga ctcaggtcat caaaatgaaa gccctcatct ttgcagctgc tggcctcctg    240
cttctgttgc ccacttttg tcagagtggc atggaaaatg atacaaacaa cttggcaaag    300
ccaaccttac ccattaagac ctttcgtgga gctcccccaa attcttttga agagttcccc    360
ttttctgcct tggaaggctg acaggagcc acgattactg taaaaattaa gtgccctgaa    420
gaaagtgctt cacatctcca tgtgaaaaat gctaccatgg ggtacctgac cagctcctta    480
agtactaaac tgatacctgc catctacctc ctggtgtttg tagttggtgt cccgccaat    540 gctgtgaccc tgtggatgct tttcttcagg accagatcca tctgtaccac tgtattctac    600
accaacctgg ccattgcaga ttttcttttt tgtgttacat tgcccttttaa gatagcttat    660 catctcaatg ggaacaactg ggtatttgga gaggtcctgt gccgggccac cacagtcatc    720
ttctatggca acatgtactg ctccattctg ctccttgcct gcatcagcat caaccgctac    780
ctggccatcg tccatccttt cacctaccgg ggcctgccca agcacaccta tgccttggta    840
acatgtggac tggtgtgggc aacagttttc ttatatatgc tgccattttt catactgaag    900
caggaatatt atcttgttca gccagacatc accacctgcc atgatgttca caacacttgc    960
gagtcctcat ctcccttcca actctattac ttcatctcct tggcattctt tggattctta   1020
attccatttg tgcttatcat ctactgctat gcagccatca tccggacact taatgcatac   1080
gatcatagat ggttgtggta tgttaaggcg agtctcctca tccttgtgat ttttaccatt   1140
tgctttgctc caagcaatat tattcttatt attcaccatg ctaactacta ctacaacaac   1200
actgatggct tatatttat atatctcata gctttgtgcc tgggtagtct taatagttgc   1260
ttagatccat tcctttattt tctcatgtca aaaaccagaa atcactccac tgcttacctt   1320
acaaaatagt gaaatgatct tagagaacaa ggacagccat cacagagaac gtctgttttc   1380
aagaacaaca taagcatagt gcaaggagct ccatttccga gctcctaaga aatatgcttc   1440
aaaggtcaaa cattacaaaa gcattagtag tttgtttgtt tgttttttgag actgagtctc   1500 actttatcac ccagactggc gtgcagtggc actatcttgg ctcattgcaa cctctgcctc   1560
ccaggtcagc ctcccaagta gctgggatta caccaccatg cccagctact aaaaatactt   1620
gtatttttag tagagacggg gtttcaccat gttgaccagg ctggtcttga actcctgacc   1680
tcaagtgatc ttccggcctc agcctcccaa agtgctggat tacaggcgtg agccactgag   1740
ccagccagca ttagtaattt ttaaaaacac tttatcagta ttttaaaaat gttaatgcag   1800
gagaaaagat atcacaactc tatggaaaat gacatttcca tttgccttat tgctacttca   1860
agctctttaa atcaccatct tccctatttc tgtgagtggt attgccatcc ttgacatttg   1920
acatcatttt ttattctttg gtctcttttg actctcatgc tggtggctgc ctcatcaact   1980
gattctatct ttgtagggtc cctcaccagg gtctttatc tagtttcacc tttgccttct   2040
ttttcctttt ttaatagaa gacagtgtct cgcttcgtca cctggctgaa gtgcagtagc   2100
ctgatcatag ctcacttcag cctccaactc ctgggctcaa gcaatcctgc tgtctcagcc   2160
tcccaagtaa ctaagactac aggcatgcac caccataccc aactaatttt attttttatt   2220
ttttgcagag atggagtctc actgttgccc aggctggtct tgaactcctg gtctcgagtg   2280
atcttcctat ctcagcctcc caaagtgctg ggactacagg catgagccac tacgtccagg   2340
ccacctctac cttctaacca ttctctccac tgccagccta ccctccacca cttcacaagt   2400
cctgccagat taatcttcct tagatatcag ttaggataca tcactaaaac atttccacta   2460
actccactgt ttctataata aatcataaat ctttagcctg gcattcaagg ctaacttgct   2520
aatcacactt cccattaaac cttgcttatg atataggcac caaccaaacc tcttgctctg   2580
```

```
ctatatctcc actctgcctc agactgaaaa gctagtccta acgtctttgc cttaattctg    2640 ttcattttt caagtccttg aaggaccatt cttccctgat tctcaggcta gaagtgtcac     2700
ttttcttatc tgtacttcca aagcactttc gtatatttt attatggcat ttatatatag    2760
ttcatttata tttaaatttt aattccatga acaatcaagt accaagtata atggagaagg    2820
tgctcatcct ctgccttcct tgagcttctg ggtgatgcca ggcccaagtc tttgtggcac    2880
ccagctccat gctttgaata ctatgtggct gaatgaattt ttaaaatctc aaagcagtta    2940
aacagcagga aagcccatta acttcgtact gaaaaagcaa catactgtga tgatacggga    3000
tgacatcatt tcaggttggg catacaaaaa agtaaggaag ctaaactaag actatactca    3060
ccaggccatt tagaagtttt aaataatgcc tccactatt tttttcttag acatagcttt     3120
taatggggaa atggaatttt gttattaata cccattatat tcctgtaagt aaatgactat    3180 ttttcccta actcagtgat tagacaggaa ggaagacatt agtgattaga caggagggaa     3240
gatattagtg attagacagc agggaagata ttagtggtaa agagtgaatg atagtagtga    3300
atataaatgg ggctgaggaa actttaagca taaaagattc ctgagatgac tttacaagtc    3360
tgtacgaatc tgccttgact gtatatttca tactgcccaa caaaacaata aaaaacaatt    3420
ttaaatgcaa aaaaaaaaaa aaaaaa                                         3446
```

<210> SEQ ID NO 18
<211> LENGTH: 11628
<212> TYPE: DNA
<213> ORGANISM: Artificial Sequence
<220> FEATURE:
<223> OTHER INFORMATION: CDK6 (Genbank accession No: NM_001259)

<400> SEQUENCE: 18

```
aacctctccg cgcgaagacg gcttcagccc tgcagggaaa gaaaagtgca atgattctgg     60
actgagacgc gcttgggcag aggctatgta atcgtgtctg tgttgaggac ttcgcttcga    120
ggagggaaga ggagggatcg gctcgctcct ccggcggcgg cggcggcggc gactctgcag    180
gcggagtttc gcggcggcgg caccagggtt acgccagccc cgcggggagg tctctccatc    240
cagcttctgc agcggcgaaa gccccagcgc ccgagcgcct gagccggcgg ggagcaagta    300
aagctagacc gatctccggg gagccccgga gtaggcgagc ggcggccgcc agctagttga    360
gcgcaccccc cgcccgcccc agcggcgccg cggcgggcgg cgtccaggcg gcatggagaa    420
ggacggcctg tgccgcgctg accagcagta cgaatgcgtg gcggagatcg gggagggcgc    480
ctatgggaag gtgttcaagg cccgcgactt gaagaacgga ggccgtttcg tggcgttgaa    540
gcgcgtgcgg gtgcagaccg gcgaggaggg catgccgctc tccaccatcc gcgaggtggc    600
ggtgctgagg cacctggaga ccttcgagca ccccaacgtg gtcaggttgt tgatgtgtg    660 cacagtgtca cgaacagaca gagaaaccaa actaactta gtgtttgaac atgtcgatca     720
agacttgacc acttacttgg ataaagttcc agagcctgga gtgcccactg aaaccataaa    780
ggatatgatg tttcagcttc tccgaggtct ggactttctt cattcacacc gagtagtgca    840
tcgcgatcta aaaccacaga acattctggt gaccagcagc ggacaaataa aactcgctga    900
cttcggcctt gcccgcatct atagtttcca gatggctcta acctcagtgg tcgtcacgct    960
gtggtacaga gcacccgaag tcttgctcca gtccagctac gccaccccg tggatctctg   1020 gagtgttggc tgcatatttg cagaaatgtt tcgtagaaag cctcttttc gtggaagttc    1080 agatgttgat caactaggaa aaatcttgga cgtgattgga ctcccaggag aagaagactg    1140
```

-continued

```
gcctagagat gttgcccttc ccaggcaggc ttttcattca aaatctgccc aaccaattga    1200
gaagtttgta acagatatcg atgaactagg caaagaccta cttctgaagt gtttgacatt    1260
taacccagcc aaaagaatat ctgcctacag tgccctgtct cacccatact tccaggacct    1320
ggaaaggtgc aaagaaaacc tggattccca cctgccgccc agccagaaca cctcggagct    1380
gaatacagcc tgaggcctca gcagccgcct aagctgatcc tgcggagaa caccttggt     1440 ggcttatggg tcccctcag caagccctac agagctgtgg aggattgcta tctgaggcc     1500 ttccagctgc tgtcttctgg acaggctctg cttctccaag aaaccgcct agtttactgt    1560 tttgaaatca atgcaagagt gattgcagct ttatgttcat ttgtttgttt gtttgtctgt    1620
ttgtttcaag aacctggaaa aattccagaa gaagagaagc tgctgaccaa ttgtgctgcc    1680
atttgatttt tctaaccttg aatgctgcca gtgtggagtg ggtaatccag gcacagctga    1740
gttatgatgt aatctctctg cagctgccgg gcctgatttg gtacttttga gtgtgtgtgt    1800
gcatgtgtgt gtgtgtgtgt gtgtgtgtgt gtgtgtatgt gagagattct gtgatctttt   1860
aaagtgttac tttttgtaaa cgacaagaat aattcaattt taaagactca aggtggtcag   1920
taaataacag gcatttgttc actgaaggtg attcaccaaa atagtcttct caaattagaa    1980
agttaacccc atgtcctcag catttctttt ctggccaaaa gcagtaaatt tgctagcagt   2040
aaaagatgaa gttttataca cacagcaaaa aggagaaaaa attctagtat atttttaagag   2100 atgtgcatgc attctattta gtcttcagaa tgctgaattt acttgttgta agtctatttt    2160
aaccttctgt atgacatcat gctttatcat ttcttttgga aaatagcctg taagcttttt   2220
attacttgct ataggtttag ggagtgtacc tcagatagat tttaaaaaaa agaatagaaa   2280 gcctttatttt cctggtttga aattcctttc ttcccttttt ttgttgttgt tattgttgtt    2340
tgttgttgtt attttgtttt tgttttaggg aatttgtcag aaactctttc ctgttttggt    2400
ttggagagta gttctctcta actagagaca ggagtggcct tgaaattttc ctcatctatt    2460
acactgtact ttctgccaca cactgccttg ttggcaaagt atccatcttg tctatctccc    2520
ggcacttctg aaatatattg ctaccattgt ataactaata acagattgct taagctgttc   2580
ccatgcacca cctgtttgct tgcttttcaat gaacctttca taaattcgca gtctcagctt   2640
atggtttatg gcctcgattc tgcaaaccta acagggtcac atatgttctc taatgcagtc   2700
cttctacctg tgtttactt ttgttaccta aataatgagt aggatcttgt tttgttttat    2760
caccagcaca cagattgcta taaactgtta ctttgtgaat tacatttta tagaagatat    2820 tttcagtgtc tttacctgag ggtatgtctt tagctatgtt ttagggccat acatttactc    2880
tatcaaatga tcttttctcc atccccagg ctgtgcttat ttctagtgcc ttgtgctcac    2940
tcctgctctc tacagagcca gcctggcctg ggcattgtaa acagcttttc cttttctct    3000 tactgttttc tctacagtcc tttatatttc ataccatctc tgccttataa gtggtttagt    3060
gctcagttgg ctctagtaac cagaggacac agaaagtatc ttttggaaag tttagccacc    3120
tgtgctttct gactcagagt gcatgcaaca gttagatcat gcaacagtta gattatgttt    3180
agggttagga ttttcaaaga atggaggttg ctgcactcag aaaataattc agatcatgtt    3240
tatgcattat taagttgtac tgaattcttt gcagcttaat gtgatatatg actatcttga    3300
acaagagaaa aaactaggag atgtttctcc tgaagagctt ttggggttgg gaactattct    3360 ttttaattg ctgtactact taacattgtt ctaattcagt agcttgagga acaggaacat     3420
tgttttctag agcaagataa taaggagat gggccataca aatgttttct actttcgttg    3480
tgacaacatt gattaggtgt tgtcagtact ataaatgctt gagatataat gaatccacag    3540
```

```
cattcaaggt caggtctact caaagtctca catggaaaag tgagttctgc ctttcctttg    3600
atcgagggtc aaaatacaaa gacattttgg ctagggccta caaattgaat ttaaaaactc    3660
actgcactga ttcatctgag cttttggtt agtattcatg ctagagtga acatagcttt       3720 agttttgct gttgtaaaag tgttttcata agttcactca agaaaatgc agctgttctg       3780 aactggaatt tttcagcatt ctttagaatt ttaaatgagt agagagctca acttttattc    3840
ctagcatctg cttttgactc atttctaggc agtgcttatg aagaaaatt aaagcacaaa     3900 cattctggca ttcaatcgtt ggcagattat cttctgatga cacagaatga aagggcatct   3960
cagcctctct gaactttgta aaatctgtc cccagttctt ccatcggtgt agttgttgca     4020
tttgagtgaa tactctcttg atttatgtat tttatgtcca gattcgccat ttctgaaatc    4080
cagatccaac acaagcagtc ttgccgttag ggcattttga agcagatagt agagtaagaa   4140
cttagtgact acagcttatt cttctgtaac atatggtttc aaacatcttt gccaaaagct   4200
aagcagtggt gaactgaaaa gggcatattg ccccaaggtt acactgaagc agctcatagc  4260
aagttaaaat attgtgacag atttgaaatc atgtttgaat ttcatagtag gaccagtaca  4320
agaatgtccc tgctagtttc tgtttgatgt ttggttctgg cggctcaggc attttgggaa   4380
ctgttgcaca gggtggagtc aaaacaacct acatataaaa agagaaaaag agaaacttgt   4440
ccatttagct ttcataagaa atcccatggc aaagggtaat aaaaaggacc taatcttaaa   4500
aatacaattt ctaagcactt gtaagaaccc agtgggttgg agcctccac tttgtccctc     4560 ctttgaagtg gatgggaact caaggtgcaa agaacctgtt ttggaagaaa gcttggggcc   4620
atttcagccc cctgtattct catgatttc tctcaggaag cacacactgt gaatggcaga    4680
cttttcattt agccccaggt gacttactaa aaatagttga aaattattca cctaagaata   4740
gaatctcagc attgtgttaa ataaaaatga aagctttaga aggcatgaga tgttcctatc   4800
ttaaataaag catgtttctt ttctatagag aaatgtatag tttgactctc cagaatgtac  4860
tatccatctt gatgagaaaa ctcttaaata gtaccaaaca ttttgaactt taaattatgt   4920
atttaaagtg agtgtttaag aaactgtagc tgcttctttt acaagtggtg cctattaaag   4980
tcagtaatgg ccattattgt tccattgtgg aaattaaatt atgtaagctt cctaatatca    5040
taaacatatt aaaattcttc taaaatattg cttttctttt aagtgacaat ttgactattc   5100
ttatgataag cacatgagag tgtcttacat tttccaaaag caggctttaa ttgcatagtt   5160
gagtctagga aaaataatg ttaaaagtga atatgccacc ataattactt aattatgtta    5220
gtatagaaac tacagaatat ttaccctgga aagaaaatat tggaatgtta ttataaactc  5280
ttagatattt atataattca aaagaatgca tgtttcacat tgtgacagat aaagatgtat   5340
gatttctaag gctttaaaaa ttattcataa aacagtgggc aatagataaa ggaaattctg  5400
gagaaaatga aggtatttaa agggtagttt caaagctata tatttttga aggatatatt     5460 ctttatgaac aaatatattg taaaaattta actaaggtc atctggtaac tgtgggatta    5520
atatggtcga aaacaaatgt tatggagaag ctgtcccaag caaactaaat tacctgtact   5580
tttttcccat ttcaagggaa gaggcaacca catgaagcaa tacttcttac acatgcctaa   5640
gaacgttcat tgaaaaaata aatttttaaa aggcatgtgt ttcctatgcc accaatactt   5700
ttgaaaaatt gtgaacctta cccaaaacca tttatcatgt ccattaagta tatttgggta   5760
tataattagg aagatattta catgttccat ctccacagtg gaaaaactta ttgaggctac   5820
caaagtgtgc caagaaatgt aagtccttag agtaattaga aatgctgttt tcctcaaaag   5880
```

```
catgagaaac tagcattttc atttcttatt tactcccttt ctatatcaat gcaattcaca      5940
acccaatttt aatacatccc tatatctcaa gcatttctat cttgtacttt ttcagaaaat      6000
aaaccaaaaa taatcctttg gtctctctat cttctgacct ttgtaagcaa cagaaatgta      6060
aaaacagaag gggtccaatt tttacacgtt tttttctcaa gtagcctttc tggggatttt      6120
tattttctta atgaagtgcc aatcagcttt tcaaaatgtt ttctatttct cagcatttcc      6180
aggaagtgat aacgtttagc taaatgagta aagtggact tccttcaaca tattgttacc      6240
ttgtctagcc ttaggaagaa acaagagcc acctgaaaat aaatacaggc tcttttcgag      6300
catctgctga atactgtta cagcaatttg aagttgatgt ggtaggaaag gaaggtgact      6360
tttcttgcaa aagtctttct aaacattcac actgtcctaa gagatgagct ttcttgtttt      6420
attccggtat attccacaag gtggcacttt tagagaaaaa caaatctgat gaagactaaa      6480
gaggtacttc taaagagat ttcattctaa ctttatttt ctgcgcatat ttaactcttt      6540
cctagcactt gtttttggg atgattaata gtctctataa tgttctgtaa cttcaatatt      6600
ttacttgtta cctaggttct gaacaattgt ctgcaaataa attgttctta aggatggata      6660
atacacccat tttgatcatt taagtaaaga aagcctagtc attcattcag tcaagaaaaa      6720 attttgaag tacccagtta ccttactttt ctagattaaa acaggcttag ttactaaaaa      6780
ggcagtcctc atctgtgaac aggatagttt cgttagaagt ataaaactcc tttagtggcc      6840
ccagttaaaa cacacatacc ctctctgctg ctttcaaatt ccctagcatg gtggcctttc      6900
aacattgatt aaattttaaa atcctaattt aaagatcagg tgagcaaaat gagtagcaca      6960
tcagtaattc agtagacaaa acttttgtct gaaaaattgc tgtattgaaa cagagccta      7020 aaataccaaa agaccaggta atttaacat ttgtggaatc acaaatgtaa attcataaga      7080
agctctaatt aaaaaaaaa agtctgaagt atatgagcat aacaacttag gagtgtgtct      7140
acatacttaa cttttgaagt tttttggcaa ctttatatac ttttttaaa tttacaagtc      7200 tacttaaaga cttcttatac cccaaatgat taagttaatt ttagaggtca cctttctcac      7260
agcagtgtca cttgaaattt agtagggaag atattgcag tattttcag tttccttagc      7320 acagcaccac agaaagcagc ttattccttt tgagtggcag acactcgacg gtgcctgccc      7380
aactttcctc ctgagtggca agcagatgag tctcagtaat tcatactgaa ccaaaatgcc      7440
acatacacta ggggcagtca gaaactggct gagaaatccc ccgcctcatt cgcccctctg      7500
ctcccaggaa ctagagtcca gttaaagccc ctatgcgaaa ggccgaattc caccccaggg      7560
tttgttataa cagtggccag tctgaacccc atttgctcgt gctcaaaact tgattcccac      7620
ttgaaagcct tccgggcgcg ctgcctcgtt gccccgcccc tttggcagga gagaggcagt      7680
gggcgaggcc gggctgggc cccgcctccc actcacctgc cggtgcctga aattatgtgc      7740
ggccccgcgg gctgctttcc gaggtcagag tgccctgctg ctgtctcaga ggcatctgtt      7800
ctgcaaatct taggaagaaa aatgtcccta gtagcaaacg ggtgtcttct gtgcataaat      7860
aagtacaaca caattctccg aaagttcggg taaaaagaga tgcggtagca gctgccctgt      7920
gtgaagctgt ctaccccgca tctctcaggc gctaagctca gtttttgttt ttgttttgt      7980 tttttaaag aaaagatgta taattgcagg aattttttt tatttttta ttttccatca      8040 ttctatatat gtgatggtga aagatatgcc tggaaaagtt ttgtttgaa aagtttattt      8100 tctgcttcgt cttcagttgg caaaagctct caattcttta gcttccagtt tcttttctct      8160 cttttttcttt gttaggtaat taaaggtatg taaacaaatt atctcatgta gcaggggatt      8220
ttcatgttga gaggaatctt ccgtgtgagt tgtttggtca cacaaataac cctttctcaa      8280
```

```
ttttaggagt tggattgtc aaatgtaggt ttttctcaaa gggggcatat aactacatat    8340
tgactgccaa gaactatgac tgtagcacta atcagcacac atagagccac acaattattt    8400
aatttctaac tctctgtggt ccctagaaaa attccgttga tgtgcttagg ttaaagttct    8460
gaagataccc gttgtaccct tacttgaaag tttctaatct taagttttat gaaatgcaat    8520
aatatgtatc agctagcaat atttctgtga tcaccaacaa ctctcagttt gatcttaaag    8580
tctgaataat aaaacaaatc ccagcagtaa tacattctt aaacctcaca gtgcatgata     8640
tatcttttca ttctgatcct gtgtttgcaa aaatatacac atgtatatca tagttcctca    8700 cttttattc atttgttttc ctattacctg tagtaaatat attagttagt acatggaatt     8760
tatagcatca gctaccccca ggaacagcac ctgacaggcg ggggattttt tttcaagttg    8820
ttctacattt gcataaatta tttctattat tattcatgta tgttatttat ttctgaatca    8880
cactagtcct gtgaaagtac aactgaaggc agaaagtgtt aggattttgc atctaatgtt    8940
cattatcatg gtattgatgg acctaagaaa ataaaaatta gactaagccc ccaaataagc    9000
tgcatgcatt tgtaacatga ttagtagatt tgaatatata gatgtagtat tttgggtatc    9060
taggtgtttt atcattatgt aaaggaatta aagtaaagga ctttgtagtt gttttttatta   9120 aatatgcata tagtagagtg caaaaatata gcaaaaataa aaactaaagg tagaaaagca    9180
ttttagatat gccttaattt agaaactgtg ccaggtggcc ctcggaatag atgccaggca    9240
gagaccagtg cctgggtggt gcctcctctt gtctgccctc atgaagaagc ttccctcacg    9300
tgatgtagtg ccctcgtagg tgtcatgtgg agtagtggga acaggcagta ctgttgagag    9360
gagagcagtg tgagagtttt tctgtagaag cagaactgtc agcttgtgcc ttgaggcttc    9420
cagaacgtgt cagatggaga agtccaagtt tccatgcttc aggcaactta gctgtgtaca    9480
gaagcaatcc agtgtggtaa taaaaagcaa ggattgcctg tataatttat tataaaataa    9540
aagggatttt aacaaccaac aattcccaac acctcaaaag cttgttgcat tttttggtat    9600
ttgaggtttt tatctgaagg ttaaagggca agtgtttggt atagaagagc agtatgtgtt    9660
aagaaaagaa aaatattggt tcacgtagag tgcaaattag aactagaaag ttttatacga    9720 ttatcattt gagatgtgtt aaagtaggtt ttcactgtaa aatgtattag tgtttctgca     9780
ttgccatagg gcctggttaa aactttctct taggtttcag gaagactgtc acatacagta    9840 agctttttc cttctgactt ataatagaaa atgttttgaa agtaaaaaaa aaaaatctaa     9900
tttggaaatt tgacttgtta gtttctgtgt ttgaaatcat ggttctagaa atgtagaaat    9960
tgtgtatatc agatactcat ctaggctgtg tgaaccagcc caagatgacc aacatccccca  10020 cacctctaca tctctgtccc ctgtatctct tcctttctac cactaaagtg ttccctgcta   10080
ccatcctggc ttgtccacat ggtgctctcc atcttcctcc acatcatgga ccacaggtgt   10140
gcctgtctag gcctggccac cactcccaac ttgacctagc cacattcatc tagagatggt   10200
tcctgatgct gggcacagac tgtgctcatg gcacccatta gaaatgcctc tagcatcttt   10260
gtatgcatct tgatttttaa accaagtcat tgtacagagc attcagtttt ggctgtggta   10320
ccaagagaaa aactaatcaa gaatataaac cacattccag gctgctgttt tctctccatc   10380
tacaggccac acttttactg tatttcttca tacttgaaat tcattctgct attttcatat   10440
cagggtacag acttataagg gtgcatgttc cttaaaggtg cataattatt cttattccgt   10500
ttgcttatat tgctacagaa tgctctgttt tggtgctttg agttctgcag acccaagaag   10560
cagtgtggaa attcactgcc tgggacacag tcttataaga atgttggcag gtgactttgt   10620
```

```
atcagatgtt gcttctcttt tctctgtaca cagattgaga gttaccacag tggcctgtcg   10680
ggtccaccct gtgggtgcag cacagctctc tgaaagcaag aaccttccta cctattctaa   10740 cgttttttgcc ctctaagaaa aatggcctca ggtatggtat agacatagca agaggggaag   10800
ggctgtctca ctctagcaac catccctcca ttacacacag aaagccctct tgaagcaaaa   10860
gaagaagaaa gaaagaaagc ttatctctaa ggctactgtc ttcagaatgc tctgagctga   10920
atgctcttgc tccttttccca agaggcagat gaaaatatag ccagtttatc tatacccttc   10980
ctatctgagg aggagaatag aaaagtaggg taaatatgta acgtaaaata tgtcattcaa   11040
ggaccaccaa aactttaagt accctatcat taaaaatctg gttttaaaag tagctcaagt   11100
aagggatgct ttgtgaccca gggtttctga agtcagatag ccattcttac ctgcccctta   11160
ctctgactta ttgggaaagg gagaactgca gtggtgtttc tgttgcagtg gcaaaggtaa   11220
catgtcagaa aattcagagg gttgcatacc aataatcctt tggaaactgg atgtcttact   11280
gggtgctaga atgaaaatgt aggtatttat tgtcagatga tgaagttcat tgttttttc   11340 aaaattggtg ttgaaatatc actgtccaat gtgttcactt atgtgaaagc taaattgaat   11400
gaggcaaaaa gagcaaatag tttgtatatt tgtaatacct tttgtatttc ttacaataaa   11460
aatattggta gcaaataaaa ataataaaaa caataacttt aaactgcttt ctggagatga   11520
attactctcc tggctatttt cttttttact ttaatgtaaa atgagtataa ctgtagtgag   11580
taaaattcat taaattccaa gttttagcag aaaaaaaaaa aaaaaaaa                11628
```

<210> SEQ ID NO 19
<211> LENGTH: 1416
<212> TYPE: DNA
<213> ORGANISM: Artificial Sequence
<220> FEATURE:
<223> OTHER INFORMATION: AKR1B1 (Genbank accession No: NM_001628)

<400> SEQUENCE: 19

```
acgggctatt taaaggtacg cgccgcggcc aaggccgcac cgtactgggc gggggtctgg     60
ggagcgcagc agccatggca agccgtctcc tgctcaacaa cggcgccaag atgcccatcc    120
tggggttggg tacctggaag tcccctccag ggcaggtgac tgaggccgtg aaggtggcca    180
ttgacgtcgg gtaccgccac atcgactgtg cccatgtgta ccagaatgag aatgaggtgg    240
gggtggccat tcaggagaag ctcagggagc aggtggtgaa gcgtgaggag ctcttcatcg    300
tcagcaagct gtggtgcacg taccatgaga agggcctggt gaaggagcc tgccagaaga    360 cactcagcga cctgaagctg gactacctgg acctctacct tattcactgg ccgactggct    420
ttaagcctgg gaaggaattt tcccattgg atgagtcggg caatgtggtt cccagtgaca    480
ccaacattct ggacacgtgg gcggccatgg aagagctggt ggatgaaggg ctggtgaaag    540
ctattggcat ctccaacttc aaccatctcc aggtggagat gatcttaaac aaacctggct    600
tgaagtataa gcctgcagtt aaccagattg agtgccaccc atatctcact caggagaagt    660
taatccagta ctgccagtcc aaaggcatcg tggtgaccgc ctacagcccc ctcggctctc    720
ctgacaggcc ctgggccaag cccgaggacc cttctctcct ggaggatccc aggatcaagg    780
cgatcgcagc caagcacaat aaaactacag cccaggtcct gatccggttc cccatgcaga    840
ggaacttggt ggtgatcccc aagtctgtga caccagaacg cattgctgag aactttaagg    900
tctttgactt tgaactgagc agccaggata tgaccacctt actcagctac aacaggaact    960
ggagggtctg tgccttgttg agctgtacct cccacaagga ttacccccttc catgaagagt   1020 tttgaagctg tggttgcctg ctcgtcccca agtgacctat acctgtgttt cttgcctcat   1080
```

```
tttttttccctt gcaaatgtag tatggcctgt gtcactcagc agtgggacag caacctgtag    1140
agtggccagc gagggcgtgt ctagcttgat gttggatctc aagagccctg tcagtagagt    1200
agaagtctct tccagtttgc tttgcccttc tttctaccct gctggggaaa gtacaacctg    1260 aataccctttt tctgaccaaa gagaagcaaa atctaccagg tcaaaatagt gccactaacg    1320
gttgagtttt gactgcttgg aactggaatc ctttcagcaa gacttctctt tgcctcaaat    1380
aaaaagtgct tttgtgagaa aaaaaaaaaa aaaaaa                              1416
```

<210> SEQ ID NO 20
<211> LENGTH: 3056
<212> TYPE: DNA
<213> ORGANISM: Artificial Sequence
<220> FEATURE:
<223> OTHER INFORMATION: MMP8 (Genbank accession No: NM_002424)

<400> SEQUENCE: 20

```
gacacatgat gctgtgaacg tcagggtgct cgccagggaa gggccctacc cagagggaca      60
gaaagaaagc caggaggggt agagtttgaa gagaagatca tgttctccct gaagacgctt     120
ccatttctgc tcttactcca tgtgcagatt tccaaggcct ttcctgtatc ttctaaagag     180
aaaaatacaa aaactgttca ggactacctg gaaaagttct accaattacc aagcaaccag     240
tatcagtcta caaggaagaa tggcactaat gtgatcgttg aaaagcttaa agaaatgcag     300
cgattttttg ggttgaatgt gacggggaag ccaaatgagg aaactctgga catgatgaaa     360
aagcctcgct gtggagtgcc tgacagtggt ggttttatgt taaccccagg aaaccccaag     420
tgggaacgca ctaacttgac ctacaggatt cgaaactata ccccacagct gtcagaggct     480
gaggtagaaa gagctatcaa ggatgccttt gaactctgga gtgttgcatc acctctcatc     540
ttcaccagga tctcacaggg agaggcagat atcaacattg cttttttacca aagagatcac     600 ggtgacaatt ctccatttga tggacccaat ggaatccttg ctcatgcctt tcagccaggc     660
caaggtattg gaggagatgc tcattttgat gccgaagaaa catggaccaa cacctccgca     720
aattacaact tgtttcttgt tgctgctcat gaatttggcc attctttggg gctcgctcac     780
tcctctgacc ctggtgcctt gatgtatccc aactatgctt tcagggaaac cagcaactac     840
tcactccctc aagatgacat cgatggcatt caggccatct atggactttc aagcaaccct     900
atccaaccta ctggaccaag cacacccaaa ccctgtgacc ccagtttgac atttgatgct     960
atcaccacac tccgtggaga atatttcc tttaaagaca ggtacttctg gagaaggcat    1020
cctcagctac aaagagtcga aatgaatttt atttctctat tctggccatc ccttccaact    1080
ggtatacagg ctgcttatga agattttgac agagacctca ttttcctatt taaaggcaac    1140
caatactggg ctctgagtgg ctatgatatt ctgcaaggtt atcccaagga tatatcaaac    1200
tatggcttcc ccagcagcgt ccaagcaatt gacgcagctg ttttctacag aagtaaaaca    1260
tacttctttg taaatgacca attctggaga tatgataacc aaagacaatt catggagcca    1320
ggttatccca aaagcatatc aggtgccttt ccaggaatag agagtaaagt tgatgcagtt    1380
ttccagcaag aacatttctt ccatgtcttc agtggaccaa gatattacgc atttgatctt    1440
attgctcaga gagttaccag agttgcaaga ggcaataaat ggcttaactg tagatatggc    1500
tgaagcaaaa tcaaatgtgg ctgtatccac tttcagaatg ttgaagggaa gttcagcaag    1560
cattttcgtt acattgtgtc ctgcttatac ttttctcaat attaagtcat tgtttcccat    1620
cactgtatcc attctacctg tcctccgtga aaatatgttt ggaatattcc actatttgca    1680
```

```
gaggcttatt cagttcttac acattccatc ttacattagt gattccatca aagagaagga    1740
aagtaagcct ttttgtcacc tcaatattta ctatttcaat acttacatat ctgacttcta    1800
ggatttattg ttatattact tgcctatctg acttcataca tccctcagtt tcttaaaatg    1860
tcctatgtat atcttctaca tgcaatttag aactagattt tggttagaag taaggattat    1920
aaacaaccta gacagtaccc ttggcccttta cagaaaatat ggtgctgttt tctacccttg    1980
gaaagaaatg tagatgatat gtttcgtggg ttgaattgtg tcccccataa aagatatgtt    2040
gaagttctaa ccccaggtac ccatgaatgt gagcttacca gggtctttgc agatgtaatt    2100
agttaagtta aggtgagatc acactgaatt agggtgggct ctaaatccat tatgactgtt    2160
gttcttataa gaagaagaga ggcatagtca cctaggggag gaggccgtat gaagacagag    2220
gcagagattg gagtgacgca tctccaagcc aaggaattcc aaggactgta agccaccagt    2280
agaagctttg aagaggcaag gaaggattcc ctccaatagc cttcaagtgt gaccctgctg    2340
acacctgcag aattcggact tctatcctcc aaaaccgtga gggaataaat ttcctttgtt    2400
ttaagccacc aactttgcaa tactttgtta cagcaaccct agacatgagg tactagacac    2460
agtacatcta cacatatgaa aatgaatcaa cacagaatgc agaagtagaa cccttgctaa    2520
ggactactgg gcatcttccc aggacagcag ccaaaagaga accaccactt cctctcctgc    2580
ctcctccttg ctctctccta gagtccaaac ccaaatgggc cagttggatc tgatgttcgt    2640 cagttctttta cttctatttc ctggggtact caggagggca cacactatag ataacttggg    2700
ttagctgcat aaaattcaat gtctcattaa gttgcattaa actgagctta gatgtgtaag    2760
tttgctaacg gatgggtttt tttgttaaga actataggat ttatgggacc aagtctagcg    2820
agtccagata tcaaaatcat tataatgtta tatttgctgt tattagaata taatatagct    2880
tattatacaa taaatatgta gactgtaaaa tatatttctc actagtacct cctatttct    2940 ttctctgttg aagtttttaa atcccacaga taattaaatt ggcacctttta tgcttgttca    3000 aaaattaaaa taatctatta aataagttca aattaaagat ttttacttca aatgac        3056
```

<210> SEQ ID NO 21
<211> LENGTH: 1239
<212> TYPE: DNA
<213> ORGANISM: Artificial Sequence
<220> FEATURE:
<223> OTHER INFORMATION: ID1 (Genbank accession No: NM_181353)

<400> SEQUENCE: 21

```
actctcattc cacgttctta actgttccat tttccgtatc tgcttcgggc ttccacctca      60 ttttttttcgc tttgcccatt ctgtttcagc cagtcgccaa gaatcatgaa agtcgccagt     120
ggcagcaccg ccaccgccgc cgcgggcccc agctgcgcgc tgaaggccgg caagacagcg     180
agcggtgcgg gcgaggtggt gcgctgtctg tctgagcaga gcgtggccat ctcgcgctgc     240
gccgggggcg ccggggcgcg cctgcctgcc ctgctggacg agcagcaggt aaacgtgctg     300
ctctacgaca tgaacggctg ttactcacgc ctcaaggagc tggtgcccac cctgcccag      360 aaccgcaagg tgagcaaggt ggagattctc cagcacgtca tcgactacat cagggacctt     420
cagttggagc tgaactcgga atccgaagtt ggaaccccg gggccgagg gctgccggtc       480 cgggctccgc tcagcaccct caacggcgag atcagcgccc tgacggccga ggtgagatcc     540
agatccgacc actagatcat ccttataccg acggggaaac ggaggccaga gagggcgtgg     600
gcgcttgcac cacttccgtc ccatccttgc gggtacctgg ctatgcgggg gtgcctaagg     660
agcctggaaa aagcgctccc ccgtcgtgct tcctggggaa gggggcgttc gctgcgctcg     720
```

```
gagcggcgtc ccttccaacc cgccggtctc atttcttctc gttttcacag gcggcatgcg    780
ttcctgcgga cgatcgcatc ttgtgtcgct gaagcgcctc ccccagggac cggcggaccc    840
cagccatcca gggggcaaga ggaattacgt gctctgtggg tctcccccaa cgcgcctcgc    900
cggatctgag ggagaacaag accgatcggc ggccactgcg cccttaactg catccagcct    960
ggggctgagg ctgaggcact ggcgaggaga gggcgctcct ctctgcacac ctactagtca   1020
ccagagactt taggggtgg gattccactc gtgtgtttct attttttgaa aagcagacat   1080
tttaaaaaat ggtcacgttt ggtgcttctc agatttctga ggaaattgct ttgtattgta   1140
tattacaatg atcaccgact gaaaatattg ttttacaata gttctgtggg gctgtttttt   1200
tgttattaaa caaataattt agatggtggt aaaaaaaaa                           1239
```

<210> SEQ ID NO 22
<211> LENGTH: 3271
<212> TYPE: DNA
<213> ORGANISM: Artificial Sequence
<220> FEATURE:
<223> OTHER INFORMATION: NEFM (Genbank accession No: NM_005382)

<400> SEQUENCE: 22

```
gctgtgacag ccacacgccc caaggcctcc aagatgagct acacgttgga ctcgctgggc     60
aacccgtccg cctaccggcg ggtaaccgag acccgctcga gcttcagccg cgtcagcggc    120
tccccgtcca gtggcttccg ctcgcagtcg tggtcccgcg gctcgcccag caccgtgtcc    180
tcctcctata gcgcagcat gctcgccccg cgcctcgctt acagtctcggc catgctcagc    240 tccgccgaga gcagccttga cttcagccag tcctcgtccc tgctcaacgg cggctccgga    300
cccggcggcg actacaagct gtcccgctcc aacgagaagg agcagctgca ggggctgaac    360
gaccgctttg ccggctacat agagaaggtg cactacctgg agcagcagaa taaggagatt    420
gaggcggaga tccaggcgct gcggcagaag caggcctcgc acgcccagct gggcgacgcg    480
tacgaccagg agatccgcga gctgcgcgcc accctggaga tggtgaacca cgagaaggct    540
caggtgcagc tggactcgga ccacctggag gaagacatcc accggctcaa ggagcgcttt    600
gaggaggagg cgcggttgcg cgacgacact gaggcggcca tccgcgcgct cgcaaagac    660 atcgaggagg cgtcgctggt caaggtggag ctggacaaga aggtgcagtc gctgcaggat    720
gaggtggcct tcctgcggag caaccacgag gaggaggtgg ccgaccttct ggcccagatc    780
caggcatcgc acatcacggt ggagcgcaaa gactacctga agacagacat ctcgacggcg    840
ctgaaggaaa tccgctccca gctcgaaagc cactcagacc agaatatgca ccaggccgaa    900
gagtggttca atgccgcta cgccaagctc accgaggcgg ccgagcagaa caaggaggcc    960
atccgctccg ccaaggaaga gatcgccgag taccggcgcc agctgcagtc caagagcatc   1020
gagctagagt cggtgcgcgg caccaaggag tccctggagc ggcagctcag cgacatcgag   1080
gagcgccaca ccacgacctt cagcagctac caggacacca tccagcagct ggaaaatgag   1140
cttcggggca caaagtggga aatggctcgt catttgcgcg aataccagga cctcctcaac   1200
gtcaagatgg ctctggatat agaaatcgct gcgtacagaa aactcctgga gggtgaagag   1260
actagattta gcacatttgc aggaagcatc actgggccac tgtatacaca ccgaccccca   1320
atcacaatat ccagtaagat tcagaaaccc aaggtggaag ctcccaagct taaggtccaa   1380
cacaaatttg tcgaggagat catagaggaa accaaagtgg aggatgagaa gtcagaaatg   1440
gaagaggccc tgacagccat tacagaggaa ttggccgttt ccatgaagga agagaagaaa   1500
```

| | |
|---|---|
| gaagcagcag aagaaaagga agaggaaccc gaagctgaag aagaagaagt agctgccaaa | 1560 |
| aagtctccag tgaaagcaac tgcacctgaa gttaaagaag aggaaggga aaaggaggaa | 1620 |
| gaagaaggcc aggaagaaga ggaggaagaa gatgagggag ctaagtcaga ccaagccgaa | 1680 |
| gagggaggat ccgagaagga aggctctagt gaaaaagagg aaggtgagca ggaagaagga | 1740 |
| gaaacagaag ctgaagctga aggagaggaa gccgaagcta aagaggaaaa gaaagtggag | 1800 |
| gaaaagagtg aggaagtggc taccaaggag gagctggtgg cagatgccaa ggtgaaaaag | 1860 |
| ccagaaaaag ccaagtctcc tgtgccaaaa tcaccagtgg aagagaaagg caagtctcct | 1920 |
| gtgcccaagt caccagtgga agagaaaggc aagtctcctg tgcccaagtc accagtggaa | 1980 |
| gagaaaggca gtctcctgt gccgaaatca ccagtggaag agaaaggcaa gtctcctgtg | 2040 |
| tcaaaatcac cagtggaaga gaaagccaaa tctcctgtgc aaaatcacc agtggaagag | 2100 |
| gcaaagtcaa aagcagaagt ggggaaaggt gaacagaaag aggaagaaga aaaggaagtc | 2160 |
| aaggaagctc ccaaggaaga gaaggtagag aaaaaggaag agaaaccaaa ggatgtgcca | 2220 |
| gagaagaaga agctgagtc ccctgtaaag gaggaagctg tggcagaggt ggtcaccatc | 2280 |
| accaaatcgg taaaggtgca cttggagaaa gagaccaaag aagaggggaa gccactgcag | 2340 |
| caggagaaag agaaggagaa agcggggagga gagggaggaa gtgaggagga agggagtgat | 2400 |
| aaaggtgcca agggatccag gaaggaagac atagctgtca atggggaggt agaaggaaaa | 2460 |
| gaggaggtag agcaggagac caaggaaaaa ggcagtggga gggaagagga gaaaggcgtt | 2520 |
| gtcaccaatg gcctagactt gagcccagca gatgaaaaga agggggtga taaaagtgag | 2580 |
| gagaaagtgg tggtgaccaa aacggtagaa aaaatcacca gtgaggggg agatggtgct | 2640 |
| accaaataca tcactaaatc tgtaaccgtc actcaaaagg ttgaagagca tgaagagacc | 2700 |
| tttgaggaga aactagtgtc tactaaaaag gtagaaaaag tcacttcaca cgccatagta | 2760 |
| aaggaagtca cccagagtga ctaagatttg agtccattgc aaaaggttaa gccatatgac | 2820 |
| aatttcaaaa tgcatgtgat tggcagcttc aaaacagaac gggttctccc atggggctc | 2880 |
| cagacattgt attttacttt gtgcaatatg aggggactgc atgcaagctc agggtgctcc | 2940 |
| ctcctcagtc tttgggggat tcaaatgcat gatattgtat gtacctggga aatttgccga | 3000 |
| tttcctaagc tgttggaagg gggtcactta agggggatg tcttgagatg tattatgcaa | 3060 |
| agtaccaact gagccaaaaa caataaacga aacacagaac tcagccttaa gaaagctata | 3120 |
| tatgaataat tatgtttacc tcactggtgc atttaaaatg gacttttgtt catgggagaa | 3180 |
| cctcgttgac atgcacagtt tgcaatctta tgttgatcga tgttaaacgt cacagcagta | 3240 |
| cttgctcaat aaaggtcata ttggaaacat a | 3271 |

<210> SEQ ID NO 23
<211> LENGTH: 2212
<212> TYPE: DNA
<213> ORGANISM: Artificial Sequence
<220> FEATURE:
<223> OTHER INFORMATION: ATP1B1 (Genbank accession No: NM_001677)

<400> SEQUENCE: 23

| | |
|---|---|
| cagcggcgcg tcctgcctgc agagagccag gccggagaag ccgagcggcg cagaggacgc | 60 |
| cagggcgcgc gccgcagcca cccaccctcc ggaccgcggc agctgctgac ccgccatcgc | 120 |
| catggcccgc gggaaagcca aggaggaggg cagctggaag aaattcatct ggaactcaga | 180 |
| gaagaaggag tttctgggca ggaccggtgg cagttggttt aagatccttc tattctacgt | 240 |
| aatattttat ggctgcctgg ctggcatctt catcggaacc atccaagtga tgctgctcac | 300 |

```
catcagtgaa tttaagccca catatcagga ccgagtggcc ccgccaggat taacacagat    360
tcctcagatc cagaagactg aaatttcctt tcgtcctaat gatcccaaga gctatgaggc    420
atatgtactg aacatagtta ggttcctgga aaagtacaaa gattcagccc agagggatga    480
catgattttt gaagattgtg gcgatgtgcc cagtgaaccg aaagaacgag gagacttaa     540 tcatgaacga ggagagcgaa aggtctgcag attcaagctt gaatggctgg gaaattgctc    600
tggattaaat gatgaaactt atggctacaa agagggcaaa ccgtgcatta ttataaagct    660
caaccgagtt ctaggcttca aacctaagcc tcccaagaat gagtccttgg agacttaccc    720
agtgatgaag tataacccaa atgtccttcc cgttcagtgc actggcaagc gagatgaaga    780
taaggataaa gttggaaatg tggagtattt tggactgggc aactcccctg gttttcctct    840
gcagtattat ccgtactatg gcaaactcct gcagcccaaa tacctgcagc cctgctggc     900 cgtacagttc accaatctta ccatggacac tgaaattcgc atagagtgta aggcgtacgg    960
tgagaacatt gggtacagtg agaagaccg ttttcaggga cgttttgatg taaaaattga    1020
agttaagagc tgatcacaag cacaaatctt tcccactagc catttaataa gttaaaaaaa    1080
gatacaaaaa caaaaaccta ctagtcttga acaaactgtc atacgtatgg gacctacact    1140
taatctatat gctttacact agctttctgc atttaatagg ttagaatgta aattaaagtg    1200
tagcaatagc aacaaaatat ttattctact gtaaatgaca aaagaaaag aaaaattgag    1260 ccttgggacg tgcccatttt tactgtaaat tatgattccg taactgactt gtagtaagca    1320
gtgtttctgg cccctaagta ttgctgcctt gtgtatttta tttagtgtac agtactacag    1380
gtgcatactc tggtcatttt tcaagccatg tttattgta tctgttttct actttatgtg     1440
agcaaggttt gctgtccaag gtgtaaatat tcaacgggaa taaaactggc atggtaattt    1500
tttttttttt ttttttttg tttttggct cttcaaagg taatgcccca tcgatgagca      1560 ttttttaacat actccatagt cttttcctgt ggtgttaggt ctttatttt attttttcc    1620 tggggggctgg ggtgggggtt tgtcatgggg gaactgccct ttaaatttta agtgacacta    1680
cagaaaaaca caaaaggtg atgggttgtg ttatgcttgt attgaatgct gtcttgacat     1740
ctcttgcctt gtcctccggt atgttctaaa gctgtgtctg agatctggat ctgcccatca    1800
ctttggctag tgacagggct aattaatttg ctttatacat tttcttttac ttttccttttt   1860 tcctttctgg aggcatcaca tgctggtgct gtgtctttat gaatgtttta accattttca    1920
tggtggaaga atttttatatt tatgcagttg tacaatttta tttttttctg caagaaaaag    1980
tgtaatgtat gaaataaacc aaagtcactt gtttgaaaat aaatctttat tttgaacttt    2040
ataaaaagca atgcagtacc ccatagactg gtgttaaatg ttgtctacag tgcaaaatcc    2100
atgttctaac atatgtaata attgccagga gtacagtgct cttgttgatc ttgtattcag    2160
tcaggttaaa acaacggaca ataaaagaat gaacacattc aaaaaaaaaa aa            2212
```

<210> SEQ ID NO 24
<211> LENGTH: 2354
<212> TYPE: DNA
<213> ORGANISM: Artificial Sequence
<220> FEATURE:
<223> OTHER INFORMATION: TNFRSF11B (Genbank accession No: NM_002546)

<400> SEQUENCE: 24

```
tttttttccc ctgctctccc aggggccaga caccaccgcc ccaccctca cgccccacct     60 ccctggggga tcctttccgc cccagccctg aaagcgttaa ccctggagct ttctgcacac    120
```

```
ccccccgaccg ctcccgccca agcttcctaa aaaagaaagg tgcaaagttt ggtccaggat    180
agaaaaatga ctgatcaaag gcaggcgata cttcctgttg ccgggacgct atatataacg    240
tgatgagcgc acgggctgcg gagacgcacc ggagcgctcg cccagccgcc gcctccaagc    300
ccctgaggtt tccggggacc acaatgaaca acttgctgtg ctgcgcgctc gtgtttctgg    360
acatctccat taagtggacc acccaggaaa cgtttcctcc aaagtacctt cattatgacg    420
aagaaacctc tcatcagctg ttgtgtgaca aatgtcctcc tggtacctac ctaaaacaac    480
actgtacagc aaagtggaag accgtgtgcg ccccttgccc tgaccactac tacacagaca    540
gctggcacac cagtgacgag tgtctatact gcagccccgt gtgcaaggag ctgcagtacg    600
tcaagcagga gtgcaatcgc acccacaacc gcgtgtgcga atgcaaggaa gggcgctacc    660
ttgagataga gttctgcttg aaacatagga gctgccctcc tggatttgga gtggtgcaag    720
ctggaacccc agagcgaaat acagtttgca aaagatgtcc agatgggttc ttctcaaatg    780
agacgtcatc taaagcaccc tgtagaaaac acacaaattg cagtgtcttt ggtctcctgc    840
taactcagaa aggaaatgca acacgacaac atatgttcc cggaaacagt gaatcaactc    900
aaaaatgtgg aatagatgtt accctgtgtg aggaggcatt cttcaggttt gctgttccta    960
caaagtttac gcctaactgg cttagtgtct tggtagacaa tttgcctggc accaaagtaa   1020
acgcagagag tgtagagagg ataaaacggc aacacagctc acaagaacag actttccagc   1080
tgctgaagtt atggaaacat caaaacaaag accaagatat agtcaagaag atcatccaag   1140
atattgacct ctgtgaaaac agcgtgcagc ggcacattgg acatgctaac ctcaccttcg   1200
agcagcttcg tagcttgatg gaaagcttac cgggaaagaa agtgggagca gaagacattg   1260
aaaaaacaat aaaggcatgc aaacccagtg accagatcct gaagctgctc agtttgtggc   1320
gaataaaaaa tggcgaccaa gacaccttga agggcctaat gcacgcacta aagcactcaa   1380
agacgtacca ctttcccaaa actgtcactc agagtctaaa gaagaccatc aggttccttc   1440
acagcttcac aatgtacaaa ttgtatcaga agttatttt agaaatgata ggtaaccagg   1500
tccaatcagt aaaaataagc tgcttataac tggaaatggc cattgagctg tttcctcaca   1560
attggcgaga tcccatggat gagtaaactg tttctcaggc acttgaggct ttcagtgata   1620
tctttctcat taccagtgac taattttgcc acagggtact aaaagaaact atgatgtgga   1680
gaaaggacta acatctcctc caataaaccc caaatggtta atccaactgt cagatctgga   1740
tcgttatcta ctgactatat tttcccttat tactgcttgc agtaattcaa ctggaaatta   1800
aaaaaaaaaa actagactcc attgtgcctt actaaatatg ggaatgtcta acttaaatag   1860
ctttgagatt tcagctatgc tagaggcttt tattagaaag ccatattttt ttctgtaaaa   1920
gttactaata tatctgtaac actattacag tattgctatt tatattcatt cagatataag   1980
atttgtacat attatcatcc tataaagaaa cggtatgact taattttaga aagaaaatta   2040
tattctgttt attatgacaa atgaaagaga aatatatat ttttaatgga aagtttgtag   2100
cattttctcta ataggtactg ccatatttt ctgtgtggag tatttttata attttatctg   2160
tataagctgt aatatcattt tatagaaaat gcattattta gtcaattgtt taatgttgga   2220
aaacatatga aatataaatt atctgaatat tagatgctct gagaaattga atgtaccta   2280
tttaaaagat tttatggttt tataactata taaatgacat tattaaagtt ttcaaattat   2340
tttttaaaaa aaaa                                                    2354

<210> SEQ ID NO 25
<211> LENGTH: 3569
```

<212> TYPE: DNA
<213> ORGANISM: Artificial Sequence
<220> FEATURE:
<223> OTHER INFORMATION: TNFRSF10D (Genbank accession No: NM_003840)

<400> SEQUENCE: 25

| | | | | | |
|---|---|---|---|---|---|
| ggcagtgtag | ctgcgagaac | ctttgcacgc | gcacaaacta | cggggacgat | ttctgattga | 60 |
| tttttggcgc | tttcgatcca | ccctcctccc | ttctcatggg | actttgggga | caaagcgtcc | 120 |
| cgaccgcctc | gagcgctcga | gcagggcgct | atccaggagc | caggacagcg | tcggaacca | 180 |
| gaccatggct | cctggacccc | aagatcctta | agttcgtcgt | cttcatcgtc | gcggttctgc | 240 |
| tgccggtccg | ggttgactct | gccaccatcc | cccggcagga | cgaagttccc | cagcagacag | 300 |
| tggccccaca | gcaacagagg | cgcagcctca | aggaggagga | gtgtccagca | ggatctcata | 360 |
| gatcagaata | tactggagcc | tgtaaccccgt | gcacagaggg | tgtggattac | accattgctt | 420 |
| ccaacaattt | gccttcttgc | ctgctatgta | cagtttgtaa | atcaggtcaa | acaaataaaa | 480 |
| gttcctgtac | cacgaccaga | gacaccgtgt | gtcagtgtga | aaaaggaagc | ttccaggata | 540 |
| aaaactcccc | tgagatgtgc | cggacgtgta | gaacagggtg | tcccagaggg | atggtcaagg | 600 |
| tcagtaattg | tacgccccgg | agtgacatca | agtgcaaaaa | tgaatcagct | gccagttcca | 660 |
| ctgggaaaac | cccagcagcg | gaggagacag | tgaccaccat | cctggggatg | cttgcctctc | 720 |
| cctatcacta | ccttatcatc | atagtggttt | tagtcatcat | tttagctgtg | gttgtggttg | 780 |
| gcttttcatg | tcggaagaaa | ttcatttctt | acctcaaagg | catctgctca | ggtggtggag | 840 |
| gaggtcccga | acgtgtgcac | agagtccttt | tccggcggcg | ttcatgtcct | tcacgagttc | 900 |
| ctggggcgga | ggacaatgcc | cgcaacgaga | ccctgagtaa | cagatacttg | cagcccaccc | 960 |
| aggtctctga | gcaggaaatc | caaggtcagg | agctggcaga | gctaacaggt | gtgactgtag | 1020 |
| agttgccaga | ggagccacag | cgtctgctgg | aacaggcaga | agctgaaggg | tgtcagagga | 1080 |
| ggaggctgct | ggttccagtg | aatgacgctg | actccgctga | catcagcacc | ttgctggatg | 1140 |
| cctcggcaac | actggaagaa | ggacatgcaa | aggaaacaat | tcaggaccaa | ctggtgggct | 1200 |
| ccgaaaagct | cttttatgaa | gaagatgagg | caggctctgc | tacgtcctgc | ctgtgaaaga | 1260 |
| atctcttcag | gaaaccagag | cttccctcat | ttacctttc | tcctacaaag | ggaagcagcc | 1320 |
| tggaagaaac | agtccagtac | ttgacccatg | ccccaacaaa | ctctactatc | caatatgggg | 1380 |
| cagcttacca | atggtcctag | aactttgtta | acgcacttgg | agtaattttt | atgaaatact | 1440 |
| gcgtgtgata | agcaaacggg | agaaatttat | atcagattct | tggctgcata | gttatacgat | 1500 |
| tgtgtattaa | gggtcgtttt | aggccacatg | cggtggctca | tgcctgtaat | cccagcactt | 1560 |
| tgataggctg | aggcaggtgg | attgcttgag | ctcgggagtt | tgagaccagc | ctcatcaaca | 1620 |
| cagtgaaact | ccatctcaat | ttaaaaagaa | aaaagtggt | tttaggatgt | cattctttgc | 1680 |
| agttcttcat | catgagacaa | gtctttttt | ctgcttctta | tattgcaagc | tccatctcta | 1740 |
| ctggtgtgtg | catttaatga | catctaacta | cagatgccgc | acagccacaa | tgctttgcct | 1800 |
| tatagttttt | taactttaga | acgggattat | cttgttatta | cctgtatttt | cagtttcgga | 1860 |
| tattttgac | ttaatgatga | gattatcaag | acgtagccct | atgctaagtc | atgagcatat | 1920 |
| ggacttacga | gggttcgact | tagagttttg | agctttaaga | taggattatt | ggggcttacc | 1980 |
| cccaccttaa | ttagagaaac | atttatattg | cttactactg | taggctgtac | atctctttc | 2040 |
| cgatttttgt | ataatgatgt | aaacatggaa | aaacttaggg | aaatgcactt | attaggctgt | 2100 |
| ttacatgggt | tgcctggata | caaatcagca | gtcaaaaatg | actaaaaata | taactagtga | 2160 |

-continued

| | |
|---|---|
| cggagggaga aatcctccct ctgtgggagg cacttactgc attccagttc tccctcctgc | 2220 |
| gccctgagac tggaccaggg tttgatggct ggcagcttct caaggggcag cttgtcttac | 2280 |
| ttgttaattt tagaggtata tagccatatt tatttataaa taaatattta tttatttatt | 2340 |
| tataagtaga tgtttacata tgcccaggat tttgaagagc ctggtatctt tgggaagcca | 2400 |
| tgtgtctggt ttgtcgtgct gggacagtca tgggactgca tcttccgact tgtccacagc | 2460 |
| agatgaggac agtgagaatt aagttagatc cgagactgcg aagagcttct ctttcaagcg | 2520 |
| ccattacagt tgaacgttag tgaatcttga gcctcatttg ggctcagggc agagcaggtg | 2580 |
| tttatctgcc ccggcatctg ccatggcatc aagagggaag agtggacggt gcttgggaat | 2640 |
| ggtgtgaaat ggttgccgac tcaggcatgg atgggcccct ctcgcttctg gtggtctgtg | 2700 |
| aactgagtcc ctgggatgcc ttttagggca gagattcctg agctgcgttt tagggtacag | 2760 |
| attccctgtt tgaggagctt ggcccctctg taagcatctg actcatctca gagatatcaa | 2820 |
| ttcttaaaca ctgtgacaac aggatctaaa atggctgaca catttgtcct tgtgtcacgt | 2880 |
| tccattattt tatttaaaaa cctcagtaat cgttttagct tctttccagc aaactcttct | 2940 |
| ccacagtagc ccagtcgtgg taggataaat tacggatata gtcattctag gggtttcagt | 3000 |
| cttttccatc tcaaggcatt gtgtgttttg ttccgggact ggtttggctg ggacaaagtt | 3060 |
| agaactgcct gaagttcgca cattcagatt gttgtgtcca tggagtttta ggaggggatg | 3120 |
| gcctttccgg tcttcgcact tccatcctct cccacttcca tctggcgtcc cacaccttgt | 3180 |
| cccctgcact tctggatgac acagggtgct gctgcctcct agtctttgcc tttgctgggc | 3240 |
| cttctgtgca ggagacttgg tctcaaagct cagagagagc cagtccggtc ccagctcctt | 3300 |
| tgtcccttcc tcagaggcct tccttgaaga tgcatctaga ctaccagcct tatcagtgtt | 3360 |
| taagcttatt cctttaacat aagcttcctg acaacatgaa attgttgggg ttttttggcg | 3420 |
| ttggttgatt tgtttaggtt ttgctttata cccgggccaa atagcacata acacctggtt | 3480 |
| atatatgaaa tactcatatg tttatgacca aaataaatat gaaacctcat attaaaaaaa | 3540 |
| aaaaaaaaaa aaaaaaaaa aaaaaaaa | 3569 |

<210> SEQ ID NO 26
<211> LENGTH: 862
<212> TYPE: DNA
<213> ORGANISM: Artificial Sequence
<220> FEATURE:
<223> OTHER INFORMATION: BEX1 (Genbank accession No: NM_018476)

<400> SEQUENCE: 26

| | |
|---|---|
| cttggcggtg acgcacggcc ctcacgtgac cgggagctgc agagctacgc agccttcggt | 60 |
| gcagtcgtca ctcgtgtctc gctaccagct ccccgctgcc ctgcgctcgg cgggctggca | 120 |
| tccggcccgg gggaaagcgg accagccctt ctgcaggtct gcggggccaa gtgtcccggc | 180 |
| ggcgcacctc gtggcgagaa tcgggagaag gaggagacta caaggatagg cccaggagta | 240 |
| atggagtcca aagagaaacg agcagtaaac agtctcagca tggaaaatgc caaccaagaa | 300 |
| aatgaagaaa aggagcaagt tgctaataaa ggggagccct tggccctccc tttggatgct | 360 |
| ggtgaatact gtgtgcctag aggaaatcgt aggcggttcc gcgttaggca gcccatcctg | 420 |
| cagtatagat gggatatgat gcataggctt ggagaaccac aggcaaggat gagagaagag | 480 |
| aatatgaaaa ggattgggga ggaggtgaga cagctgatgg aaaagctgag ggaaaagcag | 540 |
| ttgagtcata gtctgcgggc agtcagcact gaccccctc accatgacca tcatgatgag | 600 |
| ttttgcctta tgccctgaat cctgatggtt tccctaaagt tattacggaa acagacccct | 660 |

```
gctttcgaat ttacatgttc atgatgtgcc cttgttgtaa acctttacct gtcacttgtt      720
tacgtgggtc tcctattacc agcttctaat tgaatattgt gttttgaac cagtctgtaa       780 gatttttgtt agcagaagaa ttttacctat tgcatggaaa gatgctcatt atagtgaagt     840
taataaagca cctttaaaaa gc                                              862

<210> SEQ ID NO 27
<211> LENGTH: 1718
<212> TYPE: DNA
<213> ORGANISM: Artificial Sequence
<220> FEATURE:
<223> OTHER INFORMATION: IL8 (Genbank accession No: NM_000584)

<400> SEQUENCE: 27
gagggtgcat aagttctcta gtagggtgat gatataaaaa gccaccggag cactccataa      60
ggcacaaact ttcagagaca gcagagcaca caagcttcta ggacaagagc caggaagaaa     120
ccaccggaag gaaccatctc actgtgtgta aacatgactt ccaagctggc cgtggctctc     180
ttggcagcct tcctgatttc tgcagctctg tgtgaaggtg cagttttgcc aaggagtgct     240
aaagaactta gatgtcagtg cataaagaca tactccaaac ctttccaccc caaatttatc     300
aaagaactga gagtgattga gagtggacca cactgcgcca acacagaaat tattgtaaag     360
ctttctgatg aagagagagct ctgtctggac cccaaggaaa actgggtgca gaggggttgtg    420 gagaagtttt tgaagagggc tgagaattca taaaaaaatt cattctctgt ggtatccaag     480
aatcagtgaa gatgccagtg aaacttcaag caaatctact tcaacacttc atgtattgtg     540
tgggtctgtt gtagggttgc cagatgcaat acaagattcc tggttaaatt tgaatttcag     600
taaacaatga atagtttttc attgtaccat gaaatatcca gaacatactt atatgtaaag     660
tattatttat ttgaatctac aaaaaacaac aaataatttt taaatataag gattttccta     720
gatattgcac gggagaatat acaaatagca aaattgaggc caagggccaa gagaatatcc     780
gaactttaat ttcaggaatt gaatgggttt gctagaatgt gatatttgaa gcatcacata     840
aaaatgatgg gacaataaat tttgccataa agtcaaattt agctggaaat cctggatttt     900
tttctgttaa atctggcaac cctagtctgc tagccaggat ccacaagtcc ttgttccact     960
gtgccttggt ttctccttta tttctaagtg gaaaaagtat tagccaccat cttacctcac    1020
agtgatgttg tgaggacatg tggaagcact ttaagttttt tcatcataac ataaattatt    1080
ttcaagtgta acttattaac ctatttatta tttatgtatt tatttaagca tcaaatattt    1140
gtgcaagaat ttggaaaaat agaagatgaa tcattgattg aatagttata agatgttat     1200 agtaaattta ttttattta gatattaaat gatgtttat tagataaatt tcaatcaggg      1260
tttttagatt aaacaaacaa acaattgggt acccagttaa attttcattt cagataaaca    1320
acaaataatt ttttagtata agtacattat tgtttatctg aattttaat tgaactaaca     1380 atcctagttt gatactccca gtcttgtcat tgccagctgt gttggtagtg ctgtgttgaa    1440
ttacggaata atgagttaga actattaaaa cagccaaaac tccacagtca atattagtaa    1500
tttcttgctg gttgaaactt gtttattatg tacaaataga ttcttataat attatttaaa    1560
tgactgcatt tttaaataca aggctttata ttttaaactt taagatgttt ttatgtgctc    1620
tccaaatttt ttttactgtt tctgattgta tggaaatata aagtaaaata tgaaacattt    1680
aaaatataat ttgttgtcaa agtaaaaaaa aaaaaaaa                            1718

<210> SEQ ID NO 28
```

<211> LENGTH: 1677
<212> TYPE: DNA
<213> ORGANISM: Artificial Sequence
<220> FEATURE:
<223> OTHER INFORMATION: CXCL6 (Genbank accession No: NM_002993)

<400> SEQUENCE: 28

| | | | | | |
|---|---|---|---|---|---|
| accccttctt | tccacactgc | ccctgagtt | cagggaattt | ccccagcatc | ccaaagcttg | 60 |
| agtttcctgc | cagtcgggag | ggatgaatgc | agataaaggg | agtgcagaag | gcacgaggaa | 120 |
| accaaagtgc | tctgtatcct | ccagtctccg | cgcctccacc | cagctcagga | acccgcgaac | 180 |
| cctctcttga | ccactatgag | cctcccgtcc | agccgcgcgg | ccgtgtccc | gggtccttcg | 240 |
| ggctccttgt | gcgcgctgct | cgcgctgctg | ctcctgctga | cgccgccggg | gcccctcgcc | 300 |
| agcgctggtc | ctgtctctgc | tgtgctgaca | gagctgcgtt | gcacttgttt | acgcgttacg | 360 |
| ctgagagtaa | accccaaaac | gattggtaaa | ctgcaggtgt | tccccgcagg | cccgcagtgc | 420 |
| tccaaggtgg | aagtggtagc | ctccctgaag | aacgggaagc | aagtttgtct | ggacccggaa | 480 |
| gcccctttc | taaagaaagt | catccagaaa | attttggaca | gtggaaacaa | gaaaaactga | 540 |
| gtaacaaaaa | agaccatgca | tcataaaatt | gcccagtctt | cagcggagca | gttttctgga | 600 |
| gatccctgga | cccagtaaga | ataagaagga | agggttggtt | ttttccatt | tctacatgg | 660 |
| attccctact | tgaagagtg | tggggaaag | cctacgcttc | tccctgaagt | ttacagctca | 720 |
| gctaatgaag | tactaatata | gtatttccac | tatttactgt | tattttacct | gataagttat | 780 |
| tgaaccctttt | ggcaattgac | catattgtga | gcaaagaatc | actggttatt | agtctttcaa | 840 |
| tgaatattga | attgaagata | actattgtat | ttctatcata | cattccttaa | agtcttaccg | 900 |
| aaaaggctgt | ggatttcgta | tggaaataat | gttttattag | tgtgctgttg | agggaggtat | 960 |
| cctgttgttc | ttactcactc | ttctcataaa | ataggaaata | ttttagttct | gtttcttggg | 1020 |
| gaatatgtta | ctctttaccc | taggatgcta | tttaagttgt | actgtattag | aacactgggt | 1080 |
| gtgtcatacc | gttatctgtg | cagaatatat | ttccttattc | agaatttcta | aaaatttaag | 1140 |
| ttctgtaagg | gctaatatat | tctcttccta | tggttttaga | cgtttgatgt | cttcttagta | 1200 |
| tggcataatg | tcatgattta | ctcattaaac | tttgattttg | tatgctattt | tttcactata | 1260 |
| ggatgactat | aattctggtc | actaaatata | cactttagat | agatgaagaa | gcccaaaaac | 1320 |
| agataaattc | ctgattgcta | atttacatag | aaatgtattc | tcttggtttt | ttaaataaaa | 1380 |
| gcaaaattaa | caatgatctg | tgctctgaaa | gttttgaaaa | tatatttgaa | caatttgaat | 1440 |
| ataaattcat | catttagtcc | tcaaaatata | tatagcattg | ctaagatttt | cagatatcta | 1500 |
| ttgtggatct | tttaaaggtt | ttgaccattt | tgttatgagg | aattatacat | gtatcacatt | 1560 |
| cactatatta | aaattgcact | tttattttt | cctgtgtgtc | atgttggttt | ttggtacttg | 1620 |
| tattgtcatt | tggagaaaca | ataaaagatt | tctaaaccaa | aaaaaaaaa | aaaaaaa | 1677 |

<210> SEQ ID NO 29
<211> LENGTH: 3072
<212> TYPE: DNA
<213> ORGANISM: Artificial Sequence
<220> FEATURE:
<223> OTHER INFORMATION: CD105 (NM_001114753)

<400> SEQUENCE: 29

| | | | | | |
|---|---|---|---|---|---|
| ctctacccgg | ttggcaggcg | gcctggccca | gcccttctc | taaggaagcg | catttcctgc | 60 |
| ctccctgggc | cggccgggct | ggatgagccg | ggagctcct | gctgccggtc | ataccacagc | 120 |
| cttcatctgc | gccctggggc | caggactgct | gctgtcactg | ccatccattg | gagcccagca | 180 |

```
cccctcccc gcccatcctt cggacagcaa ctccagccca gccccgcgtc cctgtgtcca    240
cttctcctga cccctcggcc gccacccag aaggctggag cagggacgcc gtcgctccgg    300
ccgcctgctc ccctcgggtc cccgtgcgag cccacgccgg ccccggtgcc cgcccgcagc    360
cctgccactg gacacaggat aaggcccagc gcacaggccc ccacgtggac agcatggacc    420
gcggcacgct ccctctggct gttgccctgc tgctggccag ctgcagcctc agccccacaa    480
gtcttgcaga aacagtccat gtgaccttc agcctgtggg cccgagagg ggcgaggtga    540 catataccac tagccaggtc tcgaagggct gcgtggctca ggcccccaat gccatccttg    600
aagtccatgt cctcttcctg gagttcccaa cgggcccgtc acagtggag ctgactctcc    660 aggcatccaa gcaaaatggc acctggcccc gagaggtgct tctggtcctc agtgtaaaca    720
gcagtgtctt cctgcatctc caggccctgg gaatcccact gcacttggcc tacaattcca    780
gcctggtcac cttccaagag cccccggggg tcaacaccac agagctgcca tccttcccca    840
agacccagat ccttgagtgg gcagctgaga ggggccccat cacctctgct gctgagctga    900
atgaccccca gagcatcctc ctccgactgg gccaagccca ggggtcactg tccttctgca    960
tgctggaagc cagccaggac atgggccgca cgctcgagtg gcggccgcgt actccagcct   1020
tggtccgggg ctgccacttg aaggcgtgg ccggccacaa ggaggcgcac atcctgaggg   1080
tcctgccggg ccactcggcc gggccccgga cggtgacggt gaaggtggaa ctgagctgcg   1140
cacccgggga tctcgatgcc gtcctcatcc tgcagggtcc ccctacgtg tcctggctca   1200 tcgacgccaa ccacaacatg cagatctgga ccactggaga atactccttc aagatctttc   1260
cagagaaaaa cattcgtggc ttcaagctcc cagacacacc tcaaggcctc ctgggggagg   1320
cccggatgct caatgccagc attgtggcat ccttcgtgga gctaccgctg ccagcattg    1380 tctcacttca tgcctccagc tgcggtggta ggctgcagac ctcacccgca ccgatccaga   1440
ccactcctcc caaggacact tgtagcccgg agctgctcat gtccttgatc cagacaaagt   1500
gtgccgacga cgccatgacc ctggtactaa agaaagagct tgttgcgcat ttgaagtgca   1560
ccatcacggg cctgaccttc tgggacccca gctgtgaggc agaggacagg ggtgacaagt   1620 tgtcttgcg cagtgcttac tccagctgtg gcatgcaggt gtcagcaagt atgatcagca   1680
atgaggcggt ggtcaatatc ctgtcgagct catcaccaca gcggaaaaag gtgcactgcc   1740
tcaacatgga cagcctctct ttccagctgg gcctctacct cagcccacac ttcctccagg   1800
cctccaacac catcgagccg gggcagcaga gctttgtgca ggtcagagtg tccccatccg   1860
tctccgagtt cctgctccag ttagacagct gccacctgga cttggggcct gagggaggca   1920
ccgtggaact catccagggc cgggcggcca agggcaactg tgtgagcctg ctgtccccaa   1980
gccccgaggg tgacccgcgc ttcagcttcc tcctccactt ctacacagta cccatacca    2040 aaaccggcac cctcagctgc acggtagccc tgcgtcccaa gaccgggtct caagaccagg   2100
aagtccatag gactgtcttc atgcgcttga acatcatcag ccctgacctg tctggttgca   2160
caagcaaagg cctcgtcctg cccgccgtgc tgggcatcac ctttggtgcc ttcctcatcg   2220 ggcctgct cactgctgca ctctggtaca tctactcgca cacgcgttcc cccagcaagc    2280
gggagcccgt ggtggcggtg gctgccccgg cctcctcgga gagcagcagc accaaccaca   2340
gcatcgggag cacccagagc acccctgct ccaccagcag catggcatag cccggcccc    2400 ccgcgctcgc ccagcaggag agactgagca gccgccagct gggagcactg gtgtgaactc   2460
accctgggag ccagtcctcc actcgaccca gaatggagcc tgctctccgc gcctacccctt   2520
```

| | | |
|---|---|---|
| cccgcctccc tctcagaggc ctgctgccag tgcagccact ggcttggaac accttggggt | 2580 | |
| ccctccaccc cacagaacct tcaacccagt gggtctggga tatggctgcc caggagacag | 2640 | |
| accacttgcc acgctgttgt aaaaacccaa gtccctgtca tttgaacctg gatccagcac | 2700 | |
| tggtgaactg agctgggcag aaggggagaa cttgaaacag attcaggcca gcccagccag | 2760 | |
| gccaacagca cctccccgct gggaagagaa gagggcccag cccagagcca cctggatcta | 2820 | |
| tccctgcggc ctccacacct gaacttgcct aactaactgg caggggagac aggagcctag | 2880 | |
| cggagcccag cctgggagcc cagagggtgg caagaacagt gggcgttggg agcctagctc | 2940 | |
| ctgccacatg gagccccctc tgccggtcgg cagccagca gagggggagt agccaagctg | 3000 | |
| cttgtcctgg gcctgcccct gtgtattcac caccaataaa tcagaccatg aaaccagtga | 3060 | |
| aaaaaaaaaa aa | 3072 | |

<210> SEQ ID NO 30
<211> LENGTH: 4086
<212> TYPE: DNA
<213> ORGANISM: Artificial Sequence
<220> FEATURE:
<223> OTHER INFORMATION: CD73 (NM_002526)

<400> SEQUENCE: 30

| | | |
|---|---|---|
| actcctcctc tctgccctc agctcgctca tctttcttcc cgccccctct cttttccttc | 60 | |
| tttggttctt tgaagtgatg agctagcgca accacaaacc atacattcct tttgtagaaa | 120 | |
| aacccgtgcc tcgaatgagg cgagactcag agaggaccca ggcgcggggc ggaccctcc | 180 | |
| aattccttcc tcgcgccccc gaaagagcgg cgcaccagca gccgaactgc cggcgcccag | 240 | |
| gctccctggt ccggccggga tgcggccggt acccgctccc cgccgggaac aacctctcca | 300 | |
| ctcttcctgc agggagctgg tgccagccga cagccgcgcc agggccgctc cgggtaccag | 360 | |
| ggtcggatcg ggtgacgtcg cgaacttgcg cctggccgcc aagccggcct ccaggctgaa | 420 | |
| gaaggacccg cccggccttt gacccgggcc ccgcccctcc agccggggca ccgagccccg | 480 | |
| gccctagctg ctcgccccta ctcgccggca ctcgcccggc tcgcccgctt cgcacccag | 540 | |
| ttcacgcgcc acagctatgt gtccccgagc cgcgcgggcg cccgcgacgc tactcctcgc | 600 | |
| cctgggcgcg gtgctgtggc ctgcggctgg cgcctgggag cttacgattt tgcacaccaa | 660 | |
| cgacgtgcac agccggctgg agcagaccag cgaggactcc agcaagtgcg tcaacgccag | 720 | |
| ccgctgcatg ggtggcgtgg ctcggctctt caccaaggtt cagcagatcc gccgcgccga | 780 | |
| acccaacgtg ctgctgctgg acgccggcga ccagtaccag ggcactatct ggttcaccgt | 840 | |
| gtacaagggc gccgaggtgg cgcacttcat gaacgccctg cgctacgatg ccatggcact | 900 | |
| gggaaatcat gaatttgata atggtgtgga aggactgatc gagccactcc tcaaagaggc | 960 | |
| caaatttcca attctgagtg caaacattaa agcaaagggg ccactagcat ctcaaatatc | 1020 | |
| aggactttat ttgccatata agttcttcc tgttggtgat gaagttgtgg gaatcgttgg | 1080 | |
| atacacttcc aaagaaaccc ctttttctctc aaatccaggg acaaatttag tgtttgaaga | 1140 | |
| tgaaatcact gcattacaac ctgaagtaga taagttaaaa actctaaatg tgaacaaaat | 1200 | |
| tattgcactg ggacattcgg gttttgaaat ggataaactc atcgctcaga aagtgagggg | 1260 | |
| tgtggacgtc gtggtgggag acactccaa cacatttctt tacacaggca atccaccttc | 1320 | |
| caaagaggtg cctgctggga gtacccatt catagtcact tctgatgatg gcgcgaaggt | 1380 | |
| tcctgtagtc caggcctatg cttttggcaa ataccctaggc tatctgaaga tcgagtttga | 1440 | |
| tgaaagagga aacgtcatct cttcccatgg aaatccatt cttctaaaca gcagcattcc | 1500 | |

```
tgaagatcca agcataaaag cagacattaa caaatggagg ataaaattgg ataattattc    1560
tacccaggaa ttagggaaaa caattgtcta tctggatggc tcctctcaat catgccgctt    1620
tagagaatgc aacatgggca acctgatttg tgatgcaatg attaacaaca acctgagaca    1680 cacgcgatgaa atgttctgga accacgtatc catgtgcatt ttaaatggag gtggtatccg    1740
gtcgcccatt gatgaacgca acaatggcac aattacctgg gagaacctgg ctgctgtatt    1800 gcccttttgga ggcacatttg acctagtcca gttaaaaggt tccaccctga agaaggcctt    1860
tgagcatagc gtgcaccgct acggccagtc cactggagag ttcctgcagg tgggcggaat    1920
ccatgtggtg tatgatcttt cccgaaaacc tggagacaga gtagtcaaat tagatgttct    1980
ttgcaccaag tgtcgagtgc ccagttatga ccctctcaaa atggacgagg tatataaggt    2040
gatcctccca aacttcctgg ccaatggtgg agatgggttc cagatgataa aagatgaatt    2100
attaagacat gactctggtg accaagatat caacgtggtt tctacatata tctccaaaat    2160
gaaagtaatt tatccagcag ttgaaggtcg gatcaagttt tccacaggaa gtcactgcca    2220
tggaagcttt tctttaatat ttcttttcact ttgggcagtg atctttgttt tataccaata    2280
gccaaaaatt ctccttgcct ttaatgtgtg aaactgcatt ttttcaagtg agattcaaat    2340 ctgccttttta ggacctggct ttgtgacagc aaaaaccatc tttacaggct cctagaagct    2400
gaaggttaga gcattataaa atgaagagac agacatgatt actcagggtc agcaacctag    2460
tgagttagaa aaaaaattaa catagggccc tataaggaga aagccaacta tgttaagttt    2520
acgtgtccaa attttaatga aattttacta acaattttaa accatatttt tcttcttcat    2580
atccatttct aatccatcaa acagcttatg tttacataaa attttatcat tcacaaggaa    2640
gttttaagca cactgtctca tttgatatcc acaacttatt tttggtagga agagagatg    2700 ttttttcccac ctgtcagatg aaaaaactga agctcaaaaa gggttgactt gaccatacag    2760
ctaatgctga cagatccaag acctagacct aggtcttttg aactcaagtc cagcattctc    2820
aactatatca agttactgtt cagaatactt aatatctcct ctcttcataa ttatcaatag    2880
ccccaagctc atggatgaca aatctctgct ttatttcttg tctctatttt ttcactttat    2940
agctcctgtt ataatagcaa gtttaatggt ataaacacag gataccatcc tctcttgcaa    3000
cacccatgtg cctttgatga gtcaggtagc aagctgtagt agataatgag aaaggccaga    3060
ggctgcaaaa gacagtcaaa ggacacgaga gaaggaagg ggaagaacag gactccagga    3120
ctgttttata ttatagaaaa gcaagagcta aagagcattt acacatgtta aacagatact    3180
tgttaagcat agtgcctgac acacggcatt agctgttatt ttatgagatt ccatcagctc    3240
tgcctctgtc ctctttcttc taacatgaag gtatcatgag aagagaacct tctaacataa    3300
gctgtaattc taaacctgca cttgtccctc tccagcaaga ggctagcact gaattcattc    3360
tactcatact acacacccag ttatggaatg tccagagttc tcgaagaaaa taaatgactt    3420
taggaagagg tatacatttt ttaagtcgct ctgcctccaa atctgaacag tcactgtaaa    3480
tcattcttaa gcccagatat gagaacttct gctggaaagt gggaccctct gagtgggtgg    3540
tcagaaaata cccatgctga tgaaatgacc tatgcccaaa gaacaaatac ttaacgtggg    3600
agtggaacca catgagcctg ctcagctctg cataagtaat tcaagaaatg ggaggcttca    3660
ccttaaaaac agtgtgcaaa tggcagctag aggttttgat aggaagtatg tttgtttctt    3720 agtgttttaca aatattaagt actcttgata caaaatatac ttttaaactt cataaccttt    3780
ttataaaagt tgttgcagca aaataatagc ctcggttcta tgcatatatg gattagctat    3840
```

-continued

| | |
|---|---|
| aaaaaatgtc aataagattg tacaaggaaa attagagaaa gtcacattta gggtttattt | 3900 |
| tttacacttg gccagtaaaa tagggtaaat cctattagaa ttttttaaag aactttttt | 3960 |
| aagtttccta atctgtgtg tgtattgtga agtggtataa gaaatgactt tgaaccactt | 4020 |
| tgcaattgta gattcccaac aataaaattg aagataagct ctttggtcaa aaaaaaaaaa | 4080 |
| aaaaaa | 4086 |

<210> SEQ ID NO 31
<211> LENGTH: 2413
<212> TYPE: DNA
<213> ORGANISM: Artificial Sequence
<220> FEATURE:
<223> OTHER INFORMATION: CD90 (NM_006288)

<400> SEQUENCE: 31

| | |
|---|---|
| tttggttttc ccacagactc ctgaagaata ggtcagaaga aagggttaaa gccttaaaag | 60 |
| gggaacaacc attgcgggc tcagggagga ggataatgtt ctttgggctg ccgcaccctg | 120 |
| atccccgggg tcccgaaccc tcccgtccct ggccaggcct gccagccaca gggtgagggc | 180 |
| cccctccgc cgcaacctgc cactctcaca ccaatgcggg accgccttct cttccttccc | 240 |
| cacccccac cccaccctgc cgtccttct cccccaatct ccgcctctga ttggctgagc | 300 |
| ccccggctcc ccgctccccc tctcctccat ccccggtgaa aactgcgggc tccgagctgg | 360 |
| gtgcagcaac cggaggcggc ggcgcgtctg gaggaggctg cagcagcgga agaccccagt | 420 |
| ccagatccag gactgagatc ccagaaccat gaacctggcc atcagcatcg ctctcctgct | 480 |
| aacagtcttg caggtctccc gagggcagaa ggtgaccagc ctaacggcct gcctagtgga | 540 |
| ccagagcctt cgtctggact gccgccatga aataccagc agttcaccca tccagtacga | 600 |
| gttcagcctg acccgtgaga caaagaagca cgtgctcttt ggcactgtgg gggtgcctga | 660 |
| gcacacatac cgctcccgaa ccaacttcac cagcaaatac aacatgaagg tcctctactt | 720 |
| atccgccttc actagcaagg acgagggcac ctacacgtgt gcactccacc actctggcca | 780 |
| ttccccaccc atctcctccc agaacgtcac agtgctcaga acaaactgg tcaagtgtga | 840 |
| gggcatcagc ctgctggctc agaacacctc gtggctgctg ctgctcctgc tctccctctc | 900 |
| cctcctccag gccacggatt tcatgtccct gtgactggtg gggcccatgg aggagacagg | 960 |
| aagcctcaag ttccagtgca gagatcctac ttctctgagt cagctgaccc cctcccccca | 1020 |
| atccctcaaa ccttgaggag aagtggggac cccacccctc atcaggagtt ccagtgctgc | 1080 |
| atgcgattat ctaccacgt ccacgcggcc acctcaccct ctccgcacac ctctggctgt | 1140 |
| cttttttgtac tttttgttcc agagctgctt ctgtctggtt tatttaggtt ttatccttcc | 1200 |
| ttttctttga gagttcgtga agagggaagc caggattggg gacctgatgg agagtgagag | 1260 |
| catgtgaggg gtagtgggat ggtggggtac cagccactgg aggggtcatc cttgcccatc | 1320 |
| gggaccagaa acctgggaga gacttggatg aggagtggtt gggctgtgcc tgggcctagc | 1380 |
| acggacatgg tctgtcctga cagcactcct cggcaggcat ggctggtgcc tgaagacccc | 1440 |
| agatgtgagg gcaccaccaa gaatttgtgg cctaccttgt gagggagaga actgagcatc | 1500 |
| tccagcattc tcagccacaa ccaaaaaaaa ataaaagggg cagccctcct taccactgtg | 1560 |
| gaagtccctc agaggccttg ggcatgacc cagtgaagat gcaggtttga ccaggaaagc | 1620 |
| agcgctagtg gagggttgga gaaggaggta aaggatgagg gttcatcatc cctccctgcc | 1680 |
| taaggaagct aaaagcatgg ccctgctgcc cctccctgcc tccacccaca gtggagaggg | 1740 |
| ctacaaagga ggacaagacc ctctcaggct gtcccaagct cccaagagct tccagagctc | 1800 |

| | | |
|---|---|---|
| tgacccacag cctccaagtc aggtggggtg gagtcccaga gctgcacagg gtttggccca | 1860 | |
| agtttctaag ggaggcactt cctccctcg cccatcagtg ccagcccctg ctggctggtg | 1920 | |
| cctgagcccc tcagacagcc ccctgccccg caggcctgcc ttctcaggga cttctgcggg | 1980 | |
| gcctgaggca agccatggag tgagacccag gagccggaca cttctcagga aatggctttt | 2040 | |
| cccaaccccc agcccccacc cggtggttct tcctgttctg tgactgtgta tagtgccacc | 2100 | |
| acagcttatg gcatctcatt gaggacaaag aaaactgcac aataaaacca agcctctgga | 2160 | |
| atctgtcctc gtgtccacct ggccttcgct cctccagcag tgcctgcctg ccccgcttc | 2220 | |
| gctgggtct ccacgggtga ggctggggaa cgccacctct tcctcttccc tgacttctcc | 2280 | |
| ccaaccactt agtagcaacg ctaccccagg ggctaatgac tgcacactgg gcttcttttc | 2340 | |
| agaatgaccc taacgagaca catttgccca aataaacgaa catcccatgt ctgctgaaaa | 2400 | |
| aaaaaaaaaa aaa | 2413 | |

<210> SEQ ID NO 32
<211> LENGTH: 1818
<212> TYPE: DNA
<213> ORGANISM: Artificial Sequence
<220> FEATURE:
<223> OTHER INFORMATION: CD90 (NM_033209)

<400> SEQUENCE: 32

| | | |
|---|---|---|
| caaccggagg cggcggcgcg tctggaggag gctgcagcag cggaagaccc cagtccagat | 60 | |
| ccaggactga gatcccagaa ccatgaacct ggccatcagc atcgctctcc tgctaacagt | 120 | |
| cttgcaggtc tcccgagggc agaaggtgac cagcctaacg gcctgcctag tggaccagag | 180 | |
| ccttcgtctg gactgccgcc atgagaatac cagcagttca cccatccagt acgagttcag | 240 | |
| cctgacccgt gagacaaaga gcacgtgct ctttggcact gtggggtgc ctgagcacac | 300 | |
| ataccgctcc cgaaccaact tcaccagcaa atacaacatg aaggtcctct acttatccgc | 360 | |
| cttcactagc aaggacgagg gcacctacac gtgtgcactc caccactctg gccattcccc | 420 | |
| acccatctcc tcccagaacg tcacagtgct cagagacaaa ctggtcaagt gtgagggcat | 480 | |
| cagcctgctg gctcagaaca cctcgtggct gctgctgctc ctgctctccc tctccctcct | 540 | |
| ccaggccacg gatttcatgt ccctgtgact ggtggggccc atggaggaga caggaagcct | 600 | |
| caagttccag tgcagagatc ctacttctct gagtcagctg accccctccc cgcaatccct | 660 | |
| caaaccttga ggagaagtgg ggaccccacc cctcatcagg agttccagtg ctgcatgcga | 720 | |
| ttatctaccc acgtccacgc ggccaccttca ccctctccgc acacctctgg ctgtcttttt | 780 | |
| gtacttttg ttccagagct gcttctgtct ggtttattta ggttttatcc ttcctttct | 840 | |
| ttgagagttc gtgaagaggg aagccaggat tggggacctg atggagagtg agagcatgtg | 900 | |
| aggggtagtg ggatggtggg gtaccagcca ctggaggggt catccttgcc catcgggacc | 960 | |
| agaaacctgg gagagacttg gatgaggagt ggttgggctg tgcctgggcc tagcacggac | 1020 | |
| atggtctgtc ctgacagcac tcctcggcag gcatggctgg tgcctgaaga ccccagatgt | 1080 | |
| gagggcacca ccaagaattt gtggcctacc ttgtgaggga gagaactgag catctccagc | 1140 | |
| attctcagcc acaaccaaaa aaaaataaaa agggcagccc tccttaccac tgtgaagtc | 1200 | |
| cctcagaggc cttggggcat gacccagtga agatgcaggt ttgaccagga aagcagcgct | 1260 | |
| agtggagggt tggagaagga ggtaaaggat gagggttcat catccctccc tgcctaagga | 1320 | |
| agctaaaagc atggccctgc tgccctccc tgcctccacc cacagtggag agggctacaa | 1380 | |

| aggaggacaa gaccctctca ggctgtccca agctcccaag agcttccaga gctctgaccc | 1440 |
| acagcctcca agtcaggtgg ggtggagtcc cagagctgca cagggtttgg cccaagtttc | 1500 |
| taagggaggc acttcctccc ctcgcccatc agtgccagcc cctgctggct ggtgcctgag | 1560 |
| cccctcagac agcccctgc cccgcaggcc tgccttctca gggacttctg cggggcctga | 1620 |
| ggcaagccat ggagtgagac ccaggagccg acacttctc aggaaatggc ttttcccaac | 1680 |
| ccccagcccc cacccggtgg ttcttcctgt tctgtgactg tgtatagtgc caccacaagc | 1740 |
| ttatggcatc tcattgagga caaagaaaac tgcacaataa aaccaaagcc tctggaatcc | 1800 |
| gaaaaaaaaa aaaaaaaa | 1818 |

<210> SEQ ID NO 33
<211> LENGTH: 5429
<212> TYPE: DNA
<213> ORGANISM: Artificial Sequence
<220> FEATURE:
<223> OTHER INFORMATION: CD45 (NM_002838)

<400> SEQUENCE: 33

| agaacaactt ttttgacttc ctgcaaagag gacccttaca gtattttgg agaagttagt | 60 |
| aaaaccgaat ctgacatcat cacctagcag ttcatgcagc tagcaagtgg tttgttctta | 120 |
| gggtaacaga ggaggaaatt gttcctcgtc tgataagaca acagtggaga aaggacgcat | 180 |
| gctgtttctt agggacacgg ctgacttcca gatatgacca tgtatttgtg cttaaactc | 240 |
| ttggcatttg gctttgcctt tctggacaca gaagtatttg tgacagggca agcccaaca | 300 |
| ccttccccca ctggattgac tacagcaaag atgcccagtg ttccactttc aagtgacccc | 360 |
| ttacctactc acaccactgc attctcaccc gcaagcacct ttgaaagaga aaatgacttc | 420 |
| tcagagacca caacttctct tagtccagac aatacttcca cccaagtatc cccggactct | 480 |
| ttggataatg ctagtgcttt taataccaca ggtgtttcat cagtacagac gcctcacctt | 540 |
| cccacgcacg cagactcgca gacgccctct gctggaactg acacgcagac attcagcggc | 600 |
| tccgccgcca atgcaaaact caaccctacc ccaggcagca atgctatctc agatgtccca | 660 |
| ggagagagga gtacagccag cacctttcct acagacccag tttccccatt gacaaccacc | 720 |
| ctcagccttg cacaccacag ctctgctgcc ttacctgcac gcacctccaa caccaccatc | 780 |
| acagcgaaca cctcagatgc ctaccttaat gcctctgaaa caaccactct gagcccttct | 840 |
| ggaagcgctg tcatttcaac cacaacaata gctactactc catctaagcc aacatgtgat | 900 |
| gaaaaatatg caaacatcac tgtggattac ttatataaca aggaaactaa attatttaca | 960 |
| gcaaagctaa atgttaatga atgtgggaa tgtggaaaca atacttgcac aaacaatgag | 1020 |
| gtgcataacc ttacagaatg taaaaatgcg tctgtttcca tatctcataa ttcatgtact | 1080 |
| gctcctgata agacattaat attagatgtg ccaccagggg ttgaaaagtt tcagttacat | 1140 |
| gattgtacac aagttgaaaa agcagatact actatttgtt taaaatggaa aaatattgaa | 1200 |
| acctttactt gtgatacaca gaatattacc tacagatttc agtgtggtaa tatgatattt | 1260 |
| gataataaag aaattaaatt agaaaacctt gaaccgaac atgagtataa gtgtgactca | 1320 |
| gaaatactct ataataacca caagtttact aacgcaagta aaattattaa aacagatttt | 1380 |
| gggagtccag gagagcctca gattattttt tgtagaagtg aagctgcaca tcaaggagta | 1440 |
| attacctgga atccccctca aagatcattt catcaatttta ccctctgtta tataaaagag | 1500 |
| acagaaaaag attgcctcaa tctggataaa aacctgatca aatatgattt gcaaattta | 1560 |
| aaaccttata cgaaatatgt tttatcatta catgcctaca tcattgcaaa agtgcaacgt | 1620 |

```
aatggaagtg ctgcaatgtg tcatttcaca actaaaagtg ctcctccaag ccaggtctgg    1680
aacatgactg tctccatgac atcagataat agtatgcatg tcaagtgtag gcctcccagg    1740
gaccgtaatg gcccccatga acgttaccat ttggaagttg aagctggaaa tactctggtt    1800
agaaatgagt cgcataagaa ttgcgatttc cgtgtaaaag atcttcaata ttcaacagac    1860
tacactttta aggcctattt tcacaatgga gactatcctg agaacccctt tattttacat    1920
cattcaacat cttataattc taaggcactg atagcatttc tggcatttct gattattgtg    1980
acatcaatag ccctgcttgt tgttctctac aaaatctatg atctacataa gaaaagatcc    2040
tgcaatttag atgaacagca ggagcttgtt gaaagggatg atgaaaaaca actgatgaat    2100
gtggagccaa tccatgcaga tattttgttg gaaacttata agaggaagat tgctgatgaa    2160
ggaagacttt ttctggctga atttcagagc atcccgcggg tgttcagcaa gtttcctata    2220
aaggaagctc gaaagccctt taaccagaat aaaaaccgtt atgttgacat tcttccttat    2280
gattataacc gtgttgaact ctctgagata acggagatg cagggtcaaa ctacataaat    2340
gccagctata ttgatggttt caaagaaccc aggaaataca ttgctgcaca aggtcccagg    2400
gatgaaactt tgatgatttt ctggaggatg atttgggaac agaaagccac agttattgtc    2460
atggtcactc gatgtgaaga aggaaacagg aacaagtgtg cagaatactg gccgtcaatg    2520
gaagagggca ctcgggcttt tggagatgtt gttgtaaaga tcaaccagca caaaagatgt    2580
ccagattaca tcattcagaa attgaacatt gtaaataaaa aagaaaaagc aactggaaga    2640
gaggtgactc acattcagtt caccagctgg ccagaccacg gggtgcctga ggatcctcac    2700
ttgctcctca aactgagaag gagagtgaat gccttcagca atttcttcag tggtcccatt    2760
gtggtgcact gcagtgctgg tgttgggcgc acaggaacct atatcggaat tgatgccatg    2820
ctagaaggcc tggaagccga gaacaaagtg gatgtttatg gttatgttgt caagctaagg    2880
cgacagagat gcctgatggt tcaagtagag gcccagtaca tcttgatcca tcaggctttg    2940
gtggaataca atcagtttgg agaaacagaa gtgaatttgt ctgaattaca tccatatcta    3000
cataacatga gaaaagggaa tccacccagt gagccgtctc cactagaggc tgaattccag    3060
agacttcctt catataggag ctggaggaca cagcacattg gaaatcaaga agaaaataaa    3120
agtaaaaaca ggaattctaa tgtcatccca tatgactata acagagtgcc acttaaacat    3180
gagctggaaa tgagtaaaga gagtgagcat gattcagatg aatcctctga tgatgacagt    3240
gattcagagg aaccaagcaa atacatcaat gcatcttta taatgagcta ctggaaacct    3300
gaagtgatga ttgctgctca gggaccactg aaggagacca ttggtgactt ttggcagatg    3360
atcttccaaa gaaagtcaa agttattgtt atgctgacag aactgaaaca tggagaccag    3420
gaaatctgtg ctcagtactg gggagaagga agcaaacat atggagatat tgaagttgac    3480
ctgaaagaca cagacaaatc ttcaacttat accttcgtg tctttgaact gagacattcc    3540
aagaggaaag actctcgaac tgtgtaccag taccaatata caaactggag tgtggagcag    3600
cttcctgcag aacccaagga attaatctct atgattcagg tcgtcaaaca aaaacttccc    3660
cagaagaatt cctctgaagg gaacaagcat cacaagagta cacctctact cattcactgc    3720
agggatggat ctcagcaaac gggaatattt tgtgctttgt taaatctctt agaaagtgcg    3780
gaaacagaag aggtagtgga tattttcaa gtggtaaaag ctctacgcaa agctaggcca    3840
ggcatggttt ccacattcga gcaatatcaa ttcctatatg acgtcattgc cagcacctac    3900
cctgctcaga atggacaagt aaagaaaaac aaccatcaag aagataaaat tgaatttgat    3960
```

| | |
|---|---|
| aatgaagtgg acaaagtaaa gcaggatgct aattgtgtta atccacttgg tgccccagaa | 4020 |
| aagctccctg aagcaaagga acaggctgaa ggttctgaac ccacgagtgg cactgagggg | 4080 |
| ccagaacatt ctgtcaatgg tcctgcaagt ccagctttaa atcaaggttc ataggaaaag | 4140 |
| acataaatga ggaaactcca aacctcctgt tagctgttat ttctattttt gtagaagtag | 4200 |
| gaagtgaaaa taggtataca gtggattaat taaatgcagc gaaccaatat ttgtagaagg | 4260 |
| gttatatttt actactgtgg aaaaatattt aagatagttt tgccagaaca gtttgtacag | 4320 |
| acgtatgctt atttttaaaat tttatctctt attcagtaaa aaacaacttc tttgtaatcg | 4380 |
| ttatgtgtgt atatgtatgt gtgtatgggt gtgtgtttgt gtgagagaca gagaaagaga | 4440 |
| gagaattctt tcaagtgaat ctaaaagctt ttgcttttcc tttgttttta tgaagaaaaa | 4500 |
| atacatttta tattgaagt gttaacttag cttgaaggat ctgttttttaa aaatcataaa | 4560 |
| ctgtgtgcag actcaataaa atcatgtaca tttctgaaat gacctcaaga tgtcctcctt | 4620 |
| gttctactca tatatatcta tcttatatag tttactattt tacttctaga gatagtacat | 4680 |
| aaaggtggta tgtgtgtgta tgctactaca aaaaagttgt taactaaatt aacattggga | 4740 |
| aatcttatat tccatatatt agcatttagt ccaatgtctt tttaagctta tttaattaaa | 4800 |
| aaatttccag tgagcttatc atgctgtctt tacatggggt tttcaatttt gcatgctcga | 4860 |
| ttattccctg tacaatattt aaaatttatt gcttgatact tttgacaaca aattaggttt | 4920 |
| tgtacaattg aacttaaata aatgtcatta aaataaataa atgcaatatg tattaatatt | 4980 |
| cattgtataa aaatagaaga atacaaacat atttgttaaa tatttacata tgaaatttaa | 5040 |
| tatagctatt tttatggaat ttttcattga tatgaaaaat atgatattgc atatgcatag | 5100 |
| ttcccatgtt aaatcccatt cataactttc attaaagcat ttactttgaa tttctccaat | 5160 |
| gcttagaatg ttttttaccag gaatggatgt cgctaatcat aataaaattc aaccattatt | 5220 |
| tttttcttgt ttataataca ttgtgttata tgttcaaata tgaaatgtgt atgcacctat | 5280 |
| tgaaatatgt ttaatgcatt tattaacatt tgcaggacac ttttacaggc cccaattatc | 5340 |
| caatagtcta ataattgttt aagatctaga aaaaaaaaat caagaatagt ggtattttc | 5400 |
| atgaagtaat aaaaactcgt tttggtgaa | 5429 |

<210> SEQ ID NO 34
<211> LENGTH: 2621
<212> TYPE: DNA
<213> ORGANISM: Artificial Sequence
<220> FEATURE:
<223> OTHER INFORMATION: CD34 (NM_001025109)

<400> SEQUENCE: 34

| | |
|---|---|
| ccttttttgg cctcgacggc ggcaacccag cctccctcct aacgccctcc gcctttggga | 60 |
| ccaaccaggg gagctcaagt tagtagcagc caaggagagg cgctgccttg ccaagactaa | 120 |
| aaagggaggg gagaagagag gaaaaaagca agaatccccc acccctctcc cgggcggagg | 180 |
| gggcgggaag agcgcgtcct ggccaagccg agtagtgtct tccactcggt gcgtctctct | 240 |
| aggagccgcg cgggaaggat gctggtccgc aggggcgcgc gcgcagggcc caggatgccg | 300 |
| cggggctgga ccgcgctttg cttgctgagt ttgctgcctt ctgggttcat gagtcttgac | 360 |
| aacaacggta ctgctacccc agagttacct acccagggaa catttttcaaa tgtttctaca | 420 |
| aatgtatcct accaagaaac tacaacacct agtaccttg gaagtaccag cctgcaccct | 480 |
| gtgtctcaac atggcaatga ggccacaaca aacatcacag aaacgacagt caaattcaca | 540 |
| tctacctctg tgataaacctc agtttatgga aacacaaact cttctgtcca gtcacagacc | 600 |

```
tctgtaatca gcacagtgtt caccacccca gccaacgttt caactccaga gacaaccttg    660
aagcctagcc tgtcacctgg aaatgtttca gacctttcaa ccactagcac tagccttgca    720
acatctccca ctaaacccta tacatcatct tctcctatcc taagtgacat caaggcagaa    780
atcaaatgtt caggcatcag agaagtgaaa ttgactcagg gcatctgcct ggagcaaaat    840
aagacctcca gctgtgcgga gtttaagaag dacaggggag agggcctggc ccgagtgctg    900 tgtgggagg agcaggctga tgctgatgct ggggcccagg tatgctccct gctccttgcc    960
cagtctgagg tgaggcctca gtgtctactg ctggtcttgg ccaacagaac agaaatttcc   1020
agcaaactcc aacttatgaa aaagcaccaa tctgacctga aaaagctggg gatcctagat   1080
ttcactgagc aagatgttgc aagccaccag agctattccc aaaagaccct gattgcactg   1140
gtcacctcgg gagccctgct ggctgtcttg ggcatcactg ctatttcct gatgaatcgc    1200 cgcagctgga gccccacagg agaaaggctg ggcgaagacc cttattacac ggaaaacggt   1260
ggaggccagg gctatagctc aggacctggg acctcccctg aggctcaggg aaaggccagt   1320
gtgaaccgag gggctcagga aaacgggacc ggccaggcca cctccagaaa cggccattca   1380
gcaagacaac acgtggtggc tgataccgaa ttgtgactcg gctaggtggg caaggctgg    1440 gcagtgtccg agagagcacc cctctctgca tctgaccacg tgctacccc atgctggagg    1500 tgacatctct tacgcccaac ccttccccac tgcacacacc tcagaggctg ttcttggggc   1560
cctacacctt gaggaggggc aggtaaactc ctgtccttta cacattcggc tccctggagc   1620
cagactctgg tcttctttgg gtaaacgtgt gacgggggaa agccaaggtc tggagaagct   1680
cccaggaaca atcgatggcc ttgcagcact cacacaggac cccctttccc tacccctcc    1740 tctctgccgc aatacaggaa ccccagggg aaagatgagc ttttctaggc tacaattttc    1800
tcccaggaag ctttgatttt taccgtttct tccctgtatt ttctttctct actttgagga   1860
aaccaaagta acctttttgca cctgctctct tgtaatgata tagccagaaa acgtgttgc    1920 cttgaaccac ttccctcatc tctcctccaa gacactgtgg acttggtcac cagctcctcc   1980
cttgttctct aagttccact gagctccatg tgcccctct accatttgca gagtcctgca   2040
cagttttctg gctggagcct agaacaggcc tcccaagttt taggacaaac agctcagttc   2100
tagtctctct ggggccacac agaaactctt tttgggctcc ttttctccc tctggatcaa    2160 agtaggcagg accatgggac caggtcttgg agctgagcct ctcacctgta ctcttccgaa   2220
aaatcctctt cctctgaggc tggatcctag ccttatcctc tgatctccat ggcttcctcc   2280
tccctcctgc cgactcctgg gttgagctgt tgcctcagtc ccccaacaga tgctttctg    2340 tctctgcctc cctcaccctg agcccttcc ttgctctgca ccccatatg gtcatagccc    2400 agatcagctc ctaaccctta tcaccagctg cctcttctgt gggtgaccca ggtccttgtt   2460
tgctgttgat ttctttccag aggggttgag cagggatcct ggtttcaatg acggttggaa   2520
atagaaattt ccagagaaga gagtattggg tagatatttt ttctgaatac aaagtgatgt   2580
gtttaaatac tgcaattaaa gtgatactga aacacaaaaa a                       2621
```

<210> SEQ ID NO 35
<211> LENGTH: 1648
<212> TYPE: DNA
<213> ORGANISM: Artificial Sequence
<220> FEATURE:
<223> OTHER INFORMATION: CD14 (NM_000591)

<400> SEQUENCE: 35

```
cagagaaggc ttaggctccc gagtcaacag ggcattcacc gcctggggcg cctgagtcat      60
caggacactg ccaggagaca cagaacccta gatgccctgc agaatccttc ctgttacggt     120
ccccctccct gaaacatcct tcattgcaat atttccagga aaggaagggg gctggctcgg     180
aggaagagag gtggggaggt gatcagggtt cacagaggag ggaactgaat gacatcccag     240
gattacataa actgtcagag gcagccgaag agttcacaag tgtgaagcct ggaagccggc     300
gggtgccgct gtgtaggaaa gaagctaaag cacttccaga gcctgtccgg agctcagagg     360
ttcggaagac ttatcgacca tggagcgcgc gtcctgcttg ttgctgctgc tgctgccgct     420
ggtgcacgtc tctgcgacca cgccagaacc ttgtgagctg gacgatgaag atttccgctg     480
cgtctgcaac ttctccgaac tcagcccga ctggtccgaa gccttccagt gtgtgtctgc      540
agtagaggtg gagatccatg ccggcggtct caacctagag ccgtttctaa agcgcgtcga     600
tgcggacgcc gacccgcggc agtatgctga cacggtcaag gctctccgcg tgcggcggct     660
cacagtggga gccgcacagg ttcctgctca gctactggta ggcgccctgc gtgtgctagc     720
gtactcccgc ctcaaggaac tgacgctcga ggacctaaaa ataaccggca ccatgcctcc     780
gctgcctctg gaagccacag gacttgcact ttccagcttg cgcctacgca acgtgtcgtg     840
ggcgacaggg cgttcttggc tcgccgagct gcagcagtgg ctcaagccag gcctcaaggt     900
actgagcatt gcccaagcac actcgcctgc cttttcctgc gaacaggttc gcgccttccc     960
ggcccttacc agcctagacc tgtctgacaa tcctggactg ggcgaacgcg gactgatggc    1020
ggctctctgt ccccacaagt tcccggccat ccagaatcta gcgctgcgca acacaggaat    1080
ggagacgccc acaggcgtgt gcgccgcact ggcggcggca ggtgtgcagc cccacagcct    1140
agacctcagc cacaactcgc tgcgcgccac cgtaaaccct agcgctccga gatgcatgtg    1200
gtccagcgcc ctgaactccc tcaatctgtc gttcgctggg ctggaacagg tgcctaaagg    1260
actgccagcc aagctcagag tgctcgatct cagctgcaac agactgaaca gggcgccgca    1320
gcctgacgag ctgccgagg tggataacct gacactggac gggaatccct tcctggtccc    1380
tggaactgcc ctcccccacg agggctcaat gaactccggc gtggtccag cctgtgcacg    1440
ttcgaccctg tcggtggggg tgtcgggaac cctggtgctg ctccaagggg cccgggcttt   1500
tgcctaagat ccaagacaga ataatgaatg gactcaaact gccttggctt caggggagtc    1560
ccgtcaggac gttgaggact tttcgaccaa ttcaaccctt tgccccacct ttattaaaat    1620
cttaaacaac gggtcaaaaa aaaaaaaa                                       1648

<210> SEQ ID NO 36
<211> LENGTH: 4742
<212> TYPE: DNA
<213> ORGANISM: Artificial Sequence
<220> FEATURE:
<223> OTHER INFORMATION: CD11b (NM_000632)

<400> SEQUENCE: 36
ttttctgccc ttctttgctt tggtggcttc cttgtggttc ctcagtggtg cctgcaaccc      60
ctggttcacc tccttccagg ttctggctcc ttccagccat ggctctcaga gtccttctgt     120
taacagcctt gacctatgt catgggttca acttggacac tgaaaacgca atgaccttcc     180
aagagaacgc aaggggcttc gggcagagcg tggtccagct tcagggatcc agggtggtgg     240
ttggagcccc caggagata gtggctgcca accaaagggg cagcctctac cagtgcgact     300
acagcacagg ctcatgcgag cccatccgcc tgcaggtccc cgtggaggcc gtgaacatgt     360
ccctgggcct gtccctggca gccaccacca gccccctca gctgctggcc tgtggtccca     420
```

```
ccgtgcacca gacttgcagt gagaacacgt atgtgaaagg gctctgcttc ctgtttggat      480
ccaacctacg gcagcagccc cagaagttcc cagaggccct ccgagggtgt cctcaagagg      540
atagtgacat tgccttcttg attgatggct ctggtagcat catcccacat gactttcggc      600
ggatgaagga gtttgtctca actgtgatgg agcaattaaa aaagtccaaa accttgttct      660
ctttgatgca gtactctgaa gaattccgga ttcactttac cttcaaagag ttccagaaca      720
accctaaccc aagatcactg gtgaagccaa taacgcagct gcttgggcgg acacacacgg      780
ccacgggcat ccgcaaagtg gtacgagagc tgtttaacat caccaacgga gcccgaaaga      840
atgcctttaa gatcctagtt gtcatcacgg atggagaaaa gtttggcgat cccttgggat      900
atgaggatgt catccctgag gcagacagag agggagtcat tcgctacgtc attggggtgg      960
gagatgcctt ccgcagtgag aaatcccgcc aagagcttaa taccatcgca tccaagccgc     1020
ctcgtgatca cgtgttccag gtgaataact ttgaggctct gaagaccatt cagaaccagc     1080
ttcgggagaa gatctttgcg atcgagggta ctcagacagg aagtagcagc tcctttgagc     1140
atgagatgtc tcaggaaggc ttcagcgctg ccatcacctc taatggcccc ttgctgagca     1200
ctgtggggag ctatgactgg gctggtggag tctttctata tacatcaaag gagaaaagca     1260
ccttcatcaa catgaccaga gtggattcag acatgaatga tgcttacttg ggttatgctg     1320
ccgccatcat cttacggaac cgggtgcaaa gcctggttct gggggcacct cgatatcagc     1380
acatcggcct ggtagcgatg ttcaggcaga acactggcat gtgggagtcc aacgctaatg     1440
tcaagggcac ccagatcggc gcctacttcg gggcctccct ctgctccgtg gacgtggaca     1500
gcaacggcag caccgacctg gtcctcatcg ggcccccca ttactacgag cagacccgag     1560
ggggccaggt gtccgtgtgc cccttgccca ggggagggc tcggtggcag tgtgatgctg     1620
ttctctacgg ggagcagggc caaccctggg gccgctttgg ggcagcccta acagtgctgg     1680
gggacgtaaa tgggacaag ctgacgacg tggccattgg ggccccagga gaggaggaca     1740
accggggtgc tgtttacctg tttcacggaa cctcaggatc tggcatcagc ccctcccata     1800
gccagcggat agcaggctcc aagctctctc ccaggctcca gtattttggt cagtcactga     1860
gtgggggcca ggacctcaca atggatggac tggtagacct gactgtagga gcccaggggc     1920
acgtgctgct gctcaggtcc cagccagtac tgagagtcaa ggcaatcatg gagttcaatc     1980
ccagggaagt ggcaaggaat gtatttgagt gtaatgatca ggtggtgaaa ggcaaggaag     2040
ccggagaggt cagagtctgc ctccatgtcc agaagagcac acgggatcgg ctaagagaag     2100
gacagatcca gagtgttgtg acttatgacc tggctctgga ctccggccgc ccacattccc     2160
gcgccgtctt caatgagaca aagaacagca cacgcagaca gacacaggtc ttggggctga     2220
cccagacttg tgagaccctg aaactacagt tgccgaattg catcgaggac ccagtgagcc     2280
ccattgtgct gcgcctgaac ttctctctgg tgggaacgcc attgtctgct tcgggaacc     2340 tccggccagt gctggcggag gatgctcaga gactcttcac agccttgttt ccctttgaga     2400
agaattgtgg caatgacaac atctgccagg atgacctcag catcaccttc agtttcatga     2460
gcctggactg cctcgtggtg ggtgggcccc gggagttcaa cgtgacagtg actgtgagaa     2520
atgatggtga ggactcctac aggacacagg tcaccttctt cttcccgctt gacctgtcct     2580
accggaaggt gtccacgctc cagaaccagc gctcacagcg atcctggcgc ctggcctgtg     2640
agtctgcctc ctccaccgaa gtgtctgggg ccttgaagag caccagctgc agcataaacc     2700
accccatctt cccggaaaac tcagaggtca cctttaatat cacgtttgat gtagactcta     2760
```

| aggcttccct tggaaacaaa ctgctcctca aggccaatgt gaccagtgag aacaacatgc | 2820 |
| ccagaaccaa caaaaccgaa ttccaactgg agctgccggt gaaatatgct gtctacatgg | 2880 |
| tggtcaccag ccatggggtc tccactaaat atctcaactt cacggcctca gagaatacca | 2940 |
| gtcgggtcat gcagcatcaa tatcaggtca gcaacctggg gcagaggagc ctccccatca | 3000 |
| gcctggtgtt cttggtgccc gtccggctga accagactgt catatgggac cgcccccagg | 3060 |
| tcaccttctc cgagaacctc tcgagtacgt gccacaccaa ggagcgcttg ccctctcact | 3120 |
| ccgactttct ggctgagctt cggaaggccc ccgtggtgaa ctgctccatc gctgtctgcc | 3180 |
| agagaatcca gtgtgacatc ccgttctttg gcatccagga agaattcaat gctaccctca | 3240 |
| aaggcaacct ctcgtttgac tggtacatca agacctcgca taaccacctc ctgatcgtga | 3300 |
| gcacagctga gatcttgttt aacgattccg tgttcaccct gctgccggga caggggcgt | 3360 |
| ttgtgaggtc ccagacggag accaaagtgg agccgttcga ggtccccaac ccctgccgc | 3420 |
| tcatcgtggg cagctctgtc gggggactgc tgctcctggc cctcatcacc gccgcgctgt | 3480 |
| acaagctcgg cttcttcaag cggcaataca aggacatgat gagtgaaggg ggtccccgg | 3540 |
| gggccgaacc ccagtagcgg ctccttcccg acagagctgc ctctcggtgg ccagcaggac | 3600 |
| tctgcccaga ccacacgtag ccccaggct gctggacacg tcggacagcg aagtatcccc | 3660 |
| gacaggacgg gcttgggctt ccatttgtgt gtgtgcaagt gtgtatgtgc gtgtgtgcaa | 3720 |
| gtgtctgtgt gcaagtgtgt gcacatgtgt gcgtgtgcgt gcatgtgcac ttgcacgccc | 3780 |
| atgtgtgagt gtgtgcaagt atgtgagtgt gtccaagtgt gtgtgcgtgt gtccatgtgt | 3840 |
| gtgcaagtgt gtgcatgtgt gcgagtgtgt gcatgtgtgt gctcagggc gtgtggctca | 3900 |
| cgtgtgtgac tcagatgtct ctggcgtgtg gtaggtgac ggcagcgtag cctctccggc | 3960 |
| agaagggaac tgcctgggct cccttgtgcg tgggtgaagc cgctgctggg ttttcctccg | 4020 |
| ggagagggga cggtcaatcc tgtgggtgaa gacagaggga aacacagcag cttctctcca | 4080 |
| ctgaaagaag tgggacttcc cgtcgcctgc gagcctgcgg cctgctggag cctgcgcagc | 4140 |
| ttggatggag actccatgag aagccgtggg tggaaccagg aacctcctcc acaccagcgc | 4200 |
| tgatgcccaa taaagatgcc cactgaggaa tgatgaagct tcctttctgg attcatttat | 4260 |
| tatttcaatg tgactttaat tttttggatg gataagcttg tctatggtac aaaaatcaca | 4320 |
| aggcattcaa gtgtacagtg aaaagtctcc cttcccagat attcaagtca cctccttaaa | 4380 |
| ggtagtcaag attgtgtttt gaggtttcct tcagacagat tccaggcgat gtgcaagtgt | 4440 |
| atgcacgtgt gcacacacac cacacataca cacacacaag cttttttaca caaatggtag | 4500 |
| catactttat attggtctgt atcttgcttt ttttcaccaa tatttctcag acatcggttc | 4560 |
| atattaagac ataaattact ttttcattct tttataccgc tgcatagtat tccattgtgt | 4620 |
| gagtgtacca taatgtattt aaccagtctt cttttgatat actattttca ttctcttgtt | 4680 |
| attgcatcaa tgctgagtta ataaatcaaa tatatgtcat ttttgcatat atgtaaggat | 4740 |
| aa | 4742 |

<210> SEQ ID NO 37
<211> LENGTH: 1258
<212> TYPE: DNA
<213> ORGANISM: Artificial Sequence
<220> FEATURE:
<223> OTHER INFORMATION: CD79 (NM_001783)

<400> SEQUENCE: 37

| tccactcaca gcctgaagca tacccggcag gggctgtccc caggcccaac aagcaaaggg | 60 |

```
cccagtagcg agggccactg gagcccatct ccgggggggct gggcaggaag tagggtgggg      120
tttggggtag ggatctggta ccctgggact gctgcaactc aaactaacca acccactggg      180
agaagatgcc tgggggtcca ggagtcctcc aagctctgcc tgccaccatc ttcctcctct      240
tcctgctgtc tgctgtctac ctgggccctg ggtgccaggc cctgtggatg cacaaggtcc      300
cagcatcatt gatggtgagc ctgggggaag acgcccactt ccaatgcccg cacaatagca      360
gcaacaacgc caacgtcacc tggtggcgcg tcctccatgg caactacacg tggcccctg       420 agttcttggg cccgggcgag gaccccaatg gtacgctgat catccagaat gtgaacaaga      480
gccatggggg catatacgtg tgccgggtcc aggagggcaa cgagtcatac cagcagtcct      540
gcggcaccta cctccgcgtg cgccagccgc cccccaggcc cttcctggac atggggggagg    600 gcaccaagaa ccgaatcatc acagccgagg ggatcatcct cctgttctgc gcggtggtgc      660
ctgggacgct gctgctgttc aggaaacgat ggcagaacga aagctcgggg ttggatgccg      720
gggatgaata tgaagatgaa aacctttatg aaggcctgaa cctggacgac tgctccatgt      780
atgaggacat ctcccggggc ctccagggca cctaccagga tgtgggcagc ctcaacatag      840
gagatgtcca gctggagaag ccgtgacacc cctactcctg ccaggctgcc ccgcctgct       900 gtgcacccag ctccagtgtc tcagctcact cccctgggac attctccttt cagcccttct      960
gggggcttcc ttagtcatat tcccccagtg ggggtgtggg gggtaacctc actcttctcc      1020
aggccaggcc tccttggact ccctggggg tgtcccactc ttcttccctc taaactgccc       1080
cacctcctaa cctaatcccc ccgccccgct gcctttccca ggctcccctc accccagcgg     1140
gtaatgagcc cttaatcgct gcctctaggg gagctgattg tagcagcctc gttagtgtca     1200
ccccctcctc cctgatctgt cagggccact tagtgataat aaattcttcc caactgca       1258

<210> SEQ ID NO 38
<211> LENGTH: 1968
<212> TYPE: DNA
<213> ORGANISM: Artificial Sequence
<220> FEATURE:
<223> OTHER INFORMATION: CD19 (NM_001178098)

<400> SEQUENCE: 38
aggcccctgc ctgccccagc atccctgcg cgaagctggg tgccccggag agtctgacca      60
ccatgccacc tcctcgcctc ctcttcttcc tcctcttcct cacccccatg gaagtcaggc     120
ccgaggaacc tctagtggtg aaggtggaag agggagataa cgctgtgctg cagtgcctca     180
aggggacctc agatgccccc actcagcagc tgacctggtc tcgggagtcc ccgcttaaac     240
ccttcttaaa actcagcctg gggctgccag gcctgggaat ccacatgagg cccctggcca    300
tctggctttt catcttcaac gtctctcaac agatgggggg cttctacctg tgccagccgg    360 ggccccctc tgagaaggcc tggcagcctg gctggacagt caatgtggag ggcagcgggg     420
agctgttccg gtggaatgtt tcggacctag gtggcctggg ctgtggcctg aagaacaggt    480
cctcagaggg ccccagctcc ccttccggga agctcatgag ccccaagctg tatgtgtggg    540
ccaaagaccg ccctgagatc tgggagggag agcctccgtg tctcccaccg agggacagcc    600
tgaaccagag cctcagccag gacctcacca tggcccctgg ctccacactc tggctgtcct    660
gtggggtacc ccctgactct gtgtccaggg gccccctctc ctggacccat gtgcacccca   720
aggggcctaa gtcattgctg agcctagagc tgaaggacga tcgccggcc agagatatgt     780 gggtaatgga gacgggtctg ttgttgcccc gggccacagc tcaagacgct ggaaagtatt    840
```

```
attgtcaccg tggcaacctg accatgtcat tccacctgga gatcactgct cggccagtac    900
tatggcactg gctgctgagg actggtggct ggaaggtctc agctgtgact ttggcttatc    960
tgatcttctg cctgtgttcc cttgtgggca ttcttcatct tcaaagagcc ctggtcctga   1020
ggaggaaaag aaagcgaatg actgacccca ccaggagatt cttcaaagtg acgcctcccc   1080
caggaagcgg gccccagaac cagtacggga acgtgctgtc tctccccaca cccacctcag   1140
gcctcggacg cgcccagcgt tgggccgcag gctgggggg cactgccccg tcttatggaa    1200
acccgagcag cgacgtccag gcggatggag ccttggggtc ccggagcccg ccgggagtgg   1260
gcccagaaga agaggaaggg gagggctatg agggaacctga cagtgaggag gactccgagt   1320
tctatgagaa cgactccaac cttgggcagg accagctctc ccaggatggc agcggctacg   1380
agaaccctga ggatgagccc ctgggtcctg aggatgaaga ctccttctcc aacgctgagt   1440
cttatgagaa cgaggatgaa gagctgaccc agccggtcgc caggacaatg gacttcctga   1500
gccctcatgg gtcagcctgg gaccccagcc gggaagcaac ctccctggca gggtcccagt   1560
cctatgagga tatgagagga atcctgtatg cagcccccca gctccgctcc attcggggcc   1620
agcctggacc caatcatgag gaagatgcag actcttatga gaacatggat aatcccgatg   1680
ggccagaccc agcctgggga ggaggggcc gcatgggcac ctggagcacc aggtgatcct    1740
caggtggcca gcctggatct cctcaagtcc ccaagattca cacctgactc tgaaatctga   1800
agacctcgag cagatgatgc caacctctgg agcaatgttg cttaggatgt gtgcatgtgt   1860
gtaagtgtgt gtgtgtgtgt gtgtgtgtat acatgccagt gacacttcca gtccccttttg  1920
tattccttaa ataaactcaa tgagctcttc caatcctaaa aaaaaaa                  1968

<210> SEQ ID NO 39
<211> LENGTH: 3618
<212> TYPE: DNA
<213> ORGANISM: Artificial Sequence
<220> FEATURE:
<223> OTHER INFORMATION: HLA class II (NM_000449)

<400> SEQUENCE: 39
attcagaaaa aggaaaataa agcaacgcac gagccggctg ggccaggacc ttggggctgg     60
gctggagtga aggtggctac gagttttcca gatttaggag acttcagaaa ggtggggcag    120
atagaatgga gatggcaaag atctctttgg gcatatatgg gcctggcgaa gtaatggaat    180
aatttctaat tttcggagaa ggcaagtgcc ctcatgccgg gatggcagaa gatgagcctg    240
atgctaagag ccccaagact gggggaaggg cccccccagg tggtgctgag gctggggaac    300
ctaccaccct tcttcagagg ctccgaggta ccatttccaa ggccgtgcag aacaaagtag    360
agggatcct gcaagatgta cagaaatttt ctgacaatga caagctgtat ctctaccttc     420
agctccccct caggacccacc actggagaca aaagctcaga gccaagtaca ctgagcaatg    480
aggagtacat gtatgcctat aggtggatcc gcaaccacct ggaagagcac actgacacct    540
gtctgccaaa gcaaagtgtt tatgatgcct atcggaagta ctgtgagagt cttgcctgtt    600
gccgcccact cagcacagcc aactttggca agatcatcag agagatcttc cctgacatca    660
aagctcgaag gcttggtggc cggggccagt ccaaatattg ctacagtggc ataaggagga    720
gaccttggt gtctatgcca cccctgcctg gacttgacct aaagggttct gagagtccag    780
aaatgggccc agaagtaacc ccagcacctc gagatgaact ggtggaggca gcgtgtgccc   840
tgacctgtga ctgggcagag cggatcctga acggtccttc agttccatc gttgaggtcg    900
cccgcttcct gctacagcag catctcatct ctgcccgatc tgcacatgcc catgtgctta    960
```

-continued

```
aggccatggg gcttgctgaa gaggacgaac atgcacctcg ggaacggtca tctaaaccaa      1020
agaatggttt agagaaccca gagggtggag cccacaagaa gccagagaga ctggcccagc      1080
ctcctaagga tctggaagcc cgaactgggg ccggtcctct cgcacgtgga gagcggaaga      1140
agagtgtagt tgagagctcg gccccaggag ccaataacct gcaggttaat gccctagtgg      1200
ctcggctgcc tctgctcctt ccccgggccc ctcgctcact aattccgcca atcccagtct      1260
ctccacctat tctggccccc aggctttctt caggtgccct gaaagtggct acactgcctc      1320
tgtctagtag ggccggggca cccccagcag ctgtgcccat cattaacatg atcttaccaa      1380
ctgttcctgc tttgcctgga cctggacctg ggcctgggcg agctccacct gggggactca      1440
ctcagccccg gggcacagag aacagagagg taggcatagg tggtgaccaa ggaccacatg      1500
acaagggtgt caagaggaca gctgaagtac ctgtgagtga ggccagtggg caggctccac      1560
cagctaaagc agcaaagcag gatatagagg atacagcaag tgatgccaaa aggaaacggg      1620
ggcgccctcg aaaaaagtca ggtggaagtg gggaaaggaa ttctacccct ctcaagtcag      1680
cagctgccat ggaatctgcc cagtcctcaa ggttaccatg ggagacatgg ggctcaggag      1740
gggaaggcaa ctcagctgga ggggcagaga ggccagggcc aatgggagag ctgaaaagg      1800 gggcagtact tgcccagggt cagggagatg gtactgtttc caaggagga aggggccccg      1860 gttcccagca taccaaagaa gcagaagata aaattcccctt ggtcccctca aaagtgagtg      1920
tcatcaaggg cagcagaagc caaaaggagg ctttttcctttt ggcaaaggga gaggtagaca      1980
ctgcaccaca gggtaataaa gacttaaagg agcatgtgct tcaaagttcc ttatcccagg      2040
agcataaaga cccaaaagca caccccccat gatacaggtc tgtggggaag agtgtttata      2100
tccctacgtt aactttgcct agtagaggcc cttcttttgca cttgcttctc atttggctat      2160
tcttttccta aggaagtcca ttctcctctg tacagacagc tgagtcaccc agtctactta      2220
gtacctggtt gctgcctctg acctttcag cttgataccc tgggctttag tgtaaccaat      2280
aaatctgtag tgaccttacc tgtattccct gtgctatcct gtgggaaggt aggaatgggc      2340
taagtatgat gaatatatag gttagggatc ttttggtttt aaatcacaga aaacctaatt      2400
caaactggct taaaataaaa aggatttatt ggttcatgta actagaaagt ccataggtag      2460
tgctggctcc aggtgaagac ttgacccagt agttcagtat gtctctaaat accggactga      2520
cttttttctc actgttgcat cttctgtagg accatttaag tctgggccac ttaatggctg      2580
ccagcattcc taagattaca cttttcccca tttatgtcca atcagaaaaa gaaggcatct      2640
ttgtaccaga aatctcagca aaagccctaa tattcacact gattaggcct gggtcacatg      2700
tccaccctga ccaatcactg tggccaggag gatgatacat gctaatttgc ttattctata      2760
tcatggacaa caccttgggg gaaaagggtg ggggtcagcc tccccaaaat cacatggatt      2820
ccccaagtgg aaactaggag cagggagttg cttgggtggc cgctaacacc aggctactct      2880
tattttagct tgctaagttg agatcagcta gacctgcttt ctttttctcct cagtcttgca      2940 tttccctcaa tacaagctgt agcctctttc ctcgtttcta gtctcagaag gaaggagagg      3000
gaagccattc tcctctaggg actcttcagt ctcatttaga tgatagtccc tttttttcta      3060
cctccatatt agagatggag ctccttcctt ttcctgtttc ttaatttttg tcttctcatt      3120
cctgcttccc tctcacccta ttgccagttc caccaactag agtgaaagac ttcctagcca      3180
tttcattaaa tctattctgt atccaccagg tggcagcatc ttgtcatacg tgtcaggact      3240
taggactgcg gggtttaggt tagatgtcac ggaaaaagct agttctgtgg tcaggcggca      3300
```

-continued

```
ccaatgagaa aggaatgcag accctccaga tgtatccttg ggaaaagcag taaaccaact    3360
aatatttatt gaagacctac tttgtcctct acatagggta gcttctgtca gggaatcttg    3420
gttcttccca agaaacactg attttctttc agggagactt catgtgttca tttatttcca    3480
ccacagcaga ttttaagaaa ttataatatg taatatttga tatctataaa gagtatatct    3540
aacgtgaata aattatgaag catactaatg agtacctatg acccataaca catatacatt    3600
aaaacatttt aaatacca                                                 3618

<210> SEQ ID NO 40
<211> LENGTH: 3879
<212> TYPE: DNA
<213> ORGANISM: Artificial Sequence
<220> FEATURE:
<223> OTHER INFORMATION: CD29 (NM_002211)

<400> SEQUENCE: 40
atcagacgcg cagaggaggc ggggccgcgg ctggtttcct gccgggggc ggctctgggc      60 cgccgagtcc cctcctcccg cccctgagga ggaggagccc cgccacccg ccgcgcccga     120 cacccgggag gccccgccag ccgcgggag aggcccagcg ggagtcgcgg aacagcaggc     180
ccgagcccac cgcgccgggc cccggacgcc gcgcggaaaa gatgaattta caaccaattt     240
tctggattgg actgatcagt tcagtttgct gtgtgtttgc tcaaacagat gaaaatagat     300
gtttaaaagc aaatgccaaa tcatgtggag aatgtataca agcagggcca aattgtgggt     360
ggtgcacaaa ttcaacattt ttacaggaag gaatgcctac ttctgcacga tgtgatgatt     420
tagaagcctt aaaaaagaag ggttgccctc cagatgacat agaaaatccc agaggctcca     480
agatatataa gaaaaataaa aatgtaacca accgtagcaa aggaacagca gagaagctca     540
agccagagga tattactcag atccaaccac agcagttggt tttgcgatta agatcagggg     600
agccacagac atttacatta aaattcaaga gagctgaaga ctatcccatt gacctctact     660
accttatgga cctgtcttac tcaatgaaag acgatttgga gaatgtaaaa agtcttggaa     720
cagatctgat gaatgaaatg aggaggatta cttcggactt cagaattgga tttggctcat     780
ttgtggaaaa gactgtgatg ccttacatta gcacaacacc agctaagctc aggaacccct     840
gcacaagtga acagaactgc accagcccat ttagctacaa aaatgtgctc agtcttacta     900
ataaaggaga agtatttaat gaacttgttg gaaaacagcg catatctgga aatttggatt     960
ctccagaagg tggtttcgat gccatcatgc aagttgcagt ttgtggatca ctgattggct    1020
ggaggaatgt tacacggctg ctggtgtttt ccacagatgc cgggtttcac tttgctggag    1080
atgggaaact tggtggcatt gttttaccaa atgatggaca atgtcacctg gaaaataata    1140
tgtacacaat gagccattat tatgattatc cttctattgc tcaccttgtc agaaactga    1200 gtgaaaataa tattcagaca atttttgcag ttactgaaga atttcagcct gtttacaagg    1260
agctgaaaaa cttgatccct aagtcagcag taggaacatt atctgcaaat tctagcaatg    1320
taattcagtt gatcattgat gcatacaatt ccctttcctc agaagtcatt ttggaaaacg    1380
gcaaattgtc agaaggcgta acaataagtt acaaatctta ctgcaagaac ggggtgaatg    1440
gaacagggga aaatggaaga aaatgttcca atatttccat ggagatgag ttcaatttg     1500 aaattagcat aacttcaaat aagtgtccaa aaaggattc tgacagcttt aaaattaggc    1560
ctctgggctt tacggaggaa gtagaggtta tcttcagta catctgtgaa tgtgaatgcc    1620
aaagcgaagg catccctgaa gtcccaagt gtcatgaagg aaatgggaca tttgagtgtg    1680
gcgcgtgcag gtgcaatgaa gggcgtgttg gtagacattg tgaatgcagc acagatgaag    1740
```

```
ttaacagtga agacatggat gcttactgca ggaaagaaaa cagttcagaa atctgcagta    1800
acaatggaga gtgcgtctgc ggacagtgtg tttgtaggaa gagggataat acaaatgaaa    1860
tttattctgg caaattctgc gagtgtgata atttcaactg tgatagatcc aatggcttaa    1920
tttgtggagg aaatggtgtt tgcaagtgtc gtgtgtgtga gtgcaacccc aactacactg    1980
gcagtgcatg tgactgttct ttggatacta gtacttgtga agccagcaac ggacagatct    2040
gcaatggccg gggcatctgc gagtgtggtg tctgtaagtg tacagatccg aagtttcaag    2100
ggcaaacgtg tgagatgtgt cagacctgcc ttggtgtctg tgctgagcat aaagaatgtg    2160
ttcagtgcag agccttcaat aaaggagaaa agaaagacac atgcacacag gaatgttcct    2220
attttaacat taccaaggta gaaagtcggg acaaattacc ccagccggtc aacctgatc     2280 ctgtgtccca ttgtaaggag aaggatgttg acgactgttg gttctatttt acgtattcag    2340
tgaatgggaa caacgaggtc atggttcatg ttgtggagaa tccagagtgt cccactggtc    2400
cagacatcat tccaattgta gctggtgtgg ttgctggaat tgttcttatt ggccttgcat    2460
tactgctgat atggaagctt ttaatgataa ttcatgacag aagggagttt gctaaatttg    2520
aaaaggagaa aatgaatgcc aaatgggaca cgggtgaaaa tcctatttat aagagtgccg    2580
taacaactgt ggtcaatccg aagtatgagg gaaaatgagt actgcccgtg caaatcccac    2640
aacactgaat gcaaagtagc aatttccata gtcacagtta ggtagcttta gggcaatatt    2700
gccatggttt tactcatgtg caggttttga aaatgtacaa tatgtataat ttttaaaatg    2760
ttttattatt ttgaaaataa tgttgtaatt catgccaggg actgacaaaa gacttgagac    2820
aggatggtta ctcttgtcag ctaaggtcac attgtgcctt tttgacccttt tcttcctgga    2880 ctattgaaat caagcttatt ggattaagtg atatttctat agcgattgaa agggcaatag    2940
ttaaagtaat gagcatgatg agagtttctg ttaatcatgt attaaaactg attttttagct   3000 ttacaaatat gtcagtttgc agttatgcag aatccaaagt aaatgtcctg ctagctagtt    3060
aaggattgtt ttaaatctgt tattttgcta tttgcctgtt agacatgact gatgacatat    3120
ctgaaagaca agtatgttga gagttgctgg tgtaaaatac gtttgaaata gttgatctac    3180
aaaggccatg ggaaaaattc agagagttag gaaggaaaaa ccaatagctt taaaacctgt    3240
gtgccatttt aagagttact taatgtttgg taacttttat gccttcactt tacaaattca    3300
agccttagat aaaagaaccg agcaatttttc tgctaaaaag tccttgattt agcactattt    3360
acatacaggc catactttac aaagtatttg ctgaatgggg acctttttgag ttgaatttat    3420 tttattattt ttattttgtt taatgtctgg tgctttctgt cacctcttct aatcttttaa    3480
tgtatttgtt tgcaattttg gggtaagact ttttttatga gtactttttc tttgaagttt    3540
tagcggtcaa tttgcctttt taatgaacat gtgaagttat actgtggcta tgcaacagct    3600
ctcacctacg cgagtcttac tttgagttag tgccataaca gaccactgta tgtttacttc    3660
tcaccatttg agttgcccat cttgtttcac actagtcaca ttcttgtttt aagtgccttt    3720
agttttaaca gttcactttt tacagtgcta tttactgaag ttatttatta aatatgccta    3780
aaatacttaa atcggatgtc ttgactctga tgtatttttat caggttgtgt gcatgaaatt    3840
tttatagatt aaagaagttg aggaaaagca aaaaaaaa                            3879
```

<210> SEQ ID NO 41
<211> LENGTH: 5748
<212> TYPE: DNA
<213> ORGANISM: Artificial Sequence
<220> FEATURE:

<223> OTHER INFORMATION: CD44 (NM_000610)

<400> SEQUENCE: 41

```
gagaagaaag ccagtgcgtc tctgggcgca ggggccagtg gggctcggag gcacaggcac      60
cccgcgacac tccaggttcc ccgacccacg tccctggcag ccccgattat ttacagcctc     120
agcagagcac ggggcggggg cagaggggcc cgcccgggag ggctgctact tcttaaaacc     180
tctgcgggct gcttagtcac agccccccctt gcttgggtgt gtccttcgct cgctccctcc     240
ctccgtctta ggtcactgtt ttcaacctcg aataaaaact gcagccaact tccgaggcag     300
cctcattgcc cagcggaccc cagcctctgc caggttcggt ccgccatcct cgtcccgtcc     360
tccgccggcc cctgccccgc gcccagggat cctccagctc ctttcgcccg cgccctccgt     420
tcgctccgga caccatggac aagttttggt ggcacgcagc ctgggactc tgcctcgtgc     480
cgctgagcct ggcgcagatc gatttgaata aacctgccg ctttgcaggt gtattccacg     540
tggagaaaaa tggtcgctac agcatctctc ggacggaggc cgctgacctc tgcaaggctt     600
tcaatagcac cttgcccaca atggcccaga tggagaaagc tctgagcatc ggatttgaga     660
cctgcaggta tgggttcata gaagggcacg tggtgattcc ccggatccac cccaactcca     720
tctgtgcagc aaacaacaca ggggtgtaca tcctcacatc caacacctcc cagtatgaca     780
catattgctt caatgcttca gctccacctg aagaagattg tacatcagtc acagacctgc     840
ccaatgcctt tgatggacca attaccataa ctattgttaa ccgtgatggc acccgctatg     900
tccagaaagg agaatacaga acgaatcctg aagacatcta ccccagcaac cctactgatg     960
atgacgtgag cagcggctcc tccagtgaaa ggagcagcac ttcaggaggt tacatctttt    1020
acacccttttc tactgtacac cccatcccag acgaagacag tccctggatc accgacagca    1080
cagacagaat ccctgctacc actttgatga gcactagtgc tacagcaact gagacagcaa    1140
ccaagaggca agaaacctgg gattggtttt catggttgtt tctaccatca gagtcaaaga    1200
atcatcttca cacaacaaca caaatggctg gtacgtcttc aaataccatc tcagcaggct    1260
gggagccaaa tgaagaaaat gaagatgaaa gagacagaca cctcagtttt tctggatcag    1320
gcattgatga tgatgaagat tttatctcca gcaccatttc aaccacacca cgggcttttg    1380
accacacaaa acagaaccag gactggaccc agtggaaccc aagccattca aatccggaag    1440
tgctacttca gacaaccaca aggatgactg atgtagacag aaatggcacc actgcttatg    1500
aaggaaactg gaacccagaa gcacaccctc ccctcattca ccatgagcat catgaggaag    1560
aagagacccc acattctaca agcacaatcc aggcaactcc tagtagtaca acggaagaaa    1620
cagctaccca gaaggaacag tggtttggca acagatggca tgagggatat cgccaaacac    1680
ccaaagaaga ctcccattcg acaacaggga cagctgcagc ctcagctcat accagccatc    1740
caatgcaagg aaggacaaca ccaagcccag aggacagttc ctggactgat tcttcaacc    1800
caatctcaca ccccatggga cgaggtcatc aagcaggaag aaggatggat atggactcca    1860
gtcatagtat aacgcttcag cctactgcaa atccaaacac aggtttggtg aagatttgg    1920
acaggacagg acctctttca atgacaacgc agcagagtaa ttctcagagc ttctctacat    1980
cacatgaagg cttggaagaa gataaagacc atccaacaac ttctactctg acatcaagca    2040
ataggaatga tgtcacaggt ggaagaagag acccaaatca ttctgaaggc tcaactactt    2100
tactggaagg ttatacctct cattaccac acacgaagga agcaggacc ttcatcccag    2160
tgacctcagc taagactggg tccttttgga gttactgcag tactgttgga gattccaact    2220
ctaatgtcaa tcgttcctta tcaggagacc aagacacatt ccacccagt ggggggtccc    2280
```

```
ataccactca tggatctgaa tcagatggac actcacatgg gagtcaagaa ggtggagcaa    2340
acacaacctc tggtcctata aggacacccc aaattccaga atggctgatc atcttggcat    2400
ccctcttggc cttggctttg attcttgcag tttgcattgc agtcaacagt cgaagaaggt    2460
gtgggcagaa gaaaaagcta gtgatcaaca gtggcaatgg agctgtggag acagaaagc    2520 caagtggact caacggagag gccagcaagt ctcaggaaat ggtgcatttg gtgaacaagg    2580
agtcgtcaga aactccagac cagtttatga cagctgatga gacaaggaac ctgcagaatg    2640
tggacatgaa gattggggtg taacacctac accattatct tggaaagaaa caaccgttgg    2700
aaacataacc attacaggga gctgggacac ttaacagatg caatgtgcta ctgattgttt    2760
cattgcgaat cttttttagc ataaaatttt ctactctttt tgttttttgt gttttgttct    2820
ttaaagtcag gtccaatttg taaaaacagc attgctttct gaaattaggg cccaattaat    2880
aatcagcaag aatttgatcg ttccagttcc cacttggagg cctttcatcc ctcgggtgtg    2940
ctatggatgg cttctaacaa aaactacaca tatgtattcc tgatcgccaa ccttccccc     3000 accagctaag gacatttccc agggttaata gggcctggtc cctgggagga aatttgaatg    3060
ggtccatttt gcccttccat agcctaatcc ctgggcattg cttccactg aggttggggg    3120 ttggggtgta ctagttacac atcttcaaca gaccccctct agaaattttt cagatgcttc    3180
tgggagacac ccaaagggtg aagctattta tctgtagtaa actatttatc tgtgtttttg    3240
aaatattaaa ccctggatca gtcctttgat cagtataatt ttttaaagtt actttgtcag    3300
aggcacaaaa gggtttaaac tgattcataa taaatatctg tacttcttcg atcttcacct    3360
tttgtgctgt gattcttcag tttctaaacc agcactgtct gggtccctac aatgtatcag    3420
gaagagctga gaatggtaag gagactcttc taagtcttca tctcagagac cctgagttcc    3480
cactcagacc cactcagcca aatctcatgg aagaccaagg agggcagcac tgttttgtt    3540 ttttgttttt tgttttttt ttttgacact gtccaaaggt tttccatcct gtcctggaat    3600
cagagttgga agctgaggag cttcagcctc ttttatggtt taatggccac ctgttctctc    3660
ctgtgaaagg ctttgcaaag tcacattaag tttgcatgac ctgttatccc tggggcccta    3720
tttcatagag gctggcccta ttagtgattt ccaaaaacaa tatggaagtg ccttttgatg    3780
tcttacaata agagaagaag ccaatggaaa tgaaagagat tggcaaaggg gaaggatgat    3840
gccatgtaga tcctgtttga cattttatg gctgtatttg taaacttaaa cacaccagtg    3900
tctgttcttg atgcagttgc tatttaggat gagttaagtg cctggggagt ccctcaaaag    3960
gttaaaggga ttcccatcat tggaatctta tcaccagata ggcaagttta tgaccaaaca    4020
agagagtact ggctttatcc tctaacctca tattttctcc cacttggcaa gtcctttgtg    4080
gcatttattc atcagtcagg gtgtccgatt ggtcctagaa cttccaaagg ctgcttgtca    4140
tagaagccat tgcatctata aagcaacggc tcctgttaaa tggtatctcc tttctgaggc    4200
tcctactaaa agtcatttgt tacctaaact tatgtgctta acaggcaatg cttctcagac    4260
cacaaagcag aaagaagaag aaaagctcct gactaaatca gggctgggct tagacagagt    4320
tgatctgtag aatatcttta aaggagagat gtcaactttc tgcactattc ccagcctctg    4380
ctcctccctg tctaccctct cccctccctc tctccctcca cttcacccca caatcttgaa    4440
aaacttcctt tctcttctgt gaacatcatt ggccagatcc attttcagtg gtctggattt    4500
ctttttattt tcttttcaac ttgaaagaaa ctggacatta ggccactatg tgttgttact    4560
gccactagtg ttcaagtgcc tcttgttttc ccagagattt cctgggtctg ccagaggccc    4620
```

-continued

```
agacaggctc actcaagctc tttaactgaa aagcaacaag ccactccagg acaaggttca    4680
aaatggttac aacagcctct acctgtcgcc ccagggagaa aggggtagtg atacaagtct    4740
catagccaga gatggttttc cactccttct agatattccc aaaaagaggc tgagacagga    4800
ggttattttc aattttattt tggaattaaa tactttttc cctttattac tgttgtagtc     4860
cctcacttgg atatacctct gttttcacga tagaaataag ggaggtctag agcttctatt    4920
ccttggccat tgtcaacgga gagctggcca agtcttcaca aacccttgca acattgcctg    4980
aagtttatgg aataagatgt attctcactc ccttgatctc aagggcgtaa ctctggaagc    5040
acagcttgac tacacgtcat ttttaccaat gattttcagg tgacctgggc taagtcattt    5100
aaactgggtc tttataaaag taaaaggcca acatttaatt attttgcaaa gcaacctaag    5160
agctaaagat gtaattttc ttgcaattgt aaatctttg tgtctcctga agacttccct      5220
taaaattagc tctgagtgaa aaatcaaaag agacaaaaga catcttcgaa tccatatttc    5280
aagcctggta gaattggctt ttctagcaga acctttccaa aagttttata ttgagattca    5340
taacaacacc aagaattgat tttgtagcca acattcattc aatactgtta tatcagagga    5400
gtaggagaga ggaaacattt gacttatctg gaaaagcaaa atgtacttaa gaataagaat    5460
aacatggtcc attcaccttt atgttataga atgtctttg tgtaaatcat tgttttgag     5520
ttttcaaaga atagcccatt gttcattctt gtgctgtaca atgaccactg ttattgttac   5580
tttgactttt cagagcacac ccttcctctg gtttttgtat atttattgat ggatcaataa   5640
taatgaggaa agcatgatat gtatattgct gagttgaaag cacttattgg aaaatattaa   5700
aaggctaaca ttaaaagact aaaggaaaca gaaaaaaaaa aaaaaaaa                 5748
```

<210> SEQ ID NO 42
<211> LENGTH: 6082
<212> TYPE: DNA
<213> ORGANISM: Artificial Sequence
<220> FEATURE:
<223> OTHER INFORMATION: CD49d (NM_000885)

<400> SEQUENCE: 42

```
ataacgtctt tgtcactaaa atgttcccca gggggccttcg gcgagtcttt ttgttttggtt   60
ttttgttttt aatctgtggc tcttgataat ttatctagtg gttgcctaca cctgaaaaac    120
aagcacagt gtttaactat caacgaaaga actggacggc tccccgccgc agtcccactc     180
cccgagtttg tggctggcat ttgggccacg ccgggctggg cggtcacagc gagggggcgcg   240
cagtttgggg tcacacagct ccgcttctag gccccaacca ccgttaaaag gggaagcccg    300
tgccccatca ggtccgctct tgctgagccc agagccatcc cgcgctctgc gggctgggag    360
gcccgggcca ggacgcgagt cctgcgcagc cgaggttccc cagcgccccc tgcagccgcg    420
cgtaggcaga gacggagccc ggccctgcgc ctccgcacca cgcccgggac cccacccagc    480
ggcccgtacc cggagaagca gcgcgagcac ccgaagctcc cggctggcgg cagaaaccgg    540
gagtggggcc gggcgagtgc gcggcatccc aggccgggcc gaacgctccg cccgcggtgg    600
gccgacttcc cctcctcttc cctctctcct tcctttagcc cgctggcgcc ggacacgctg    660
cgcctcatct cttggggcgt tcttcccgt tggccaaccg tcgcatcccg tgcaactttg     720
gggtagtggc cgtttagtgt tgaatgttcc ccaccgagag cgcatggctt gggaagcgag    780
gcgcgaaccc ggccccgaa gggccgccgt ccgggagacg gtgatgctgt tgctgtgcct    840
gggggtcccg accggccgcc cctacaacgt ggacactgag agcgcgctgc tttaccaggg   900
ccccacaac acgctgttcg gctactcggt cgtgctgcac agccacgggg cgaaccgatg     960
```

-continued

```
gctcctagtg ggtgcgccca ctgccaactg gctcgccaac gcttcagtga tcaatcccgg    1020
ggcgatttac agatgcagga tcggaaagaa tcccggccag acgtgcgaac agctccagct    1080
gggtagccct aatggagaac cttgtggaaa gacttgtttg aagagagag acaatcagtg     1140 gttggggtc acactttcca gacagccagg agaaaatgga tccatcgtga cttgtgggca     1200
tagatggaaa aatatatttt acataaagaa tgaaaataag ctccccactg gtggttgcta    1260
tggagtgccc cctgatttac gaacagaact gagtaaaaga atagctccgt gttatcaaga    1320
ttatgtgaaa aaattttggag aaaattttgc atcatgtcaa gctggaatat ccagttttta   1380
cacaaaggat ttaattgtga tgggggcccc aggatcatct tactgactg gctctctttt     1440 tgtctacaat ataactacaa ataaatacaa ggctttttta gacaaacaaa atcaagtaaa    1500
atttggaagt tatttaggat attcagtcgg agctggtcat tttcggagcc agcatactac    1560
cgaagtagtc ggaggagctc ctcaacatga gcagattggt aaggcatata tattcagcat    1620
tgatgaaaaa gaactaaata tcttacatga aatgaaaggt aaaaagcttg gatcgtactt    1680
tggagcttct gtctgtgctg tggacctcaa tgcagatggc ttctcagatc tgctcgtggg    1740
agcacccatg cagagcacca tcagagagga aggaagagtg tttgtgtaca tcaactctgg    1800
ctcgggagca gtaatgaatg caatggaaac aaacctcgtt ggaagtgaca aatatgctgc    1860
aagatttggg gaatctatag ttaatcttgg cgacattgac aatgatggct ttgaagatgt    1920
tgctatcgga gctccacaag aagatgactt gcaaggtgct atttatattt acaatggccg    1980
tgcagatggc atctcgtcaa ccttctcaca gagaattgaa ggacttcaga tcagcaaatc    2040
gttaagtatg tttggacagt ctatatcagg acaaattgat gcagataata atggctatgt    2100
agatgtagca gttggtgctt ttcggtctga ttctgctgtc ttgctaagga caagacctgt    2160
agtaattgtt gacgcttctt taagccaccc tgagtcagta aatagaacga aatttgactg    2220
tgttgaaaat ggatggcctt ctgtgtgcat agatctaaca cttttgtttct catataaggg    2280 caaggaagtt ccaggttaca ttgttttgtt ttataacatg agtttggatg tgaacagaaa    2340
ggcagagtct ccaccaagat tctatttctc ttctaatgga acttctgacg tgattacagg    2400
aagcatacag gtgtccagca gagaagctaa ctgtagaaca catcaagcat ttatgcggaa    2460
agatgtgcgg gacatcctca ccccaattca gattgaagct gcttaccacc ttggtcctca    2520
tgtcatcagt aaacgaagta cagaggaatt cccaccactt cagccaattc ttcagcagaa    2580
gaaagaaaaa gacataatga aaaaaacaat aaactttgca aggttttgtg cccatgaaaa    2640
ttgttctgct gatttacagg tttctgcaaa gattgggttt tgaagccccc atgaaaataa    2700
aacatatctt gctgttggga gtatgaagac attgatgttg aatgtgtcct tgtttaatgc    2760
tggagatgat gcatatgaaa cgactctaca tgtcaaacta cccgtgggtc tttatttcat    2820
taagatttta gagctggaag agaagcaaat aaactgtgaa gtcacagata actctggcgt    2880
ggtacaactt gactgcagta ttggctatat atatgtagat catctctcaa ggatagatat    2940
tagctttctc ctggatgtga gctcactcag cagagcggaa gaggacctca gtatcacagt    3000
gcatgctacc tgtgaaaatg aagaggaaat ggacaatcta aagcacagca gagtgactgt    3060 agcaataacct ttaaaatatg aggttaagct gactgttcat gggtttgtaa acccaacttc    3120
atttgtgtat ggatcaaatg atgaaaatga gcctgaaacg tgcatggtgg agaaaatgaa    3180
cttaactttc catgttatca acactggcaa tagtatggct cccaatgtta gtgtggaaat    3240
aatggtacca aattcttta gccccccaaac tgataagctg ttcaacattt tggatgtcca    3300
```

```
gactactact ggagaatgcc actttgaaaa ttatcaaaga gtgtgtgcat tagagcagca   3360
aaagagtgca atgcagacct tgaaaggcat agtccggttc ttgtccaaga ctgataagag   3420
gctattgtac tgcataaaag ctgatccaca ttgtttaaat ttcttgtgta attttgggaa   3480
aatggaaagt ggaaaagaag ccagtgttca tatccaactg gaaggccggc catccatttt   3540
agaaatggat gagacttcag cactcaagtt tgaaataaga gcaacaggtt ttccagagcc   3600
aaatccaaga gtaattgaac taaacaagga tgagaatgtt gcgcatgttc tactggaagg   3660
actacatcat caaagaccca aacgttattt caccatagtg attatttcaa gtagcttgct   3720
acttggactt attgtacttc tgttgatctc atatgttatg tggaaggctg gcttctttaa   3780
aagacaatac aaatctatcc tacaagaaga aaacagaaga gacagttgga gttatatcaa   3840
cagtaaaagc aatgatgatt aaggacttct ttcaaattga gagaatggaa aacagaactca  3900
ggttgtagta aagaaattta aaagacactg tttacaagaa aaaatgaatt ttgtttggac   3960
ttcttttact catgatcttg tgacatatta tgtcttcatg caaggggaaa atctcagcaa   4020
tgattactct ttgagataga agaactgcaa aggtaataat acagccaaag ataatctctc   4080
agcttttaaa tgggtagaga acactaaaag cattcaattt attcaagaaa gtaagccct    4140
tgaagatatc ttgaaatgaa agtataactg agttaaatta tactggagaa gtcttagact   4200
tgaaatacta cttaccatat gtgcttgcct cagtaaaatg aaccccactg ggtgggcaga   4260
ggttcatttc aaatacatct ttgatacttg ttcaaaatat gttctttaaa aatataattt   4320
tttagagagc tgttcccaaa ttttctaacg agtggaccat tatcactta aagcccttta    4380
tttataatac atttcctacg ggctgtgttc caacaaccat ttttttttcag cagactatga   4440
atattatagt attataggcc aaactggcaa acttcagact gaacatgtac actggtttga   4500
gcttagtgaa attacttctg gataattatt ttttataat tatggatttc accatctttc    4560
tttctgtata tatacatgtg ttttatgta ggtatatatt taccattctt cctatctatt    4620
cttcctataa cacacctttta tcaagcatac ccaggagtaa tcttcaaatc tttttgttata  4680
ttctgaaaca aaagattgtg agtgttgcac tttacctgat acacgctgat ttagaaaata   4740
cagaaaccat acctcactaa taactttaaa atcaaagctg tgcaaagact agggggccta   4800
tacttcatat gtattatgta ctatgtaaaa tattgactat cacacaacta tttccttgga   4860
tgtaattctt tgttacccctt tacaagtata agtgttacct tacatggaaa cgaagaaaca   4920
aaattcataa atttaaattc ataaatttag ctgaaagata ctgattcaat ttgtatacag   4980
tgaatataaa tgagacgaca gcaaaatttt catgaaatgt aaaatatttt tatagtttgt   5040
tcatactata tgaggttcta ttttaaatga ctttctggat tttaaaaaat ttctttaaat   5100
acaatcattt ttgtaatatt tattttatgc ttatgatcta gataattgca gaatatcatt   5160
ttatctgact ctgccttcat aagagagctg tggccgaatt ttgaacatct gttataggga   5220
gtgatcaaat tagaaggcaa tgtggaaaaa caattctggg aaagatttct ttatatgaag   5280
tccctgccac tagccagcca tcctaattga tgaaagttat ctgttcacag gcctgcagtg   5340
atggtgagga atgttctgag atttgcgaag gcatttgagt agtgaaatgt aagcacaaaa   5400
cctcctgaac ccagagtgtg tatacacagg aataaacttt atgacattta tgtatttta    5460
aaaaactttg tatcgttata aaaaggctag tcattctttc aggagaacat ctaggatcat   5520
agatgaaaaa tcaagcccg atttagaact gtcttctcca ggatggtctc taaggaaatt   5580
tacatttggt tctttcctac tcagaactac tcagaaacaa ctatatattt caggttatct   5640
gagcacagtg aaagcagagt actatggttg tccaacacag gcctctcaga tacaagggga  5700
```

```
acacaattac atattgggct agattttgcc cagttcaaaa tagtatttgt tatcaactta    5760
ctttgttact tgtatcatga attttaaaac cctaccactt taagaagaca gggatgggtt    5820 attcttttt  ggcaggtagg ctatataact atgtgatttt gaaatttaac tgctctggat    5880
tagggagcag tgaatcaagg cagacttatg aaatctgtat tatatttgta acagaatata    5940
ggaaatttaa cataattgat gagctcaaat cctgaaaaat gaaagaatcc aaattatttc    6000
agaattatct aggttaaata ttgatgtatt atgatggttg caaagttttt ttgtgtgtcc    6060
aataaacaca ttgtaaaaaa aa                                            6082

<210> SEQ ID NO 43
<211> LENGTH: 576
<212> TYPE: DNA
<213> ORGANISM: Artificial Sequence
<220> FEATURE:
<223> OTHER INFORMATION: CD31 (NM_000558)

<400> SEQUENCE: 43
actcttctgg tccccacaga ctcagagaga acccaccatg gtgctgtctc ctgccgacaa      60
gaccaacgtc aaggccgcct ggggtaaggt cggcgcgcac gctggcgagt atggtgcgga     120
ggccctggag aggatgttcc tgtccttccc caccaccaag acctacttcc cgcacttcga     180
cctgagccac ggctctgccc aggttaaggg ccacggcaag aaggtggccg acgcgctgac     240
caacgccgtg gcgcacgtgg acgacatgcc caacgcgctg tccgccctga cgacctgca      300 cgcgcacaag cttcgggtgg acccggtcaa cttcaagctc ctaagccact gcctgctggt     360
gaccctggcc gcccacctcc ccgccgagtt caccccctgcg gtgcacgcct ccctggacaa    420
gttcctggct tctgtgagca ccgtgctgac ctccaaatac cgttaagctg agcctcggt     480 ggccatgctt cttgccccctt gggcctcccc ccagcccctc ctcccctttcc tgcacccgta   540 cccccgtggt ctttgaataa agtctgagtg ggcggc                               576

<210> SEQ ID NO 44
<211> LENGTH: 3220
<212> TYPE: DNA
<213> ORGANISM: Artificial Sequence
<220> FEATURE:
<223> OTHER INFORMATION: CD106 (NM_001078)

<400> SEQUENCE: 44 aaacttttt  ccctggctct gccctgggtt tcccccttgaa gggattttccc tccgcctctg     60 caacaagacc cttataaag cacagacttt ctatttcact ccgcggtatc tgcatcgggc      120
ctcactggct tcaggagctg aatacccctcc caggcacaca caggtgggac acaaataagg    180 gtttggaac  cactatttc  tcatcacgac agcaacttaa aatgcctggg aagatggtcg      240
tgatccttgg agcctcaaat atactttgga taatgtttgc agcttctcaa gcttttaaaa     300
tcgagaccac cccagaatct agatatcttg ctcagattgg tgactccgtc tcattgactt    360
gcagcaccac aggctgtgag tccccattt  tctcttggag aacccagata gatagtccac     420
tgaatgggaa ggtgacgaat gaggggacca catctacgct gacaatgaat cctgttagtt    480
ttgggaacga acactcttac ctgtgcacag caacttgtga atctaggaaa ttggaaaaag    540
gaatccaggt ggagatctac tcttttccta aggatccaga gattcatttg agtggccctc    600
tggaggctgg gaagccgatc acagtcaagt gttcagttgc tgatgtatac ccatttgaca    660
ggctggagat agacttactg aaaggagatc atctcatgaa gagtcaggaa tttctggagg    720
```

```
atgcagacag gaagtccctg gaaaccaaga gtttggaagt aacctttact cctgtcattg      780
aggatattgg aaaagttctt gtttgccgag ctaaattaca cattgatgaa atggattctg      840
tgcccacagt aaggcaggct gtaaaagaat tgcaagtcta catatcaccc aagaatacag      900
ttatttctgt gaatccatcc acaaagctgc aagaaggtgg ctctgtgacc atgacctgtt      960
ccagcgaggg tctaccagct ccagagattt tctggagtaa gaaattagat aatgggaatc     1020
tacagcacct ttctggaaat gcaactctca ccttaattgc tatgaggatg gaagattctg     1080
gaatttatgt gtgtgaagga gttaatttga ttgggaaaaa cagaaaagag gtggaattaa     1140
ttgttcaaga gaaaccattt actgttgaga tctcccctgg accccggatt gctgctcaga     1200
ttggagactc agtcatgttg acatgtagtg tcatgggctg tgaatcccca tctttctcct     1260
ggagaaccca gatagacagc cctctgagcg ggaaggtgag gagtgagggg accaattcca     1320
cgctgaccct gagccctgtg agttttgaga acgaacactc ttatctgtgc acagtgactt     1380
gtggacataa gaaactggaa aagggaatcc aggtggagct ctactcattc cctagagatc     1440
cagaaatcga gatgagtggt ggcctcgtga atgggagctc tgtcactgta agctgcaagg     1500
ttcctagcgt gtaccccctt gaccggctgg agattgaatt acttaagggg gagactattc     1560
tggagaatat agagttttg gaggatacgg atatgaaatc tctagagaac aaaagtttgg     1620
aaatgacctt catccctacc attgaagata ctggaaaagc tcttgtttgt caggctaagt     1680
tacatattga tgacatggaa ttcgaaccca acaaaggca gagtacgcaa acactttatg     1740
tcaatgttgc ccccagagat acaaccgtct tggtcagccc ttcctccatc ctggaggaag     1800
gcagttctgt gaatatgaca tgcttgagcc agggctttcc tgctccgaaa atcctgtgga     1860
gcaggcagct ccctaacggg gagctacagc ctctttctga gaatgcaact ctcaccttaa     1920
tttctacaaa aatggaagat tctggggttt atttatgtga aggaattaac caggctggaa     1980
gaagcagaaa ggaagtggaa ttaattatcc aagttactcc aaaagacata aaacttacag     2040
ctttttcctt ctgagagtgtc aaagaaggag acactgtcat catctcttgt acatgtggaa     2100
atgttccaga acatggata atcctgaaga aaaaagcgga gacaggagac acagtactaa     2160
aatctataga tggcgcctat accatccgaa aggcccagtt gaaggatgcg ggagtatatg     2220
aatgtgaatc taaaaacaaa gttggctcac aattaagaag tttaacactt gatgttcaag     2280
gaagagaaaa caacaaagac tattttttctc ctgagcttct cgtgctctat tttgcatcct     2340
ccttaataat acctgccatt ggaatgataa tttactttgc aagaaaagcc aacatgaagg     2400
ggtcatatag tcttgtagaa gcacagaagt caaaagtgta gctaatgctt gatatgttca     2460
actggagaca ctatttatct gtgcaaatcc ttgatactgc tcatcattcc ttgagaaaaa     2520
caatgagctg agaggcagac ttccctgaat gtattgaact tggaaagaaa tgcccatcta     2580
tgtcccttgc tgtgagcaag aagtcaaagt aaaacttgct gcctgaagaa cagtaactgc     2640
catcaagatg agagaactgg aggagttcct tgatctgtat atacaataac ataatttgta     2700
catatgtaaa ataaaattat gccatagcaa gattgcttaa aatagcaaca ctctatattt     2760
agattgttaa ataactagt gttgcttgga ctattataat ttaatgcatg ttaggaaaat     2820
ttcacattaa tatttgctga cagctgacct ttgtcatctt tcttctattt tattcccttt     2880
cacaaaattt tattcctata tagtttattg acaataattt caggttttgt aaagatgccg     2940
ggttttatat ttttatagac aaataataag caaagggagc actgggttga ctttcaggta     3000
ctaaatacct caacctatgg tataatggtt gactgggttt ctctgtatag tactggcatg     3060
gtacggagat gtttcacgaa gtttgttcat cagactcctg tgcaactttc ccaatgtggc     3120
```

```
ctaaaaatgc aacttctttt tattttcttt tgtaaatgtt taggttttt tgtatagtaa    3180 agtgataatt tctggaatta gaaaaaaaaa aaaaaaaaa                          3220
```

<210> SEQ ID NO 45
<211> LENGTH: 1097
<212> TYPE: DNA
<213> ORGANISM: Artificial Sequence
<220> FEATURE:
<223> OTHER INFORMATION: FABP3 (NM_004102)

<400> SEQUENCE: 45

```
gccgtcggag cccttgcacg cctgctctct tgtagcttct ctcagcctag cccagcatca     60
ctatggtgga cgctttcctg ggacctggaa agctagtgga cagcaagaat ttcgatgact    120
acatgaagtc actcggtgtg gttttgcta ccaggcaggt ggccagcatg accaagccta    180
ccacaatcat cgaaaagaat ggggacattc tcaccctaaa aacacacagc accttcaaga    240
acacagagat cagctttaag ttggggtgg agttcgatga caacagca gatgacagga     300 aggtcaagtc cattgtgaca ctggatggag ggaaacttgt tcacctgcag aaatgggacg    360
ggcaagagac cacacttgtg cgggagctaa ttgatgaaaa actcatcctg acactcaccc    420
acggcactgc agtttgcact cgcacttatg agaaagaggc atgacctgac tgcactgttg    480
ctgactacta ctctgccaat cggctacccc tcgactcagc accacattgc ctcatttctt    540
cctctgcatt ttgtacaaat ccacgaattc ttctggggtc aggtgccact gaccgggatc    600
cagttccagt tccatggtg tatgtggttt ttttttttt ttttttaactg cactcatagg    660 gtgctctgag gtcaataaag cagagccaag gccacccagt tgccttttg cctttggtaa    720 cataactctg ggagtcttgg tttatcctgt gtgtcagaga gtgggcagaa ataacggcct    780
gaaggttact gaggaagaag cactggatgg gagactgaaa tggacagtct cggagcctgt    840
taatcagctg atcaccttac acatttaata ataaaagagc tgtacctaca cgttgccttt    900
acactgcccc ccctccatgg tcaaatgacc tagttcagtc agtgatgggg cttccccagg    960
tttggctatt gaactgtcac ttcaggccca tcctacactg aaagctcttg ggtctggctg   1020
ttctctgtga aatgctgtag tctctccctt tccagaattc aggttcaggg cacagaaccc   1080
aggcttgtac catggtg                                                 1097
```

<210> SEQ ID NO 46
<211> LENGTH: 1184
<212> TYPE: DNA
<213> ORGANISM: Artificial Sequence
<220> FEATURE:
<223> OTHER INFORMATION: CXCL1 (NM_001511)

<400> SEQUENCE: 46

```
cacagagccc gggccgcagg cacctcctcg ccagctcttc cgctcctctc acagccgcca     60
gacccgcctg ctgagcccca tggcccgcgc tgctctctcc gccgcccca gcaatccccg    120 gctcctgcga gtggcactgc tgctcctgct cctggtagcc gctggccggc gcgcagcagg    180
agcgtccgtg gccactgaac tgcgctgcca gtgcttgcag accctgcagg gaattcaccc    240
caagaacatc caaagtgtga acgtgaagtc ccccggaccc cactgcgccc aaaccgaagt    300
catagccaca ctcaagaatg ggcggaaagc ttgcctcaat cctgcatccc ccatagttaa    360
gaaaatcatc gaaaagatgc tgaacagtga caaatccaac tgaccagaag ggaggaggaa    420
gctcactggt ggctgttcct gaaggaggcc ctgcccttat aggaacagaa gaggaaagag    480
```

| | |
|---|---|
| agacacagct gcagaggcca cctggattgt gcctaatgtg tttgagcatc gcttaggaga | 540 |
| agtcttctat ttatttattt attcattagt tttgaagatt ctatgttaat attttaggtg | 600 |
| taaaataatt aagggtatga ttaactctac ctgcacactg tcctattata ttcattcttt | 660 |
| ttgaaatgtc aaccccaagt tagttcaatc tggattcata tttaatttga aggtagaatg | 720 |
| ttttcaaatg ttctccagtc attatgttaa tatttctgag gagcctgcaa catgccagcc | 780 |
| actgtgatag aggctggcgg atccaagcaa atggccaatg agatcattgt gaaggcaggg | 840 |
| gaatgtatgt gcacatctgt tttgtaactg tttagatgaa tgtcagttgt tatttattga | 900 |
| aatgatttca cagtgtgtgg tcaacatttc tcatgttgaa actttaagaa ctaaaatgtt | 960 |
| ctaaatatcc cttggacatt ttatgtcttt cttgtaaggc atactgcctt gtttaatggt | 1020 |
| agttttacag tgtttctggc ttagaacaaa ggggcttaat tattgatgtt ttcatagaga | 1080 |
| atataaaaat aaagcactta tagaaaaaac tcgtttgatt tttgggggga aacaagggct | 1140 |
| accttactg gaaaatctgg tgatttataa aaaaaaaaaa aaaa | 1184 |

<210> SEQ ID NO 47
<211> LENGTH: 5008
<212> TYPE: DNA
<213> ORGANISM: Artificial Sequence
<220> FEATURE:
<223> OTHER INFORMATION: SYT14 (NM_153262)

<400> SEQUENCE: 47

| | |
|---|---|
| ccctctcgct ggcggactca gcgcgtcctc cgccagccct cgcgtctgct gcccccgcca | 60 |
| tccagttggt gcggtccatg gcgagcgcat catggcgatt gaaggtggag agagaacctg | 120 |
| tggagtacat gaacttatct gtattagaaa agtatctcca gaggcagttg gattttttgtc | 180 |
| agctgttggg gtgtttatta tcttgatgct gctccttttt ctctatatta ataagaagtt | 240 |
| ctgttttgaa aatgttggcg ggtttccaga tcttggttca gaatacagta caaggaagaa | 300 |
| ttcacaagat aaaatttata attcctacat ggacaaagat gagcatggtt catcctctga | 360 |
| aagtgaagat gaagcgctgg gtaaatatca tgaggcctta tccagaacac acaattccag | 420 |
| actaccactg gcagattcta gacaaaggaa ctatgcttgg gaaacaaggc agaaatacag | 480 |
| tcctctatcg gcagagtatg atggatacag tagtgaagca tcaatagatg aaggaaactg | 540 |
| cattcagaga atgagaagaa cacccccgct ggatgaattg cagccaccac catatcagga | 600 |
| tgacagtggt tctcccccatc tgtcatgtac accctcagaa attggggaca gtaaatgtga | 660 |
| attttcccac tgcagcaaca gtccaagatg ctcatataac aagtgcccaa gtgaaggaag | 720 |
| cacaggtcat gaaatagaaa gttttcataa taaaggatat gaagaagatg ttccaagtga | 780 |
| cagcactgca gtcctgagcc ctgaagatat gtcagctcaa ggatcatctt cgcagcttcc | 840 |
| taaacctttt gatcctgagc cagaagctaa atatggcaca ctggatgtga cttttgacta | 900 |
| tgactcacaa gaacagaagc ttctggtaac agtgacagct gtcacagaca tcccaacata | 960 |
| taacaggaca ggtggcaact catggcaagt acaccttgtt cttctaccta taagaaaaca | 1020 |
| gagagcaaaa accagcatcc agagaggacc atgccctgtc ttcacagaaa catttaaatt | 1080 |
| taatcatgtt gaatctgaga tgattggaaa ttatgcagtt cggtttagac tgtatggtgt | 1140 |
| acatcgcatg aaaaagaaa agattgtggg ggaaaagatt tttatttaa caaaattgaa | 1200 |
| tcttcaaggg aaaatgtcat tgcctgtgat attggaacct tcttacaatc attctggctg | 1260 |
| tgactcccaa atgagcgtgt cagaaatgtc gtgtagtgaa agtacatcct catgtcagtc | 1320 |
| tcttgaacat ggctcagttc cagaaattct tattggcctg cttttataatg ccacaactgg | 1380 |

```
aagactatca gcagaagtga taaaaggcag ccacttcaaa aatttggcag caaacagacc  1440
acccaataca tatgttaagt taactctact gaattccatg ggtcaagaga tgtccaaatg  1500
caagacatcc atccgcagag ggcagccaaa tccagtatat aaggaaactt ttgtctttca  1560
agtggcccta tttcagcttt ctgatgtgac actcatactg tctgtgtata acaaacgcag  1620
catgaaaaga aaagagatga taggctggat ttctttaggt ctcaacagct ctggagaaga  1680
agaactcaat cactggactg aaatgaaaga gtcaaaagga cagcaagtat gtagatggca  1740
tgcgttgcta gagtcatgat gaatagaata agcaagcagt taccatcaaa ggcagcatat  1800
ttccaattcc aacattactg tttctaccaa gtcccattag aagagctgtt ctttgaagaa  1860
tcatattcaa ccttctacca aaatgcttta agttctatgg aaagaacgtc tcatactgac  1920
ataaatgaag aaaatatgtg tatctagtag agcttgttta ggaaactgag aaacgtacac  1980
tatcattgct aaactaacag tcctccagaa atttaataag atgttttga tttgaagtta  2040
attttaattt agcaaaagag ccagtcattt tatgaaaaat caaaattata agtgatttta  2100
aaaaccagaa ttttagttgc aatacaattt taatatcacc ctacatatta tttataaaac  2160
atagtttgac tggccagtcc ctggtgtttg taatgttctt taatatgaaa aagtagttct  2220
ccaactctat cataagtcat atctaatggt gaagggtttc agtcacattg aaaattgttt  2280
tatttcaggc atgttccctt tgtgcactta ggttcattgt gcctcagttc ctctcaaaag  2340
cactaaatct aagtgcaaac aagtattcat tttcatacag gaatttttt aatatgttat  2400
ttttttaaaa gttcattttt catttgcctc cgctttcgcc tgatccaaag agaccaagtc  2460
actgtactgg tcccttgcaa gtcttctaga caggttgtac tgtagaacta cgtaactttc  2520
tgttgaaagc acttcctgta ttcttgtatt ccaatgtagg aagctaatag agcaggactt  2580
tactttcaaa tttctttcag tgattgactc ttcaaaattg cagtagtgtg aaaatacatt  2640
ttttacaaac tgaaaataca gtagataagc tgtcgaaaat ggaaacaat tcaattttaa  2700
ttttctgctc tgagtattta gtaaccaaca ctgcgtaaag caggtagcat tcaaaataag  2760
aaactgttct ctctctaaat cttcactctt acttcaattt atatttgtga tatgaagact  2820
atccagttct cagtttgaat tggaacatca tgttaaaaac agttatgaga ttccttatga  2880
agtttctagt aacttgtaac tagactttat gaaattaaca gataaagttc ttcaacgtga  2940
tgtcatcttg tgcctttcat gtaagttaaa tttgctcata cagcttgaac gttgtatttg  3000
caaaattaag ccttcgattt ttataaatgt aaagattcct cagaacagtg tcgcaagatc  3060
tttatttcct ctgaagtatg taaagttgt ataatgtgct aacttttaa tggcaaggca  3120
ctttcatttg tttttatatt taggaactct aatcaggaat attataagct gttttctttt  3180
taattttgct tcttacctaa tatatcattt tatgcatata ctttatcaga gtatgtttta  3240
tatatattaa aaatagtttc ttttttctcc ttctcatttc tagttaaaat agacaaaaac  3300
atactattta ccagttacta aaaagcagta tatcattgct tctagtccca actaagtact  3360
atatattatt gtaaactaga acttgttatt accataataa caaaacaatg cgtagatatt  3420
acttcagctt ggctgtactg aaaggcctta aagaaaccc aaaagaccg tgaacttctg  3480
tatttttta gtttaaaaaa tggcagctct atgcattcat acacatgaat tataagaaaa  3540
aatacaaatg ctatattgga tgacatgagg tttgagaatg tgtgttacag ggctgcatta  3600
aagggaaaaa tccatctttt attgttacat caatgagctt tttccaggat ttttcaaata  3660
aacaagtaag agttagaacc tgaatcaaat ggcaaaatat ctcatttaag tgttttcagc  3720
```

| | |
|---|---|
| aacagtatga aaaaagactt gaagagggga tgtagatttt actgagaaat tggacttagg | 3780 |
| catttgaagc tataatgaac tttttagact ttgaaacaac tgactgcatt gctaacaact | 3840 |
| gttatcttcc taataaaaag agttatcagt cttatctgta actgtaacag agcttagtga | 3900 |
| aacacattag taagaccagc ttggtgcttt cactcttagt gagaaaaaga cctaactaat | 3960 |
| tgttatttgt taaatctacc ttttttcaga ctattcccag aattgtgtgt gtgatttgat | 4020 |
| acatccctag ggatttatct ggcataagta tcaaatcctt catggcttaa aaattaataa | 4080 |
| acagtttttt aatatttctg gaaagaccct acctccaccc cagctgccaa gtcctcaaag | 4140 |
| attataaatt atctatatga gtgtatgtat ctgtatacac acatgcacca ttacacatac | 4200 |
| aacataaata tgtatatgta tattcatttg taaaggcaaa ggtgccctgg cttttttcaga | 4260 |
| taactgaata gaaaaacatt tcatacattt aggattattt ttctcctcta tgtatttact | 4320 |
| agatattata tttggtttgg gttgcttttct gctgctgttc tccttcacac acagcaaaat | 4380 |
| atacatttgt ttctgtagat tgacacaact tataataatt actcccaaaa agttgtctgt | 4440 |
| tcttttagaa aaggattaaa taaggctcag gggacccact tcactctact gaatctaatg | 4500 |
| tacgagacag tactactgct tctttgtgtg cttgaatttg catgaaagct taatagcaaa | 4560 |
| atcttctatc tcagtaatta tagcaaatag ggacctactg gtagggagca ggtgttggct | 4620 |
| cagaaacctg aaaagacaa cccactttca tacagttcta ttaaaatccc ctaagttttc | 4680 |
| taataaaaatg atatagtcca aatatggcaa tcgactggca tttatgggag cctctaaacc | 4740 |
| tggaattatg gggtttattt ttctcccaaa tgagctgcaa aagataatta ttgctgccca | 4800 |
| gtaaacaaaa tgtatgtcaa atcagtaaag aatttgttta gcataatatt gccttatctt | 4860 |
| tcagaagctt tcttctatat tcttgtgtct tcagtacaat ccactttgt ttgaaatcca | 4920 |
| tttgcatatt atcttactgt gcatttagtg aattctcaat aatgttgtat ttgctgacaa | 4980 |
| gaataataaa ttggaccaca attaaaaa | 5008 |

<210> SEQ ID NO 48
<211> LENGTH: 4320
<212> TYPE: DNA
<213> ORGANISM: Artificial Sequence
<220> FEATURE:
<223> OTHER INFORMATION: EDNRB (NM_001122659)

<400> SEQUENCE: 48

| | |
|---|---|
| aagaaaaaca gctgagaggg catcaggaag gagtttcgac ccgcgctggc gagtcatgag | 60 |
| cgccaagttt cccactggcg cgcaaacttg agttactttt gagcgtggat actggcgaag | 120 |
| aggctgcggg cggtattagc gtttgcagcg acttggctcg ggcagctgac ccaagtgtcc | 180 |
| tgtcttcctt cctctgcttg tctctaggct ctgaaactgc ggagcggcca ccggacgcct | 240 |
| tctggagcag gtagcagcat gcagccgcct ccaagtctgt gcggacgcgc cctggttgcg | 300 |
| ctggttcttg cctgcggcct gtcgcggatc tggggagagg agagaggctt cccgcctgac | 360 |
| agggccactc cgcttttgca aaccgcagag ataatgacgc cacccactaa gaccttatgg | 420 |
| cccaagggtt ccaacgccag tctggcgcgg tcgttggcac ctgcggaggt gcctaaagga | 480 |
| gacaggacgg caggatctcc gccacgcacc atctcccctc ccccgtgcca aggacccatc | 540 |
| gagatcaagg agactttcaa atacatcaac acggttgtgt cctgccttgt gttcgtgctg | 600 |
| gggatcatcg ggaactccac acttctgaga attatctaca agaacaagtg catgcgaaac | 660 |
| ggtcccaata tcttgatcgc cagcttggct ctggagacc tgctgcacat cgtcattgac | 720 |
| atccctatca atgtctacaa gctgctggca gaggactggc catttggagc tgagatgtgt | 780 |

```
aagctggtgc ctttcataca gaaagcctcc gtgggaatca ctgtgctgag tctatgtgct    840
ctgagtattg acagatatcg agctgttgct tcttggagta gaattaaagg aattgggtt    900
ccaaaatgga cagcagtaga aattgttttg atttgggtgg tctctgtggt tctggctgtc    960
cctgaagcca taggttttga tataattacg atggactaca aaggaagtta tctgcgaatc   1020
tgcttgcttc atcccgttca gaagacagct ttcatgcagt tttacaagac agcaaaagat   1080
tggtggctat tcagtttcta tttctgcttg ccattggcca tcactgcatt ttttatac a   1140
ctaatgacct gtgaaatgtt gagaaagaaa gtggcatgc agattgcttt aaatgatcac   1200
ctaaagcaga gacgggaagt ggccaaaacc gtcttttgcc tggtccttgt ctttgccctc   1260
tgctggcttc cccttcacct cagcaggatt ctgaagctca ctctttataa tcagaatgat   1320
cccaatagat gtgaactttt gagctttctg ttggtattgg actatattgg tatcaacatg   1380
gcttcactga attcctgcat taacccaatt gctctgtatt tggtgagcaa aagattcaaa   1440
aactgcttta gtcatgctt atgctgctgg tgccagtcat ttgaagaaaa acagtccttg   1500
gaggaaaagc agtcgtgctt aaagttcaaa gctaatgatc acggatatga caacttccgt   1560
tccagtaata aatacagctc atcttgaaag aagaactatt cactgtattt cattttcttt   1620
atattggacc gaagtcatta aaacaaaatg aaacatttgc caaaacaaaa caaaaaacta   1680
tgtatttgca cagcacacta ttaaaatatt aagtgtaatt attttaacac tcacagctac   1740
atatgacatt ttatgagctg tttacggcat ggaaagaaaa tcagtgggaa ttaagaaagc   1800
ctcgtcgtga aagcacttaa ttttttacag ttagcacttc aacatagctc ttaacaactt   1860
ccaggatatt cacacaacac ttaggcttaa aaatgagctc actcagaatt tctattcttt   1920
ctaaaaagag atttattttt aaatcaatgg gactctgata taaaggaaga ataagtcact   1980
gtaaaacaga acttttaaat gaagcttaaa ttactcaatt taaaatttta aaatccttta   2040
aaacaacttt tcaattaata ttatcacact attatcagat tgtaattaga tgcaaatgag   2100
agagcagttt agttgttgca ttttttcggac actggaaaca tttaaatgat caggagggag   2160
taacagaaag agcaaggctg ttttttgaaaa tcattacact ttcactagaa gcccaaacct   2220
cagcattctg caatatgtaa ccaacatgtc acaaacaagc agcatgtaac agactggcac   2280
atgtgccagc tgaatttaaa atataatact tttaaaaaga aaattattac atcctttaca   2340
ttcagttaag atcaaacctc acaaagagaa atagaatgtt tgaaaggcta tcccaaaaga   2400
cttttttgaa tctgtcattc acataccctg tgaagacaat actatctaca atttttttcag   2460
gattattaaa atcttcttct ttcactatcg tagcttaaac tctgttggt tttgtcatct   2520
gtaaatactt acctacatac actgcatgta gatgattaaa tgagggcagg ccctgtgctc   2580
atagctttac gatggagaga tgccagtgac ctcataataa agactgtgaa ctgcctggtg   2640
cagtgtccac atgacaaagg ggcaggtagc accctctctc acccatgctg tggttaaaat   2700
ggtttctagc atatgtataa tgctatagtt aaaatactat ttttcaaaat catacagatt   2760
agtacattta acagctacct gtaaagctta ttactaattt ttgtattatt tttgtaaata   2820
gccaatagaa aagtttgctt gacatggtgc ttttctttca tctagaggca aaactgcttt   2880
ttgagaccgt aagaacctct tagctttgtg cgttcctgcc taattttat atcttctaag   2940
caaagtgcct taggatagct tgggatgaga tgtgtgtgaa agtatgtaca agagaaaacg   3000
gaagagagag gaaatgaggt ggggttggag gaaacccatg gggacagatt cccattctta   3060
gcctaacgtt cgtcattgcc tcgtcacatc aatgcaaaag gtcctgattt tgttccagca   3120
```

-continued

| | | | | | |
|---|---|---|---|---|---|
| aaacacagtg | caatgttctc | agagtgactt | tcgaaataaa | ttgggcccaa | gagctttaac | 3180 |
| tcggtcttaa | aatatgccca | aattttact | ttgttttct | tttaataggc | tgggccacat | 3240 |
| gttggaaata | agctagtaat | gttgtttct | gtcaatattg | aatgtgatgg | tacagtaaac | 3300 |
| caaaacccaa | caatgtggcc | agaaagaaag | agcaataata | attaattcac | acaccatatg | 3360 |
| gattctattt | ataaatcacc | cacaaacttg | ttctttaatt | tcatcccaat | cacttttca | 3420 |
| gaggcctgtt | atcatagaag | tcattttaga | ctctcaattt | taaattaatt | ttgaatcact | 3480 |
| aatattttca | cagtttatta | atatattaa | tttctattta | aattttagat | tattttatt | 3540 |
| accatgtact | gaattttac | atcctgatac | cctttcttc | tccatgtcag | tatcatgttc | 3600 |
| tctaattatc | ttgccaaatt | ttgaaactac | acacaaaaag | catacttgca | ttatttataa | 3660 |
| taaaattgca | ttcagtggct | ttttaaaaaa | atgtttgatt | caaaactta | acatactgat | 3720 |
| aagtaagaaa | caattataat | ttctttacat | actcaaaacc | aagatagaaa | aaggtgctat | 3780 |
| cgttcaactt | caaaacatgt | ttcctagtat | taaggacttt | aatatagcaa | cagacaaaat | 3840 |
| tattgttaac | atggatgtta | cagctcaaaa | gatttataaa | agattttaac | ctattttctc | 3900 |
| ccttattatc | cactgctaat | gtggatgtat | gttcaaacac | cttttagtat | tgatagctta | 3960 |
| catatggcca | aaggaataca | gtttatagca | aaacatgggt | atgctgtagc | taactttata | 4020 |
| aaagtgtaat | ataacaatgt | aaaaaattat | atatctggga | ggattttg | gttgcctaaa | 4080 |
| gtggctatag | ttactgattt | tttattatgt | aagcaaaacc | aataaaaatt | taagtttttt | 4140 |
| taacaactac | cttatttttc | actgtacaga | cactaattca | ttaaatacta | attgattgtt | 4200 |
| taaaagaaat | ataatgtga | caagtggaca | ttatttatgt | taaatataca | attatcaagc | 4260 |
| aagtatgaag | ttattcaatt | aaaatgccac | atttctggtc | tctgggaaaa | aaaaaaaaa | 4320 |

<210> SEQ ID NO 49
<211> LENGTH: 1365
<212> TYPE: DNA
<213> ORGANISM: Artificial Sequence
<220> FEATURE:
<223> OTHER INFORMATION: MHC class I polypeptide-related sequence A
(NM_000247)

<400> SEQUENCE: 49

| | | | | | |
|---|---|---|---|---|---|
| cactgcttga | gccgctgaga | gggtggcgac | gtcggggcca | tggggctggg | cccggtcttc | 60 |
| ctgcttctgg | ctggcatctt | cccttttgca | cctccgggag | ctgctgctga | gcccacagt | 120 |
| cttcgttata | acctcacggt | gctgtcctgg | gatggatctg | tgcagtcagg | gtttctcact | 180 |
| gaggtacatc | tggatggtca | gcccttcctg | cgctgtgaca | ggcagaaatg | cagggcaaag | 240 |
| ccccagggac | agtgggcaga | agatgtcctg | ggaaataaga | catgggacag | agagaccaga | 300 |
| gacttgacag | ggaacggaaa | ggacctcagg | atgaccctgg | ctcatatcaa | ggaccagaaa | 360 |
| gaaggcttgc | attccctcca | ggagattagg | gtctgtgaga | tccatgaaga | caacagcacc | 420 |
| aggagctccc | agcatttcta | ctacgatggg | gagctcttcc | tctcccaaaa | cctggagact | 480 |
| aaggaatgga | caatgcccca | gtcctccaga | gctcagacct | tggccatgaa | cgtcaggaat | 540 |
| ttcttgaagg | aagatgccat | gaagaccaag | acacactatc | acgctatgca | tgcagactgc | 600 |
| ctgcaggaac | tacggcgata | tctaaaatcc | ggcgtagtcc | tgaggagaac | agtgccccc | 660 |
| atggtgaatg | tcacccgcag | cgaggcctca | gagggcaaca | ttaccgtgac | atgcagggct | 720 |
| tctggcttct | atccctggaa | tatcacactg | agctggcgtc | aggatggggt | atctttgagc | 780 |
| cacgacaccc | agcagtgggg | ggatgtcctg | cctgatggga | atggaaccta | ccagacctgg | 840 |

| | |
|---|---|
| gtggccacca ggatttgcca aggagaggag cagaggttca cctgctacat ggaacacagc | 900 |
| gggaatcaca gcactcaccc tgtgccctct gggaaagtgc tggtgcttca gagtcattgg | 960 |
| cagacattcc atgtttctgc tgttgctgct gctgctattt ttgttattat tattttctat | 1020 |
| gtccgttgtt gtaagaagaa aacatcagct gcagagggtc cagagctcgt gagcctgcag | 1080 |
| gtcctggatc aacacccagt tgggacgagt gaccacaggg atgccacaca gctcggattt | 1140 |
| cagcctctga tgtcagatct tgggtccact ggctccactg agggcgccta gactctacag | 1200 |
| ccaggcagct gggattcaat tccctgcctg gatctcacga gcactttccc tcttggtgcc | 1260 |
| tcagtttcct gacctatgaa acagagaaaa taaaagcact tatttattgt tgttggaggc | 1320 |
| tgcaaaatgt tagtagatat gaggcgtttg cagctgtacc atatt | 1365 |

<210> SEQ ID NO 50
<211> LENGTH: 2309
<212> TYPE: DNA
<213> ORGANISM: Artificial Sequence
<220> FEATURE:
<223> OTHER INFORMATION: pancreatic lipase-related protein 3
(NM_001011709)

<400> SEQUENCE: 50

| | |
|---|---|
| tgcatcattg tgaggaaaac cacttagtat tttatagtga ggtgacttta caagtaaaga | 60 |
| tcttcaagaa gatttttatg tgattaaaaa aatcagctta gatgcttgga atttggattg | 120 |
| ttgcattctt gttctttggc acatcaagag gaaaagaagt ttgctatgaa aggttagggt | 180 |
| gtttcaaaga tggtttacca tggaccagga ctttctcaac agagttggta ggtttaccct | 240 |
| ggtctccaga gaagataaac actcgtttcc tgctctacac tatacacaat cccaatgcct | 300 |
| atcaggagat cagtgcggtt aattcttcaa ctatccaagc tcatattttt ggaacagaca | 360 |
| agatcacccg tatcaacata gctggatgga aaacagatgg caaatggcag agagacatgt | 420 |
| gcaatgtgtt gctacagctg gaagataaaa attgcattaa tttagattgg atcaacggtt | 480 |
| cacgggaata catccatgct gtaaacaatc tccgtgttgt tggtgctgag gtggcttatt | 540 |
| ttattgatgt tctcatgaaa aaatttgaat attccccttc taaagtgcac ttgattggcc | 600 |
| acagcttggg agcacacctg gctggggaag ctgggtcaag gataccaggc cttggaagaa | 660 |
| taactgggtt ggacccagct gggccatttt ccacaacac tccaaaggaa gtcaggctag | 720 |
| accccctcgga tgccaacttt gttgacgtta ttcatacaaa tgcagctcgc atcctctttg | 780 |
| agcttggtgt tggaaccatt gatgcttgtg gtcatcttga cttttaccca aatggaggga | 840 |
| agcacatgcc aggatgtgaa gacttaatta cacctttact gaaatttaac ttcaatgctt | 900 |
| acaaaaaaga aatggcttcc ttctttgact gtaaccatgc ccgaagttat caatttttatg | 960 |
| ctgaaagcat tcttaatcct gatgcattta ttgcttatcc ttgtagatcc tacacatctt | 1020 |
| ttaaagcagg aaattgcttc ttttgttcca agaaggttg cccaacaatg ggtcattttg | 1080 |
| ctgatagatt tcacttcaaa aatatgaaga ctaatggatc acattatttt taaacacag | 1140 |
| ggtccctttc cccatttgcc cgttggaggc acaaattgtc tgttaaactc agtggaagcg | 1200 |
| aagtcactca aggaactgtc tttcttcgtg taggcgtggc agttaggaaa actggggagt | 1260 |
| ttgccattgt cagtggaaaa cttgagccag gcatgactta cacaaaatta atcgatgcag | 1320 |
| atgttaacgt tggaaacatt acaagtgttc agttcatctg gaaaaaacat ttgtttgaag | 1380 |
| attctcagaa taagttggga gcagaaatgg tgataaatac atctgggaaa tatggatata | 1440 |
| aatctacctt ctgtagccaa gacattatgg gacctaatat tctccagaac ctgaaaccat | 1500 |

| | |
|---|---|
| gctaatctca gatacagtct tgatggattt ctttagtagg agcaatgaag aaaagtgtct | 1560 |
| ccttccacct ggcatccaga ccaaatttga cccttgtaaa tgacttagtc atttacaagg | 1620 |
| gtcttactca gagtcaagta cgggtttgct ttttttctgt gtagaatgtt catctaactg | 1680 |
| caccttaaaa acacactgaa ccctgggaca aaagataatt actatgatct gtaggaatct | 1740 |
| ggatatcatt gacaaaatag agctgttttg gaattttcct gaataagagg aggtgatgca | 1800 |
| aatgtatgtt gagtgtataa actcactgga caaaagtaag cctctggctt gctgagtttt | 1860 |
| tgaagtatat tttcaggtat aataatcatt gttctaaaat tatataaaac tatttgttat | 1920 |
| gttgttaaat cttgctgaga caaattatga ctatagtgca tgatatatag tagattataa | 1980 |
| ccttgtgggt tgatgtgtct atctagtaat aataaaaact aatgagatgg cactagtatt | 2040 |
| tccaaggtgt tccttggtgt tcagggtgtg cacaagagag attttggagc ttatctgtta | 2100 |
| tgtgttcatc agttagcaat gggacctgaa gttcaacaac ccagggtata gccccttcc | 2160 |
| tccaaagtcc ctgccacagg agaattactc ctctccctgg gtcttgaatg ctctatggtg | 2220 |
| aatttgtatt tagcctcaag gcagcatttc atttgtaaag cacttgggta accctttgtt | 2280 |
| cttgcaataa caatattata atatttaaa | 2309 |

<210> SEQ ID NO 51
<211> LENGTH: 2974
<212> TYPE: DNA
<213> ORGANISM: Artificial Sequence
<220> FEATURE:
<223> OTHER INFORMATION: secreted frizzled-related protein 4 (NM_003014)

<400> SEQUENCE: 51

| | |
|---|---|
| gcggccgagg gggagcccgc gccgcggctg cagctgccaa gggagcgttc cgagcccacg | 60 |
| tcaggggagg tgtcgggata aatagggtcc cgcaatggcc gtggctggct gcgctccgag | 120 |
| ctgcggagtc cgggactgga gctgcccggg cgggttcgcg ccccgaaggc tgagagctgg | 180 |
| cgctgctcgt gccctgtgtg ccagacggcg gagctccgcg gccggacccc gcggccccgc | 240 |
| tttgctgccg actggagttt gggggaagaa actctcctgc gccccagagg atttcttcct | 300 |
| cggcgaaggg acagcgaaag atgagggtgg caggaagaga agggcgcttt ctgtctgccg | 360 |
| gggtcgcagc gcgagagggc agtgccatgt tcctctccat cctagtggcg ctgtgcctgt | 420 |
| ggctgcacct ggcgctgggc gtgcgcgcg cgccctgcga ggcggtgcgc atccctatgt | 480 |
| gccgcacat gccctggaac atcacgcgga tgcccaacca cctgcaccac agcacgcagg | 540 |
| agaacgccat cctggccatc gagcagtacg aggagctggt ggacgtgaac tgcagcgccg | 600 |
| tgctgcgctt cttcctctgt gccatgtacg cgcccatttg caccctggag ttcctgcacg | 660 |
| acccctatca agccgtgcaa gtcggtgtgc aacgcgcgcg cgacgactgc gagcccctca | 720 |
| tgaagatgta caaccacagc tggcccgaaa gcctggcctg cgacgagctg cctgtctatg | 780 |
| accgtggcgt gtgcatctcg cctgaagcca tcgtcacgga cctcccggag gatgttaagt | 840 |
| ggatagacat cacaccagac atgatggtac aggaaaggcc tcttgatgtt gactgtaaac | 900 |
| gcctaagccc cgatcggtgc aagtgtaaaa aggtgaagcc aactttggca acgtatctca | 960 |
| gcaaaaacta cagctatgtt attcatgcca aaataaaagc tgtgcagagg agtgctgca | 1020 |
| atgaggtcac aacggtggtg gatgtaaaag agatcttcaa gtcctcatca cccatccctc | 1080 |
| gaactcaagt cccgctcatt acaaaattctt cttgccagtg tccacacatc ctgcccatc | 1140 |
| aagatgttct catcatgtgt tacgagtggc gctcaaggat gatgcttctt gaaaattgct | 1200 |
| tagttgaaaa atgagagat cagcttagta aaagatccat acagtgggaa gagaggctgc | 1260 |

| | |
|---|---|
| aggaacagcg gagaacagtt caggacaaga agaaaacagc cgggcgcacc agtcgtagta | 1320 |
| atcccccaa accaaaggga aagcctcctg ctcccaaacc agccagtccc aagaagaaca | 1380 |
| ttaaaactag gagtgcccag aagagaacaa acccgaaaag agtgtgagct aactagtttc | 1440 |
| caaagcggag acttccgact tccttacagg atgaggctgg gcattgcctg ggacagccta | 1500 |
| tgtaaggcca tgtgcccctt gccctaacaa ctcactgcag tgctcttcat agacacatct | 1560 |
| tgcagcattt ttcttaaggc tatgcttcag tttttctttg taagccatca caagccatag | 1620 |
| tggtaggttt gcccttttggt acagaaggtg agttaaagct ggtggaaaag gcttattgca | 1680 |
| ttgcattcag agtaacctgt gtgcatactc tagaagagta gggaaaataa tgcttgttac | 1740 |
| aattcgacct aatatgtgca ttgtaaaata aatgccatat ttcaaacaaa acacgtaatt | 1800 |
| tttttacagt atgtttttatt accttttgat atctgttgtt gcaatgttag tgatgtttta | 1860 |
| aaatgtgatc gaaatataa tgcttctaag aaggaacagt agtggaatga atgtctaaaa | 1920 |
| gatctttatg tgtttatggt ctgcagaagg attttttgtga tgaaagggga ttttttgaaa | 1980 |
| aatctagaga agtagcatat ggaaaactat aatgtgtctt ttttacaatg acttcagctc | 2040 |
| tgttttagc tagaaactct aaaaacaaaa ataataataa agaaaaataa ataaaaagga | 2100 |
| gaggcagaca atgtctggat tcctgttttt tggttacctg atttcatgat catgatgctt | 2160 |
| cttgtcaaca ccctcttaag cagcaccaga aacagtgagt ttgtctgtac cattaggagt | 2220 |
| taggtactaa ttagttggct aatgctcaag tattttatac ccacaagaga ggtatgtcac | 2280 |
| tcatcttact tcccaggaca tccaccctga gaataatttg acaagcttaa aaatggcctt | 2340 |
| catgtgagtg ccaaattttg ttttcttcat ttaaatattt tctttgccta aatacatgtg | 2400 |
| agaggagtta aatataaatg tacagagagg aaagttgagg ttccacctct gaaatgagaa | 2460 |
| ttacttgaca gttgggatac tttaatcaga aaaaagaac ttatcttgca gcattttatc | 2520 |
| aacaaatttc ataattgtgg acaattggag gcatttattt taaaaaacaa ttttattggc | 2580 |
| cttttgctaa cacagtaagc atgtattctc tataaggcat tcaataaatg cacaacgccc | 2640 |
| aaaggaaata aaatcctatc taatcctact ctccactaca cagaggtaat cactattagt | 2700 |
| attttggcat attattctcc aggtgtttct tatgcactta taaaatgatt tgaacaaata | 2760 |
| aaactaggaa cctgctatac atgtgtttca taacctgcct cctttgcttg gcccttttatt | 2820 |
| gagataagtt ttcctgtcaa gaaagcagaa accatctcat ttctaacagc tgtgttatat | 2880 |
| tccatagtat gcattactca acaaactgtt gtgctattgg atacttaggt ggtttcttca | 2940 |
| ctgacaatac tgaataaaca tctcaatagt caaa | 2974 |

<210> SEQ ID NO 52
<211> LENGTH: 9443
<212> TYPE: DNA
<213> ORGANISM: Artificial Sequence
<220> FEATURE:
<223> OTHER INFORMATION: Sestrin 3 (NM_144665)

<400> SEQUENCE: 52

| | |
|---|---|
| agccgccgcc gtctccgccg tcgctggggc agctgccgcg gtggtcgcct ctggcagtgc | 60 |
| cgctagcttt caggcagtcg cctctcctcc cgacatcccg ccttgaggag gctgaggcgg | 120 |
| aatcgcggct ggcggcgggg ggacggaccg gccctgcagt ggccgcagtg acagcccgga | 180 |
| cccggccctc cgcccgctct cgcctcggcg cccgcagcca cgatgaaccg gggcggcggc | 240 |
| agcccgtcgg ccgccgccaa ctacctgctc tgtaccaact gccggaaagt gctgcggaag | 300 |

-continued

```
gataaaagaa tcagagtgtc tcaacccttg acaagaggac caagtgcctt tattccagag    360
aaggaagttg tccaagcaaa cacagtggat gaacgtacta actttcttgt ggaagaatac    420
tctacatccg gtcgtctgga caacatcaca caggtcatga gtttacacac tcagtacctg    480
gagtctttct tgcggagcca gttttacatg ttgcgcatgg atggtcccct tcctctacca    540
tacaggcact atattgcaat aatggctgca gctagacatc agtgttctta cttaataaac    600
atgcatgtgg atgaattttt aaagactgga ggtattgctg agtggttgaa tggtttggaa    660
tatgtgccac aaagactgaa aaatcttaat gaaattaata agctgctagc acatcgacct    720
tggctgatca caaagagca cattcagaaa cttgtcaaaa ctggagaaaa taattggtct    780
ctgcctgaac tggtacatgc tgtggtcctc ctggcacatt atcatgcttt ggcaagcttt    840
gttttggta gtggtatcaa tccagagaga gatccagaaa tctccaatgg attcaggcta    900
atatcagtca acaatttctg cgtttgtgat cttgctaatg acaacaacat agagaatgca    960
tctctttcag gcagcaactt tgggattgtg gattctctaa gtgagctaga ggccttaatg   1020
gaaaggatga aaagacttca agaagaaagg gaagatgaag aggcgtctca agaagaaatg   1080
agcactcgtt ttgaaaagga gaagaaagaa agtcttttttg tggtctctgg agatactttt   1140
cattcatttc ctcattcaga ttttgaggat gacatgatta aacatctga tgtctctcga    1200
tatattgaag accctggttt tgggtatgaa gactttgcca gacgaggaga agagcatttg   1260
ccaacattcc gagctcagga ctatacctgg gaaaatcatg ggttctccct ggtgaacaga   1320
ctttattctg acattggaca tcttcttgat gaaaagtttc ggatggtcta caatctcaca   1380
tataacacta tggccaccca tgaggatgtt gacacaacca tgctgcgcag agctttattt   1440
aactatgttc actgtatgtt tggaatcagg tatgatgact atgattatgg agaagttaat   1500
caattacttg aaagaagcct gaaggttac attaagacag tgacctgcta tcctgagaga   1560
actacaaaac gcatgtatga tagttactgg cggcagttca aacactcaga aaaagttcat   1620
gtcaatctac ttttaatgga agcacgaatg caagctgaac ttctttatgc tcttcgtgcc   1680
ataactcggc atttgacctg aagtatcacc caaggaaaat gtcatacatg tgtaaagacc   1740
tttcacataa gataaacatt gaagctattt gtgatatagc atcaaaaatt attcagttct   1800
ctagtgtcaa agtttagccg tttgtttttt ttttttttgtt tttgcggct gtaatgtgca   1860
atgatgtgtt ttatttctcct tgatgcttaa cattactaac aattgcaaaa ataatactga   1920
ggagcactac tttgcattgt ttgtagttgg agttttggat actgatcata aatcatgaat   1980
ctggcgtatt aatgcttaac ttcagcgcct ttgggttgtg tgtatgtgta ttttttctcc   2040
ccccacccccg ccctttttt tttaagaata aggacaagtg cttacaatct gctcaagcaa   2100
ttgtttttca gatattggaa ttcagcaaag agtgacctct ctggccattc taaaacttta   2160
atgttgtgtc ctaaatctgg tggaggaaaa gcatgcgctg ttgaaccaag ctgctcactg   2220
gacacatatt tgtgtcccca ggagattatt tgtcaggcac tgtttttat ttgtttgttt   2280
gttcatttat tgttgttta ctgctattgg cgataacatg aaatgtgata cagctattgc   2340
ccataattta atgtgaaatt aatcatgatg aattctatag catgctactg aaatgccaaa   2400
ttcagctatt ttctttctct tctaaaatgg aagtttcagt tttccatatc agatgtatat   2460
aagtggaatt ataacacaat cctatcactg acagtaatcc tcagtcacct taaataatca   2520
gtgctcacag tgctgcttac agttcattta gttggcacat ataaacctgt acccacacaa   2580
gactgaccaa aaattttctt tgcacatttt tcctttctca tagttttttt ctatatttcg   2640
ttaagcaaag gaaggttaat atgcctattt ttcctgttag gcttttagaa attattttcc   2700
```

```
atgactttg ttcttataat aggttagaca gtttattttt caaaggtaaa aattgtgttt       2760
ctatgcatta atgtgattga actacaaaaa cagagtgcaa tatgttcaaa aaatactcaa       2820
ctaaactttc cccctgtcat atcactgcaa aagtgtcctt ttaaacagag ccataaagaa       2880
atttttttca aatttcttta ttgcacaggc ttttttcagt tttacctttc tgggattgaa       2940
caatgttcct ttcataatgc caaagcattc ccttccccag aaaaatctcc ttggacaact       3000
ggtttaaaaa cgttattaag tcataggggga ggaataagcg gccaaaaagt cacattttttg       3060 cattggttta cgttgcttga ttagactatc ttcagagagc acattatgtg tttatagctt       3120
taatttgtat tatgtcaatg aaccagtgaa gtgcctaaag agatgcttac aactatccag       3180
taggacacaa ctgcactgct tttttaaacac tttttggtta gttaagggtg acttgaattg       3240
tacacataca tgctaattttt tgaaaactta tccatttttc atagtaaata atatagataa       3300
aattttctgt tagagttccc gcaaatattt cattttagac ttacttgtga tataagattt       3360
aacttttctt ttgtgaaaga atcgtgaact agtgtttcat gaaatcattt tcctcttcca       3420
tttatcatcc tcctctggta caatatattg ggttgctttc ttttagattt tgttccagat       3480
aggaaaacaa atatgactgt atacttatta acataaggta gttctgcatt tttggattcc       3540
aggatcctgt ttgaaatctt ccatgtgagg aaaaaattac taatattttt aaagacaggg       3600 tggtttatttt aaagagatta ttcagagaac ttgtgccata tctcgtctgt tttattgcat       3660
atgccatatg ttaactttta ttcaatatta cattatgtag atatgtaata caagaaaat       3720 atttaggaga atggcaaaac acaatgggca acataaatgt ccatttgact tacctaactt       3780
cacaactttc aagttgagga tgtcatttat tcttgaattt gttttttttac tagatgctttt       3840 caattaatag ccctatatttt ttgtgcaggc gaactgtata acaggataaa aaatgatttg       3900
tatgtattga aaaggaggag aaattctcac agaacaccat atgagcttta gaccaaaagg       3960
ggaaacaagg tttaagtaac taaaatggcc acttagtttg tgtttatttt tttccctgga       4020
aatgtaagta gttggagttt aggctatgga aatattagtg cctttaatag atctctttcc       4080
ttgcaaagtt tcttttttagc tcagcattga tctatcttat caataggaaa ataagttgac       4140
ttggaactat aaacaaaaac aacaccatat atttatgaac ctcagtgaac cagcctagaa       4200
aaattgactt ctgcaggtgc taaagcacct actaatacgc agcatgcaca gcatttcagg       4260
ttgtgaatac cattttacaa cgagtttgct gttaactctc tttatccaat gcaaacttga       4320
aattctgatg cggttttcca gggtggtatt ttttcagagt attgaattta ctatttagta       4380
atttatagta tagcttttta tattaaaatg tgatattttt aaaagagata tctggttcaa       4440
ttggtataat gacgtgatta tgcaatatgc tgatctacac cttgcgctca cattgtgcca       4500
aacttaaatg tgcaagtgta cgtgagaaaa gcacatgtga atgtgaattc tttaattctt       4560
tgcttattat gttaaaatta gtcttcatag tccactgatg tgtatgcttg aataatgtct       4620
atttactttg gaatttcaag atttccagct tcaatggtaa tttataattt ctcagatcac       4680
cttaagaaat attgagatac tctcccacct gaaaataatc tgttctttaa cccacctgac       4740
tatgggagta gccaggcagg tgcctcactg gcttcttcag acgaggcttc ctcaggtgga       4800
tatatgacta ttaggggaaa agaggctttt gagacagctt attacctcct tccccttttt       4860
gaactaagta cattgtctca gtcccagtat gaatttgtcc catttggggt atttttaaaa       4920
taaaagatgg ctaacatgga atctgggggca tagccttggc ctttaattat ggttgtaagc       4980
ccaaataatg gcagagaaac acagggctgt ttttacaaca gaaaactcaa tataagtttt       5040
```

```
atataagaat cctataaaat ttgaaccaga gctcctattt agttgttata atgtctccta    5100
aagatcttaa atgcttctaa aagctaatta ttattccaga gcaactttt ccttttcccc    5160 cttataaagt ttttttttaa atccaaaatc ttagatttct gtgccacagc aaaataaaat    5220
gatcaacaat taaagatctg tacttaaaat agtacaccat ttttagtgga gggagggtgc    5280
atgcctatat gatggtaaga ttcttttgaa ctctaaggac aattcctcat ggaaaaata    5340 aatttcagtg catattataa aaatgatttg cactgtgtta gcaaaataag gtgttttagg    5400
ttgtatttta aagacaattc taaatcattt ctctggaaag caagaccta aattcttctc    5460 tttaatagaa ctgcttttat gcaaagagat ggtcttaaca tggactaaac agtacataac    5520
aataatgttt gttatgtaaa tagtatatca catttgctta gtagcacaat tcaacagcag    5580
gctgaaagtc gtggctcctc tgctcagatt gagttttaag ttacctaatt tatgtaatca    5640
gaatctattc taggtggccg tcaacgtaaa ctgtgtttcc ctattatatc cctctggaga    5700
ctgagaatca aattaaatag tcttcttca aagcagtact gtaacatgaa tgtatttatc    5760
tcagtcaaca gaacttatat gcccactgta tgtggagctt atttcaatgc taatttggct    5820
tagttagcag acctagaatc tgcccaggtg agacctagaa caaaaatagc tggggtgaaa    5880
tggataagag aggtagaggt atatgtcaag gcagagccct atgaggaagg aagagttttc    5940
aaagaatatg aggaacatag tgctgagagt gtggctgcct tcagcaccgt acacctaatc    6000
tagagaaaat atttcccatg tgggaggtcc tgtctgcatt cagtccaccc ttttctgcct    6060
gcttcttcct ccaagtgcct caacctctac atgctcactc tcctcccctt ccctcagccc    6120
atcttggtct aagcagcttt cacaatccaa accaaacatc accagccacc cgctgataag    6180
tcaccagcat ttactttcct gagttacttt ttctccattc attgagacta tggattcatc    6240
ccaactcctt ctaaatccct caaccatcca gctatattt ggctaacctt tgccctagac    6300
actctaccag atgttaatgc agtatcaagt gtaaattgtg tcaccctatt ctgttctacc    6360
cttttccctg ctgccgaaat atcttgctct cctctacctc atccccaaag agcctataaa    6420
ttcagagtat ccaacctttt catggattca ctcactgttg ttcagtaata caacttccat    6480
attttaaata aatcataaaa gatttttgcc ttctatcaaa gtaggaaact ttatatttat    6540
acatgataca gaaattgaac tatttctatc gttcagaatt tagcatataa caggatttta    6600
aagtgattga attgccatcc taacttggat ttgtattagg ttatgaatga atactgttgt    6660
tagtccaagc tatttgaatg taaagttaaa attctccagc aatccagaat gacttgtaac    6720
ccttcagtgg aatgggaaat ttctggtatg caaatagggt ggtgttccag acatttgttt    6780
tattggtggt gtttgggcct tgaaacacat ttctaataga atgacatatg caaagggta    6840 tttagatggt cctatgggat cacagaagcc catatgattt aaaatataga taaaataaca    6900
caaaattggg tacataaggg tttaaccagg cttttcctggg ttagactaag cctctaacct    6960
ctgttcctat cctgttctta tgggaggaaa aaaatgttc catgggatga aagaaaatg    7020 cattgacttt gtagtcttta ttctcctagc cgcacttcgg gtatatccag aaggaagagg    7080
aaatgcaaag aggaagaaga tgtaatagtt cttctctcca gctaggtgca cttgaggttg    7140
ttcataaatg taaaattatg tcaggtttct aacatgggac actgcacaca gttgtctgac    7200
ctgatgaacc atcccatttg aaagtataga ttattattat ttcttgtagt atttggttgt    7260
tttccatctc attcatgaac aactcaacct gatagtagta tccaataaat gcctttcagg    7320
gctcaggaat gaattgacat cctagttaag aaatgagact taataatgga gactgaatga    7380
ggcggtttgt attaaattat atgccatgaa gtgttcattt tagctttaac ctaattatga    7440
```

```
ctgtaccacc atgaagtaca gaatgaaaaa ttatatatat ggggggggaaa cagaatgaat    7500 atctgattct tttgaatgct tgtggaaatc tttgagatcg tgcagggcat accacaaaat    7560
agcctttaga acagataccc aattttacag ttcataggac aacatcaaac attagtaagt    7620
ctaaataaga tgaatagaat ttttgttatg taaattttgc tagaacagtc tattttcttg    7680 caccccctcaa gttaacctct taaaaaaatg aatgtataat ttctaccgaa agaatatcag    7740
agagaatctc tctggcctat agtgttaaaa tattgttcac aaatcctgat tagttaagtg    7800
catacattat gaaacttaca gaataaaact tattatacat ctctttctta aattaatatc    7860
tttacacatt tcaactggc tccccaagtc tgataaggaa ggattaaaag aaaaaagaaa    7920
tgtattagtt gggtggccaa ggagtttcct ttgtaatgtt gagagacttc cgctttctga    7980
atttcgctgg ttctctaagg taaaagagtt aaatagtacc cttgttcacc aaggaaagtg    8040
atccaaacta tatatctagt gcagatattt cctttgcatt atttagtctt ctctggagag    8100
aaaatacagt ttcccttcc tctttctctt cacattact cttttcaacc caaaataaga    8160
gacatagaaa gcaaaccaca gccagtttgg catcttctca gtgctactag tataggcaca    8220
tacacataca cagtctcagc aaggttataa agaaccctgt caggtccact tgcaacatgg    8280
ccttgctact tggattagct cctttaagcc tgaaaataac tttcctggtc atggaagaac    8340
tggacgcatc ttttaactta tgaaatagaa gttgaacttg aaaactcttt ttaaaaaatc    8400
ctggttttgc aggacagcta cataatgaat gtatatatta agactgtagc tgaattgcac    8460
atgaaatcag attgccaact tcttgactt caatgttaga catttatcct taagttgtga    8520
gcgatatatg tagcatgctg tgaaatgtct gttatagctc tttaattcat cagtattaat    8580
acagaattat catttgcgtt tcttggtact ttttattcaa tgtaatcaga agctgtgatg    8640
ttttgccttt gtagtcctgt gctttgttac tgtaattttt ttttttttt tacgaagcac    8700 gtgactggac taatgtaagg cagatgacgt gatctttaag actgctatat atatcagtct    8760
cttactctat aaggtttaa attagaataa gcttttatca aatagataat tgatgcaatt    8820
taggattcac gcaagtttca gtgtcaaatg gcggtcttat agtttcaatt ctgaaaatag    8880
caaacttaat aaacagccac tttaaacttg ttctggcaaa ccagaccctg ctgtagatat    8940
agtctaaggt agttaaccat ataagccttt tcaactctta atgccctcca catgaatcag    9000
cagttaagaa ggttctagaa cccatgaaag cttttgtatg tattactagg ttttgttttt    9060
cttatgtttg ctgattttac agttctgact aaagctgacc taaatggatc agtttatgtg    9120
taatattcta gtgctttaat gactcttttt ttctttggag ggagggtaac attatttgga    9180
cagatgcaga aggaactgtt agtgagtcaa gacaaacaca tctgaaataa aggaactgtg    9240
tattaacatg ttaacaattc ataactgcac tttttatgac attttgaaaa tctatttata    9300
ggtacagaac aatgggtttt gttaaactgt atcacattta tacttgcaga aatttatttc    9360
attgttatta gtaggaattt tattggttca ataaaattgg caaaactgaa caccaatcat    9420
ttgcctactt tgtttatact gga                                            9443
```

<210> SEQ ID NO 53
<211> LENGTH: 2974
<212> TYPE: DNA
<213> ORGANISM: Artificial Sequence
<220> FEATURE:
<223> OTHER INFORMATION: EGF-like repeats and discoidin I-like domains 3 (NM_005711)

<400> SEQUENCE: 53

-continued

```
agaagccccg cagccgccgc gcggagaaca gcgacagccg agcgcccggt ccgcctgtct      60
gccggtgggt ctgcctgccc gcgcagcaga cccggggcgg ccgcgggagc ccgcgccccg     120
cccgccgcgc ctctgccggg acccacccgc agcggagggc tgagcccgcc ggcggctccc     180
cggagctcac ccacctccgc gcgccggagc gcaggcaaaa ggggaggaaa ggctcctctc     240
tttagtcacc actctcgccc tctccaagaa tttgtttaac aaagcgctga ggaaagagaa     300
cgtcttcttg aattctttag tagggcgga gtctgctgct gccctgcgct gccacctcgg     360
ctacactgcc ctccgcgacg accctgacc agccggggtc acgtccggga cgggatca      420
tgaagcgctc ggtagccgtc tggctcttgg tcgggctcag cctcggtgtc cccagttcg      480
gcaaaggtga tatttgtgat cccaatccat gtgaaaatgg aggtatctgt tgccaggat     540
tggctgatgg ttccttttcc tgtgagtgtc cagatggctt cacagacccc aactgttcta    600
gtgttgtgga ggttgcatca gatgaagaag aaccaacttc agcaggtccc tgcactccta    660
atccatgcca taatggagga acctgtgaaa taagtgaagc ataccgaggg gatacattca    720
taggctatgt ttgtaaatgt ccccgaggat ttaatgggat tcactgtcag cacaacataa    780
atgaatgcga agttgagcct tgcaaaaatg gtggaatatg tacagatctt gttgctaact    840
attcctgtga gtgcccaggc gaatttatgg gaagaaattg tcaatacaaa tgctcaggcc    900
cactgggaat tgaaggtgga attatatcaa accagcaaat cacagcttcc tctactcacc    960
gagctctttt tggactccaa aaatggtatc cctactatgc acgtcttaat aagaagggc    1020
ttataaatgc gtggacagct gcagaaaatg acagatggcc gtggattcag ataaatttgc    1080
aaaggaaaat gagagttact ggtgtgatta cccaaggagc caagaggatt ggaagcccag    1140
agtatataaa atcctacaaa attgcctaca gtaatgatgg aaagacttgg gcaatgtaca    1200
aagtgaaagg caccaatgaa gacatggtgt tcgtggaaa cattgataac aacactccat    1260
atgctaactc tttcacaccc cccataaaag ctcagtatgt aagactctat ccccaagttt    1320
gtcgaagaca ttgcactttg cgaatggaac ttcttggctg tgaactgtcg ggttgttctg    1380
agcctctggg tatgaaatca ggacatatac aagactatca gatcactgcc tccagcatct    1440
tcagaacgct caacatggac atgttcactt gggaaccaag gaaagctcgg ctggacaagc    1500
aaggcaaagt gaatgcctgg acctctggcc acaatgacca gtcacaatgg ttacaggtgg    1560
atcttcttgt tccaaccaaa gtgactgcca tcattacaca aggagctaaa gattttggtc    1620
atgtacagtt tgttggctcc tacaaactgg cttacagcaa tgatggagaa cactggactg    1680
tataccagga tgaaaagcaa agaaaagata aggttttcca gggaaatttt gacaatgaca    1740
ctcacagaaa aaatgtcatc gaccctccca tctatgcacg acacataaga atccttcctt    1800
ggtcctggta cggaggatc acattgcggt cagagctgct gggctgcaca gaggaggaat    1860
gaggggaggc tacatttcac aaccctcttc cctatttccc taaaagtatc tccatggaat    1920
gaactgtgca aaatctgtag gaactgaat ggtttttttt ttttttttcat gaaaaagtgc    1980
tcaaattatg gtaggcaact aacggtgttt ttaaggggt ctaagcctgc cttttcaatg    2040
atttaatttg attttatttt atccgtcaaa tctcttaagt aacaacacat taagtgtgaa    2100
ttacttttct ctcattgttt cctgaattat tcgcattggt agaaatatat tagggaaaga    2160
aagtagcctt cttttatag caagagtaaa aaagtctcaa agtcatcaaa taagagcaag    2220
agttgataga gcttttacaa tcaatactca cctaattctg ataaaaggaa tactgcaatg    2280
ttagcaataa gttttttcct tctgtaatga ctctacgtta tcctgttcc ctgtgcctac    2340
```

-continued

```
caaacactgt caatgtttat tacaaaattt taaagaagaa tatgtaacat gcagtactga      2400
tattataatt ctcattttac tttcattatt tctaataaga gattatgtga cttcttttc       2460 ttttagttct attctacatt cttaatattg tatattacct gaataattca atttttttct      2520
aattgaattt cctattagtt gactaaaaga agtgtcatgt ttactcatat atgtagaaca      2580
tgactgccta tcagtagatt gatctgtatt taatattcgt taattaaatc tgcagtttta      2640
tttttgaagg aagccataac tatttaattt ccaaataatt gcttcataaa gaatcccata     2700
ctctcagttt gcacaaaaga acaaaaaata tatatgtctc tttaaattta aatcttcatt     2760
tagatggtaa ttacatatcc ttatatttac tttaaaaaat cggcttattt gtttatttta     2820
taaaaatttt agcaaagaaa tattaatata gtgctgcata gtttggccaa gcatactcat     2880
catttctttg ttcagctcca catttcctgt gaaactaaca tcttattgag atttgaaact     2940
ggtggtagtt tcccaggaag gcacaggtgg agtt                                 2974

<210> SEQ ID NO 54
<211> LENGTH: 1251
<212> TYPE: DNA
<213> ORGANISM: Artificial Sequence
<220> FEATURE:
<223> OTHER INFORMATION: aldo-keto reductase family 1, member C3
      (3-alpha hydroxysteroid dehydrogenase, type II) (NM_003739)

<400> SEQUENCE: 54
gcccattgtt tttgtaatct ctgaggagaa gcagcagcaa acatttgcta gtcagacaag        60
tgacagggaa tggattccaa acaccagtgt gtaaagctaa atgatggcca cttcatgcct       120
gtattgggat ttggcaccta tgcacctcca gaggttccga gaagtaaagc tttggaggtc       180
acaaaattag caatagaagc tgggttccgc catatagatt ctgctcattt atacaataat       240
gaggagcagg ttggactggc catccgaagc aagattgcag atggcagtgt gaagagagaa       300
gacatattct acacttcaaa gctttggtcc acttttcatc gaccagagtt ggtccgacca       360
gccttggaaa actcactgaa gaaagctcaa ttggactatg ttgacctcta tcttattcat       420
tctccaatgt ctctaaagcc aggtgaggaa cttccaccaa cagatgaaaa tggaaaagta       480
atatttgaca tagtggatct ctgtaccacc tgggaggcca tggagaagtg taaggatgca       540
ggattggcca agtccattgg ggtgtcaaac ttcaaccgca ggcagctgga gatgatcctc       600
aacaagccag gactcaagta caagcctgtc tgcaaccagg tagaatgtca tccgtatttc       660
aaccggagta aattgctaga tttctgcaag tcgaaagata ttgttctggt tgcctatagt       720
gctctgggat ctcaacgaga caaacgatgg gtggacccga actccccggt gctcttggag       780
gacccagtcc tttgtgcctt ggcaaaaaag cacaagcgaa ccccagccct gattgccctg       840
cgctaccagc tgcagcgtgg ggttgtggtc ctggccaaga gctacaatga gcagcgcatc       900
agacagaacg tgcaggtttt tgagttccag ttgactgcag aggacatgaa agccatagat       960
ggcctagaca gaaatctcca ctatttttaac agtgatagtt ttgctagcca ccctaattat      1020
ccatattcag atgaatatta acatggaggg ctttgcctga tgtctaccag aagccctgtg      1080
tgtggatggt gacgcagagg acgtctctat gccggtgact ggacatatca cctctactta      1140
aatccgtcct gtttagcgac ttcagtcaac tacagctgag tccataggcc agaaagacaa      1200
taaattttta tcattttgaa ataaaaaaaa aaaaaaaaa aaaaaaaaa a                  1251
```

IMMORTALIZED MESENCHYMAL STROMAL CELL FROM ADIPOSE TISSUE

CROSS-REFERENCE TO RELATED APPLICATION

This application is a continuation of U.S. application Ser. No. 12/972,315, filed Dec. 17, 2010, which claims priority to Korean Patent Application No. 10-2010-0058273, filed Jun. 18, 2010, the entire contents of which are incorporated herein by reference.

BACKGROUND OF THE INVENTION

1. Field of the Invention

The present invention relates to a composition for diagnosing a Parkinson's disease comprising mesenchymal stromal cells derived from adipose tissue, a method of providing information for diagnosing Parkinson's disease and/or extent of disease progression using mesenchymal stromal cells derived from adipose tissue, a biomarker for diagnosing a Parkinson's disease, aa method of screening an agent treating Parkinson's disease where the agent targets the biomarker, and an immortalized mesenchymal stromal cell from adipose tissue.

2. Description of the Related Art

Parkinson's disease (PD) is a secondarily common neurodegenerative disease which about one percent of old people aged over 60 suffers from, but the cause of disease has not yet been determined.

It has been suggested that Parkinson's disease has some connections with the selective loss of dopaminergic neurons in substantia nigra, and with the extensive neuron changes causing various complex motile and immotile symptoms.

A genetic mutation of disease-causing gene such as α-synuclein, parkin, Parkinson disease autosomal recessive, early onset 7 (DJ-1), or phosphatase and tensin homologue (PTEN)-induced putative kinase 1 (PINK1) is mentioned as a cause of familial Parkinson's disease.

Parkin acts as E3 ligase in ubiquitin-proteasomal system, protects against the oxidative stress, and helps the maintenance of mitochondrial function. The mutation in Parkin gene can cause a hereditary early-onset of Parkinson's disease.

The correlation between mitochondrial dysfunction and Parkinson's disease can be observed as the widely known disease-causing mechanism in PD patient subgroup involves aberrant shape and dysfunction of mitochondria.

The damage of mitochondrial function increases an oxidative stress and associates with the control of calcium homeostasis and cell apoptosis pathway. The oxidative stress can be defined as one of causes inducing apoptosis of dopaminergic neuronal cells of the substantia nigra in Parkinson's disease patient.

Parkinson's disease associated gene products including α-synuclein, Parkin, PINK', DJ-1 and the like can be found in mitochondria and play a critical role in the mitochondrial dysfunction and oxidative stress.

The methods of diagnosing Parkinson's disease and determining extent of the disease progression include a method of imaging brain nigros-triatal region with a magnetic resonance image (MRI) analysis, a positron emission tomography (PET), a single photon emission computed tomography (SPECT), and the like, and a method of analyzing a sample taken from brain tissue with a biomarker. However, such methods still lead to inaccurate analysis of results, and unwanted pain and a risk to patient from directly taking a sample form brain tissue.

SUMMARY OF THE INVENTION

To solve the problems in the art, the present inventors found that Parkinson's disease could be diagnosed by using the mesenchymal stromal cell derived from adipose tissue, developed a technology for accurately diagnosing Parkinson's disease without directly taking brain tissue, and completed the present invention by developing a biomarker for diagnosing Parkinson's disease using the technology.

Therefore, an embodiment of the present invention provides a composition for diagnosing Parkinson's disease comprising the mesenchymal stromal cell derived from adipose tissue.

Another embodiment provides a method of providing an information for diagnosing Parkinson's disease and determining extent of the progression of Parkinson's disease.

Further embodiment of the present invention provides a biomarker for diagnosing Parkinson's disease where the biomarker is obtained from the mesenchymal stromal cell derived from the adipose tissue.

Still another embodiment of the present invention provides a method of screening a drug treating Parkinson's disease where the drug targets the biomarker.

Another embodiment provides an immortalized mesenchymal stromal cell from adipose tissue

DETAILED DESCRIPTION OF THE EMBODIMENTS

The present invention can provide a tool for understanding and determining the brain physiological states without isolating the brain tissue from Parkinson's disease patient, by performing the transcriptome microarray analysis of mesenchymal stromal cell derived from early-passage adipose tissue taken from human subject with early-onset (congenital) hereditary Parkinson's disease such as Parkin-deficient PD, as well as late-onset (acquired) Idiopathic Parkinson's disease (idiopathic PD).

The present inventors completed the present invention by separating a human mesenchymal stromal cell derived from human adipose tissue (hAD-MSC), from a subject with Idiopathic PD or Parkin-deficient Parkinson's disease, and comparing the gene expression pattern of the mesenchymal stromal cell with that of non-Parkinson's disease. The human adipose tissue is abundant and easily accessible source for mesenchymal stem cells (MSC).

Hereinafter, hAD-MSC obtained from a patient with idiopathic Parkinson's disease is referred to as 'PD,' hAD-MSC obtained from a patient with Parkin-deficient Parkinson's disease as 'Parkin,' and hAD-MSC obtained from a patient who has pituitary adenoma without Parkinson's disease as 'non-PD' or 'PA.' Initially, by analyzing differentially-expressed gene (DEG) among three groups, 413 genes are confirmed to be differentially expressed, and then classified into three groups of non-PD, PD and Parkin. In addition, DEG are analyzed and divided to seven clusters according to K-mean clustering analysis, and the GENBANK accession numbers are listed in Tables 6a-6e. In addition, the functional groups of human biomarker candidates are organized, and non-PD vs. PD and non-PD vs. Parkin are compared. Finally, the PD associated DEGs which are regulated differently due to the oxidative stress are classified into one of groups among non-PD, PD and Parkin categories.

The knowledge of selective gene expression pattern in Parkinson's disease patient gained from the present invention can be helpful for obtaining the physiological information and early-diagnosis of Parkinson's disease, and developing an effective target specific drug for treating the Parkinson's disease by using the genes as a biomarker.

First of all, the present invention relates to a composition for diagnosing a disease, comprising mesenchymal stromal cells derived from adipose tissue, where the disease is selected from the group consisting of Parkinson's disease, Alzheimer's disease, Huntington's disease, hereditary dystonia, hereditary dyskinesia, and metabolic disease. The present inventors found that the presence of Parkinson's disease and the extent of disease progression could be diagnosed without separating the brain tissue from Parkinson's disease patient by assaying the gene expression pattern of mesenchymal stromal cell derived from adipose tissue, since the gene expression is very similar to that of brain tissue. In accordance with the present invention, the use of adipose tissue-derived mesenchymal stromal cell for diagnosing the Parkinson's disease removes the step of dangerous separation of brain tissue from the subject. The diagnosing method using the adipose tissue-derived mesenchymal stromal cells can be widely applied for diagnosing various diseases such as Alzheimer's disease, Huntington's disease, hereditary dystonia, hereditary dyskinesia, and metabolic disease.

The subject includes any kind of mammals, and preferably human beings who are suffering or are likely to suffer from Parkinson's disease, Alzheimer's disease, Huntington's disease, hereditary dystonia, hereditary dyskinesia, and metabolic disease. Since one of the common causes of the diseases is adipose tissue (Human Lipodystrophies: Genetic and Acquired Diseases of Adipose Tissue; Capeau J, et al.; 2010; PUBMED), the application of following diagnosing technology for Parkinson's disease can be extended to diseases listed above.

The adipose tissue can be one separated from mammals, preferably human. The separated region is not limited to a particular region of body and can include any regions of a body such as breast and abdominal region. For more accurate analysis, the separated adipose tissue can be used preferably after eliminating cell debris and blood cell.

Hereinafter, the term, adipose tissue can be separated or unseparated one from a live body, and includes an adipose cell.

In an embodiment of the present invention, the mesenchymal stromal cells (hAD-MSC) can be, for example, but are not limited thereto, cells showing the mononuclear cell properties which are confirmed by positive expression of human integrin beta-1 marker CD29, phagocytic glycoprotein-1 marker CD44, and human integrin alpha-4 marker CD49d, and at the same time expressing slightly primitive hematopoietic precursors and vascular endothelial marker CD34, vascular endothelial marker CD31 and vascular adhesion molecule 1, (VCAM-1) marker CD106.

The Parkinson's diseases which can be detected by using the composition of the present invention includes all kinds of the Parkinson's diseases such as an acquired Idiopathic Parkinson's disease, congenital, familial Parkinson's disease (for examples, Parkin, α-synuclein, phosphatase and tensin homologue (PTEN)-induced putative kinase 1 (PINK1, a mitochondrial kinase), Parkinson disease autosomal recessive, early onset 7 (DJ-1), Leucine-rich repeat kinase 2 (LRRK2), and High temperature requirement protein A2 (HTRA2) deficient).

In another embodiment of the present invention, a method of diagnosing Parkinson's disease using the mesenchymal stromal cells derived from the adipose tissue is provided.

More specifically, the method comprises the steps of separating a mesenchymal stromal cell derived from adipose tissue of a subject, assaying a gene expression pattern of the mesenchymal stromal cell; and determining the presence of disease by analyzing the assayed result or the disease progression degree by analyzing the assayed result.

The assaying step of gene expression pattern of hAD-MSC can be performed by any methods of analyzing gene expression which are used commonly in the art. For examples, the assaying of gene expression can be carried out by microarray analysis, Reverse transcriptase Polymerase Chain Reaction (RT-PCR), Real time Polymerase Chain Reaction (real time PCR), genomics, proteomics, microRNA assay, SNP analysis, mitochondrial assay, functional assay and the like, but not limited thereto.

As a result of the molecular biological studies in the present invention, a high-throughput microarray analysis of hAD-MSC obtained from a patient with Idiopathic Parkinson's disease, a patient with Parkin-deficient Parkinson's disease, and a patient with non-Parkinson's disease can be established, and the analysis result is compared with that of a patient with non-Parkinson's disease (control group) to identify the gene groups which are differentially expressed between a patient with Idiopathic Parkinson's disease and/or a patient with Parkin-deficient Parkinson's disease. Thus, the identified genes in a patient with non-Parkinson's disease, a patient with Idiopathic Parkinson's disease and a patient with Parkin-deficient Parkinson's disease can contribute to the understanding of physiological symptoms of Parkinson's disease, and can provide a useful tool for developing the early-diagnosis and effective treatment of Parkinson's disease targeting the human biomarker.

The mitochondrial dysfunction and increased oxygen stress are shown in subgroup of Parkinson's disease patient, and these suggest the important effect of mitochondrial dysfunction and oxygen stress on onset of Parkinson's disease. Thus, the mitochondria can be effective target for developing a biomarker of Parkinson's disease. The biochemical methods of detecting the potential biomarker of Parkinson's disease include the gene screening method, mitochondria complex I measurement, blood level of alpha-synuclein and isoforms measurement. Gene test tools which are commercially available for detecting mitochondria mutant genes such as Parkin, PINK1, and alpha-synuclein can be used. Furthermore, Coenzyme Q10, antioxidant and electron transporter (electron transporter chain component) act as an electron transporter for mitochondria complex I and II.

The genes which show differential expression at least two times in non-PD patient vs. Parkin, and non-PD vs. PD, and Parkin vs. PD are identified with hierarchical clustering analysis (FIG. 4), and summarized in table 4 to select the PD-related genes (SCUBE3, IL8, ATP1B1, TNFRSF11B, FABP3, CXCL1). IL8 and CXCL1 are chemokines which act a basic role in development, homeostasis and immune systems, and involve in inflammation of cranial nerve of Parkinson's disease patient. SCUBE3 accompanies an important molecule in dopaminergic neuron of ventral midbrain, and TNFRSF11B involves in an inflammation in neurodegeneration of Parkinson's disease. The single heterozygous mutation of ATP is suggested to be related with a cause of early-onset of Parkinson's disease. Finally, FABP3 has been used as a diagnostic marker for Parkinson's disease. The PD-related genes in non-PD vs. Parkin and Parkin vs. PD are summarized in Table 5 (SYT14, LGR5, TGFB3, ITGA2, F2RL2, DRD1, PENK, GNA14, EDNRB, HSPA2, SLC6A6, AKR1B1, and PRG4). SYT14 is a transmembrane protein involved with control of membrane trafficking. LGR5, F2RL2, DRD1, GNA14 and EDNRB involve in a signal pathway of G-protein, TGFB3 involves in a susceptibility of Parkinson's disease patient, and ITGA2 in a neuronal adhesion. An increased expression of PENK can be a cause of treatment-related dyskinesia in Parkinson's disease patient. Parkin, as a substrate for parkin, mediates the ubiquitination of HSPA2 and a molecular chaperone. SLC6A6, also known as taurine, is a neurotransmitter. Taurine is a beta-amino acid abundantly located in substantia nigra (SN), and functions as a neurotransmitter in substantia. The immunoreactivity of AKR1B1 is generated in human cerebral cortex and hippocampus, and PRG4 relates with the inclusions of Parkinson's disease.

The comparison analysis of seven regulating sequences of K-mean clustering genes in non-PD, PD and Parkin are shown in FIG. 5b. The names and GENBANK accession numbers of PD-related genes showing the increased or decreased gene expression are summarized in Tables 6a-6e. The genes showing the increased gene expression pattern are shown in Table 6a (ITGA8, CTSH, CCRL1), Table 6b (TGFB3, DRD1, GNA14, PENK, PRG4, LGR5, HLA-DPA1), and Table 6e (SCUBE3, HSPA2, TGFB3, DRD1, GNA14, PENK, PRG4, LGR5, RELN, EDNRB, ITGA2, SLC6A6, F2RL2, CDK6, AKR1B1, MMP8, ID1, NEFM, ATP1B1, TNFRSF11B, TNFRSF10D), and the genes showing the decreased gene expression pattern are shown in Table 6c (BEX1) and Table 6d (IL8, CXCL6). The change in gene expression seems to be due to the mitochondria activity change between late-onset of Idiopathic Parkinson's disease and congenital early-onset of Parkinson's disease or due to compensation therebetween. These data also suggest the potential biomarker for the onset of Parkinson's disease. The molecular functional groups in non-PD vs. PD and non-PD vs. Parkin are determined and shown in FIG. 8a to FIG. 8d, and the genes which show the change in the gene expression level in Idiopathic Parkinson's disease patient and Parkin-deficient Parkinson's disease patient can provide a potential human biomarker candidate for detecting a disease onset and a selective vulnerability.

In addition, after analyzing of genes differentially expressed due to the oxygen stress in PD, the genes and the clusters taken from Cluster Nos. 2 to 6 are shown in Table 9. Interestingly, genes showing a linear increase of gene expression were discovered in all groups, which may be explained by an increased compensation against vulnerability caused by oxygen stress in pathology of Idiopathic PD and Parkin-deficient PD.

Based on these results, when there is an increased expression of at least one selected from the group consisting of ITGA8, CTSH, CCRL1, TGFB3, DRD1, GNA14, PENK, PRG4, LGR5, HLA-DPA1, SCUBE3, HSPA2, RELN, EDNRB, ITGA2, SLC6A6, F2RL2, CDK6, AKR1B1, MMP8, ID1, NEFM, ATP1B1, TNFRSF11B, and TNFRSF10D in mesenchymal stromal cells derived from adipose cell of a patent, or when where is an decreased expression of at least one selected from the group consisting of BEX1, IL8, and CXCL6 in mesenchymal stromal cells derived from adipose cell of a patent, it is possible to determine the presence of the Parkinson's Disease. Parkinson's disease includes late-onset (acquired) Parkinson's disease (Idiopathic Parkinson's disease), or early-onset (congenital, familial, hereditary) Parkinson's disease (for examples, Parkin, α-synuclein, phosphatase and tensin homologue (PTEN)-induced putative kinase 1 (PINK1, a mitochondrial kinase), Parkinson disease autosomal recessive, early onset 7 (DJ-1), Leucine-rich repeat kinase 2 (LRRK2), or High temperature requirement protein A2 (HTRA2) deficient Parkinson's disease and etc).

In an embodiment of the present invention, the increase and decrease of the gene expressions can be measured by the amount of protein expressed. When the amount is about 1.5 to 3 times higher than that of normal group without Parkinson's disease, the result can be determined to be significant.

In an embodiment of the present invention, a method of screening a drug treating Parkinson's disease, in which the drug targets the biomarker in mesenchymal stromal cells derived from adipose tissue, is provided.

More specifically, the method comprises the steps of contacting a drug candidate with a mesenchymal stromal cell derived from adipose tissue; and assaying a gene expression pattern of the mesenchymal stromal cell; and determining the drug candidate as a drug treating Parkinson's disease in case that there is a difference of gene expression pattern in the mesenchymal stromal cells between the treatment and non-treatment of the drug candidate, wherein at least gene is selected from the group consisting of ITGA8, CTSH, CCRL1, TGFB3, DRD1, GNA14, PENK, PRG4, LGR5, HLA-DPA1, SCUBE3, HSPA2, RELN, EDNRB, ITGA2, SLC6A6, F2RL2, CDK6, AKR1B1, MMP8, ID1, NEFM, ATP1B1, TNFRSF11B, TNFRSF10D, BEX1, IL8, and CXCL6.

For example, when the group treated with the drug candidate shows the increased gene expression (preferably, at least an increase of two-fold) of at least one selected from the group consisting of ITGA8, CTSH, CCRL1, TGFB3, DRD1, GNA14, PENK, PRG4, LGR5, HLA-DPA1, SCUBE3, HSPA2, RELN, EDNRB, ITGA2, SLC6A6, F2RL2, CDK6, AKR1B1, MMP8, ID1, NEFM, ATP1B1, TNFRSF11B, TNFRSF10D and the like, or the decreased gene expression (preferably, at least a decrease of two-fold) of at least one selected from the group consisting of BEX1, IL8, CXCL6 and the like, compared to that of the group untreated with the drug candidate, the drug candidate can be determined as a drug for treating Parkinson's disease, for examples, late-onset (acquired) Parkinson's Disease (Idiopathic Parkinson's Disease), or early-onset (congenital, familial, hereditary) Parkinson's Disease (for examples, Parkin, α-synuclein, phosphatase and tensin homologue (PTEN)-induced putative kinase 1 (PINK1, a mitochondrial kinase), Parkinson disease autosomal recessive, early onset 7 (DJ-1), Leucine-rich repeat kinase 2 (LRRK2), or High temperature requirement protein A2 (HTRA2) deficient Parkinson's disease, etc.

The increase or decrease of gene expression can be measured by any method of measuring the gene expression level which has been known generally in the art, for examples but not limited to, microarray assay, Reverse transcriptase polymerase chain reaction (RT-PCR), Real time PCR, genomics, proteomics, microRNA assay, SNP analysis, mitochondrial assay, functional assay and the like.

The data obtained in the present invention provide a predictable scenario for onset of Parkinson's disease. In conclusion, the gene expression analysis of the mesenchymal stromal cells derived from the human adipose tissue can identify specific molecular functional groups of the genes which are affected by the mitochondrial dysfunction and oxidative stress. Thus, the present invention provides a technology for diagnosing Parkinson's disease and/or determining its extent of disease progression using the mesenchymal stromal cell derived from adipose tissue instead of brain tissue, for. The genes which show the change in gene expression in Idiopathic or Parkin-deficient (familial) Parkinson's disease patient compared to the non-Parkinson's disease can be identified by using such technology, and can be used both as a biomarker as well as a target for developing a drug treating Parkinson's disease.

BRIEF DESCRIPTION OF DRAWINGS

FIG. 4 is a Venn diagram of Differentially Expressed Gene (DEG) between the control group (non-PD, PA) and test group with Parkinson's disease.

FIG. 5a is a result of hierarchical clustering analysis of the genes showing the gene expression level at least two times higher between non-PD, PD and Parkin groups.

FIG. 11b is the result of western blot analysis showing successful separation of mitochondria in the assay of FIG. 11a.

FIG. 14b represents a western blot analysis showing the change in the gene expression of mTOR as an autophagy maker in immortalization-culture stage of the cells in non-PD, PD, and Parkin of FIG. 14a.

FIG. 14c represents a western blot analysis showing the change in the gene expression of S6K as an autophagy maker in immortalization-culture stage of the cells in non-PD, PD, and Parkin of FIG. 14a.

FIG. 15b is a graph showing the quantitative analysis of the result.

FIG. 16b is a graph showing the quantitative analysis of the change in the gene expression of autophagy markers in immortalization-culture stage of the cells in non-PD, PD, and Parkin.

EXAMPLE

Figure 1A:
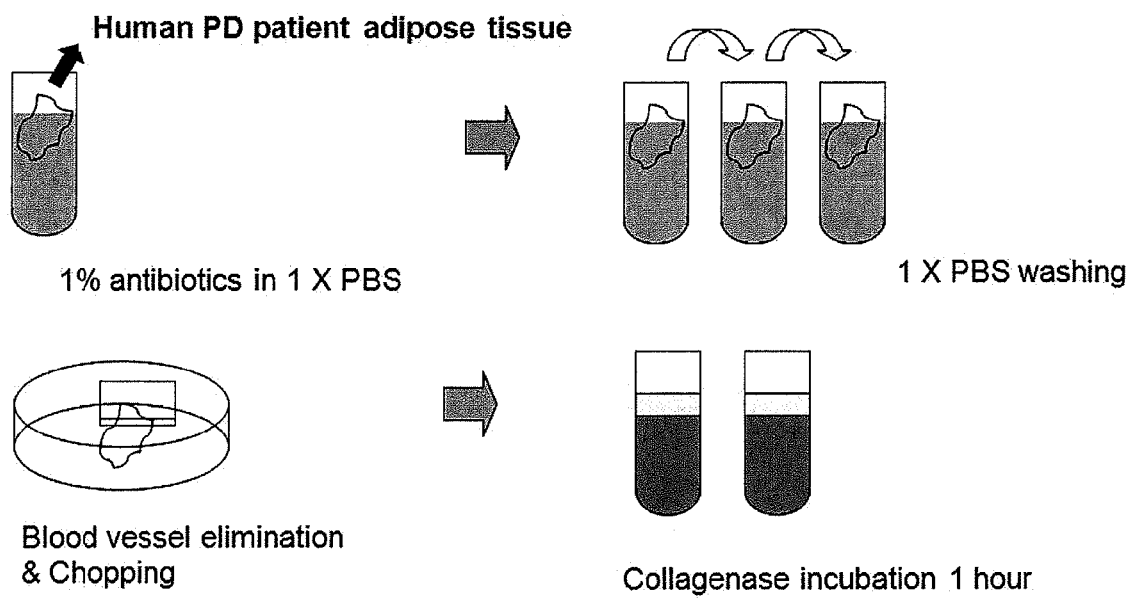
FIGS. 1a and 1b show the procedure of separating and culturing the mesenchymal stromal cells derived from adipose tissue of human patient with Parkinson's disease.

The present invention is further explained in more detail with reference to the following examples. These examples, however, should not be interpreted as limiting the scope of the present invention in any manner.

Example 1

Preparation of the Mesenchymal Stromal Cell Derived from the Adipose Tissue 1.1. Separation and Culture of the Mesenchymal Stromal Cells Derived from the Adipose Tissue The adipose tissue-derived mesenchymal stromal cells (hAD-MSC) were separated from Idiopathic Parkinson's disease (Idiopathic PD) patient, Parkin-deficient Parkinson's disease (Parkin-deficient PD) patient, and a pituitary adenoma patient who did not suffer from Parkinson's disease, and then subsequently were cultured. Hereinafter, otherwise particularly defined, hAD-MSC obtained from Idiopathic PD patient is referred to as "PD," hAD-MSC obtained from Parkin-deficient Parkinson's disease patient to as "Parkin", and hAD-MSC obtained from Parkinson's disease to as "non-PD" or "PA."

These tests were performed under the permission of Institutional Review Board of Seoul National University Hospital (IRB No. 0707-024-212) and the written consent of the patients. During the performance of Deep Brain Stimulation (DBS) surgery of Idiopathic PD patient, and Parkin-deficient PD patient, the adipose tissue under the skin of clavicle was taken in order to compare with that of a pituitary adenoma patient (control group) who did not suffer from Parkinson's disease.

The adipose tissue was added to 1% antibiotic/antimyotic (Gibco®Invitrogen, Carlsbad, Calif.) in sterilized PBS (phosphate-buffered saline, pH7.4) and transferred to test room. The adipose tissue was washed with PBS three times to remove tissue debris and red blood cell, and then finely cut into small pieces. The adipose tissue was digested with 0.075% collagenase Type I (Sigma-Aldrich, St. Louis, Mo., USA) at 37° C. for 1 hour, inactivated with the same volume of DMEM/10% Fetal Bovine Serum (FBS) (Gibco®Invitrogen, Carlsbad, Calif.), and centrifuged at 1200×g for 10 minutes. The obtained pellet was cultured in three times volume of red blood lysis buffer (QIAGEN, valencia, CA, USA) at 37° C. for 10 minutes, and filtered with 100 μm strainer. The filtrate was centrifuged at 1200×g for 10 minutes. The resultant pellet was washed with PBS and centrifuged at 1200×g for 10 minutes. Finally, the obtained pellet was resuspended in Mesenchymal Stem cell Expansion medium (Millipore, SCM015, Billerica, Mass., USA) and placed onto 25T culture flask. After the cells were cultured in Mesenchymal Stem cell Expansion medium (Millipore, SCM015, Billerica, Mass., USA) at 37° C. for 48 hours, the cells were washed with PBS and the unattached cells were removed. The culture medium was replaced with new medium every three days.

As a result, the hAD-MSC was obtained, wherein two cells are obtained from a pituitary adenoma patient who did not suffer from Parkinson's Disease (PA1 and PA2), two cells are obtained from Idiopathic PD (PD1 and PD2), and two cells are obtained from Parkin-deficient PD (Parkin1 and Parkin2).

Figure 1B:
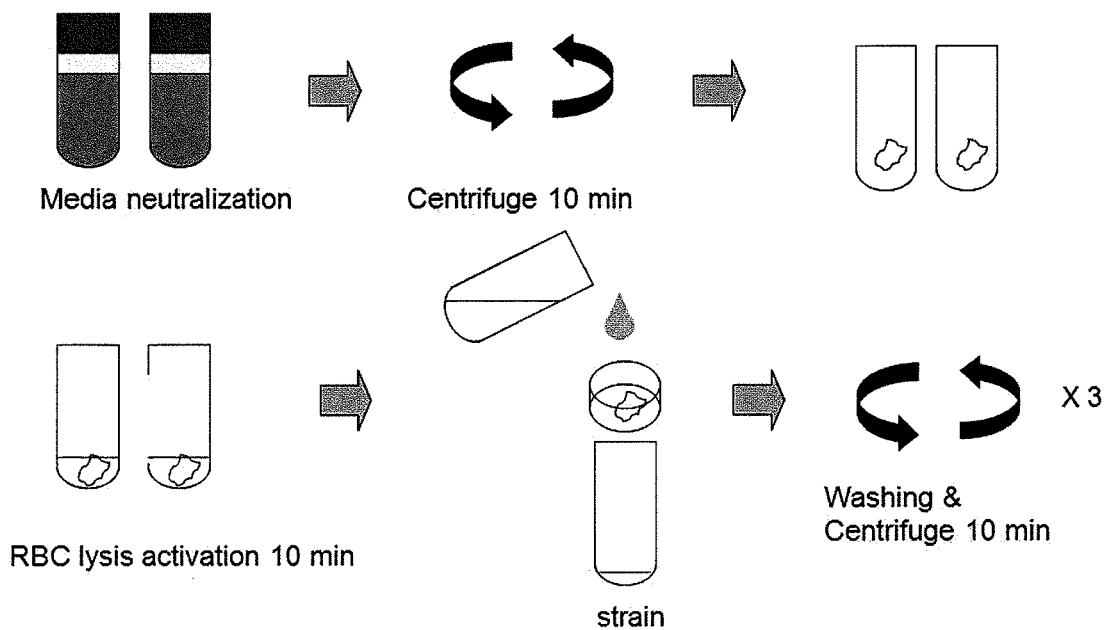
Figure 2:
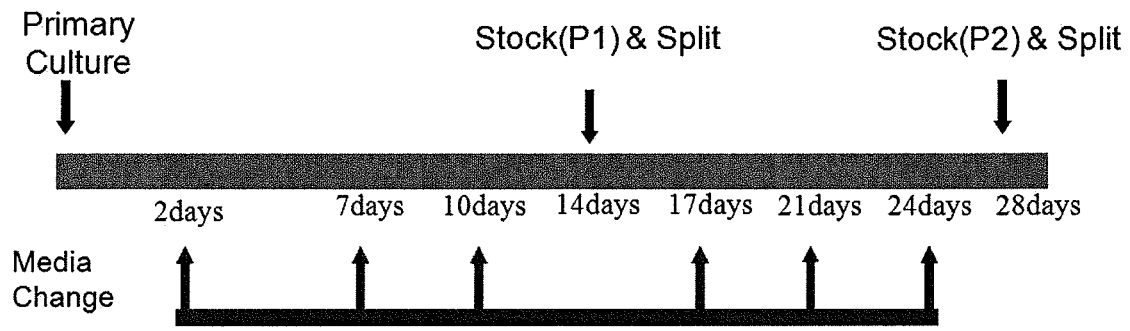
FIG. 2 represents schematically the procedure of preparing a stock by culturing the mesenchymal stromal cells derived from adipose tissue of human patient with Parkinson's disease.
Figure 3:
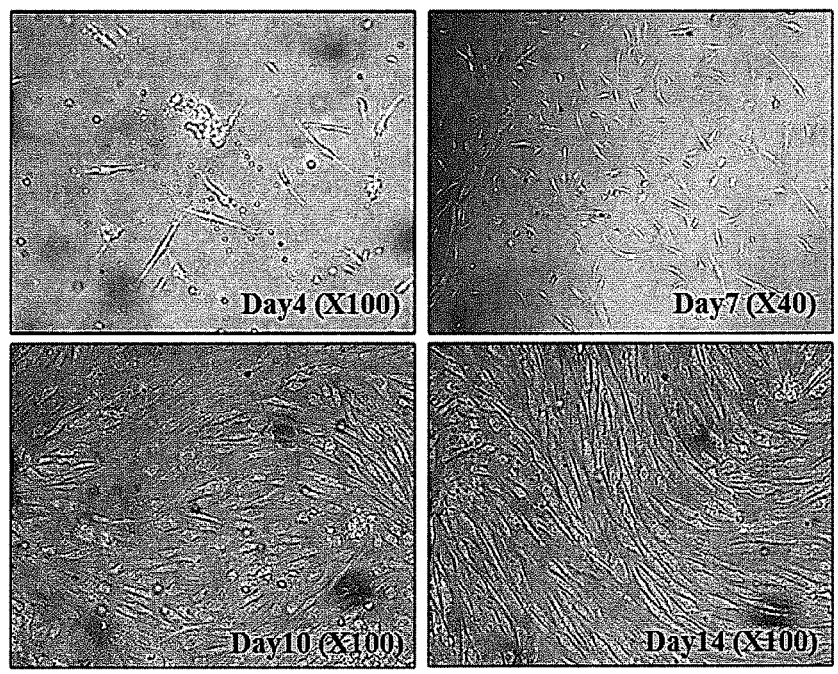
FIG. 3 is a picture showing the transient change in cell morphology of the mesenchymal stromal cells derived from adipose tissue of human patient with Parkinson's disease based on culture time variations.

The culture procedure is shown schematically in FIGS. 1a and 1b. FIG. 2 represents schematically the procedure of preparing stock by culturing mesenchymal stromal cells derived from adipose tissue of human patient with Parkinson's disease. FIG. 3 is a picture showing the transient change in cell morphology of mesenchymal stromal cells derived from adipose tissue of human patient with Parkinson's disease according to the culture time variations. In FIG. 3, the pictures of cell morphology of adipose tissue-derived mesenchymal stromal cells were taken every day during continuous culture.

The information on the cell culture of mesenchymal stromal cells derived from adipose tissue obtained from Idiopathic PD patient, Parkin-deficient PD patient, and control group are summarized at Tables 1 to 3:

TABLE 1

Culture information of adipose tissue obtained from Idiopathic PD patient

| Patient No. | Labeling | Culture Date |
|---|---|---|
| 1 | FSC-PD#2 | 2007 Mar. 9 |
| 2 | FSC-PD#3 | 2007 Apr. 2 |
| 3 | FSC-PD#5 | 2007 Aug. 13 |
| 4 | FSC-PD#6 | 2007 Oct. 22 |
| 5 | FSC-PD#7 | 2007 Oct. 29 |
| 6 | FSC-PD#8 | 2007 Nov. 19 |
| 7 | FSC-PD#9 | 2008 Mar. 24 |
| 8 | FSC-PD#10 | 2008 Jul. 7 |
| 9 | FSC-PD#11 | 2008 Aug. 29 |
| 10 | FSC0714 | 2008 Jul. 14 |
| 11 | FSC0721 | 2008 Jul. 21 |
| 12 | FSC0829 | 2008 Aug. 29 |
| 13 | FSC1006 | 2008 Oct. 6 |
| 14 | FSC0119 | 2009 Jan. 19 |
| 15 | FSC0209 | 2009 Feb. 9 |
| 16 | FSC0420 | 2009 Apr. 20 |
| 17 | FSC0427 | 2009 Apr. 27 |
| 18 | FSC0601 | 2009 Jun. 1 |
| 19 | FSC0622 | 2009 Jun. 22 |
| 20 | FSC0918 | 2009 Sep. 18 |
| 21 | FSC1123 | 2009 Nov. 23 |

TABLE 2

Culture information of adipose tissue obtained from Parkin-deficient PD patient

| Patient | Labeling | Culture Date |
|---|---|---|
| 1 | FSC-parkin | 2007 May 17 |
| 2 | gFSC | 2008 Jun. 2 |

TABLE 3

Culture information of adipose tissue obtained from control group

| Patient No. | Labeling | Culture Date |
|---|---|---|
| 1 | FSC-#1 | 2006 Nov. 22 |
| 2 | FSC-#2 | 2006 Nov. 23 |
| 3 | FSC-#3 | 2006 Dec. 18 |
| 4 | FSC-#4 | 2006 Dec. 18 |
| 5 | FSC-#7 | 2007 Jan. 3 |
| 6 | FSC-#8 | 2007 Jan. 22 |
| 7 | FSC-#9 | 2007 Jan. 31 |
| 8 | FSC-#11 | 2007 Feb. 15 |
| 9 | FSC-#12 | 2007 Feb. 26 |
| 10 | FSC-#14 | 2007 Mar. 15 |
| 11 | FSC-#15 | 2007 Apr. 20 |
| 12 | FSC-#17 | 2007 Oct. 2 |
| 13 | FSC-#18 | 2007 Oct. 4 |
| 14 | FSC-#19 | 2008 Mar. 25 |
| 15 | FSC1013 | 2008 Oct. 13 |
| 16 | FSC1014 | 2008 Oct. 14 |
| 17 | FSC1103 | 2008 Nov. 3 |
| 18 | FSC1104 | 2008 Nov. 4 |
| 19 | FSC0629 | 2009 Jun. 29 |
| 20 | FSC0630 | 2009 Jun. 30 |
| 21 | FSC0706 | 2009 Jul. 6 |
| 22 | FSC1019 | 2009 Oct. 19 |
| 23 | FSC1102 | 2009 Nov. 2 |
| 24 | FSC1109 | 2009 Nov. 9 |
| 25 | FSC1201 | 2009 Dec. 1 |

1.2. Fluorescence-Activated Cell Sorter (FACS) Analysis

The hAD-MSC culture was separated with PBS and subsequently cultured with following primary antibodies (culture medium: Mesenchymal Stem cell Expansion medium (Millipore, SCM015, Billerica, Mass., USA), culture temperature: 37° C.).

Primary Antibody:
Anti-CD29, anti-CD44, anti-CD34, anti-CD31 (DakoCytomation, Carpinteria, Calif., USA), anti- and CD49d, anti-CD106 (Chemicon, Temecula, Calif., USA).

The cells were cultured on ice for 30 minutes, and then washed with 0.5% BSA and 2 mM EDTA in BSA (Sigma-Aldrich, St. Louis, Mo., USA). The morphological characteristics of hAD-MSC and quantitative analysis were performed by FACS SCAN flow cytometer (Becton Dickinson, San Diego, Calif., USA) and CellQuest software (Becton Dickinson, San Diego, Calif., USA).

Figure 17:
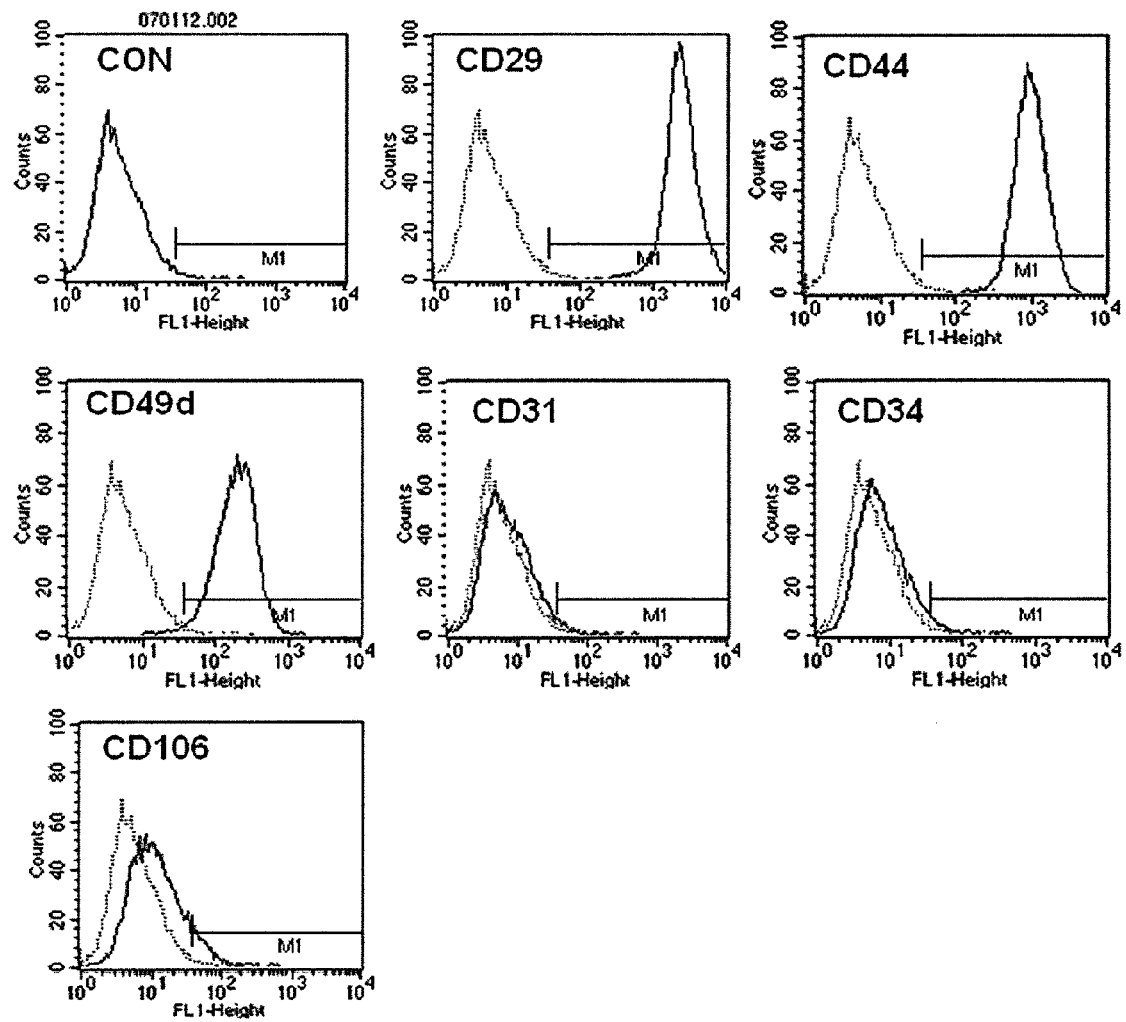
FIG. 17 shows an analysis result of properties of the mesenchymal stromal cells derived from the adipose tissue.

The results are shown in FIG. 17. hAD-MSC obtained from idiopathic PD patient, Parkin-deficient PD patient, and control group were separated and cultured. Then, the cells showed the characteristics of mononuclear cell based on the expression of human integrin beta-1 marker CD29, phagocytic glycoprotein-1 marker CD44, and human integrin alpha-4 marker CD49d. In addition, the cells expressed slightly primitive hematopoietic precursors and vascular endothelial marker CD34, vascular endothelial marker CD31 and vascular adhesion molecule 1, (VCAM-1) marker CD106.

1.3. Preparation of RNA Sample

According to manufacturer's manual, the RNA sample was prepared. Specifically, whole RNA was separated with RNE-ASY Mini Kit columns (Qiagen, Hilden, Germany) according to the manufacturer's manual. The quantity of RNA was assessed with Agilent 2100 bioanalyser using RNA 6000 NANO CHIP (Agilent Technologies, Amstelveen, The Netherlands) and determined with ND-1000 Spectrophotometer (NanoDrop Technologies, Inc., DE, USA).

1.4. Analysis of hAD-MSC Properties hAD-MSC was separated from Idiopathic PD patient, Parkin-deficient PD patient, and the control group and cultured. In flow cytometry analysis, at least 95% of MSC (≥95%) expressed CD105, CD73 and CD90, and the cells were deficient in the expression of CD45, CD34, CD14 or CD11b; CD79☐ or CD19; and HLA class II (positive at most 2%) (M Dominici, K Le Blanc, I Mueller, I Slaper-Cortenbach, F Marini, D Krause, et al, Minimal criteria for defining multipotent mesenchymal stromal cells. The International Society for Cellular Therapy position statement, *Cytotherapy*, 8, 315-7, 2006). The accession numbers of the genes are summarized in following table:

| Gene name | Gene accession number |
| --- | --- |
| CD105 | NM_001114753 |
| CD73 | NM_002526 |
| CD90 | NM_006288 NM_033209 |
| CD45 | NM_002838 |
| CD34 | NM_001025109 |
| CD14 | NM_000591 |
| CD11b | NM_000632 |
| CD79 | NM_001783 |
| CD19 | NM_001178098 |
| HLA class II | NM_000449 |

The cells should be able to differentiate into osteoblasts cell, adipose cell (adipocytes) and chondroblasts under the standard in vitro differentiation condition (M Dominici, K Le Blanc, I Mueller, I Slaper-Cortenbach, F Marini, D Krause, et al, Minimal criteria for defining multipotent mesenchymal stromal cells. The International Society for Cellular Therapy position statement, Cytotherapy, 8, 315-7, 2006).

The separated hAD-MSC were cultured at Mesenchymal Stem cell Expansion medium (Millipore, SCM015, Billerica, Mass., USA) at 37° C., and the expression profile of human integrin beta-1 marker CD29, phagocytic glycoprotein-1 marker CD44, and human integrin alpha-4 marker CD49d were analyzed with FACS analysis method. The result is shown in FIG. 17. CON in FIG. 17 shows FACS analysis result of mesenchymal stromal cells themselves.

The accession numbers of the genes utilized are summarized in following table:

| Gene name | Gene accession number |
| --- | --- |
| CD29 | NM_002211 |
| CD44 | NM_000610 |
| CD49d | NM_000885 |
| CD34 | NM_001025109 |
| CD31 | NM_000558 |
| CD106 | NM_001078 |

The positive expression of the genes confirmed that the cells showed the properties of the mononuclear cell. The cells expressed a small amount of primitive hematopoietic precursors and vascular endothelial marker CD34, vascular endothelial marker CD31 and vascular adhesion molecule 1, (VCAM-1) marker CD106.

Example 2

Gene Profiling of Adipose Tissue-Derived Mesenchymal Stromal Cell 2.1. cDNA Microarray Analysis The gene expression analysis was performed with Affymetrix GeneChip® Human Gene 1.0 ST oligonucleotide array (DNA LINK, INC (Seoul, Korea)).

According to AFFYMETRIX manufactor's protocol (www.affymetrix.com), 300 ng of RNA was added to each sample. Namely, 300 ng of all RNA per a sample was changed into double stranded cDNA. The double stranded cDNA was obtained by using SUPERSCRIPT II Reverse Transcriptase, DNA polymerase I and random hexamer inserted by T7 promoter (AFFYMETRIX GENECHIP® WT cDNA Synthesis and Amplipicaition Kit, Cat No. 900672). An amplified RNA (cDNA) was produced by in vitro transcription (IVT) with IVT Enzyme Mix (AFFYMETRIX GENECHIP® WT cDNA Synthesis and Amplipicaition Kit, Cat No. 900672), and separated with AFFYMETRIX sample cleanup module. The amplified cRNA was mixed with IVT cRNA binding buffer and 100% EtOH, and bonded in cRNA cleanup spin column. The column was washed with cRNA wash buffer, and then eluted with RNase-free water.

cDNA was reproduced with dNTP mixture including dUTP AFFYMETRIX GENECHIP® WT cDNA Synthesis and Amplipicaition Kit, Cat No. 900672), according to the random-primed reverse transcription. Then, the produced cDNA was fragmented by using UDG and APE 1 restriction enzyme (AFFYMETRIX GENECHIP® WT Terminal Labeling Kit, Cat No. 900670), and the end labeling was performed by inserting biotinylated dideoxynucleotide with TdT (Terminal deoxynucleotidyl transferase) enzyme.

According to Gene Chip Whole Transcript (WT) Sense Target Labeling Assay Manual (AFFYMETRIX), the end-labeled and fragmented cDNA was hybridized at 60 r/min, at 45° C., for 16 hours with GENECHIP® Human Gene 1.0 ST array. Then, the array was stained and washed in GENECHIP Fluidics Station 450 (AFFYMETRIX), and scanned with GENECHIP Array scanner 3000 7G (AFFYMETRIX).

2.2. Classification of DEG Included in Three Groups of Non-PD (Control Group), Idiopathic PD and Parkin-Deficient PD To identify DEG based on two-fold gene expression difference between non-PD vs. Parkin, non-PD vs. PD and Parkin vs. PD, hierarchical clustering analysis (Eisen M B, Spellman P T, Brown P O, Botstein D, 1998) Cluster analysis and display of genome-wide expression patterns. Genetics Vol. 95, Issue 25, 14863-14868) was performed. The hierarchical clustering analysis is data-mining algorithm used for defining similarity or dissimilarity of expressed genes. By using all genes showing the gene expression difference of two-fold between three groups of non-PD, PD, Parkin as a standard, the hierarchical clustering analysis was carried out to identify the gene having high similarity and the Euclidean distance was used as a similarity measurement.

The obtain result is shown as a Venn diagram in FIG. 4. In order to identify genes showing expression level difference of at least two-fold between the groups of non-PD, PD and Parkin, after selecting genes showing expression level difference of at least two-fold in each non-PD vs Parkin, non-PD vs PD, and Parkin vs PD, and comparing with the results among non-PD vs Parkin, non-PD vs PD, and Parkin vs PD, the genes that showed the similar level of difference in each comparison were selected and shown in FIG. 4.

For example, the genes having gene expression level of at least two times higher between the groups of non-PD vs. Parkin were 109 genes which included 20 genes showing two-fold expression in comparison of non-PD vs. Parkin and 16 genes showing two-fold expression level in all three comparisons.

Differentially-expressed genes were 413 genes where 109 genes were for non-PD vs. Parkin, 233 genes for non-PD vs. PD and 335 genes for Parkin vs. PD. Particularly, 6 genes which had been already known as PD-related gene were selected from 16 common genes in the center of non-PD vs. Parkin vs. PD, and their GENBANK accession numbers are listed in Table 4.

TABLE 4

| GENBANK Accession No. | Gene name (Gene symbol) | Fold Change (log2 ratio) | | | Function |
|---|---|---|---|---|---|
| | | non-PD vs. Parkin | non-PD vs. PD | Parkin vs. PD | |
| NM_152753 | signal peptide, CUB domain, EGF-like 3 (SCUBE3) | 2.0097 | −1.6452 | −3.6549 | protein hetero-homo-oligomerization |
| NM_000584 | interleukin 8 (IL8) | −1.5026 | −3.5819 | −2.0792 | angiogenesis/cell motility |
| NM_001677 | ATPase, Na+/K+ transporting, β1 polypeptide (ATP1B1) | 1.1420 | −2.1375 | −3.2796 | ion transport |
| NM_002546 | tumor necrosis factor receptor superfamily, member 11b(TNFRSF11B) | 1.2471 | −1.6420 | −2.8891 | apoptosis/inflammation response |
| NM_004102 | fatty acid binding protein 3, muscle and heart (mammary-derived growth inhibitor) (FABP3) | −1.4108 | 1.7890 | 3.1998 | phosphatidylcholine biosynthetic process |
| NM_001511 | chemokine (C-X-C motif) ligand 1 (melanoma growth stimulating activity, α) (CXCL1) | −1.0412 | −2.9751 | −1.9339 | chemotaxis/immune response |

In addition, 13 genes which have been known as Parkinson's disease-related gene are selected from 56 genes in groups of non-PD vs. Parkin and Parkin vs. PD, and their GENBANK accession numbers are shown in Table 5. The genes do not include 16 genes which are common in three groups.

TABLE 5

| GENBANK Accession No | Gene name (Gene symbol) | Fold Change (log2 ratio) | | Function |
|---|---|---|---|---|
| | | non-PD vs. Parkin | Parkin vs. PD | |
| NM_153262 | synaptotagmin XIV (SYT14) | 1.6903 | −1.5708 | membrane trafficking |
| NM_003667 | leucine-rich repeat-containing G protein-coupled receptor 5 (LGR5) | 2.1567 | −2.1239 | G-protein signaling |
| NM_003239 | transforming growth factor, β3 (TGFB3) | 1.1171 | −1.0345 | cell growth/aging |
| NM_002203 | integrin α2 (ITGA2) | 1.3831 | −1.8448 | cell adhesion |
| NM_004101 | coagulation factor II (thrombin) receptor-like 2 (F2RL2) | 1.6712 | −2.2182 | G-protein signaling |
| NM_000794 | dopamine receptor D1 (DRD1) | 1.1496 | −1.1496 | G-protein signaling |
| NM_006211 | proenkephalin (PENK) | 1.9852 | −1.9852 | neuropeptide signaling |
| NM_004297 | G protein α14 (GNA14) | 2.5842 | −2.5842 | G-protein signaling |
| NM_001122659 | endothelin receptor type B (EDNRB) | 1.0755 | −1.6347 | G-protein signaling |
| NM_021979 | heat shock 70 kDa protein 2 (HSPA2) | 1.0932 | −1.4480 | response to unfolded protein |
| NM_003043 | solute carrier family 6, member 6 (SLC6A6) | 1.0595 | −1.3053 | amino acid metabolic process |
| NM_001628 | aldo-keto reductase family 1, member B1 (aldose reductase) (AKR1B1) | 1.1052 | −1.3105 | metabolic process |
| NM_005807 | proteoglycan 4 (PRG4) | 3.8210 | −4.4772 | cell proliferation |

2.3. Clustering Analysis and Result

After finally washing and staining, the image was scanned with AFFYMETRIX GENECHIP® Human Gene 1.0 ST array using AFFYMETRIX Model 3000 G7 scanner. The image data was extracted by AFFYMETRIX Commnad Console software 1.1. The raw excel file was used for obtaining the expression extent data in the next step. The expression data was obtained by Expression Console software version 1.1. The data normalization was performed with Robust Multi-Average (RMA) algorithm in Expression Console software. The genes showing the increase of gene expression level of at least two fold between the test group and the control group were selected and used in the subsequent step.

The gene expression level of the selected genes was measured with Hierarchical clustering in MEV (MultiExperiment Viewer) software 4.0 (TM4: a free, open-source system for microarray data management and analysis. Biotechniques. 2003 February; 34(2):374-8.). To classify the genes as common gene groups having similar expression pattern, K-mean Clustering was performed (A Soukas, P Cohen, N D Socci, J M Friedman, Leptin-specific patterns of gene expression in white adipose tissue, Genes Dev, 14, 963-80 (2000)). The K-mean Clustering is a method used for classifying, based on their patterns, the common gene expression groups having the genes of similar expression pattern in hierarchical clustering analysis.

The genes which are differentially expressed were analyzed biologically with Web-based DAVID (the Database for Annotation, Visualization, and Integrated Discovery; DAVID Bioinformatics Resources 6.7, Systematic and integrative analysis of large gene lists using DAVID Bioinformatics Resources. (2009) Nat Protoc. 4(1):44-57.). The genes were classified on the basis of Gene ontology, Panther ontology database (DAVID Bioinformatics Resources 6.7).

Based on the similarity measured by the K-mean clustering analysis between non-PD, PD and Parkin groups, the expressed genes were classified. The expression pattern graphs were reorganized to seven clusters (FIG. 5b).

Figure 5B:
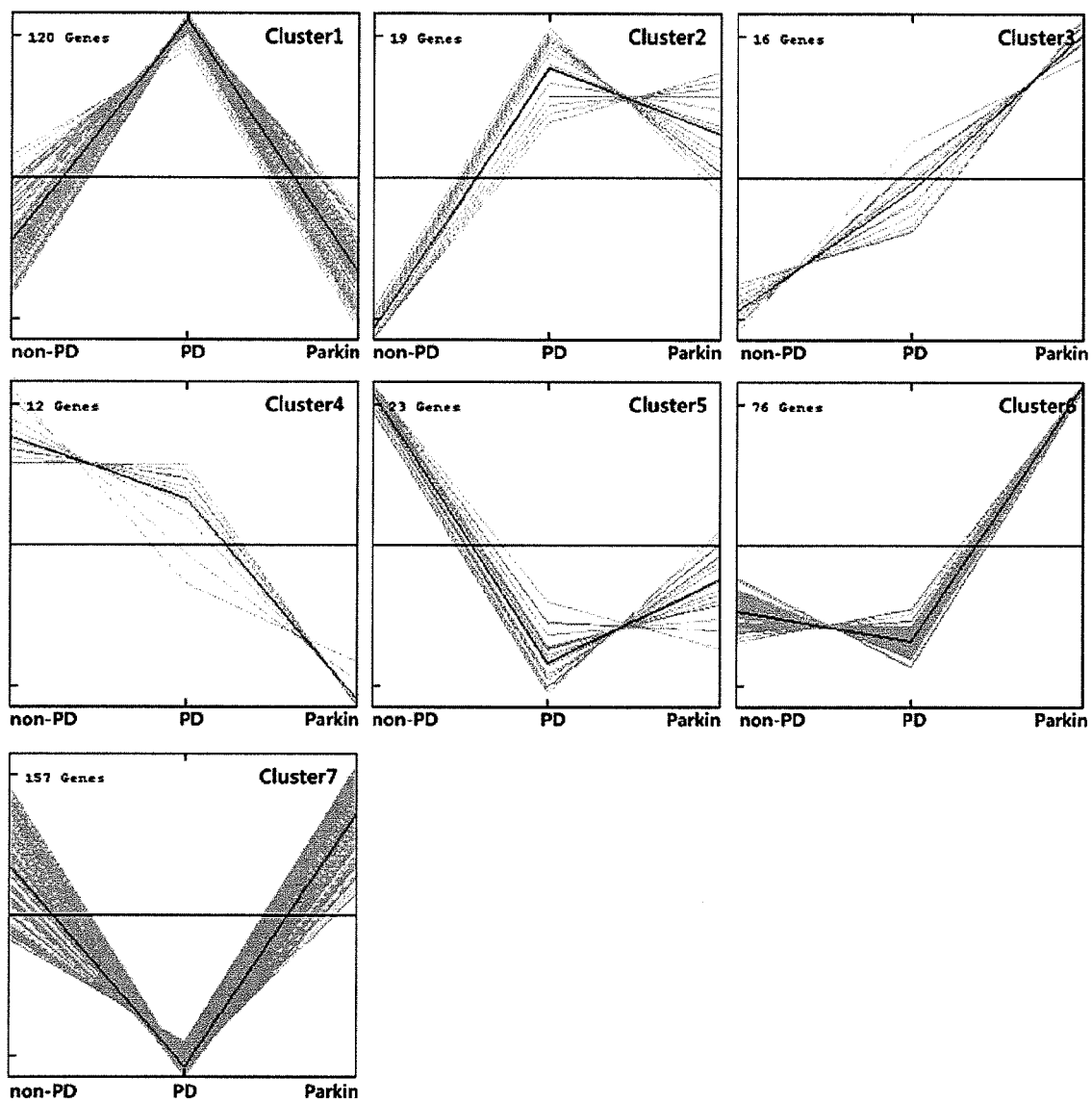
FIG. 5b shows the seven clusters obtained by reorganizing the expression pattern graphs which are classified through the K-mean clustering analysis of non-PD, PD and Parkin.

FIG. 5a showed a result of Hierarchical Clustering by using the signals of 413 genes which represent the difference in gene expression between the groups of PA, PD, and Parkin. The result confirmed the whole profile of clusters showing the difference in gene expression between the groups of PA, PD, and Parkin, and the expected several patterns of the clusters. FIG. 5b showed classified clusters showing similar gene expression pattern, when 7 patterns of clusters were classified according to the result of hierarchical clustering analysis. The number of pattern was determined by the smallest optimized number which was obtained after performing repetitive simulation with various pattern numbers.

Specifically, the gene names and their genbank accession number of Cluster 2, 3, 4, 5 and 6 were summarized in Tables 6a-6e.

TABLE 6a

Cluster 2: Increase

| no | Gene name (non-PD < PD = Parkin) | Gene symbol | Genbank accession No |
|---|---|---|---|
| 1 | interleukin α8 | ITGA8 | NM_003638 |
| 2 | cathepsin H | CTSH | NM_004390 |
| 3 | chemokine (C-C motif) receptor-like 1 | CCRL1 | NM_178445 |

TABLE 6b

Cluster 3: Increase

| no | Gene name (non-PD ≤ PD < Parkin) | Gene symbol | Genbank accession No |
|---|---|---|---|
| 1 | transforming growth factor, β3 | TGFB3 | NM_003239 |
| 2 | dopamine receptor D1 | DRD1 | NM_000794 |
| 3 | G protein α14 | GNA14 | NM_004297 |
| 4 | proenkephalin | PENK | NM_006211 |
| 5 | proteoglycan 4 | PRG4 | NM_005807 |
| 6 | leucine-rich repeat-containing G-protein coupled receptor 5 | LGR5 | NM_003667 |
| 7 | major histocompatibility complex, class II, DP α1 | HLA-DPA1 | NM_033554 |

TABLE 6c

Cluster 4: Decrease

| no | Gene name (non-PD ≥ PD > Parkin) | Gene symbol | Genbank accession No |
|---|---|---|---|
| 1 | brain expressed, X-linked 1 | BEX1 | NM_018476 |

TABLE 6d

Cluster 5: Decrease

| no | Gene name (non-PD > PD = Parkin) | Gene symbol | Genbank accession No |
|---|---|---|---|
| 1 | interleukin 8 | IL8 | NM_000584 |
| 2 | chemokine (C-X-C motif) ligand 6 (granulocyte chemotactic protein 2) | CXCL6 | NM_002993 |

TABLE 6e

Cluster 6: Increase

| no | Gene name (non-PD ≥ PD < Parkin) | Gene symbol | Genbank accession No |
|---|---|---|---|
| 1 | signal peptide, CUB domain, EGF-like 3 | SCUBE3 | NM_152753 |
| 2 | heat shock 70 kDa protein 2 | HSPA2 | NM_021979 |
| 3 | transforming growth factor, β3 | TGFB3 | NM_003239 |
| 4 | dopamine receptor D1 | DRD1 | NM_000794 |
| 5 | G protein α14 | GNA14 | NM_004297 |
| 6 | proenkephalin | PENK | NM_006211 |
| 7 | proteoglycan 4 | PRG4 | NM_005807 |
| 8 | leucine-rich repeat-containing G-protein coupled receptor 5 | LGR5 | NM_003667 |
| 9 | reelin | RELN | NM_005045 |
| 10 | endothelin receptor type B | EDNRB | NM_001122659 |
| 11 | Integrin α2 | ITGA2 | NM_002203 |
| 12 | solute carrier family 6, member 6 | SLC6A6 | NM_003043 |
| 13 | coagulation factor II (thrombin) receptor-like 2 | F2RL2 | NM_004101 |
| 14 | cyclin-dependent kinase 6 | CDK6 | NM_001259 |
| 15 | aldo-keto reductase family 1, member B1 (aldose reductase) | AKR1B1 | NM_001628 |
| 16 | matrix metallopeptidease 8 | MMP8 | NM_002424 |
| 17 | inhibitor of DNA binding 1, dominant negative helix-loop-helix protein | ID1 | NM_181353 |
| 18 | neurofilament, medium polypeptide | NEFM | NM_005382 |
| 19 | ATPase, Na$^+$/K$^+$ transporting, β1 polypeptide | ATP1B1 | NM_001677 |

TABLE 6e-continued

Cluster 6: Increase

| no | Gene name (non-PD ≥ PD < Parkin) | Gene symbol | Genbank accession No |
|---|---|---|---|
| 20 | tumor necrosis factor receptor superfamily, member 11b | TNFRSF11B | NM_002546 |
| 21 | tumor necrosis factor receptor superfamily, member 10d, decoy with truncated death domain | TNFRSF10D | NM_003840 |

The increased pattern of gene expression was shown in Clusters 2, 3, and 6, and the decreased pattern was shown in Clusters 4 and 5. The gene data showing greatest linear-increase of gene expression (Cluster 3) and the genes showing greatest linear-decrease of gene expression (Cluster 4) could provide the numerical values of severe Parkinson's disease and a guidance for a search for the human biomarker diagnosing early-stage of Parkinson's disease.

The gene expression result is described in detail hereinafter.

Figure 6:
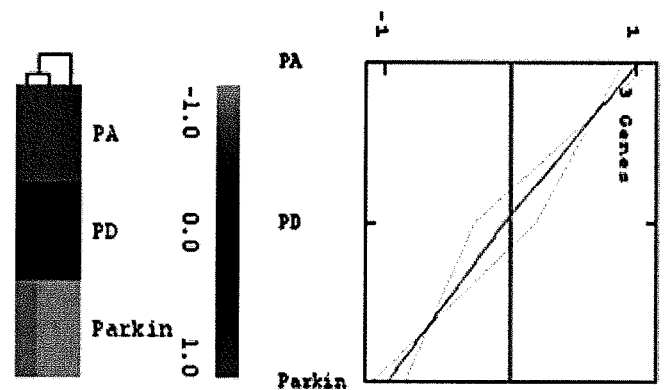
FIG. 6 represents the clustering analysis result of the genes showing linearly-decreased gene expression between non-PD, PD, and Parkin groups.

Firstly, the genes which showed the linear decrease of gene expression amount in the order of PA>PD>Parkin were Cluster 4 in Table 7 and FIG. 6.

TABLE 7

| Gene name | Function | Genbank accession # |
|---|---|---|
| brain expressed, X-linked 1 | multicellular organismal development//nervous system development// cell differentiation | NM_018476 |

As shown in FIG. 6, gene expression amount of gene X-linked 1 (NM_018476) showed a linear decrease in PA, PD, and Parkin. FIG. 6 is a pattern graph and Heat map showing a result of Hierarchical Clustering of the genes separated with K-mean Clustering Analysis.

Figure 7:
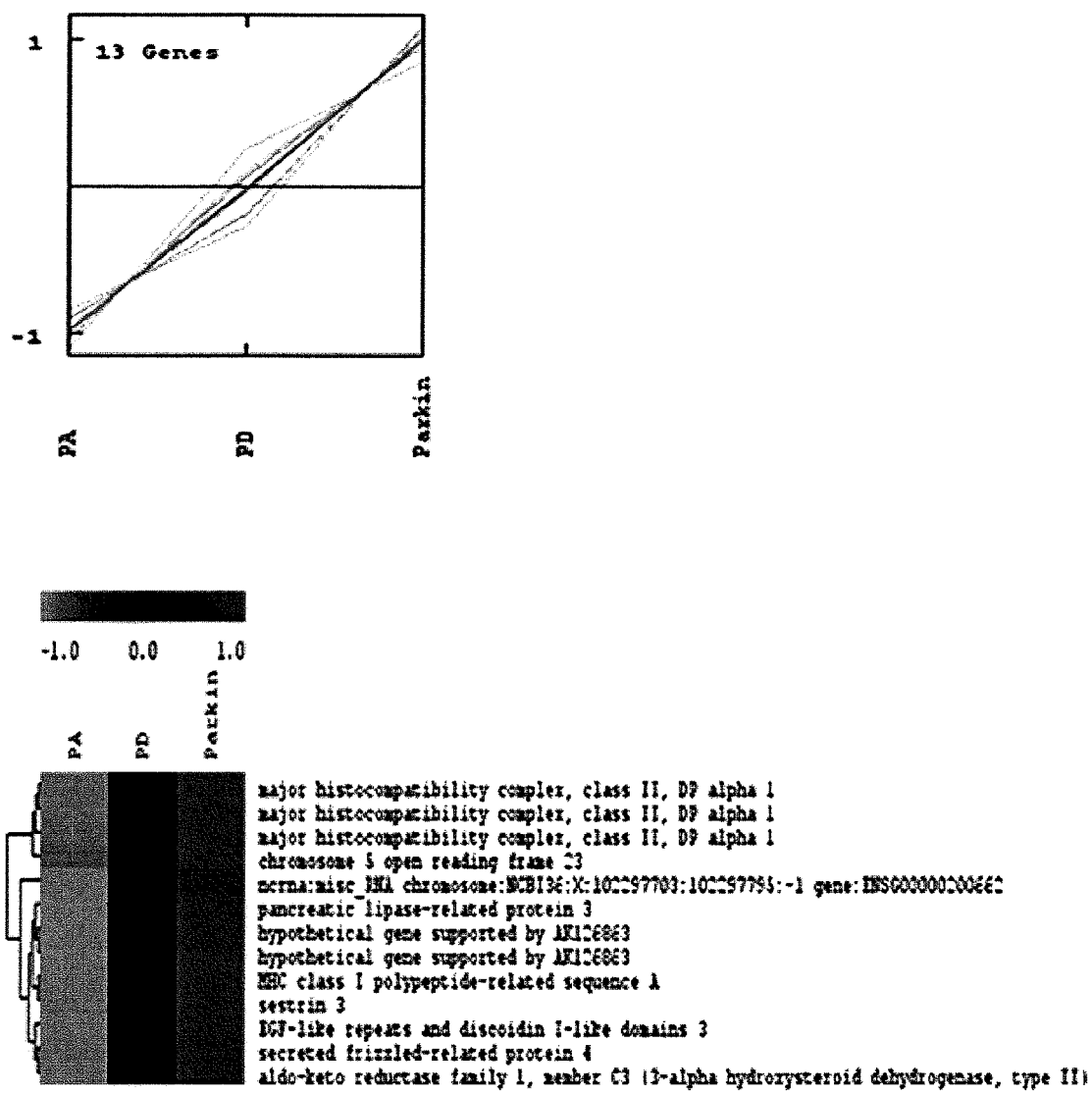
FIG. 7 represents the clustering analysis result of the genes showing linearly-increased gene expression between non-PD, PD, and Parkin groups.
Figure 8A:
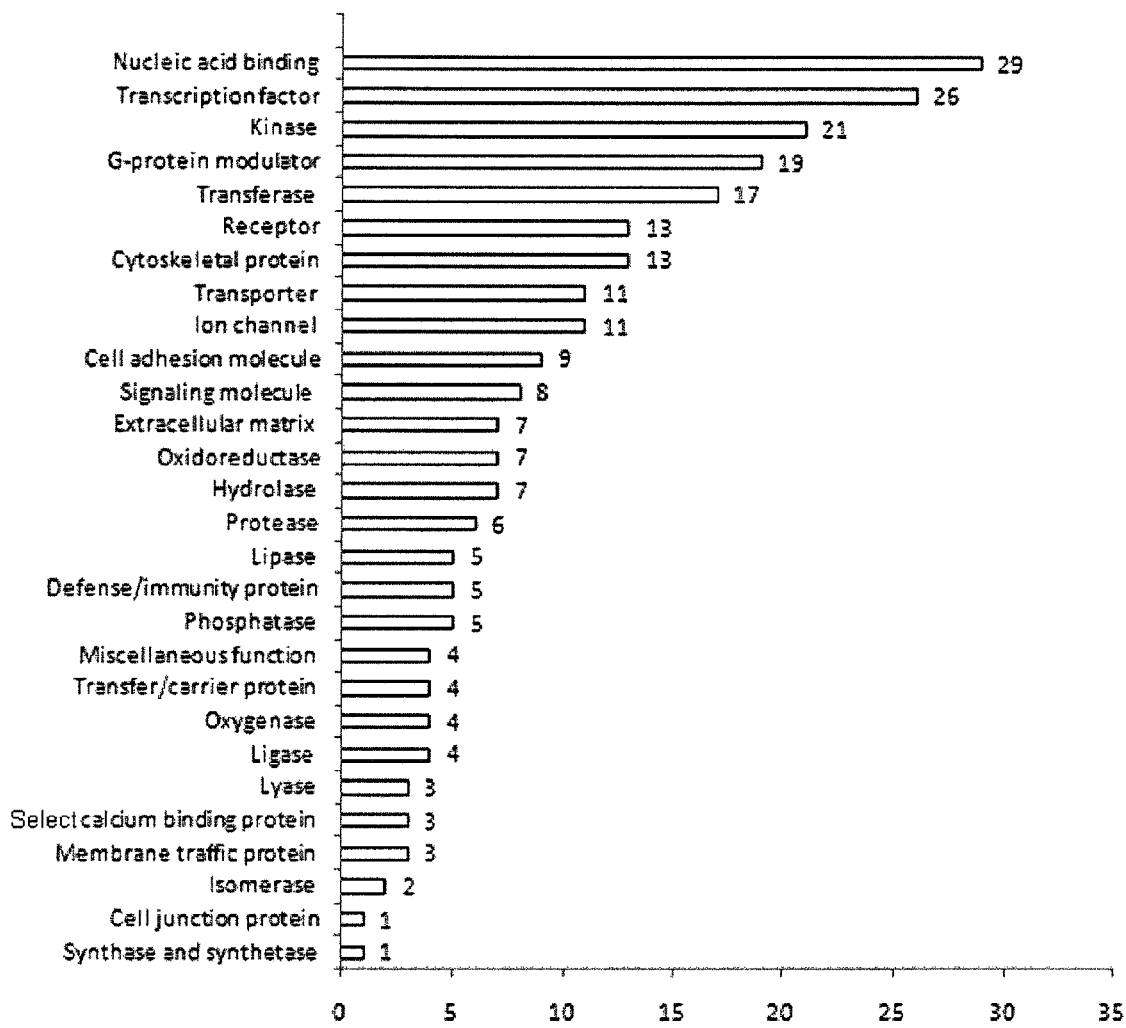
FIG. 8a to 8d show the result classifying human biomarker which are obtained by reprogramming the molecular functional groups by using Gene Ontology and Panther database system between non-PD vs. PD and non-PD vs. Parkin.
Figure 8B:
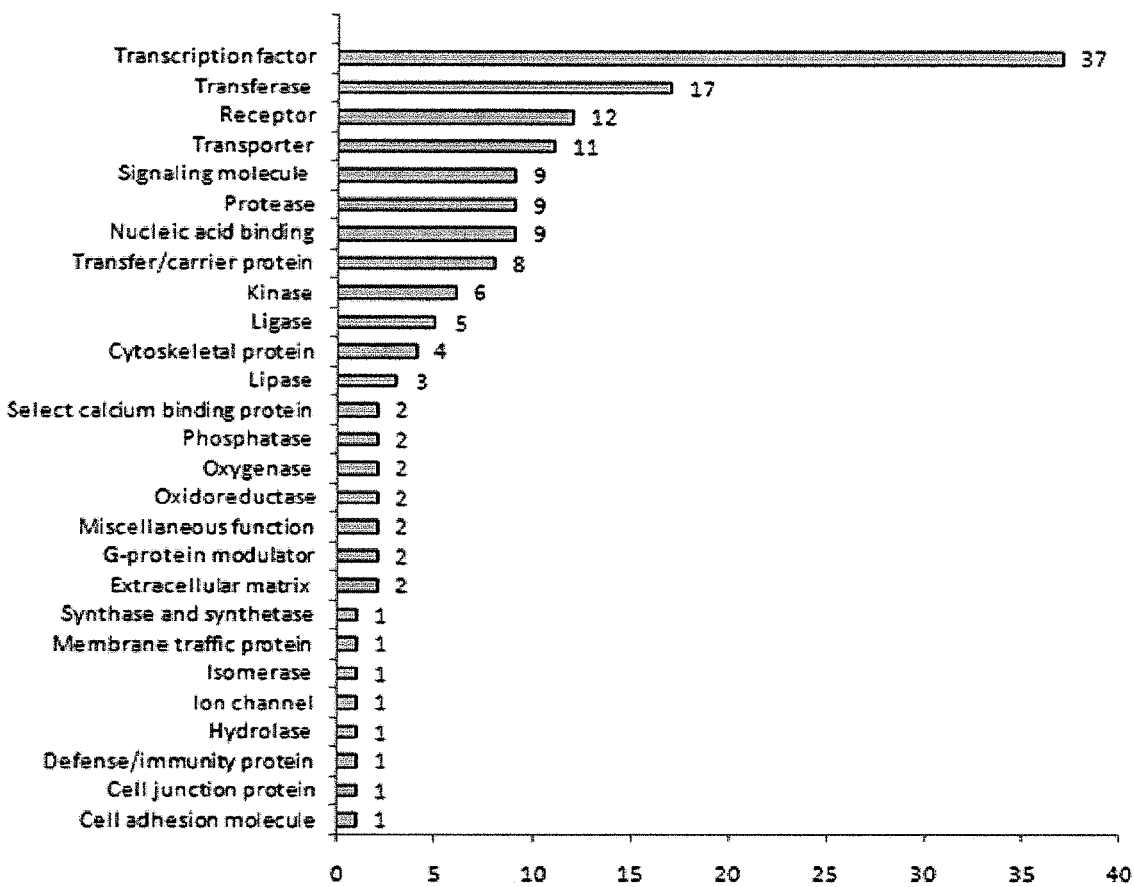
Figure 8C:
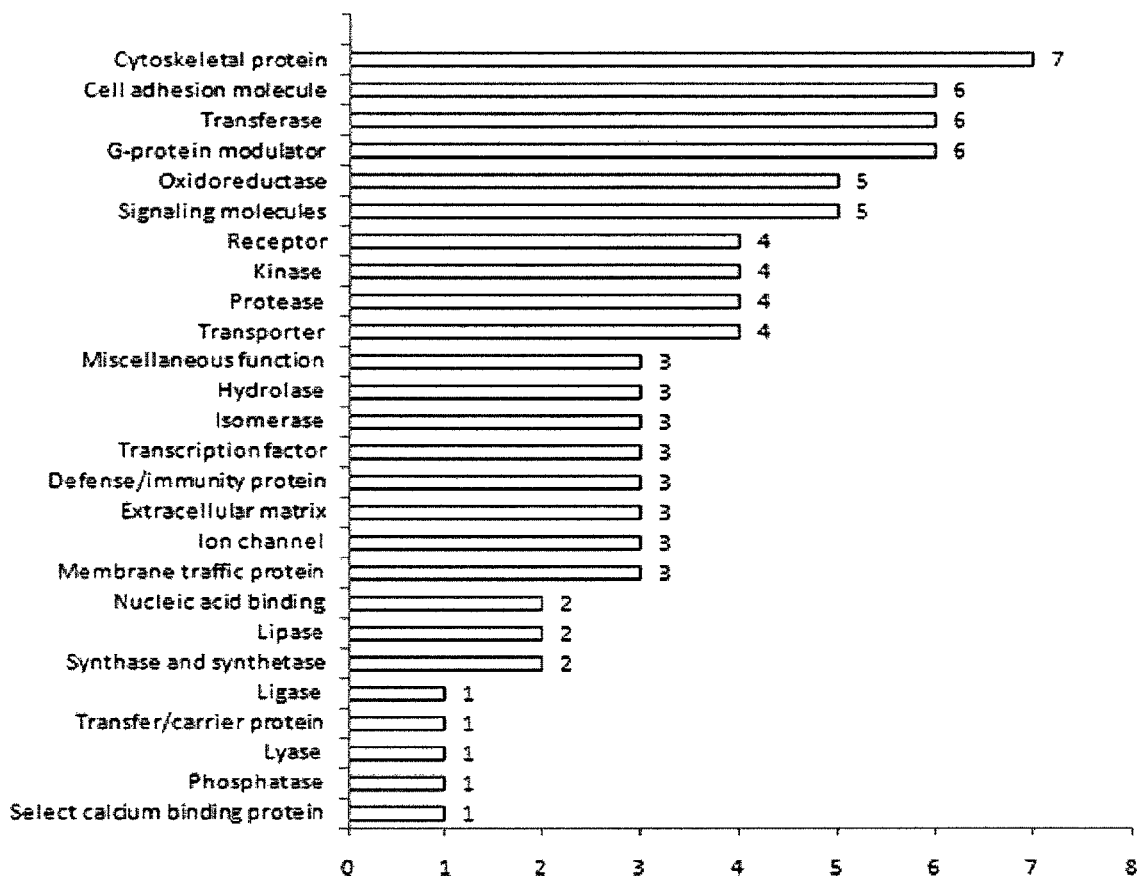
Figure 8D:
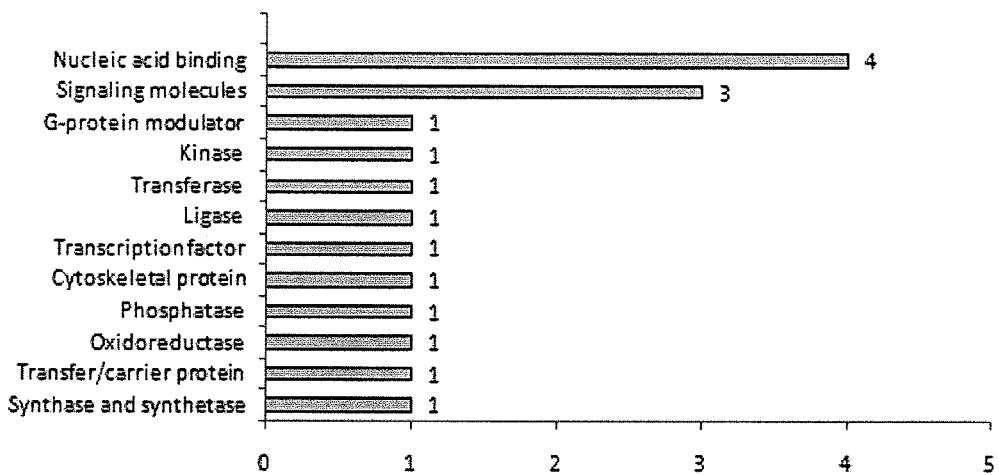

The genes of Cluster 3 showed a linear increase of gene expression amount in the order of PA<PD<Parkin, as shown in Table 8 and FIG. 7.

TABLE 8

| Gene name | Function | Genbank accession # |
|---|---|---|
| major histo-compatibility complex, class II, DP alpha 1 | antigen processing and presentation of peptide or polysaccharide antigen via MHC class II//immune response | NM_033554 |
| MHC class I polypeptide-related sequence A | antigen processing and presentation of peptide antigen via MHC class I// response to stress//immune response//cellular defense response//cell recognition// antigen processing and presentation | NM_000247 |
| pancreatic lipase-related protein 3 | lipid catabolic process | NM_001011709 |
| secreted frizzled-related protein 4 | signal transduction// embryo implantation//Wnt receptor signaling pathway//cell differentiation | NM_003014 |

TABLE 8-continued

| Gene name | Function | Genbank accession # |
|---|---|---|
| Sestrin 3 | cell cycle arrest | NM_144665 |
| EGF-like repeats and discoidin I-like domains 3 | cell adhesion//multicellular organismal development// angiogenesis | NM_005711 |
| aldo-keto reductase family 1, member C3 (3-alpha hydroxysteroid dehydrogenase, type II) | prostaglandin metabolic process | NM_003739 |

FIG. 7 is a result of clustering of the genes which showed a linear increase of gene expression in non-PD, PD, and Parkin.

2.4. Reprogramming of Functional Group of Human Biomarker Candidate Among Non-PD Vs. PD and Non-PD Vs. Parkin The functional groups among non-PD vs. PD and non-PD vs. Parkin were reprogrammed, and the human biomarker candidates were classified by using the genes obtained from Gene Ontology and Panther database system (DAVID Bioinformatics Resources 6.7) (FIGS. 8a to 8d). FIGS. 8a to 8d represented the number of genes which were reclassified as biologically-functional groups from the genes having the gene expression level of at least two-fold between the three groups of non-PD, PD, Parkin.

The biological categories included transcription factor, nucleic acid binding, receptor, kinase, oxido-reduction protein, signal molecule, cell adhesion molecule and the like.

The genetic functional groups which showed up-regulation (FIG. 8a) or down-regulation (FIG. 8b) in Idiopathic PD patient were compared with those of non-PD patient (control group). The genetic functional groups which showed up-regulation (FIG. 8c) or down-regulation (FIG. 8d) in Parkin (parkin deficiency) patient were compared with those of non-PD patient (control group). These graphs represented human biomarker candidate which were re-classified according to the biological functions and notable up-regulation or down-regulation in idiopathic PD patient and parkin-deficiency PD patient.

2.5. Genes Regulated Differentially in Non-PD, PD and Parkin Patients Due to the Oxidative Stress It has not been known which genes show selective sensitivity to the oxidative stress and how those genes affect the cell. PD-related genes which are differentially regulated by the oxidative stress are analyzed in non-PD, PD and Parkin groups. The genes regulated differentially by the oxidative stress were classified again as a functional group from the genes showing the gene expression level of at least two-fold between the groups of non-PD, PD, and Parkin, and then the PD-related genes were selected.

These groups included oxidoreductase, endoplasmic reticulum/ubiquitin-like, exocytosis/membrane trafficking, apoptosis/cell survival, structure/transport, translation, nuclear/transcriptional, and cell cycle. The PD-related genes in K-mean clustering 2 and 6 were classified again to change the cluster number. The genes which were differentially expressed between non-PD, PD and Parkin because of the oxidative stress are summarized in Table 9.

TABLE 9

| Putative Function | K-mean clustering |
|---|---|
| Group I: oxidoreductase | |
| aldo-keto reductase family 1, member B1 (aldose reductase) (AKR1B1) | 6 |
| Group II: endoplasmic reticulum/ubiquitin-like | |
| dopamine receptor D1 (DRD1) | 6 |
| Group III: exocytosis/membrane trafficking | |
| major histocompatibility complex, class II, DP α1 (HLA-DPA1) | 3 |
| synaptotagmin XIV (SYT14) | 6 |
| Group IV: apoptosis/cell survival | |
| actin, α, cardiac muscle 1 (ACTC1) | 2 |
| clusterin (CLU) | 2 |
| transforming growth factor, β3 (TGFB3) | 6 |
| Group V: structure/transport | |
| major histocompatibility complex, class II, DP α1 (HLA-DPA1) | 3 |
| transforming growth factor, β3 (TGFB3) | 6 |
| solute carrier family 6, member 6 (SLC6A6) | 6 |
| aldo-keto reductase family 1, member B1 (aldose reductase) (AKR1B1) | 6 |
| signal peptide, CUB domain, EGF-like 3 (SCUBE3) | 6 |
| Group VI: translation | |
| angiotensin II receptor, type 1 (AGTR1) | 2 |
| reelin (RELN) | 6 |
| G protein α14 (GNA14) | 6 |
| solute carrier family 6, member 6 (SLC6A6) | 6 |
| Group VII: nuclear/transcriptional | |
| integrin α2 (ITGA2) | 6 |
| transforming growth factor, β3 (TGFB3) | 6 |
| dopamine receptor D1 (DRD1) | 6 |
| Group VIII: cell cycle | |
| heat shock 70 kDa protein 2 (HSPA2) | 6 |

Surprisingly, the selective gene expression of the groups in Clusters 2, 3, and 6 increased linearly between non-PD, PD and Parkin patients, and the groups belonged to AKR1B1 (oxidoreductase), DRD1 (endoplasmic reticulum/ubiquitin-like), HLA-DPA1 and SYT14 (exocytosis/membrane trafficking), ACTC1, CLU and TGFB3 (apoptosis/cell survival), HLA-DPA1, TGFB3, SLC6A6, AKR1B1 and SCUBE (structure/transport), AGTR1, RELN, GNA14 and SLC6A6 (translation), ITGA2, TGFB3 and DRD1 (nuclear/transcriptional), and HSPA2 (cell cycle). The GENBANK accession numbers of the genes are summarized in the following table.

| Gene name | Gene accession number |
|---|---|
| AKR1B1 | NM_001628 |
| DRD1 | NM_000794 |
| HLA-DPA1 | NM_033554 |
| SYT14 | NM_153262 |
| ACTC1 | NM_005159 |
| CLU | NM_001831 |
| TGFB3 | NM_003239 |
| SLC6A6 | NM_003043 |
| SCUBE3 | NM_152753 |
| AGTR1 | NM_000685 |
| RELN | NM_005045 |
| GNA14 | NM_004297 |
| ITGA2 | NM_002203 |
| HSPA2 | NM_021979 |

The obtained data can assist the understanding of mitochondrial dysfunction and oxidative stress in Idiopathic and Parkin-derived Parkinson's disease, and provide a useful guidance for investigation of additional functional properties.

2.6. Immortalization of Mesenchymal Stromal Cells Derived from Adipose Tissue of Parkinson's Disease Patient with pGRN145 Including hTERT The cells of non-PD, PD, Parkin in Example 1.1 were spread again on the 24-well plate to reach 90 percent of confluence without adding antibiotics on one day before transfecting. 50 μL of serum-free OPTI-MEM I Medium (Gibco BRL, Gaithersburg, Md.) including 1 μg of pGRN145 DNA (Geron Corporation, Menlo Park, Calif., USA), and 50 μL of OPTI-MEM I Medium including 2 mL of LIPOFECTAMINE LTX Reagent (Gibco) were mixed and added to each well, and replaced with new media after culturing at 37° C. for 24 hr. After 48 hours, the transfected cells were cultured in media including Hygromycin-B (30 μg/mL) for 2 to 3 weeks, and the final concentration was reduced to be 10 μg/mL. The clones derived from one cell were selected.

The cell shapes of non-PD, PD, and Parkin cells belonging to the selected clones were compared before immortalization, after immortalization, 6-month culture and one-year culture with human telomerase reverse transcriptase (hTERT).

The objected immortalized cells were deposited at Korean cell line bank located at 28 Yungdon-dong, Chongrno-gu, Seoul 110-799, Republic of Korea on Nov. 17, 2010, and then assigned with the accession numbers of KCLRF-BP-00239 (PA1), KCLRF-BP-00240 (PA2), KCLRF-BP-00241 (PD1), KCLRF-BP-00242 (PD2), KCLRF-BP-00243 (Pakin1), and KCLRF-BP-00244 (Pakin2).

Figure 9:
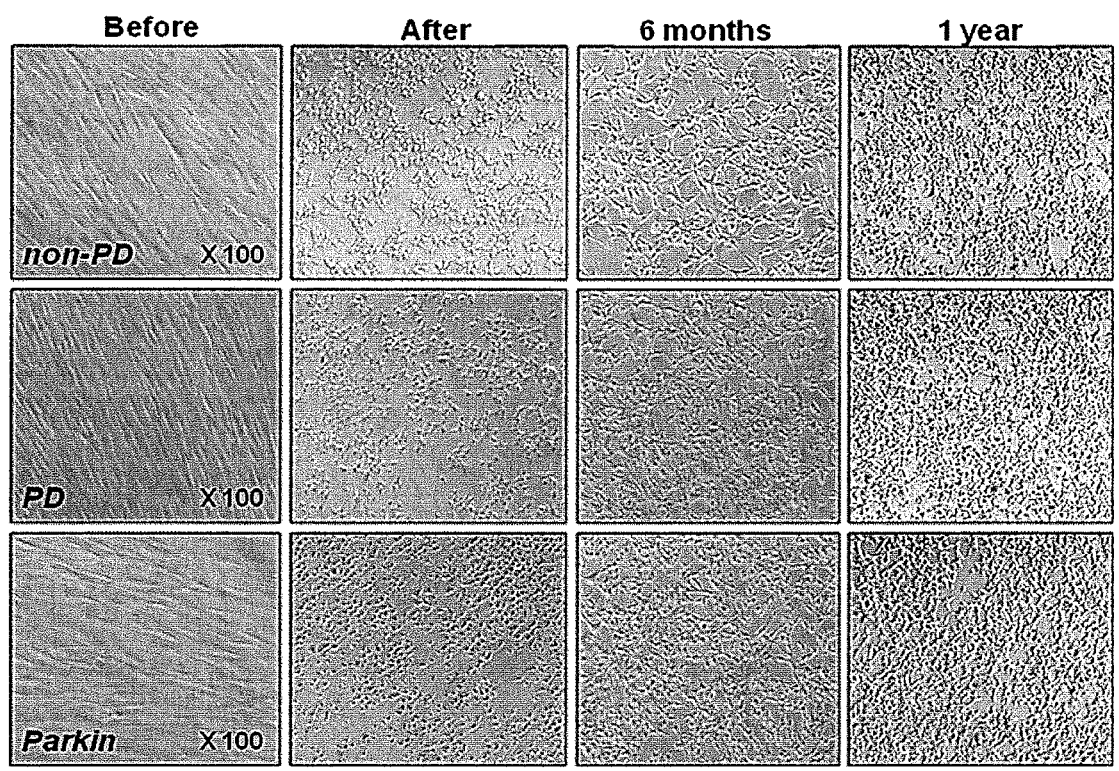
FIG. 9 shows the comparison of cell morphology before and after immortalization with hTERT in non-PD, PD, and Parkin group.
After: the cell morphology shortly after immortalization with hTERT.
6 months: the cell morphology after immortalization with hTERT and culturing for 6 months.
1 year: the cell morphology after immortalization with hTERT and culturing for 1 year.

The result is described in FIG. 9. In FIG. 9, non-PD (PA) represents the shape of cell having Accession No. KCLRF-BP-00239 (PA1) before and after immortalization, PD is for the shape of cell having Accession No. KCLRF-BP-00241 (PD1) before and after immortalization, and Parkin is for the shape of cell having Accession No. KCLRF-BP-00243 (Pakin1) before and after immortalization.

Figure 10:
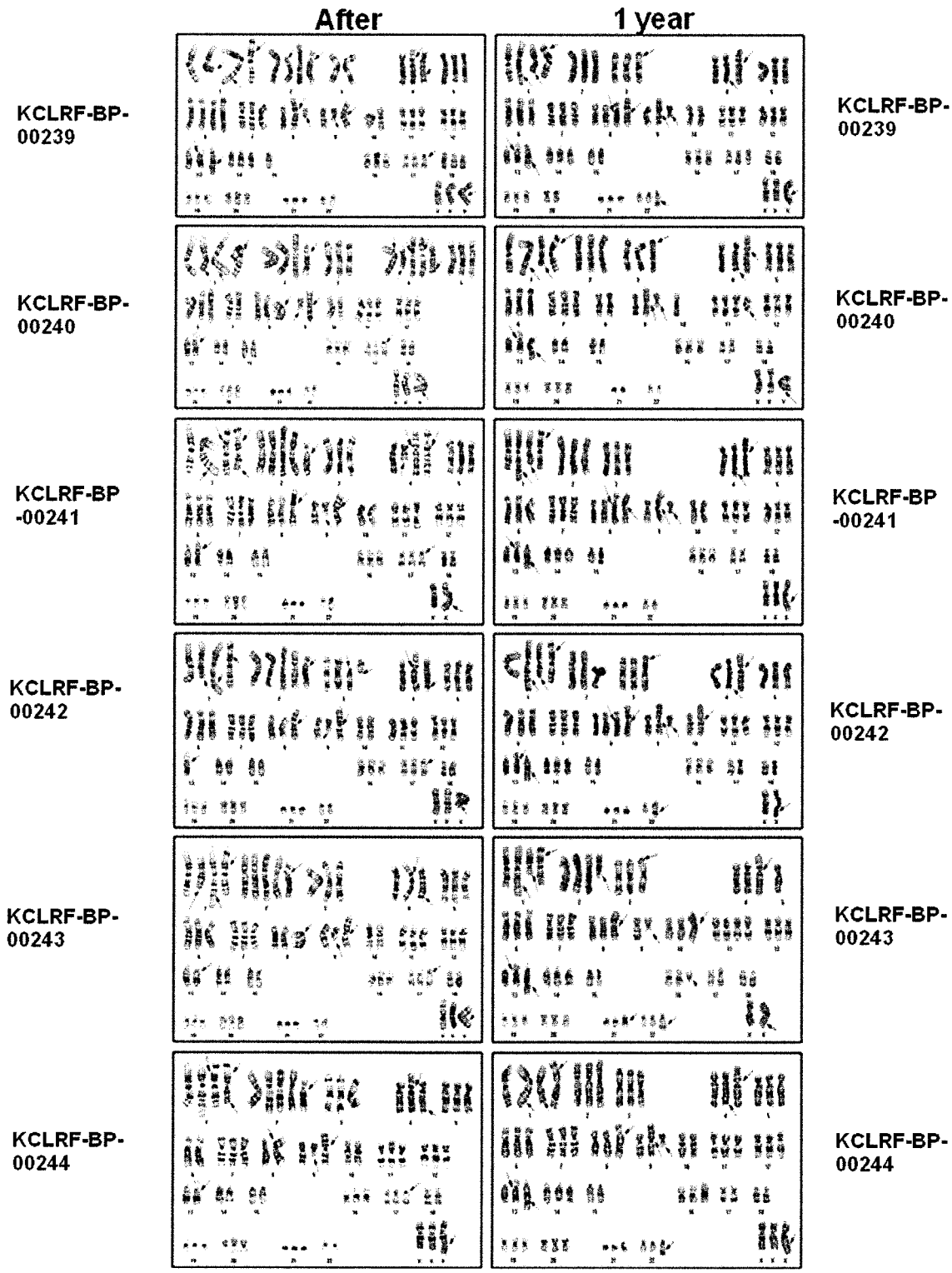
FIG. 10 shows a result of chromosomal structure (karyotype) analysis.
after: the karyotype analysis result shortly after immortalization with hTERT.
1 year: the karyotype analysis result after immortalization with hTERT and culturing for 1 year.

The chromosomal structure of the cells obtained shortly after the immortalization and after culturing the immortalized non-PD, PD, and Parkin for a year were analyzed and shown in FIG. 10. The chromosomal structure of the cells before immortalization was normal, and thus was not analyzed. From top to bottom in FIG. 10, non-PD (PA) represents the state of immortalized cell having Accession Nos. KCLRF-BP-00239 (PA1) and KCLRF-BP-00240 (PA2), PD represents the state of immortalized cell having Accession Nos. KCLRF-BP-00241 (PD1) and KCLRF-BP-00242 (PD2), and Parkin represent the state of immortalized cell having Accession Nos. KCLRF-BP-00243 (Pakin1) and KCLRF-BP-00244 (Pakin2).

Specifically, the cell division at metaphase of mitosis was restrained with colcemid (Gibco) Stoc solution. That is, the cells were collected from the supernatant obtained by centrifuging at 1500 rpm, shocked with 0.075M KCl hypotonic, and fixed with the addition of Canoy's fixative including methanol and acetic acid at a mixing ratio of 3:1, and Giemsa staining GTG banding). The prepared cell slide was analyzed with Karyotype Analysis program: ChIPS-Karyo (Chromosome Image Processing System) (GenDix, Inc. Seoul, Korea), and the analyzed result is shown in FIG. 10.

As shown in FIG. 10, the immortalized cell showed abnormal karyotype compared with the non-immortalized cell.

2.7. Separation of Mitochondria from the Cultured Cell for Mitochondria Complex I, II, IV and Citrate Synthase Assays The non-PD, PD, and Parkin cells immortalized with hTERT were washed with PBS and suspended in 10 mM Tris, pH 7.6 including protease inhibitor cocktail. The cells were blocked with 1-mL syringe, added with 1.5M sucrose and centrifuged at 600×g, 2° C. for 10 minutes. Then, the supernatant were centrifuged again at 14,000×g, 2° C. for 10 minutes and the obtained pellet were washed with protease inhibitor cocktail in 10 mM Tris (pH 7.6). The mitochondria pellets were re-suspended in 10 mM Tris (pH 7.6) including protease inhibitor cocktail and subsequently preserved in ice before use.

Complex I Assay:

The activity of complex I was analyzed with spectrometer at 600 nm by using 240 μL reagent including 25 mM potassium phosphate, 3.5 g/L BSA, 60 μM DCIP, 70 μM decylubiquinone, 1.0 μM antimycine-A, and 3.2 mM NADH, pH 7.8.

Figure 11A:
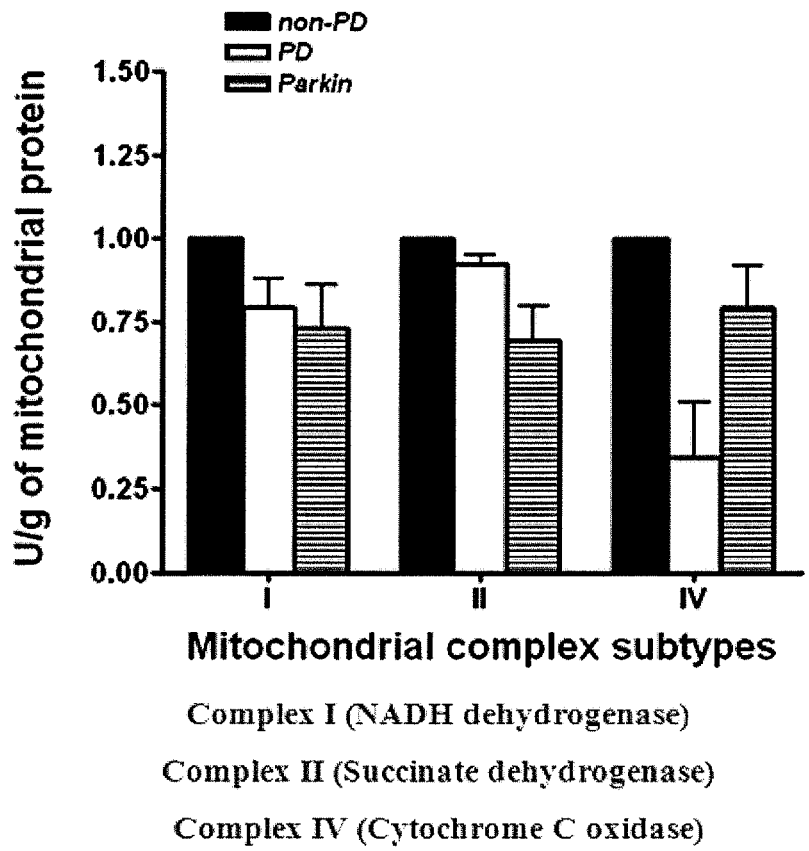
FIG. 11a shows a result of biochemical enzyme assay of mitochondria respiration chain of immortalized cell.
Figure 11B:
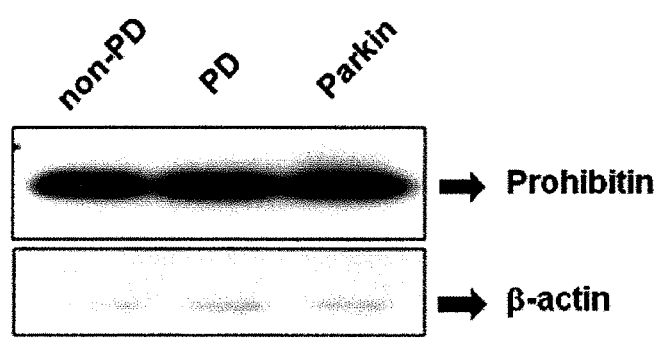

Namely, the obtained mitochondria sample (1 μg/10 μL) was added to a buffer solution without NADH, incubated at 37° C. for 3 minutes, and then added with 5 μL of 160 mM NADH. The absorbance was measured at 37° C. for 5 minutes at 30 second-intervals, and after 5 minutes, and 2.5 μL rotenone (100 μM of rotenone dissolved in 1 mM in dimethylsulfoxide and 10 mM Tris, pH 7.6) was added thereto. Then, the absorbance was measured at 37° C. for 5 minutes at 30 second-intervals. The results are shown in FIG. 11.

Complex II Assay:

The activity of complex II was analyzed with spectrometer at 600 nm with 240 μL reagent including 80 mM potassium phosphate, 1 g/L BSA, 2 mM EDTA, 0.2 mM ATP, 10 mM succinate, 0.3 mM potassium cyanide, 60 μM DCIP, 50 μM decylubiquinone, antimycine-A, and 3 μM rotenone, pH 7.8.

Specifically, the obtained mitochondria sample (1 μg/10 μL) was added to a buffer solution without succinate and potassium cyanide, incubated at 37° C. for 10 minutes, and then 20 μL of 1.5M succinate and 0.75 μL of 0.1M KCN were added thereto. The absorbance was measured at 37° C. for 5 minutes at 30 second-intervals, and BLANK was detected in the presence of 5 mM malonate. The result is shown in FIG. 11.

Complex IV Assay:

The activity of complex IV was analyzed with spectrometer at 550 nm with 240 μL reagent including 30 mM potassium phosphate, 2.5 mM dodecylmaltoside, and 34 μM ferrocytochrome c, pH 7.4

Specifically, the obtained mitochondria sample (1 μg/10 μL) was added to a buffer solution and shortly after, the absorbance was measured at 30° C. for 5 minutes at 30 second-intervals, and BLANK was detected in the presence of 1 mM KCN. The result is shown in FIG. 11.

Citrate Synthase Assay:

The activity of citrate synthase was analyzed with spectrometer at 412 nm with 2404 reagent (pH 7.5) including 50 mM Tris-HCl, 0.2 mM 5,5'-dithiobis-(2-nitrobenzoic acid), 0.1 mM acetyl-CoA and 0.5 mM oxaloacetate.

Specifically, the obtained mitochondria sample (1 μg/10 μL) was added to a buffer solution without oxaloacetate, and incubated at 30° C. for 5 minutes. After adding by 2.5 μL of 50 mM oxaloacetate, the absorbance was measured at 37° C. for 5 minutes at 30 second-intervals. The result is shown in FIG. 11. This assay began with the addition of oxaloacetate, and for a control group, water was added in the equal amount.

As represented in FIG. 11, the result of biochemical analysis for mitochondrial respiration chain of immortalized cell confirmed that the activities of PD and Parkin decreased compared with Non-PD activity.

2.8. Electron Microscopy Analysis

Figure 12:
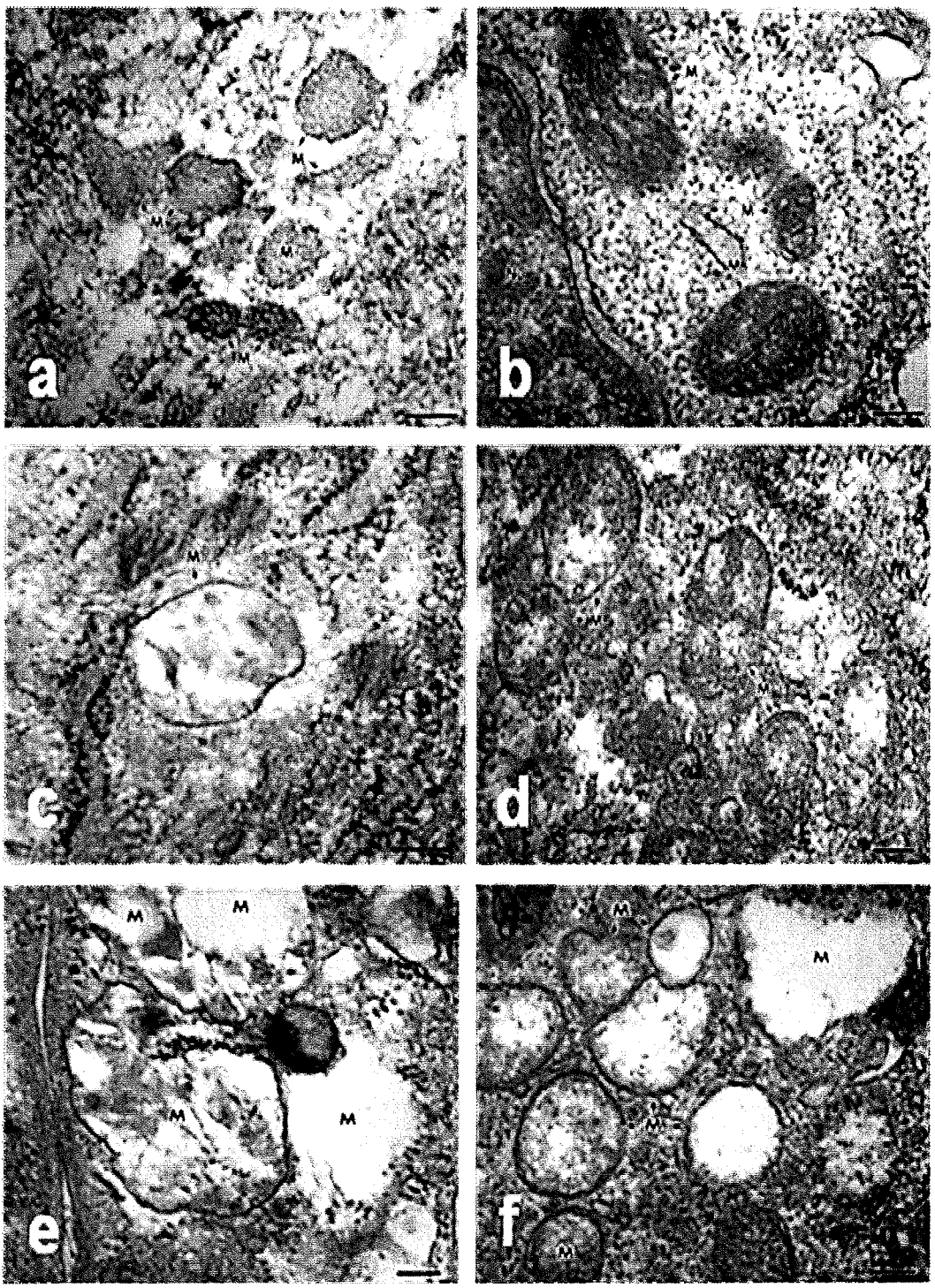
FIG. 12 is electronic microscopic images of mitochondria in early-culture stage and immortalization-culture stage of the cells (a, b: mitochondria in Non-PD; c, d: mitochondria in PD; and e, f: mitochondria in Parkin).

The non-PD, PD, and Parkin cells immortalized with hTERT were washed with PBS and fixed with 0.1% glutaraldehyde and 4% paraformaldehyde in PBS at 4° C. for 2 hours. The cells were collected and centrifuged at 2000×g, at 4° C. and for 3 minutes to obtain pellets. The prepared pellets were re-suspended in warm 1% agar and centrifuged at 2000×g at 4° C. for 3 minutes to obtain the pellets again. Then, the pellets were washed with PBS three times, and the cell pellets embedded with agar were fixed again with 1% osmium tetroxide for 2 hours and washed with PBS three times. The cell pellets embedded with agar was dehydrated in ethanol and fixed again with Epon 812. The ultrathin (70 nm) sections were collected on Formvar/carbon-coated nickel grids, stained with 2.5% uranyl acetate for 7 minutes and with lead citrate for 2.5 minutes, and then were observed with JEOL JEM-1011 electron microscope. The results are shown in FIG. 12. The comparison of mitochondrial shape of primary-cultured non-PD, PD and Parkin cell and immortalized non-PD, PD and Parkin cell showed that the mitochondria shape of non-PD (non-Parkinson's disease) patient was normal, but those of PD (Idiopathic Parkinson's disease) patient and Parkin (parkin-deficient Parkinson's disease) patient were damaged gradually. This suggested the mitochondrial damage is an important cause of Parkinson's disease.

2.9. Western Blot Analysis

Figure 13A:
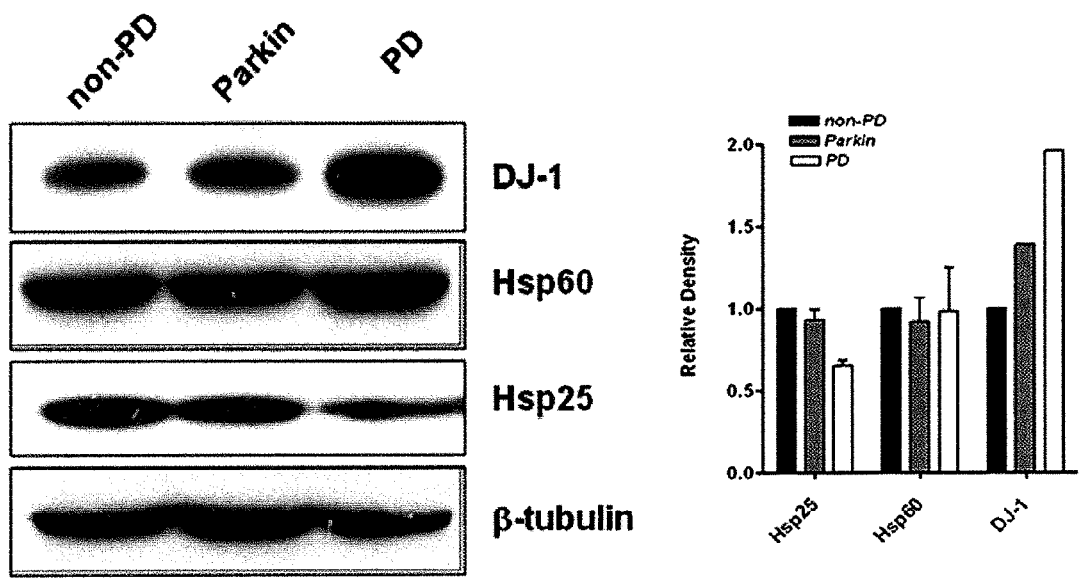
FIG. 13a represents a result of western blot analysis (left side) which shows the change in the gene expression of mitochondrial markers in early-culture stage of non-PD, PD, and Parkin groups, and a graph (right side) showing the quantitative analysis of the result.

The cells (The primary-cultured mesenchymal stromal cells derived from non-PD, PD, and Parkin patients were used in FIG. 13a, and immortalized mesenchymal stromal cells derived from non-PD, PD, and Parkin patients were used in FIGS. 13b, 13c, 14a, 15a, and 16a) were washed with cold PBS and divided into lysis buffer (cell signaling) and PMSF. The divided products were centrifuged at 15,000×g at 4° C. for 20 minutes. The products were analyzed quantitatively with Bradford reagent (Bio-Rad, Hercules, Calif.). The protein which was used in the same amount as other primary-cultured cells, and immortalized cells were loaded on SDS-PAGE, transferred to PVDF membrane (Millipore), and blocked with 5% non-fat dry milk in TBST. The proteins on the membrane were detected by chemical luminescence with X-ray film using ECL-Plus substrate (GE Healthcare, Buckinghamshire, USA). Antibodies of Hsp25, Hsp60 and Hsp90 were obtained from Santa Cruz Biotechnology (Santa Cruz, Calif., USA) and antibodies of DJ-1, P-mTOR, mTOR, P-S6K, S6K, LC3-I, and LC3-II were obtained from Chemicon (Temecula, Calif., USA). Prohibitin and β-actin (Santa Cruz) were used as internal control. The western blot analysis was performed with National Institutes of Health image processing and analyzing program (ImageJ, v1.38).

Figure 13B:
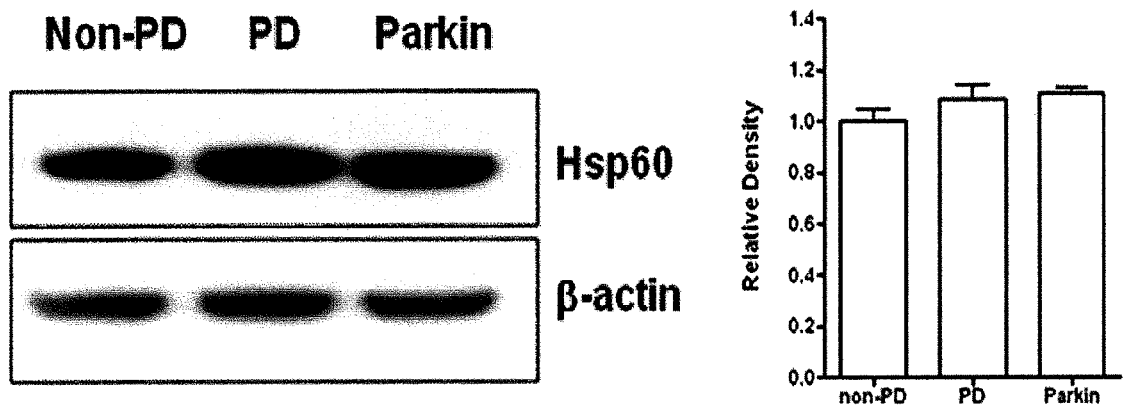
FIG. 13b represents the change in the gene expression of HSP60 as mitochondria marker in immortalization-culture stage of the cells in non-PD, PD, and Parkin (left side) and a graph (right side) showing the quantitative analysis of the result.
Figure 13C:
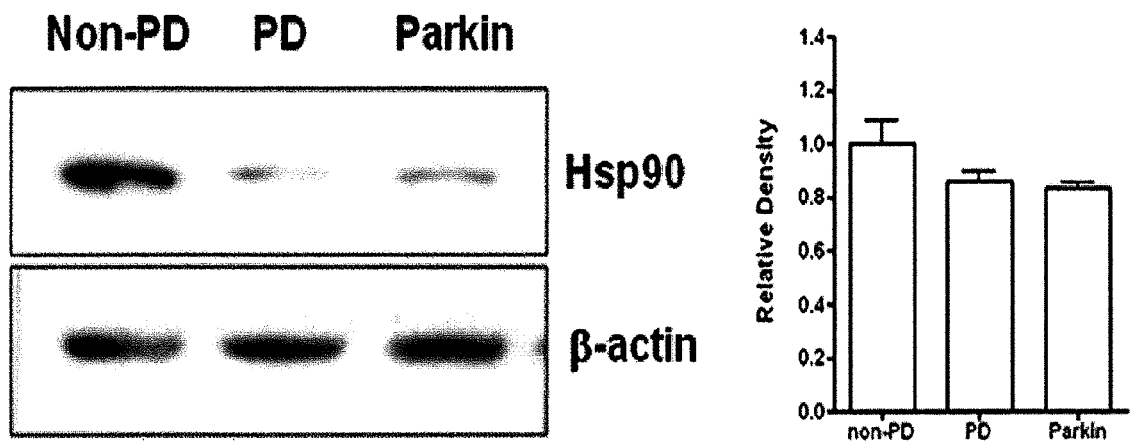
FIG. 13c represents the change in the gene expression of HSP90 as mitochondria marker in immortalization-culture stage of the cells in non-PD, PD, and Parkin (left side) and a graph (right side) showing the quantitative analysis of the result.
Figure 14A:
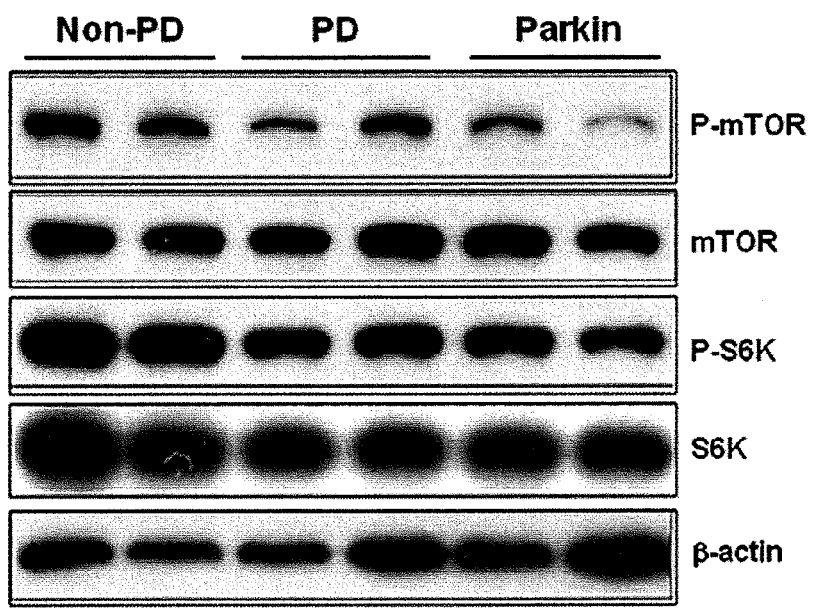
FIG. 14a represents a western blot analysis showing the change in the gene expression of autophagy makers in immortalization-culture stage of the cells in non-PD, PD, and Parkin.
Figure 14B:
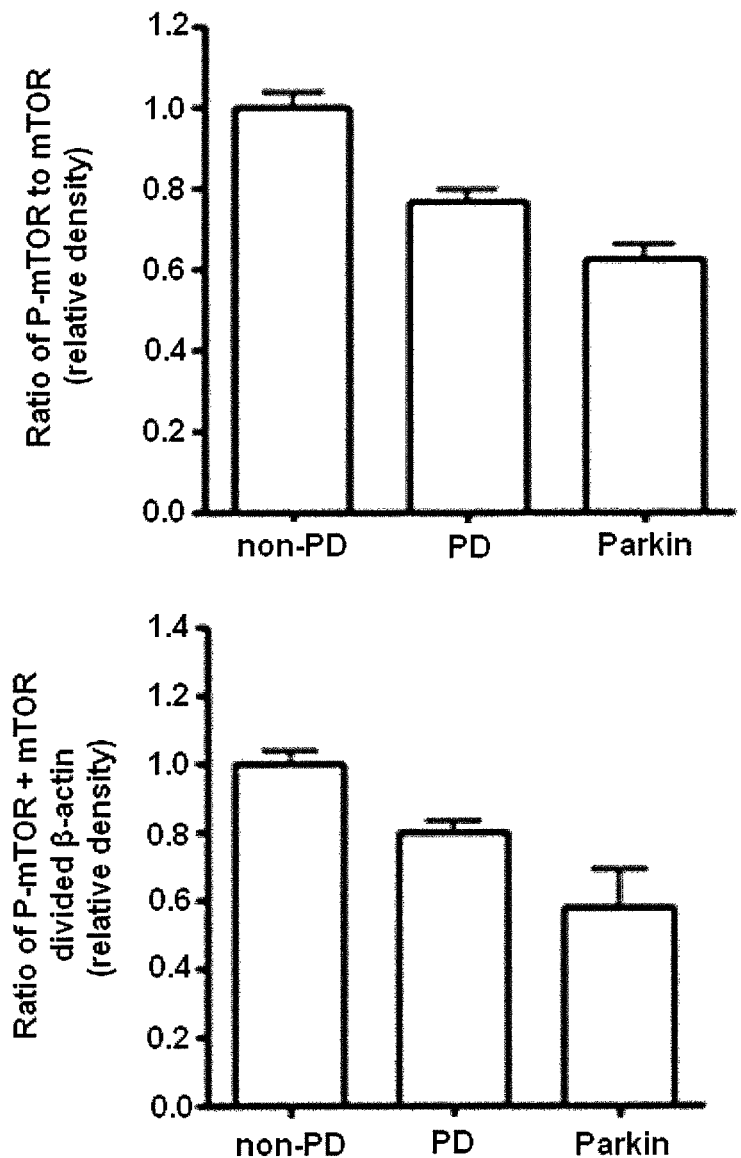
Figure 14C:
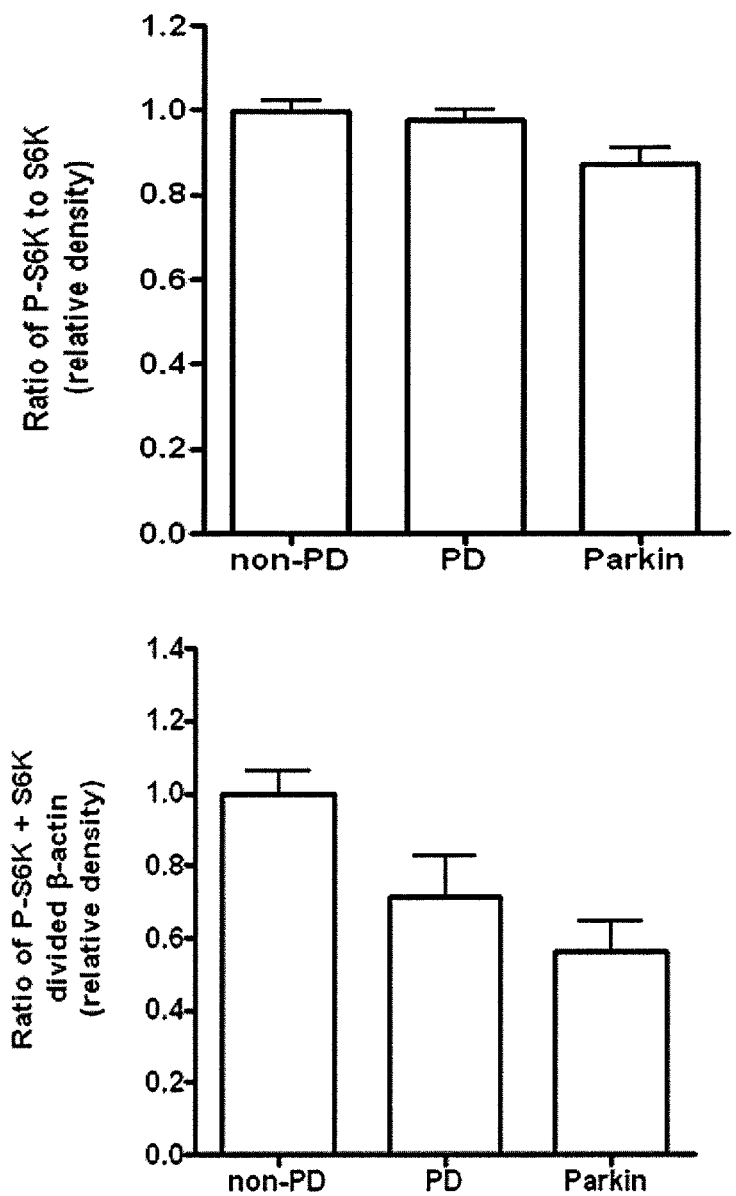
Figure 15A:
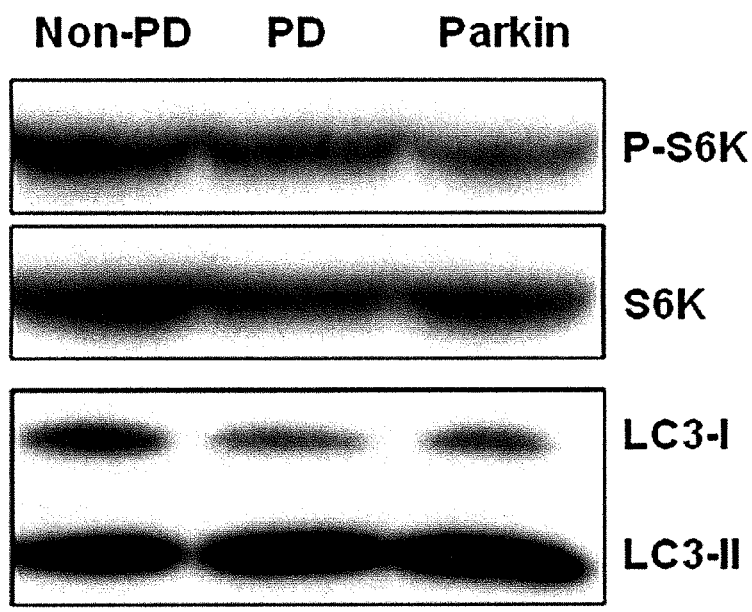
FIG. 15a represents a western blot analysis showing the change in the gene expression of autophagy markers in immortalization-culture stage of the cells in non-PD, PD, and Parkin.
Figure 16A:
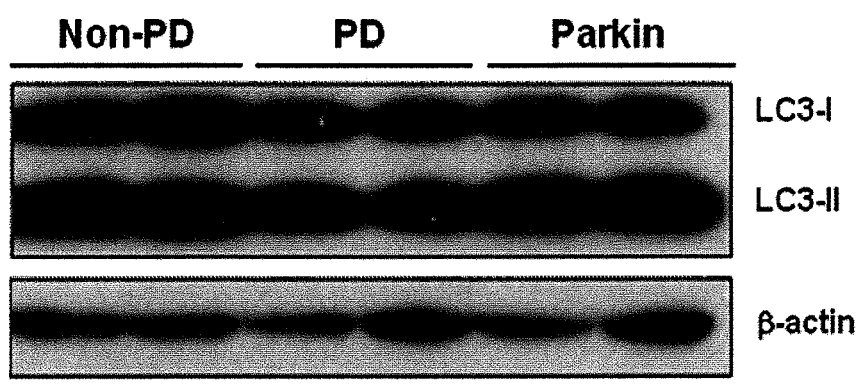
FIG. 16a represents western blot analysis showing the change in the gene expression of autophagy markers in immortalization-culture stage of the cells in non-PD, PD, and Parkin.

The obtained results are shown in FIGS. 13a-13c, 14a-14c, 15a-15b and 16a-16b. FIG. 13a represents the change in the gene expression of mitochondrial markers, DJ-1, Hsp60, and Hsp25 in the primary-cultured mesenchymal stromal cells derived from non-PD, PD, and Parkin patients. FIG. 13b represents the change in the gene expression of mitochondrial markers, Hsp60 in immortalized mesenchymal stromal cells derived from non-PD, PD, and Parkin patients. FIG. 13c represents the change in the gene expression of mitochondrial markers, Hsp90 in immortalized mesenchymal stromal cells derived from non-PD, PD, and Parkin patients. FIG. 14a represents the change in the gene expression of autophagy marker, mTOR, and S6K in immortalized mesenchymal stromal cells derived from non-PD, PD, and Parkin patients. FIG. 14b and FIG. 14c are the graphs showing the quantitative analysis of FIG. 14a. FIG. 15a represents the change in the gene expression of autophagy marker, mTOR, and S6K in immortalized mesenchymal stromal cells derived from non-PD, PD, and Parkin patients. FIG. 15b is the graph showing the quantitative analysis of FIG. 15a. FIG. 16a represents the change in the gene expression of autophagy marker, LC3 (LC3-I, LC3-II) in immortalized mesenchymal stromal cells derived from non-PD, PD, and Parkin patients. FIG. 16b is the graph showing the quantitative analysis of FIG. 16a.

What is claimed is:

1. An immortalized mesenchymal stromal cell, which is prepared by immortalizing a mesenchymal stromal cell separated from human adipose tissue of a patient without Parkinson's disease using human telomerase reverse transcriptase, and has an abnormal karyotype, wherein the immortalized mesenchymal stromal cell is a cell deposited with the Korean Cell Line Research Foundation under Accession No. KCLRF-BP-00239 or KCLRF-BP-00240.

2. An immortalized mesenchymal stromal cell, which is prepared by immortalizing a mesenchymal stromal cell separated from human adipose tissue of patient with Idiopathic Parkinson's disease using human telomerase reverse transcriptase, and has an abnormal karyotype, wherein the immortalized mesenchymal stromal cell is a cell deposited with the Korean Cell Line Research Foundation under Accession No. KCLRF-BP-00241 or KCLRF-BP-00242.

3. The immortalized mesenchymal stromal cell of claim 2, which has decreased mitochondrial activity compared with that of the immortalized mesenchymal stromal cell deposited with the Korean Cell Line Research Foundation under Accession No. KCLRF-BP-00239 or KCLRF-BP-00240.

4. An immortalized mesenchymal stromal cell, which is prepared by immortalizing a mesenchymal stromal cell separated from human adipose tissue of patient with Parkin-deficient Parkinson's disease using human telomerase reverse transcriptase, and has an abnormal karyotype, wherein the immortalized mesenchymal stromal cell is a cell deposited with the Korean Cell Line Research Foundation under Accession No. KCLRF-BP-00243 or KCLRF-BP-00244.

5. The immortalized mesenchymal stromal cell of claim 4, which has decreased mitochondrial activity compared with that of the immortalized mesenchymal stromal cell deposited with the Korean Cell Line Research Foundation under Accession No. KCLRF-BP-00239 or KCLRF-BP-00240.

* * * * *